United States Patent
Innocenti et al.

(10) Patent No.: US 11,028,448 B2
(45) Date of Patent: Jun. 8, 2021

(54) METHODS OF IDENTIFYING RISK OF VASCULAR ENDOTHELIAL GROWTH FACTOR (VEGF) PATHWAY INHIBITOR-INDUCED HYPERTENSION

(71) Applicants: The University of North Carolina at Chapel Hill, Chapel Hill, NC (US); Duke University, Durham, NC (US)

(72) Inventors: Federico Innocenti, Chapel Hill, NC (US); Julia Quintanilha, Chapel Hill, NC (US); Danyu Lin, Chapel Hill, NC (US); Kouros Owzar, Durham, NC (US); Jin Wang, Chapel Hill, NC (US)

(73) Assignees: The University of North Carolina at Chapel Hill, Chapel Hill, NC (US); Duke University, Durham, NC (US)

( * ) Notice: Subject to any disclaimer, the term of this patent is extended or adjusted under 35 U.S.C. 154(b) by 0 days.

(21) Appl. No.: 16/932,002

(22) Filed: Jul. 17, 2020

(65) Prior Publication Data
US 2021/0085745 A1 Mar. 25, 2021

Related U.S. Application Data

(60) Provisional application No. 62/903,442, filed on Sep. 20, 2019.

(51) Int. Cl.
*C12Q 1/6886* (2018.01)
*C12Q 1/6883* (2018.01)

(52) U.S. Cl.
CPC ......... *C12Q 1/6886* (2013.01); *C12Q 1/6883* (2013.01); *C12Q 2600/106* (2013.01); *C12Q 2600/156* (2013.01)

(58) Field of Classification Search
None
See application file for complete search history.

(56) References Cited

FOREIGN PATENT DOCUMENTS

WO   WO 2011/084791 A2   7/2011
WO   WO 2013/030168 A1   3/2013

OTHER PUBLICATIONS

Talbert, M.E. Thesis Dissertation. "Positional Cloning of Adiposity Genes in Ethnic Minorities of the Insulin Resistance Atherosclerosis Family Study", available via URL: <wakespace.lib.wfu.edu/bitstream/handle/10339/14758/TalbertThesisonedocument1.pdf> (Year: 2009).*
McCarthy et al J Hypertension. 2010. Vo. 28, e-Supplement A, e341-e342, Abstract pp. 21.315 (Year: 2010).*
An et al. Incidence and risk of significantly raised blood pressure in cancer patients treated with bevacizumab: An updated meta-analysis. Eur J Clin Pharmacol 2010, 66, 813-821.
Banerjee et al. Genomic imbalances in key ion channel genes and telomere shortening in sudden cardiac death victims. Cytogenet Genome Res 2009; 122: 350-355.
Berger et al. Autophagy-related polymorphisms predict hypertension in patients with metastatic colorectal cancer treated with FOLFIRI and bevacizumab: Results from TRIBE and FIRE-3 trials. Eur J Cancer. 2017;77:13-20.
Berger et al. The safety of monoclonal antibodies for treatment of colorectal cancer. *Expert Opin Drug Saf* 2016, 15, 799-808.
Chiu et al. Identification of rare variants for hypertension with incorporation of linkage information. BMC Proc. Jun. 17, 2014;8(Suppl 1):S109.
Crona et al. Genetic variants of VEGFA and FLT4 are determinants of survival in renal cell carcinoma patients treated with sorafenib. Cancer Res 2019;79:231-41. https://doi.org/10.1158/0008-5472.CAN-18-1089.
Crucitta et al., "Endothelia nitric oxide synthase c.-813C>T predicts for proteinuria in metastatic breast cancer patients treated with bevacizumab-based chemotherapy." Cancer Chemotherapy and Pharmacology 2019, 84:1219-1227.
Etienne-Grimaldi et al. "Prospective analysis of the impact of VEGF-A gene polymorphisms on the pharmacodynamics of bevacizumab-based therapy in metastatic breast cancer patients." *Br J Clin Pharmacol* 2011, 71, 921-928.
Fava et al., "Vanin-1 I26T Polymorphism and Hypertension in Two Large Urban-Based Prospective Studies in Swedes." Genetics, Genomics and Proteomics 2010, Poster Session 21, abstracts e341-e342.
Frey et al. "Genetic predisposition to bevacizumab-induced hypertension." *Gynecol Oncol* 2017, 147, 621-625.
Gampenrieder et al. "Endothelin-1 genetic polymorphism as predictive marker for bevacizumab in metastatic breast cancer." Pharmacogenomics J 2017, 17, 344-350.
Jain et al. "Hypertension and hand-foot skin reactions related to VEGFR2 genotype and improved clinical outcome following bevacizumab and sorafenib." J Exp. Chn Cancer Res 2010, 29, 95.
Keating, "Bevacizumab: A review of Its Use in Advanced Cancer." Drugs 2014, 74:1891-1925.
Lambrechts et al. "Genetic markers of bevacizumab-induced hypertension." Angiogenesis 2014, 17, 685-694.
Li et al. "Bevacizumab-induced hypertension: Clinical presentation and molecular understanding." *Pharmacol Ther* 2018, 182, 152-160.
Li et al. Identification of a genomic region between SLC29A1 and HsP90AB1 associated with risk of bevacizumab-induced hypertension: CALGB 80405 (Alliance). Clin Cancer Res 2018; 24: 4734-4744.
Martens et al. Alterations in rat interlobar artery membrane potential and K+ channels in genetic and nongenetic hypertension. Circ Res 1996; 79: 295-301.
McCarthy et al. Two further blood pressure loci identified in ion channel genes with a gene-centric approach. Circ Cardiovasc Genet. Dec. 2014;7(6):873-9.

(Continued)

*Primary Examiner* — Carla J Myers
(74) *Attorney, Agent, or Firm* — Casimir Jones, S.C.; Lisa V. Mueller

(57) ABSTRACT

The disclosure relates to methods of identifying subjects at risk of developing bevacizumab-induced toxicities such as proteinuria and/or hypertension involving measuring nucleic acid or gene mutations in a sample obtained from the subject.

6 Claims, 16 Drawing Sheets

(56) References Cited

OTHER PUBLICATIONS

Mir et al. An Observational Study of Bevacizumab-Induced Hypertension as a Clinical Biomarker of Antitumor Activity. Oncologist 2011; 16: 1325-1332.
Morita et al. "Association between bevacizumab-related hypertension and vascular endothelial growth factor (VEGF) gene polymorphisms in Japanese patients with metastatic colorectal cancer." Cancer Chemother Pharmacol 2013, 71, 405-411.
Robinson et al. Hypertension induced by vascular endothelial growth factor signaling pathway inhibition: Mechanisms and potential use as a biomarker, 2010. Semin Nephrol. 30:591-601.
Salvatore, "IL-8 and eNOS polymorphisms predict bevacizumab-based first line treatment oucomes in RAS mutant metastatic colorectal cancer patients." Oncotarget 2017, 8(10): 16887-16898.
Schneider et al. "Association of vascular endothelial growth factor and vascular endothelial growth factor receptor-2 genetic polymorphisms with outcome in a trial of paclitaxel compared with paclitaxel plus bevacizumab in advanced breast cancer: ECOG 2100." J Chn Oncol 2008, 28, 4672-4678.
Schneider et al. "Genetic variant predicts bevacizumab-induced hypertension in ECOG-5103 and ECOG-2100." *Br J Cancer* 2014, 111, 1241-1248.
Sibertin-Blanc et al. "Vascular Endothelial Growth Factor A c. 237C T polymorphism is associated with bevacizumab efficacy and related hypertension in metastatic colorectal cancer." Dig Liver Dis 2015, 47, 331-337.
Sobey Potassium channel function in vascular disease. Arterioscler Thromb Vasc Biol 2001; 21: 28-38.
Syrigos et al. Bevacizumab-induced hypertension: pathogenesis and management. *Biodrugs* 2011, 25, 159-169.
Tesařová et al. Proteinuria and hypertension in patients treated with inhibitors of the VEGF signalling pathway—incidence, mechanisms and management. *Folia Biol (Praha)* 2013, 59, 15-25.
Tur et al. Deletion of Kvβ1.1 subunit leads to electrical and haemodynamic changes causing cardiac hypertrophy in female murine hearts. Exp Physiol 2016; 101: 494-508.
Zhu. Risks of Proteinuria and Hypertension With Bevacizumab, an Antibody Against Vascular Endothelial Growth Factor: Systematic Review and Meta-Analysis. *Am J Kidney Dis* 2007, 49, 186-19.

* cited by examiner

Proteinuria grade ≥2

Hypertension grade ≥2

Composite toxicity grade ≥2

Hypertension, rs2350620

Hypertension, rs6770663

METHODS OF IDENTIFYING RISK OF VASCULAR ENDOTHELIAL GROWTH FACTOR (VEGF) PATHWAY INHIBITOR-INDUCED HYPERTENSION

CROSS REFERENCE TO RELATED APPLICATION

This application claims priority to U.S. Provisional Application No. 62/903,442, filed Sep. 20, 2019, which is hereby incorporated by reference in its entirety.

STATEMENT OF GOVERNMENTAL INTEREST

Tis invention was made with government support under Grant Numbers CA180821, CA180882, CA196171, CA233327, CA233253, CA233373, CA139280 and CA140390 awarded by the National Institutes of Health. The government has certain rights in the invention.

FIELD

The present disclosure relates to methods of identifying patients at risk of developing bevacizumab-induced toxicities. In particular, the disclosure relates methods of identifying patients at risk of developing bevacizumab-induced proteinuria and/or hypertension involving measuring nucleic acid mutations in a sample obtained from the patient.

BACKGROUND

Bevacizumab is a recombinant humanized monoclonal antibody that targets vascular endothelial growth factor (VEGF), inhibiting its binding to its receptors VEGFR1 and VEGFR2. It was approved by the U.S. Food and Drug Administration (FDA) in 2004 and by the European Medicines Agency in 2005 for the treatment of metastatic colorectal cancer. The FDA has also approved its use for the treatment of advanced non-squamous lung cancer, metastatic renal cell carcinoma, recurrent glioblastoma, advanced cervical cancer and platinum-resistant ovarian cancer.[1] Bevacizumab antitumor efficacy relies on its inhibition of the VEGF-signaling pathway involved in endothelial survival, vascular permeability and therefore angiogenesis.[2]

Despite the demonstrated efficacy of bevacizumab in combination with other therapies, patients frequently experience toxicity that limits the duration of therapy with bevacizumab and the efficacy of the regimen. The most frequent toxicities are hypertension and proteinuria, with a prevalence that varies in different studies (proteinuria 21%-41%, hypertension 3%-43).[3-5] Although hypertension and proteinuria are usually asymptomatic, they can be occasionally life threatening.[4,5]

The underlying mechanisms of how bevacizumab induces hypertension and proteinuria are not well understood, but they are postulated to involve nitric oxide (NO) inhibition and increases in peripheral vascular resistance, renal dysfunction and glomerular damage by inhibition of VEGF produced by podocytes. It is not clear whether the occurrence of proteinuria shares the same mechanism responsible for hypertension, or whether the kidney damage is a secondary effect.[6]

Currently, there are no validated biomarkers to predict bevacizumab-induced hypertension or proteinuria. Previous genetic studies of bevacizumab-induced hypertension focused on a few single-nucleotide polymorphisms (SNPs) in genes of the VEGF pathway.[7-14]

Despite the reported associations, none of the studies generated robust enough evidence to use these markers in the clinic, mostly because the biomarker signal was not concordant across multiple studies.[16] Accordingly, what is needed are robust biomarkers and methods of identifying patients at risk of bevacizumab-induced hypertension and/or proteinuria that can be reproduced in different studies.

SUMMARY

Provided herein are methods for determining risk and/or treating a subject.

In one aspect, provided herein is a method including detecting a mutation in one or more nucleic acids in a sample obtained from a subject who is undergoing therapy or is a candidate for therapy with a VEGF-pathway inhibitor.

In another aspect, provided herein is a method of predicting the risk of developing one or more VEGF-pathway inhibitor-induced toxicities in a subject, including detecting a mutation in one or more nucleic acids in a sample obtained from the subject who is undergoing therapy or is a candidate for therapy with a VEGF-pathway inhibitor, and determining the risk of developing one or more VEGF-pathway inhibitor-induced toxicities in the subject based upon the presence or absence of the mutation in the one or more nucleic acids in the sample.

In another aspect, provided herein is a method of treating a subject, comprising detecting a mutation in one or more nucleic acids in a sample obtained from a subject who is undergoing therapy or is a candidate for therapy with a VEGF-pathway inhibitor; determining the risk of developing one or more VEGF-pathway inhibitor-induced toxicities in the subject based upon the presence or absence of the mutation in the one or more nucleic acids in the sample; and modulating therapy with a VEGF-pathway inhibitor and/or providing the subject with one or more supportive therapies based upon the determined risk of developing one or more VEGF-pathway inhibitor-induced toxicities in the subject.

In another aspect, provided herein is a method for treating or preventing a VEGF pathway inhibitor-induced toxicity in a subject in need of treatment with a VEGF-pathway inhibitor, the method comprising identifying the subject as having a genetic mutation that confers a risk of developing the VEGF pathway inhibitor-induced toxicity, and treating the subject with a supportive and/or prophylactic therapy for the toxicity in addition to the VEGF-pathway inhibitor.

In another aspect, provided herein is a method for treating a subject having a disease or disorder, wherein the disease or disorder is indicated for treatment with a VEGF pathway inhibitor, the method comprising identifying the subject as having a genetic mutation that confers a risk of developing a VEGF pathway inhibitor-induced toxicity, treating the subject with a supportive and/or prophylactic therapy to prevent or reduce the toxicity, and treating the subject with the VEGF-pathway inhibitor.

In embodiments, the mutation is in a gene selected from the group consisting of KCNAB1, DNAH5, TRIO, RIPK4, IL17F, ASPH, TTMA, EPB41L3 and SLC25A24. In embodiments, the genetic mutation is a SNP. In embodiments, the genetic mutation is a mutation that lowers expression of KCNAB1 relative to wild type.

In embodiments, the SNP is selected from the group consisting of rs339947, rs12482855, rs13135230, rs2350620, rs11662763, rs6770663, rs408130, rs418173, rs12482855, rs444904, and rs427554. In embodiments, the base identified at rs339947 is an adenine, the base identified at rs12482855 is an adenine, the base identified at rs11662763 is an adenine, the base identified at rs408130 is an adenine, the base identified at rs418173 is an adenine, the base identified at rs12482855 is an adenine, the base identified at rs13135230 is an adenine, the base identified at rs11662763 is an adenine, the base identified at rs6770663 is a guanine, the base identified at rs444904 is an adenine, the base identified at rs427554 is an adenine, the base identified at rs2350620 is a guanine, or the base identified at rs11662763 is an adenine. In embodiments, the toxicity comprises hypertension and the SNP is rs677063, wherein the base identified at rs6770663 is a guanine.

In embodiments, the toxicity comprises hypertension, proteinuria, or both. In embodiments, the methods provided herein comprise administering a prophylactic and/or supportive therapy to prevent or reduce the toxicity. In embodiments, the prophylactic and/or supportive therapy is administered to the patient prior to and/or concurrently with administration of the VEGF pathway inhibitor. In embodiments, the methods comprise delaying the initiation of treatment with the VEGF pathway inhibitor until the prophylactic and/or supportive therapy has been administered to the subject for at least 1, 2, 3, 4, 5, 6, 7, 8, 9, 10, 11, 12, 13, 14, or more days, and/or until the subjects hypertension or proteinuria or other condition associated with the toxicity is reduced and/or resolved and/or under control. In embodiments, the methods comprise adding one or more prophylactic and/or supportive therapy to the subject's treatment regimen; switching the subject to a different prophylactic and/or supportive therapy; and/or increasing the dose and/or frequency of dosing of an anti-hypertensive agent relative to the dose administered to the subject prior to treatment with the VEGF pathway inhibitor. For example, in embodiments, a subject may have already been undergoing a treatment regimen with a prophylactic and/or supportive therapy for the condition associated with the toxicity risk. In such situations, the methods may comprise adding one or more additional prophylactic and/or supportive therapy, switching to a different class of drug for the prophylactic and/or supportive therapy, switching to a different drug within the same class for the prophylactic and/or supportive therapy, and/or increasing the dose and/or frequency of dosing with the prophylactic and/or supportive therapy, when the subject is identified as being at risk of developing the toxicity upon treatment with a VEGF pathway inhibitor.

In embodiments, the methods provided herein comprise modulating the dose of the VEGF pathway inhibitor. For example, in embodiments, the methods comprise reducing the total dosing amount, mg/kg dosing amount, or frequency of dosing of the VEGF pathway inhibitor. In embodiments, modulating the dose of the VEGF pathway inhibitor comprises starting at a dose lower than the recommended starting dose and maintaining the low dose or increasing the dose as appropriate with close monitoring for signs of the toxicity. In embodiments, the dose modulation is for the duration of treatment of the VEGF pathway inhibitor. In embodiments, the dose modulation is for a portion of the treatment with the VEGF pathway inhibitor, for example while symptoms of the toxicity persist. In embodiments, the methods comprise monitoring the subject for signs and symptoms of the toxicity or for worsening severity of the toxicity.

In embodiments, the toxicity comprises hypertension. In embodiments, the methods comprise monitoring the blood pressure of the subject, and/or monitoring the blood pressure of the subject more frequently than the blood pressure would be monitored in a patient who does not have the risk factor for the toxicity as provided herein. In embodiments, the toxicity comprises proteinuria. In embodiments, the toxicity comprises monitoring for proteinuria. In embodiments, monitoring for proteinuria comprises a urine dipstick and sulfosalicyclic acid test, a 24 hour urine collection test assay, or a spot albumin or protein-to-creatinine ratio test. In embodiments, the prophylactic and/or supportive therapy is an anti-hypertensive agent and/or an agent that treats or prevents proteinuria (e.g., a proteinuria medication). In embodiments, the anti-hypertensive agent or proteinuria medication is selected from the group consisting of loop diuretics, thiazide diuretics, thiazide-like diuretics, potassium-sparing diuretics, calcium channel blockers, ACE inhibitors, angiotensin 11 receptor antagonists, adrenergic receptor antagonists, vasodilators, renin inhibitors, aldosterone receptor antagonists, alpha-2 adrenergic receptor agonists, and endothelium receptor blockers.

In embodiments, the VEGF pathway inhibitor is any drug or therapeutic agent that inhibits, interferes with, or alters the VEGF pathway. For example, the VEGF pathway inhibitor may be an antibody, an antibody-like molecule, a small molecule, a soluble protein, a peptide, or the like that interferes with the VEGF-VEGFR interaction. In embodiments, the VEGF pathway inhibitor is selected from the group consisting of bevacizumab, bevacizumab-awwb, bevacizumab-bvzr, ranibizumab, aflibercept, ziv-aflibercept, lenalidomide, lenvatinib, ramucirumab, cabozantinib, pazopanib, sunitinib malate, regorafenib, axitinib, tipiracil and trifluridine, ponatinib, vandetanib, sorafenib, everolimus, thalidomide, temsirolimus, interferon alfa, interferon alfa-2B, interferon alfa-N3, peginterferon alfa-2B, peginterferon alfa-2A, rhEndostatin, cediranib, semaxanib, pomalidomide, alitretinoin, imiquimod, sinecatechins, vismodegib, sonidegib, pegaptanib sodium, dexamethasone intravitreal implant, fluocinolone acetonide, conbercept, brolucizumab-dbll, selpercatinib, nintedanib, apatinib, and motesanib. In embodiments, the VEGF pathway inhibitor is any biosimilar, generic, salt, ester, ether, isomer, mixture of isomers, complex, prodrug, or derivative of any VEGF pathway inhibitor provided herein or otherwise known in the art.

In embodiments, treating the subject with the VEGF pathway inhibitor comprises reducing exposure of the subject to the VEGF pathway inhibitor relative to the exposure of a subject treated as provided on prescribing information (e.g., the package insert or label) for the VEGF pathway inhibitor. For example, in embodiments, the methods provided herein comprise delaying initiation of treatment with the VEGF inhibitor, reducing the dose of the VEGF inhibitor, reducing the total number of doses of the VEGF inhibitor, reducing the dosing frequency of the VEGF inhibitor, and/or selecting a different VEGF pathway inhibitor (e.g., a VEGF pathway inhibitor that is less likely to be associated with the toxicity) or a non-VEGF pathway inhibitor therapy in the method of treating the subject, wherein the subject has been identified as being at risk of developing the toxicity. In embodiments, reducing the dose of the VEGF inhibitor comprises reducing the dose by about 5%, about 10%, about 25%, about 33%, about 50%, about 75%, or more relative to a reference dose, wherein the reference dose is the dose provided in prescribing information for the VEGF inhibitor. In embodiments, reducing the total number of doses of the VEGF inhibitor comprises reducing the total number of doses by about 5%, about 10%, about 25%, about 33%, about 50%, about 75%, or more relative to a reference total number of doses, wherein the reference total number of doses are total number of doses provided in prescribing information for the VEGF inhibitor. In embodiments, the methods comprise starting the subject on a lower dose and/or dosing frequency than the starting dose and/or dosing frequency recommended on the package insert for the VEGF pathway inhibitor, and titrating the dose upward to the dose and/or dosing frequency recommended on the package insert. In embodiments, such dosing comprising upward titrating is performed in combination with close monitoring of the subject for the toxicity. In embodiments, reducing the dosing frequency of the VEGF inhibitor comprises reducing the dosing frequency to about one third, about half, or about three quarters as often as the dosing frequency provided in prescribing information for the VEGF inhibitor.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated. Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

The term "single nucleotide polymorphism" or "SNP" as used interchangeably herein refer to a DNA sequence variation occurring when a single nucleotide (adenine (A), thymine (T), cytosine (C), or guanine (G)) in the genome differs between members of a species. Single nucleotides may be changed (substitution), removed (deletions) or added (insertion) to a polynucleotide sequence. Single nucleotide polymorphisms may fall within coding sequences of genes, non-coding regions of genes, or in the intergenic regions between genes. SNPs within a coding sequence may not necessarily change the amino acid sequence of the protein that is produced, due to degeneracy of the genetic code.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (e.g., a monkey, such as a cynomolgus or rhesus monkey, chimpanzee, etc.) and a human). In some embodiments, the subject may be a human or a non-human. In one embodiment, the subject is a human. The subject or patient may be undergoing various forms of treatment, such as with a VEGF-pathway inhibitor. The subject may be male or female. The subject may be of any ancestry. In some embodiments, the subject is of European ancestry.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a treatment to a subject that is not at the time of administration afflicted with the disease. "Preventing" also refers to preventing the recurrence of a disease or of one or more symptoms associated with such disease.

"Therapy" and/or "therapy regimen" generally refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. The term "providing" or "administering" as used herein with relation to a therapy (e.g. a VEGF-pathway inhibitor or a supportive therapy) may refer to providing to the subject the therapy or modulating the dose of a therapy currently being provided to the patient. For example, providing a supportive therapy may refer to increasing the dose of a supportive therapy currently being administered to the subject. The term "supportive therapies" and the like may be used interchangeably herein with "prophylactic therapies" and the like and refers to a therapy other than the therapy with the VEGF pathway inhibitor that prevents or controls (e.g., reduces the severity of or resolves) an adverse event such as hypertension or proteinuria. For example, the supportive therapy may be an anti-hypertensive agent.

DESCRIPTION OF THE DRAWINGS

These and other features, aspects, and advantages of the present disclosure will become better understood with regard to the following drawings.

DETAILED DESCRIPTION

Figure 1:
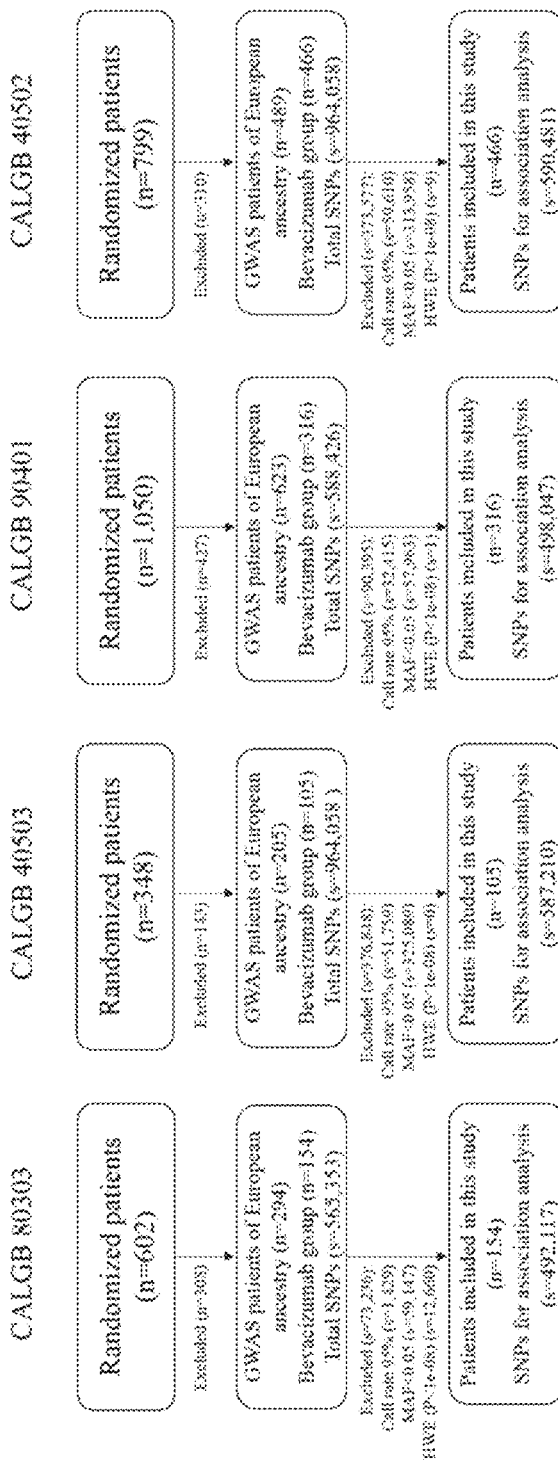
FIG. 1 shows CONSORT and quality control flowchart for CALGB 80303, 40503, 90401, and 40502. MAF minor allele frequency, HWE Hardy-Weinberg Equilibrium.

Provided herein are methods of predicting risk and/or treating a subject. In some embodiments, the methods comprise detecting one or more mutations in one or more nucleic acids in a sample obtained from the subject. In some aspects, the methods comprise detecting one or more mutations in one or more genes in a sample obtained from the subject.

In one aspect, provided herein is a method comprising detecting one or more mutations (e.g., 1, 2, 3, 4, 5, 6, 7, 8, 9 or 10 mutations) in one or more nucleic acids or genes in a sample obtained from a subject. In some embodiments, the method further comprises determining the risk of developing one or more VEGF-pathway inhibitor-induced toxicities in the subject based upon the presence or absence of one or more mutations in the one or more nucleic acids or genes in the sample.

In another aspect, provided herein is a method of predicting the risk of developing one or more toxicities induced by a therapeutic agent (e.g., a VEGF-pathway inhibitor) in a subject. The method comprises detecting one or more mutations (e.g., 1, 2, 3, 4, 5, 6, 7, 8, 9 or 10 mutations) in one or more nucleic acids or genes in a sample obtained from the subject, and determining the risk of developing one or more VEGF-pathway inhibitor-induced toxicities in the subject based upon the presence or absence of the mutation in the one or more nucleic acids or genes in the sample.

In another aspect, provided herein is a method of treating a subject comprising detecting one or more mutations in one or more nucleic acids or genes in a sample obtained from a subject, determining the risk of developing one or more VEGF-pathway inhibitor-induced toxicities in the subject based upon the presence or absence of one or more mutations in the one or more nucleic acids or genes in the sample, and modulating therapy with a VEGF-pathway inhibitor based upon the determined risk of developing one or more VEGF-pathway inhibitor-induced toxicities in the subject. Modulating the therapy may include, for example, monitoring the subject for improvement or worsening of the toxicity, administering a supportive therapy to the subject, and/or adjusting the dose of the VEGF-pathway inhibitor. For example, in embodiments, the present disclosure provides methods of treating a subject comprising detecting one or more mutations in one or more nucleic acids or genes in a sample obtained from a subject, determining the risk of hypertension or severe hypertensive crisis in the subject based upon the presence or absence of one or more mutations in the one or more nucleic acids or genes in the sample, and administering to the subject an anti-hypertensive agent prior to or concurrently with administration of the VEGF-pathway inhibitor.

In another aspect, provided herein is a method of treating a subject, comprising determining the risk of developing one or more VEGF-pathway inhibitor-induced toxicities in the subject based upon the presence or absence of one or more (e.g., 1, 2, 3, 4, 5, 6, 7, 8, 9 or 10 or more mutations) in one or more nucleic acids or genes in a sample obtained from a subject, and modulating therapy with a VEGF-pathway inhibitor based upon the determined risk of developing one or more VEGF-pathway inhibitor-induced toxicities in the subject. In some aspects, the method of treating a subject may be performed by one party. In other aspects, the method of treating a subject may be performed by two or more parties. For example, the presence or absence of one or more mutations in one or more nucleic acids in a sample may be measured by one party and a different party could modulate therapy with a VEGF-pathway inhibitor. For example, one party could analyze the sample to detect one or more mutations in nucleic acids or genes and provide information regarding these mutations to enable a second party to determine the risk in the subject and modulate therapy with the VEGF-pathway inhibitor based upon the determined risk. Alternatively, one party could analyze the sample to detect one or more mutations in nucleic acids or genes and determine the risk of developing one or more VEGF-pathway inhibitor-induced toxicities based upon the analysis, and a second party (e.g. a physician) could then modulate therapy with a VEGF-pathway inhibitor based upon the risk determination provided by the first party.

In an aspect, provided herein is a method for treating a subject having a disease or disorder associated with neovascularization or angiogenesis, the method comprising identifying the subject as having a mutation in the gene KCNAB1; treating the subject with an anti-hypertensive agent; and treating the subject with an angiogenesis inhibitor (e.g., a VEGF pathway inhibitor). In embodiments, the mutation is an SNP. In embodiments, the SNP is rs6770663. In embodiments, the base identified at rs6770663 is a guanine. In embodiments, provided herein is a method for treating a population of patients with a VEGF-pathway inhibitor, the method comprising providing a first population of patients who have a disease or disorder indicated for treatment with a VEGF-pathway inhibitor; separating patients who have the SNP rs6770663 into a second population of patients; and treating the second population of patients with an anti-hypertensive agent prior to or concurrently with administering the VEGF pathway inhibitor to the subject.

In accordance with any of the aspects and embodiments described herein, the subject may be a mammal. In particular embodiments, the subject is a human. The subject may be undergoing treatment or a candidate for treatment with a VEGF-pathway inhibitor.

Detecting a mutation in one or more nucleic acids in the sample may comprise detecting one or more single-nucleotide polymorphisms (SNPs) in the one or more nucleic acids in the sample, one or more deletions, insertions, copy number variations, inversions, or dislocations: and/or deletion of an entire gene of interest; and/or one or more mutations in one or more genes that affect the expression or function of a gene of interest. In some embodiments, the method comprises detecting a single SNP. In some embodiments, the method comprises detecting two SNPs. In yet other embodiments, the method comprises detecting three SNPs. In other embodiments, the method comprises detecting four SNPs, etc. In some embodiments, one or more SNPs is located in one or more genes provided in Table 8 or Table 9. In embodiments, the mutations provided herein that are associated with the risk of developing a VEGF-pathway-inhibitor-induced toxicity are present in one or more genes selected from the group consisting of KCNAB1 and ASPH.

KCNAB1 encodes the K* voltage activated channel subfamily 1 subunit 01 (Kv1.1-1.3) and it is highly expressed in arteries (aorta, coronary, tibial), and endothelial cells. Variant rs6770663 is located in a region of H3K4mel enhancers in the aorta (see Table 14).

In embodiments, the present disclosure provides mutations that predispose for lower expression of KCNAB1. For example, the present disclosure provides methods for treating patients with rs6770663 with a VEGF pathway inhibitor (e.g., bevacizumab), wherein the method comprises modifying the VEGF pathway inhibitor treatment by including monitoring for hypertension, prophylactically treating to prevent hypertension, and/or reducing the dosing level or dosing regimen for the VEGF pathway inhibitor in view of the patient's increased risk of hypertension. Variant rs6770663 has a frequency of about 10% in Europeans and a global frequency of 30%.

ASPH (aspartate P-hydroxylase) encodes the junctin protein which is expressed in arteries and in endothelial cells.

In some embodiments, the SNP is selected from the SNPs provided in Table 4, Table 5, Table 6, Table 7, Table 10, Table 11, Table 12, Table 13, rs444904, rs427554, or any combinations thereof. For example, one or more SNPs may be selected from the group consisting of rs339947, rs12482855, rs13135230, rs2350620, rs1662763, rs6770663, rs408130, rs418173, rs12482855, rs444904, and rs427554, or any combinations thereof. In some embodiments, a single mutation may be detected. In embodiments, more than one mutation (e.g., 2, 3, 4, 5, 6, 7, 8, 9 or 10 or more mutations) may be detected. For example, multiple SNPs may be evaluated for mutations in the subject. In embodiments, SNP rs6770663 confers susceptibility to VEGF-pathway inhibitor-induced hypertension.

The present disclosure provides data and validation of the mutations (e.g. SNPs) provided herein as clinically relevant biomarkers of VEGF pathway inhibitor toxicities. For example, the present disclosure demonstrates that mutations provided herein are biomarkers for hypertension and/or proteinuria elicited by more than one different type of VEGF pathway inhibitor. The skilled person will understand that the results provided herein apply to any angiogenesis inhibitor, e.g., any VEGF pathway inhibitor.

The methods described herein may involve determining the risk of developing one or more VEGF-pathway inhibitor-induced toxicities in the subject. Any suitable toxicity may be evaluated. VEGF inhibitor-induced toxicities include, for example, fatigue, asthenia, weight loss, pain, depression, pyrexia, chills, myalgia, neurologic-sensory neuropathy, gastrointestinal toxicities (e.g. anorexia, decreased appetite, dry mouth, stomatitis, mucositis, nausea, vomiting, diarrhea, constipation, GI perforation), skin toxicities (e.g. HFS, rash, alopecia, depigmentation, pruritus, dry skin, wound healing complications), cardiovascular toxicities (e.g. hypertension, CHF, cardiac ischemia, cerebrovascular ischemia, embolism/thrombosis, bleeding, dyspnea, cough, pneumonitis, dysphonia), myelotoxicities (e.g. anemia, hemoglobin elevation, leukopenia, neutropenia, thrombocytopenia, lymphopenia), metabolic abnormalities (e.g. bilirubin, ALT, AST, gamma-GT abnormalities, INR abnormalities, PTT abnormalities, increased alkaline phosphatase, hypoalbuminemia, lipase elevation, amylase elevation, creatinine increase, increased uric acid, proteinuria, hypophosphatemia, hypothyroidism, increased triglycerides, increased cholesterol, hyperglycemia, hypoglycemia, hypercalcemia, hypocalcemia, hyponatremia), and the like.

In particular embodiments, VEGF-pathway inhibitor-induced toxicities are selected from proteinuria, hypertension, or both. For example, determining the risk of developing one or more VEGF-pathway inhibitor-induced toxicities may comprise diagnosing the subject as having a high risk of developing proteinuria. In particular embodiments, the subject is diagnosed as having a high risk of developing proteinuria when the base identified at rs339947 is an adenine, the base identified at rs12482855 is an adenine, the base identified at rs11662763 is an adenine, the base identified at rs408130 is an adenine, the base identified at rs418173 is an adenine, or the base identified at rs12482855 is an adenine.

As another example, determining the risk of developing one or more VEGF-pathway inhibitor-induced toxicities may comprise diagnosing the subject as having a high risk of developing hypertension. In particular embodiments, the subject is diagnosed as having a high risk of developing hypertension when the base identified at rs13135230 is an adenine, the base identified at rs11662763 is an adenine, the base identified at rs6770663 is a guanine, the base identified at rs444904 is an adenine, or the base identified at rs427554 is an adenine. In embodiments, the subject is determined to be of high risk of developing hypertension when the base identified at rs6770663 is a guanine.

In some embodiments, determining the risk of developing one or more VEGF-pathway inhibitor-induced toxicities comprises diagnosing the subject as having a low risk of developing hypertension. For example, the subject may be diagnosed as having a low risk of developing hypertension when the base identified at rs2350620 is a guanine.

In some embodiments, determining the risk of developing one or more VEGF-pathway inhibitor-induced toxicities comprises diagnosing the subject as having a high risk of developing either proteinuria, or hypertension, or both (e.g. composite toxicity). For example, the subject may be diagnosed as having a high risk of developing proteinuria or hypertension or both when the base identified at rs11662763 is an adenine.

In some embodiments, the methods described herein further comprise modulating therapy with a VEGF-pathway inhibitor based upon the risk determined in the subject. For example, the method may comprise providing the subject with a VEGF-pathway inhibitor or increasing the therapeutic dose of the VEGF pathway inhibitor when the subject is determined to have a low risk of developing one or more VEGF-pathway inhibitor toxicities. For example, the method may comprise providing the subject with a VEGF-pathway inhibitor or increasing the therapeutic dose of the VEGF pathway inhibitor when the subject is diagnosed as having a low risk of developing proteinuria, hypertension, or both. In some embodiments, the method may comprise lowering the dose of a VEGF-pathway inhibitor or ceasing treatment with the VEGF-pathway inhibitor when the subject is determined to have a high risk of developing one or more VEGF-pathway inhibitor toxicities, such as a high risk of developing proteinuria, hypertension, or both. In embodiments, the method may comprise starting the subject who is determined to have a high risk of developing one or more VEGF pathway inhibitor toxicities, such as the high risk of developing proteinuria, hypertension, or both, at a lower dose and/or lower dosing frequency compared to the dose and/or regimen that is recommended on the package insert for the VEGF pathway inhibitor, monitoring the subject for the one or more toxicities, and titrating the dose and/or dosing frequency upwards, if appropriate based on the monitoring for the toxicity.

In some embodiments, the methods described herein further comprise modulating therapy with or providing the subject with one or more supportive therapies. The term "supportive therapies" refers to a therapy other than the therapy with an anti-cancer agent (e.g. a VEGF pathway inhibitor or other anti-cancer agent). For example, the supportive therapy may be an anti-hypertensive agent and/or a proteinuria medication. Suitable anti-hypertensive agents and/or proteinuria medications include, for example, diuretics, beta blockers, alpha and beta blockers, calcium channel blockers, angiotensin-converting enzyme (ACE) inhibitors, angiotensin II receptor antagonists (ARBs), adrenergic receptor antagonists, vasodilators (e.g. direct vasodilators), renin inhibitors, aldosterone receptor antagonists, alpha-2 adrenergic receptor agonists, central alpha-2 agonists and other centrally acting drugs, endothelin receptor blockers, and the like.

In embodiments, if the subject is determined to be at risk of developing one or more VEGF-pathway inhibitor toxicities, the methods provided herein comprise adding a supportive therapy to the subject's treatment regimen, increasing the dose and/or dosing frequency of a supportive therapy that is already a part of the subject's treatment regimen, and/or adding one, two, three, or more additional supportive therapies to the subject's treatment regimen. In embodiments, the added one, two, three or more additional supportive therapies may be different drugs in the same class as one another and/or as a supportive therapy that was already a part of the subject's treatment regimen; or the one, two, three, or more additional supportive therapies may be drugs in a different class as one another and/or as a supportive therapy that was already part of the subject's treatment regimen. Classes of supportive therapies are known in the art and exemplified herein, such as, for example, diuretics, beta blockers ACE inhibitors, angiotensin II receptor antagonists, calcium channel blockers, direct renin inhibitors, alpha-2 adrenergic receptor agonists, central alpha-2 agonists, and vasodilators.

Exemplary diuretics may be thiazide or thiazide-type diuretics. For example, the diuretic may be chlorthalidone, hydrochlorothiazide, indapamide, or metolazone. Chlorthalidone or hydrochlorothiazide may be administered, for example, at a dose of about 12.5 to about 50 mg/day, once daily. Indapamide may be administered, for example at a dose of about 1.25 to about 2.5 mg/day, once daily. Metolazone may be administered, for example, at a dose of about 2.5 to about 5 mg/day, once daily. Exemplary diuretics may also be loop diuretics, such as bumetanide, furosemide, or torsemide. Bumetanide may be administered, for example, twice daily at a dose of about 0.5 to about 2 mg/day. Furosemide may be administered, for example, twice daily at a dose of about 20 to about 80 mg/day. Torsemide may be administered, for example, once daily at a dose of about 5 to about 10 mg/day. Exemplary diuretics may also be potassium sparing diuretics, such as amiloride or triamterene. Amiloride may be administered, for example, once or twice daily at a dose of about 5 to about 10 mg/day. Triamterene may be administered, for example, once or twice daily at a dose of about 50 to about 100 mg/day. Exemplary diuretics may also be aldosterone antagonists, such as eplerenone or spironolactone. Eplerenone may be administered, for example, once or twice daily at a dose of about 50 to about 100 mg/day. Spironolactone may be administered, for example, twice daily at a dose of about 25 to about 100 mg/day. Exemplary diuretics may also include thiazide/potassium-sparing combination diuretics, such as hydrochlorothiazide/triamterene. Hydrochlorothiazide/triamterene may be administered once daily, for example, at a dose of about 25 mg/about 37.5 mg to about 50 mg/about 75 mg.

Exemplary beta blockers may be cardioselective (e.g., atenolol, betaxolol, bisoprolol, metoprolol (tartate), or metoprolol (succinate) extended release), noncardioselective (e.g., nadolol, propranolol, or long-acting propranolol), cardioselective and vasodilatory (e.g., nebivolol), or intrinsic and sympathomimetic activity beta-blockers (e.g., acebutolol, penbutolol, and pindolol). Atenolol may be administered, for example, once or twice daily at a dose of about 25 to about 100 mg/day. Betaxolol may be administered, for example, once daily at a dose of about 5 to about 20 mg/day. Bisoprolol may be administered, for example, once daily at a dose of about 2.5 mg to about 20 mg/day. Metoprolol (tartate) may be administered once or twice daily at a dose of about 50 to about 200 mg/day. Metoprolol (succinate) extended release may be administered, for example, once daily at a dose of about 50 to about 200 mg/day. Nadolol may be administered, for example, once daily at a dose of about 40 to about 120 mg/day. Propanolol may be administered, for example, twice daily at a dose of about 40 to about 160 mg/day. Long-acting propranolol may be administered, for example, once daily at a dose of about 60 to about 180 mg/day. Nebivolol may be administered, for example, once daily at a dose of about 5 to about 40 mg/day. Acebutolol may be administered, for example, twice daily at a dose of about 200 to about 800 mg/day. Penbutolol may be administered, for example, once daily at a dose of about 10 to about 40 mg/day. Pindolol may be administered, for example, twice daily at a dose of about 10 to about 60 mg/day. Exemplary combined alpha and beta blockers include carvedilol, carvedilol phosphate, and labetalol. Carvedilol may be administered, for example, twice daily at a dose of about 12.5 to about 50 mg/day. Carvedilol phosphate may be administered, for example, once daily at a dose of about 20 to about 80 mg/day. Labetalol may be administered, for example, twice daily at a dose of about 100 mg to about 400 mg/day.

Exemplary ACE inhibitors include benazepril, captopril, enalapril, fosinopril, lisinopril, moexipril, perindopril, quinapril, ramipril, and trandolapril. Benazepril may be administered, for example, once or twice daily at a dose of about 10 to about 40 mg/day. Captopril may be administered, for example, twice or three times daily at a dose of about 12.5 to about 150 mg/day. Enalapril may be administered, for example, once or twice daily at a dose of about 5 to about 40 mg/day. Fosinopril may be administered, for example, once daily at a dose of about 10 to about 40 mg/day. Lisinopril may be administered, for example, once daily at a dose of about 5 mg to about 40 mg/day. Moexipril may be administered, for example, once or twice daily at a dose of about 7.5 mg to about 30 mg/day. Perindopril may be administered, for example, once daily at a dose of about 2 to about 16 mg/day. Quinapril may be administered, for example, once or twice daily at a dose of about 10 to about 80 mg/day. Ramipril may be administered, for example, once or twice daily at a dose of about 2.5 to about 20 mg/day. Trandolapril may be administered, for example, once daily at a dose of about 1 to about 4 mg/day.

Exemplary angiotensin 1 receptor antagonists include candesartan, eprosartan, irbesartan, losartan, olmesartan, telmisartan, valsartan, and azilsartan. Candesartan may be administered, for example, once daily at a dose of about 8 to about 32 mg/day. Eprosartan may be administered, for example, once or twice daily at a dose of about 400 to about 800 mg/day. Irbesartan may be administered, for example, once daily at a dose of about 150 to about 300 mg/day. Losartan may be administered, for example, once daily at a dose of about 25 to about 100 mg/day. Olmesartan may be administered, for example, once daily at a dose of about 20 about 40 mg/day. Telmisartan may be administered, for example, once daily at a dose of about 20 to about 80 mg/day. Valsartan may be administered, for example, once or twice daily at a dose of about 80 to about 320 mg/day. Azilsartan may be administered, for example, once daily at a dose of about 40 to about 80 mg/day.

Exemplary calcium channel blockers may be dihydropyridines (e.g., amlodipine, felodipine, nifedipine long-acting, nisoldipine, isradipine, and nicardipine SR) or nondihydropyridines (e.g., diltiazem ER, verapamil IR, verapamil SR, and verapamil-delayed onset ER). Amlodipine may be administered, for example, once daily at a dose of about 2.5 to about 10 mg/day. Felodipine may be administered, for example, once daily at a dose of about 2.5 to about 20 mg/day. Nifedipine long acting may be administered, for example, once daily at a dose of about 30 to about 90 mg/day. Nisoldipine may be administered, for example, once daily at a dose of about 10 to about 40 mg/day. Isradipine may be administered, for example, twice daily at a dose of about 5 to about 10 mg/day. Nicardipine SR may be administered, for example, twice daily at a dose of about 60 to about 120 mg/day. Diltiazem may be administered, for example, once daily at a dose of about 120 to about 360 mg/day. Verapamil IR may be administered, for example, three times daily at a dose of about 120 to about 360 mg/day. Verapamil SR maybe administered, for example, once or twice daily at a dose of about 120 to about 360 mg/day. Verapamil-delayed onset ER may be administered, for example, once daily in the evening at a dose of about 100 to about 300 mg/day.

An exemplary direct renin inhibitor is aliskiren. Aliskiren may be administered, for example, once daily at a dose of about 150 to about 300 mg/day. Exemplary alpha-1 blockers include doxazosin, prazosin, and terazosin. Doxazosin may be administered, for example, once daily at a dose of about 1 to about 16 mg/day. Prazosin may be administered, for example, two or three times daily at a dose of about 2 to about 20 mg/day. Terazosin may be administered, for example, once or twice daily at a dose of about 1 to about 20 mg/day. Exemplary central alpha2-agonists and other centrally acting drugs include, for example, clonidine oral, clonidine patch, methyldopa, and guanfacine. Clonidine oral may be administered, for example, twice daily at a dose of about 0.1 to about 0.8 mg/day. Clonidine patch may be administered, for example, once weekly at a dose of 0.1 to about 0.3 mg. Methyldopa maybe administered, for example, twice daily at a dose of about 250 to about 1000 mg/day. Guanfacine may be administered, for example, once daily at a dose of about 0.5 to about 2 mg/day. Exemplary direct vasodilators include hydralazine and minoxidil. Hydralazine may be administered, for example, two or three times daily at a dose of about 100 to about 200 mg/day. Minoxidil may be administered, for example once, twice, or three times daily at a dose of about 5 to about 100 mg/day.

In embodiments, any two or more supportive therapies may be used in combination. The skilled person will recognize that the decision of which agents to combine should be based on the complementarity of mechanism of action, evidence of better antihypertensive effect of the combination than either individual agent, and favorable tolerability of the combination. For example, the following combinations of supportive therapies may be used in the methods provided herein: calcium antagonist and ACE inhibitor; calcium antagonist and angiotensin receptor antagonist; calcium antagonist (dihydropiridine) and beta-blocker; calcium antagonist and thiazide diuretic; thiazide diuretic and ACE inhibitor; and thiazide diuretic and angiotensin receptor antagonist.

In embodiments, a newly added supportive therapy and/or an increased dose of a supportive therapy may be administered prior to treatment with the VEGF-pathway inhibitor. For example, a subject may be identified as having a high risk of developing one or more VEGF-pathway inhibitor toxicities as provided herein, and may be administered a new supportive therapy, and additional supportive therapy, an increased dose of supportive therapy, and/or an increased frequency of dosing of a supportive therapy, for at least 1, at least 2, at least 3, at least 4, at least 5, at least 6, at least 7, at least 8, at least 9, at least 10, at least 11, at least 12, at least 13, at least 14, or more days before initiation of treatment with the VEGF-pathway inhibitor. In embodiments, the subject is monitored for evidence that the risk of developing one or more VEGF-pathway inhibitor toxicities, or that the likely severity of any such VEGF-pathway inhibitor toxicity, has been reduced prior to initiating therapy with the VEGF-pathway inhibitor. For example, in embodiments, the subject's blood pressure is monitored and the VEGF-pathway inhibitor is withheld until the subject has been determined to be in a safe range for blood pressure.

In embodiments, a subject has been identified as being at risk of developing one or more VEGF pathway inhibitor toxicities, wherein the subject's blood pressure monitoring is increased prior to, during, or following initiation of therapy with a VEGF pathway inhibitor. In embodiments, increasing blood pressure monitoring may mean increasing the intensity of monitoring. For example, increasing blood pressure monitoring may comprise increasing the frequency of monitoring. For subjects who were not currently monitoring blood pressure regularly, increasing blood pressure monitoring may mean initiating ambulatory blood pressure monitoring, and/or monitoring blood pressure more than once daily, once daily, once every 2, 3, 4, 5, or 6, days, or once weekly. For subjects who were monitoring blood pressure regularly at home, increasing blood pressure monitoring may mean initiating ambulatory blood pressure monitoring where the subject previously only periodically measured blood pressure; or may mean periodic blood pressure monitoring that is performed more often, for example, twice as often. Blood pressure monitoring may be conducted at home by the subject, using single blood pressure measurement devices and/or ambulatory blood pressure monitoring, and/or may be conducted in a hospital or clinic. Ambulatory blood pressure monitoring is blood pressure monitoring using a device that records blood pressure automatically and periodically over a period of time, for example, of 12 hours, 18 hours, 24 hours, 36 hours, 48 hours, or longer.

In some embodiments, therapy with a VEGF-pathway inhibitor may be modulated and one or more supportive therapies may be provided to the subject based upon the determined risk. For example, the method may comprise lowering the dose of a VEGF-pathway inhibitor and providing a supportive therapy to the subject when the subject is determined to have a high risk of developing one or more VEGF-pathway inhibitor-induced toxicities. In embodiments, lowering the dose of the VEGF pathway inhibitor may comprise starting the subject at a lower dose and/or lower dosing frequency compared to the recommended dose on the package insert for the VEGF pathway inhibitor, and may further comprise monitoring the subject for the toxicity and/or providing a supportive therapy for the toxicity, and titrating the dose and/or dosing frequency upwards as appropriate. In embodiments, the method may comprise lowering the dose of the VEGF-pathway inhibitor and providing an anti-hypertensive agent or increasing the dose of an anti-hypertensive agent provided to the subject when the subject is determined to have a high risk of developing VEGF-pathway inhibitor-induced hypertension. As another example, the method may comprise lowering the dose of the VEGF-pathway inhibitor and providing a proteinuria medication or increasing the dose of a proteinuria medication provided to the subject when the subject is determined to have a high risk of developing VEGF-pathway inhibitor-induced proteinuria.

VEGF-pathway inhibitors may be any suitable agent, such as an antibody or a small molecule. VEGF-pathway inhibitors include agents that inhibit any part of the VEGF pathway, including antibodies that bind to VEGF or a VEGF receptor (VEGFR), soluble proteins that bind to or otherwise block interaction of VEGF and VEGFR, small molecule drugs that interfere with the VEGF/VEGFR interaction, and kinase inhibitors. Exemplary VEGF-pathway inhibitors include, without limitation, bevacizumab, bevacizumab-awwb, bevacizumab-bvzr, ranibizumab, aflibercept, ziv-aflibercept, lenalidomide, lenvatinib, ramucirumab, cabozantinib, pazopanib, sunitinib malate, regorafenib, axitinib, tipiracil and trifluridine, ponatinib, vandetanib, sorafenib, everolimus, thalidomide, temsirolimus, interferon alfa, interferon alfa-2B, interferon alfa-N3, peginterferon alfa-2B, peginterferon alfa-2A, rhEndostatin, cediranib, semaxanib, pomalidomide, alitretinoin, imiquimod, sinecatechins, vismodegib, sonidegib, pegaptanib sodium, dexamethasone intravitreal implant, fluocinolone acetonide, conbercept, brolucizumab-dbll, selpercatinib, nintedanib, apatinib, and motesanib. VEGF-pathway inhibitors encompassed by the disclosure also include any biosimilar, generic, salt, ester, ether, isomer, mixture of isomers, complex, prodrug, or derivative of a VEGF-pathway inhibitor. The skilled person will understand how to obtain prescribing information (e.g., information from the product insert or approved label) for VEGF pathway inhibitors; exemplary prescribing information is also provided herein.

In embodiments, the VEGF-pathway inhibitor is bevacizumab (AVASTIN) or bevacizumab-awwb (MVASI) or bevacizumab-bvzr (ZIRABEV). Bevacizumab is a vascular endothelial growth factor inhibitor indicated for the treatment of metastatic colorectal cancer, in combination with intravenous fluorouracil based chemotherapy for first- or second-line treatment; metastatic colorectal cancer, in combination with fluoropyrimidine-irinotecan- or fluoropyrimidine-oxaliplatin-based chemotherapy for second-line treatment in patients who have progressed on a first-line bevacizumab-containing regimen; unresectable, locally advanced, recurrent or metastatic non-squamous non-small cell lung cancer, in combination with carboplatin and paclitaxel for first-line treatment; recurrent glioblastoma in adults: metastatic renal cell carcinoma in combination with interferon alfa; persistent, recurrent, or metastatic cervical cancer, in combination with paclitaxel and cisplatin, or paclitaxel and topotecan; and epithelial ovarian, fallopian tube, or primary peritoneal cancer (i) in combination with carboplatin and paclitaxel, followed by bevacizumab as a single agent, for stage III or IV disease following initial surgical resection, (ii) in combination with paclitaxel, pegylated liposomal doxorubicin, or topotecan for platinum-resistant recurrent disease who received no more than 2 prior chemotherapy regimens, and (iii) in combination with carboplatin and paclitaxel or carboplatin and gemcitabine, followed by bevacizumab as a single agent, for platinum sensitive recurrent disease. Bevacizumab is administered intravenously and is provided in dosage forms of 100 mg/4 mL (25 mg/mL) or 400 mg/16 mL (25 mg/mL) in a single-dose vial.

For metastatic colorectal cancer, bevacizumab is administered at a dose of 5 mg/kg every 2 weeks with bolus-IFL (irinotecan 125 mg/m$^2$, fluorouracil 500 mg/m$^2$, and leucovorin 20 mg/m given once weekly for 4 weeks every 6 weeks); 10 mg/kg every 2 weeks with FOLFOX4; or 5 mg/kg every 2 weeks or 7.5 mg/kg every 3 weeks with fluoropyrimidine-irinotecan- or fluoropyrimidine-oxaliplatin-based chemotherapy after progression on a first-line bevacizumab containing regimen. For first-line non-squamous non-small cell lung cancer, bevacizumab is administered at a dose of 15 mg/kg every 3 weeks with carboplatin and paclitaxel. For recurrent glioblastoma, bevacizumab is administered at a dose of 10 mg/kg every 2 weeks. For metastatic renal cell carcinoma, bevacizumab is administered at a dose of 10 mg/kg every 2 weeks with interferon alfa. For persistent, recurrent, or metastatic cervical cancer, bevacizumab is administered at a dose of 15 mg/kg every 3 weeks with paclitaxel and cisplatin, or paclitaxel and topotecan. For stage III or IV epithelial ovarian, fallopian tube or primary peritoneal cancer following initial surgical resection, bevacizumab is administered at a dose of 15 mg/kg every 3 weeks with carboplatin and paclitaxel for up to 6 cycles, followed by 15 mg/kg every 3 weeks as a single agent, for a total of up to 22 cycles. For platinum-resistant recurrent epithelial ovarian, fallopian tube or primary peritoneal cancer, bevacizumab is administered at a dose of 10 mg/kg every 2 weeks with paclitaxel, pegylated liposomal doxorubicin, or topotecan given every week, or 15 mg/kg every 3 weeks with topotecan given every 3 weeks. For platinum-sensitive recurrent epithelial ovarian, fallopian tube, or primary peritoneal cancer, bevacizumab is administered at a dose of 15 mg/kg every 3 weeks with carboplatin and paclitaxel for 6-8 cycles, followed by 15 mg/kg every 3 weeks as a single agent: or 15 mg/kg every 3 weeks with carboplatin and gemcitabine for 6-10 cycles, followed by 15 mg/kg every 3 weeks as a single agent.

Arterial thromboembolic events, venous thromboembolic events, hypertension, and proteinuria are among the adverse reactions that can occur in patients administered bevacizumab. For hypertension, blood pressure may be monitored and patients may be treated for the hypertension, e.g., with an anti-hypertensive agent; bevacizumab may be withheld if hypertension is not medically controlled. Bevacizumab can be resumed once controlled, but should be discontinued for hypertensive crisis or hypertensive encephalopathy. For renal injury and proteinuria, doctors are instructed to monitor urine protein and to discontinue bevacizumab for nephrotic syndrome, and withhold until less than 2 grams of protein are detectable in urine. Presently, there is no known method for identifying patients at risk of hypertension and/or proteinuria prior to treatment with bevacizumab.

In embodiments, the VEGF-pathway inhibitor is ranibizumab. Ranibizumab (LUCENTIS) is a vascular endothelial growth factor (VEGF) inhibitor, indicated for the treatment of patients with neovascular (wet) Age-Related Macular Degeneration (AMD), macular edema following retinal vein occlusion (RVO), diabetic macular edema (DME), diabetic retinopathy (DR), and myopic choroidal neovascularization (mCNV). Ranibizumab is for ophthalmic intravitreal injection. For wet AMD, 0.5 mg (0.05 mL) is recommended to be administered by intravitreal injection once a month (approximately 28 days). Although not as effective, patients may be treated with 3 monthly doses followed by less frequent dosing, or may be treated with one dose every 3 months after 4 monthly doses, with regular assessment. For macular edema following RVO, 0.5 mg (0.05 mL) is recommended to be administered by intravitreal injection once a month (approximately 28 days). For DME and DR, 0.3 mg (0.05 mL) is recommended to be administered by intravitreal injection once a month (approximately 28 days). For mCNV, 0.5 mg (0.05 mL) is recommended to be initially administered by intravitreal injection once a month (approximately 28 days) for up to three months. Patients may be retreated if needed. The dosage forms provided for ranibizumab are single-use prefilled syringe or glass vials containing 10 mg/mL solutions designed to provide 0.05 mL for intravitreal injections; or containing 6 mg/mL solution (0.3 mg). There is a potential risk of arterial thromboembolic events following intravitreal use of VEGF inhibitors.

In embodiments, the VEGF-pathway inhibitor is aflibercept. Aflibercept (EYLEA) is a vascular endothelial growth factor (VEGF) inhibitor indicated for the treatment of patients with wet AMD, macular edema following RVO, DME, and DR. For wet AMD, the recommended dose is 2 mg (0.05 mL) administered by intravitreal injection every 4 weeks (approximately every 28 days, monthly) for the first 3 months, followed by 2 mg (0.05 mL) via intravitreal injection once every 8 weeks (2 months). Some patients may need every 4 week (monthly) dosing after the first 12 weeks (3 months). Although not as effective as the recommended every 8 week dosing regimen, patients may also be treated with one dose every 12 weeks after one year of effective therapy. For macular edema following RVO, the recommended dose is 2 mg (0.05 mL) administered by intravitreal injection once every 4 weeks (approximately every 25 days, monthly). For DME and DR, the recommended dose is 2 mg (0.05 mL) administered by intravitreal injection every 4 weeks (approximately every 28 days, monthly) for the first 5 injections followed by 2 mg (0.05 mL) via intravitreal injection once every 8 weeks (2 months). Some patients may need every 4 week (monthly) dosing after the first 20 weeks (5 months). Aflibercept is provided in dosage forms for injection of 2 mg/0.05 mL solution in a single-dose pre-filled syringe or a single-dose vial. As with ranibizumab, there is a potential risk of arterial thromboembolic events following intravitreal use of aflibercept.

In embodiments, the VEGF-pathway inhibitor is ziv-aflibercept. Ziv-aflibercept (ZALTRAP) is indicated for the treatment of patients with metastatic colorectal cancer that is resistant to or has progressed following an oxaliplatin-containing regimen, a vascular endothelial growth factor inhibitor, in combination with fluorouracil, leucovorin, irinotecan (FOLFIRI). Ziv-aflibercept is administered 4 mg/kg as an intravenous infusion over 1 hour every 2 weeks in combination with FOLFIRI until disease progression or unacceptable toxicity. Ziv-aflibercept is to be administered prior to any component of the FOLFIRI regimen on the day of treatment. Arterial thromboembolic events, hypertension, and proteinuria are among the adverse effects that may be induced by zif-aflibercept administration. For hypertension, doctors may monitor blood pressure and treat hypertension; may temporarily suspend ziv-aflibercept if hypertension is not controlled (and upon resumption, permanently reduce to 2 mg/kg); and may discontinue it if hypertensive crisis develops. For proteinuria, doctors may monitor urine protein; may suspend ziv-aflibercept for proteinuria of 2 grams per 24 hours or more (to be resumed when proteinuria is less than 2 grams per 24 hours, and then permanently reduce to 2 mg/kg for recurrent proteinuria); and may discontinue it if nephrotic syndrome or thrombotic microangiopathy (TMA) develops. The provided dosage forms of ziv-aflibercept are a 100 mg/4 mL (25 mg/mL) and a 200 mg/8 mL (25 mg/mL) solution in a single-dose vial for injection.

In embodiments, the VEGF-pathway inhibitor is lenalidomide. Lenalidomide (REVLIMID) is a thalidomide analogue indicated for the treatment of adult patients with multiple myeloma (MM), in combination with dexamethasone (25 mg once daily orally on Days 1-21 of repeated 28-day cycles in combination with dexamethasone); MM, as maintenance following autologous hematopoietic stem cell transplantation (auto-HSCT) (initiated after therapy after adequate hematologic recovery (ANC at least 1000/mcL and/or platelet counts at least 75,000/mcL, recommended starting dose of 10 mg once daily continuously (Days 1-28 of repeated 28-day cycles) until disease progression or unacceptable toxicity, and after 3 cycles of maintenance therapy, the dose can be increased to 15 mg once daily if tolerated); transfusion-dependent anemia due to low- or intermediate-1-risk myelodysplastic syndromes (MDS) associated with a deletion 5q abnormality with or without additional cytogenetic abnormalities (10 mg once daily); mantle cell lymphoma (MCL) whose disease has relapsed or progressed after two prior therapies, one of which included bortezomib (25 mg once daily orally on Days 1-21 of repeated 28-day cycles); previously treated follicular lymphoma (FL), in combination with a rituximab product (20 mg once daily orally on Days 1-21 of repeated 28-day cycles for up to 12 cycles in combination with a rituximab-product); and previously treated marginal zone lymphoma (MZL), in combination with a rituximab product (20 mg once daily orally on Days 1-21 of repeated 28-day cycles for up to 12 cycles in combination with a rituximab-product). Lenalidomide is provided as 2.5 mg, 5 mg, 10 mg, 15 mg, 20 mg, and 25 mg capsules. There is significantly increased risk of deep vein thrombosis an pulmonary embolism as well as risk of myocardial infarction and stroke in patients receiving REVLIMID with dexamethasone; anti-thrombotic prophylaxis is recommended.

In embodiments, the VEGF-pathway inhibitor is lenvatinib (LENVIMA). Lenvatinib is a kinase inhibitor that is indicated for the treatment of patients with locally recurrent or metastatic, progressive, radioactive iodine-refractory differentiated thyroid cancer (DTC); combination with everolimus, for the treatment of patients with advanced renal cell carcinoma (RCC) following one prior antiangiogenic therapy; for the first-line treatment of patients with unresectable hepatocellular carcinoma (HCC); and in combination with pembrolizumab, for the treatment of patients with advanced endometrial carcinoma that is not microsatellite instability-high (MSI-H) or mismatch repair deficient (dMMR), who have disease progression following prior systemic therapy and are not candidates for curative surgery or radiation. Lenvatinib is available as 4 mg and 10 mg capsules. Lenvatinib is taken daily at a recommended dosage of 24 mg orally (for DTC), 18 mg orally with 5 mg everolimus (for RTC), and 20 mg orally with 200 mg i.v. pembrolizumab (for endometrial carcinoma). For HCC, the recommended dosage is based on body weight: 12 mg orally once daily for patients greater than or equal to 60 kg and 8 mg orally once daily for patients less than 60 kg. Doses are modified for adverse reactions as follows. For DTC, the first reduction is to 20 mg once daily, the second is to 14 mg once daily, the third is to 10 mg once daily. For RCC and endometrial carcinoma, the first reduction is to 14 mg once daily, the second is to 10 mg once daily, the third is to 8 mg once daily. For HCC patients that weigh 60 kg or more, the first reduction is to 8 mg once daily, the second reduction is to 4 mg once daily, and the third reduction is to 4 mg every other day; and for HCC patients that weight less than 60 kg, the first reduction is to 4 mg once daily, the second reduction is to 4 mg every other day, and the third is to discontinue. Hypertension, cardiac dysfunction, arterial thromboembolic events, and proteinuria are adverse reactions that may occur. For hypertension, blood pressure is monitored during treatment and lenvatinib is withheld for grade 3 hypertension despite optimal antihypertensive therapy. The drug can be resumed at a reduced dose when hypertension is controlled at less than or equal to grade 2. Lenvatinib is discontinued for grade 4 hypertension, grade 4 cardiac dysfunction, an arterial thromboembolic event of any grade, and nephrotic syndrome.

In embodiments, the VEGF-pathway inhibitor is ramucirumab. Ramucirumab (CYRAMZA) is a VEGFR2 antagonist indicated as a single agent or in combination with paclitaxel, for treatment of advanced or metastatic gastric or gastro-esophageal junction adenocarcinoma with disease progression on or after prior fluoropyrimidine- or platinum-containing chemotherapy; in combination with docetaxel, for treatment of NSCLC with disease progression on or after platinum-based chemotherapy; in combination with FOLFIRI, for the treatment of metastatic colorectal cancer with disease progression on or after prior therapy with bevacizumab, oxaliplatin, and a fluoropyrimidine; and as a single agent, for the treatment of hepatocellular carcinoma in patients who have an alpha fetoprotein of ≥400 ng/mL and have been treated with sorafenib. Ramucirumab is for intravenous infusion (first infusion over 60 minutes and if tolerated, all subsequent infusions may be administered over 30 minutes) and is supplied as a mg/10 mL (10 mg/mL) or 500 mg/50 mL (10 mg/mL) solution in a single-dose vial. Patients are premedicated with an intravenous histamine-1 receptor antagonist (e.g., diphenhydramine hydrochloride) before each infusion; or, for patients who have experienced a Grade 1 or 2 IRR, premedicate with a histamine-1 receptor antagonist, dexamethasone (or equivalent), and acetaminophen prior to each infusion. For gastric cancer, 8 mg/kg is administered every 2 weeks as a single agent or in combination with weekly paclitaxel. For non-small cell lung cancer (NSCLC), 10 mg/kg is administered on Day 1 of a 21-day cycle prior to docetaxel. For colorectal cancer, 8 mg/kg is administered every 2 weeks prior to FOLFIRI. For hepatocellular carcinoma, 8 mg/kg is administered every 2 weeks. ATEs, proteinuria, and hypertension are among the adverse events that may be induced by ramucirumab administration. For the first occurrence of increased urine protein levels greater than or equal to 2 g per 24 hours, doctors may withhold ramucirumab until urine protein level is less than 2 g per 24 hours and resume at a reduced dose (reduce 8 mg dose to 6 mg, and 10 mg dose to 8 mg). Upon a recurrence of urine protein level greater than 2 g per 24 hours following initial dose reduction, doctors may withhold ramucirumab until urine protein level is less than 2 g per 24 hours and resume at a reduced dose (reduce 6 mg dose to 5 mg, and 8 mg dose to 6 mg). Ramucirumab is permanently discontinued for urine protein levels greater than 3 g per 24 hours or nephrotic syndrome. For hypertensive adverse events, blood pressure should be monitored and hypertension should be treated. Ramucirumab should be withheld for severe hypertension until it is controlled; and should be permanently discontinued if it cannot be controlled with antihypertensive therapy and for hypertensive crisis or hypertensive encephalopathy In embodiments, the VEGF-pathway inhibitor is cabozantinib. Cabozantinib (CABOMETYX, COMETRIQ) is a kinase inhibitor. CABOMETYX is indicated for the treatment of advanced renal cell carcinoma (RCC) and patients with hepatocellular carcinoma (HCC) who have been previously treated with sorafenib CABOMETRYX is provided as 20 mg, 40 mg, and 60 mg tablets and is administered once daily at a dose of 60 mg orally. COMETRIQ® is indicated for the treatment of patients with progressive, metastatic medullary thyroid cancer (MTC). The recommended dose is 140 mg orally, once daily, and COMETRIQ is supplied as a 20 mg or 80 mg capsule.

For both CABOMETRYX and COMETRIZ, doses can be reduced if coadministered with strong CYP3A4 inhibitors (e.g., ketoconazole, ritonavir, clarithromycin), or if adverse reactions occur. For example, CABOMETRYX can be reduced from 60 mg daily to 40 mg daily, or from 40 mg daily to 20 mg daily, and if 20 mg daily is not tolerated, CABOMETRYX should be discontinued; and COMETRIZ daily administration can be reduced by 40 mg (e.g., from 140 to 100, or from 100 to 60). For coadministration with strong CYPA34 induces, CABOMETRYX should be increased by 20 mg daily (for example, from 60 mg to 80 mg daily or from 40 mg to 60 mg daily) as tolerated; and COMETRIQ should be increased by 40 mg (e.g., 140 mg to 180 mg daily or 100 mg to 140 mg daily) as tolerated. Patients are monitored for hypertension and proteinuria, and cabozantinib is interrupted for hypertension that is not adequately controlled with anti-hypertensive therapy; and is discontinued for hypertensive crisis or severe hypertension that cannot be controlled with anti-hypertensive therapy. Cabozantinib is discontinued for nephrotic syndrome.

In embodiments, the VEGF-pathway inhibitor is pazopanib. Pazopanib (VOTRIENT) is a kinase inhibitor indicated for the treatment of patients with advanced renal cell carcinoma (RCC) or advanced soft tissue sarcoma (STS) who have received prior chemotherapy. 800 mg is administered once daily. For RCC, the initial dose reduction should be 400 mg, and additional dose decrease or increase should be in 200-mg steps based on individual tolerability. For STS, a decrease or increase should be in 200-mg steps based on individual tolerability. The recommended dose for patients with moderate hepatic impairment is 200 mg orally once daily and pazopanib is not recommended in patients with severe hepatic impairment. Concomitant use with strong CYP3A4 inhibitors should be avoided; if it is warranted, the pazopanib dose should be reduced to 400 mg. VOTRIENT is provided in a dosage form of 200 mg tablets. Cardiac dysfunction, arterial thromboembolic events, venous thromboembolic events, hypertension including hypertensive crisis, and proteinuria are among the adverse events for which patients should be monitored. Blood pressure should be well controlled before initiating pazopanib.

In embodiments, the VEGF-pathway inhibitor is sunitinib. Sunitinib malate (SUTENT) is a kinase inhibitor indicated for treatment of gastrointestinal stromal tumor (GIST) after disease progression on or intolerance to imatinib mesylate, treatment of advanced RCC, adjuvant treatment of adult patients at high risk of recurrent ACC following nephrectomy, and treatment of progressive, well-differentiated pancreatic neuroendocrine tumors (pNET) in patients with unresectable locally advanced or metastatic disease. The dosage form of sunitinib malate is 12.5 mg, 25 mg, 37.5 mg, or 50 mg capsules. For GIST and advanced RCC, the treatment regimen is 50 mg orally once daily, 4 weeks on treatment followed by 2 weeks off. For adjuvant RCC, the treatment regimen is 50 mg orally once daily, 4 weeks on treatment followed by 2 weeks off for nine 6-week cycles. For pNET, the treatment regimen is 37.5 mg orally once daily, continuously without a scheduled off-treatment period. Strong CYP3A4 inhibitors such as ketoconazole may increase sunitinib plasma concentrations and coadministraiton should be avoided. A dose reduction for to a minimum of 37.5 mg (GIST and RCC) or 25 mg (pNET) daily should be considered if sunitinib must be co-administered with a strong CYP3A4 inhibitor. CYP3A4 inducers such as rifampin may decrease sunitinib plasma concentrations and coadministration should be avoided. A dose increase for to a maximum of 87.5 mg (GIST and RCC) or 62.5 mg (pNET) daily should be considered if sunitinib must be co-administered with a CYP3A4 inducer. Adverse events that may occur and should be monitored for include cardiovascular events, hypertension, and proteinuria.

In embodiments, the VEGF-pathway inhibitor is regorafenib. Regorafenib (STIVARGA) is a kinase inhibitor indicated for the treatment of patients with metastatic colorectal cancer (CRC) who have been previously treated with fluoropyrimidine-, oxaliplatin- and irinotecan-based chemotherapy, an antiVEGF therapy, and, if RAS wild-type, an anti-EGFR therapy; patients with locally advanced, unresectable or metastatic GIST who have been previously treated with imatinib mesylate and sunitinib malate; and HCC patients who have been previously treated with sorafenib. The dosage form is 40 mg tablets. The recommended dose is 160 mg orally, once daily for the first 21 days of each 28-day cycle. If dose modifications are required, the dose should be reduced in 40 mg (one tablet) increments; the lowest recommended daily dose of regorafenib is 80 mg daily. Regorafenib should be temporarily or permanently withheld for severe or uncontrolled hypertension. For cardiac ischemia and infarction, regorafenib should be withheld and resumed only after resolution of acute ischemic events.

In embodiments, the VEGF-pathway inhibitor is axitinib. Axitinib (INLYTA) is a kinase inhibitor indicated for the treatment of advanced RCC after failure of one prior systemic therapy. Axitinib is provided in a dosage form 1 mg and 5 mg tablets. The starting dose is 5 mg orally twice daily. Over the course of treatment, patients who tolerate axitinib for at least two consecutive weeks with no adverse reactions >Grade 2 (according to the CTCAE), are normotensive, and are not receiving anti-hypertension medication, may have their dose increased. When a dose increase from 5 mg twice daily is recommended, the axitinib dose may be increased to 7 mg twice daily, and further to 10 mg twice daily using the same criteria. Over the course of treatment, management of some adverse drug reactions may require temporary interruption or permanent discontinuation and/or dose reduction. If dose reduction from 5 mg twice daily is required, the recommended dose is 3 mg twice daily. If additional dose reduction is required, the recommended dose is 2 mg twice daily. If coadministration with strong CYPA4/5 inhibitors is required, the dose of axitinib should be decreased by approximately half. Blood pressure should be well-controlled prior to initiating axitinib therapy and patients should be monitored for hypertension and treated as needed. For persistent hypertension despite use of anti-hypertensive medications, the axitinib dose should be reduced. Patients should also be monitored for arterial and venous thromboembolic events, cardiac failure, and proteinuria. For moderate to severe proteinuria, the axitinib dose should be reduced or temporarily interrupted In embodiments, the VEGF-pathway inhibitor is LONSURF. LONSURF is a combination of trifluridine, a nucleoside metabolic inhibitor, and tipiracil, a thymidine phosphorylase inhibitor, and is indicated for the treatment of adult patients with metastatic colorectal cancer who have been previously treated with fluoropyrimidine-, oxaliplatin- and irinotecan-based chemotherapy, an anti-VEGF biological therapy, and if RAS wild-type, an anti-EGFR therapy; or for the treatment of metastatic gastric or gastroesophageal junction adenocarcinoma previously treated with at least two prior lines of chemotherapy that included a fluoropyrimidine, a platinum, either a taxane or irinotecan, and if appropriate, HER2/neu-targeted therapy. The dosage form of LONSURF is 15 mg trifluridine/6.14 mg tipiracil or 20 mg trifluridine/8.19 mg tipiracil. The recommended dosage is 35 mg/M2 up to a maximum of 80 mg per dose (based on the trifluridine component) orally twice daily with food on Days 1 through 5 and Days 8 through 12 of each 28-day cycle. Doses are rounded to the nearest 5 mg increment. Within a treatment cycle, LONSURF is withheld for any of the following: absolute neutrophil count (ANC) less than 500/mm$^3$ or febrile neutropenia, platelets less than 50,000/ mm³, Grade 3 or 4 non-hematologic adverse reaction. After recovery, LONSURF can be resumed after reducing the dose by 5 mg/m²/dose. A maximum of 3 dose reductions are permitted LONSURF dosage is not escalated after it has been reduced. LONSURF is discontinued in patients who are unable to tolerate a dose of 20 mg/m² orally twice daily.

In embodiments, the VEGF-pathway inhibitor is ponatinib. Ponatinib (ICLUSIG) is a kinase inhibitor indicated for treatment of adult patients with chronic phase, accelerated phase, or blast phase chronic myeloid leukemia (CML) or Ph+ ALL for whom no other tyrosine kinase inhibitor (TKI) therapy is indicated; or for treatment of adult patients with T315-positive CML (chronic phase, accelerated phase, or blast phase) or T3151-positive Philadelphia chromosome positive acute lymphoblastic leukemia (Ph+ ALL). The dosage form is 15 mg, 30 mg, and 45 mg tablets. The recommended starting dose is 45 mg taken orally once daily with or without food. Dose modifications may be made for neutropenia and thrombocytopenia that are unrelated to leukemia; or for hepatotoxicity or pancreatitis and elevation of lipase. The recommended dose is reduced to 30 mg once daily when administering ICLUSIG with strong CYP3A inhibitors. Arterial occlusion, venous thromboembolism, heart failure, hypertension, and cardiac arrhythmias are among the adverse events that can occur. Blood pressure should be monitored.

In embodiments, the VEGF-pathway inhibitor is vandetanib. Vandetanib (CAPRELSA) is a kinase inhibitor indicated for the treatment of symptomatic or progressive medullary thyroid cancer in patients with unresectable locally advanced or metastatic disease. The dosage form is 100 mg and 300 mg tablets, and the dosing regimen is 300 mg once daily. The dose can be reduced to 200 mg (two 100 mg tablets) and then to 100 mg for CTCAE Grade 3 or greater toxicities. Vandetanib should be discontinued or interrupted in the event of ischemic cerebrovascular events, hemorrhage, heart failure, diarrhea, hypertension, and/or reversible posterior leukoencephalopathy syndrome.

In embodiments, the VEGF-pathway inhibitor is sorafenib. Sorafenib (NEXAVAR) is a kinase inhibitor indicated for the treatment of unresectable HCC, advanced RCC, and locally recurrent or metastatic, progressive, differentiated thyroid carcinoma refractory to radioactive iodine treatment. The dosage form is 200 mg tablets. For dosing, 400 mg is administered orally twice daily at least 1 hour before or 2 hours after a meal. Treatment should continue until the patient is no longer clinically benefiting from therapy or until unacceptable toxicity occurs. When dose reduction is necessary, the dose may be reduced to 40 mg once daily. If additional dose reduction is required, vandetanib may be reduced to a single 400 mg dose every other day. Dermatologic toxicities, cardiovascular events, and hypertension should be monitored.

In embodiments, the VEGF-pathway inhibitor is everolimus. Everolimus is an inhibitor of mammalian target of rapamycin (mTOR) marketed as AFINITOR, AFINITOR DISPERZ, or ZORTRESS. AFFINITOR is indicated for treatment of postmenopausal women with advanced hormone receptor-positive, HER2-negative breast cancer in combination with exemestane after failure of treatment with letrozole or anastrozole; adults with progressive neuroendocrine tumors of pancreatic origin (PNET) and adults with progressive, well-differentiated, non-functional neuroendocrine tumors (NET) of gastrointestinal (GI) or lung origin that are unresectable, locally advanced or metastatic; adults with advanced RCC after failure of treatment with sunitinib or sorafenib; and adults with renal angiomyolipoma and tuberous sclerosis complex (TSC), not requiring immediate surgery. AFINITOR and AFINITOR DISPERZ are indicated for the treatment of adult and pediatric patients aged 1 year and older with TSC who have subependymal giant cell astrocytoma (SEGA) that requires therapeutic intervention but cannot be curatively resected. AFINITOR DISPERZ is also indicated for the adjunctive treatment of adult and pediatric patients aged 2 years and older with TSC associated partial-onset seizures. Zortess is indicated for prophylaxis of kidney transplant rejection (in combination with basiliximab, cyclosporine, and corticosteroids) or liver transplant rejection (in combination with tacrolimus and corticosteroids). The dosage form of AFINITOR is 2.5 mg, 5 mg, 7.5 mg, and 10 mg tablets; the dosage form of AFINITOR DISPERZ is 2 mg, 3 mg, and 5 mg tablets; the dosage form of ZORTRESS is 0.25 mg, 0.5 mg, and 0.75 mg. For breast cancer, NET, RCC, and TSC-associated angiomyolipoma, the approved dosage is 10 mg orally once daily. For TSC-associated SEGA, the approved dosage is 4.5 mg/M2 orally once daily, with dose adjustments to attain trough concentrations of 5-15 mg/mL. For kidney transplantation, the starting dose is 0.75 mg orally twice daily starting as soon as possible after transplantation; for liver transplantation the starting dose is 1.0 mg twice daily starting 30 days after transplantation. Everolimus concentrations are monitored and maintenance doses are adjusted to achieve trough concentrations within 3-8 ng/mL target range using LC/MS/MS assay method. Patients taking concomitant angiotensin-converting enzyme (ACE) inhibitors may be at increased risk of angioedema and proteinuria.

In embodiments, the VEGF-pathway inhibitor is thalidomide. Thalidomide (THALOMID) is indicated for the treatment of patients with newly diagnosed multiple myeloma (MM) in combination with dexamethasone; treatment of acute treatment of the cutaneous manifestations of moderate to severe erythema nodosum leprosum (ENL); and as a maintenance therapy for prevention and suppression of the cutaneous manifestations of ENL recurrence. Thalidomide is provided in a dosage form of 50 mg, 100 mg, 150 mg, and 200 mg. For MM, patients are administered 200 mg orally once daily, and the recommended dose of dexamethasone is 40 mg/day on days 1-4, 9-12, and 17-20 every 28 days. For ENL, patients are administered 100 to 300 mg/day for an episode of cutaneous ENL and up to 400 mg/day for severe cutaneous ENL. Dosing is continued until signs and symptoms of active reaction have subsided, usually a period of at least 2 weeks. Patients should be monitored for venous thromboembolism and ischemic heart disease (including myocardial infarction) and stroke.

In embodiments, the VEGF-pathway inhibitor is temsirolimus. Temsirolimus (TORISEL) is a kinase inhibitor indicated for treatment of advanced RCC. The dosage form is a 25 mg/mL solution for injection. The recommended dose of TORISEL is 25 mg infused over a 30-60 minute period once a week, until disease progression or unacceptable toxicity. Antihistamine pre-treatment is recommended. Temsirolimus should be held for absolute neutrophil count (ANC) <1,000/mm^3, platelet count <75,000/mm^3, or NCI CTCAE grade 3 or greater adverse reactions. Once toxicities have resolved to grade 2 or less, it may be restarted with the dose reduced by 5 mg/week to a dose no lower than 15 mg/week. The concomitant use of strong CYP3A4 inhibitors should be avoided (e.g. ketoconazole, itraconazole, clarithromycin, atazanavir, indinavir, nefazodone, nelfinavir, ritonavir, saquinavir, telithromycin, and voriconazole). Grapefruit juice may also increase plasma concentrations of sirolimus (a major metabolite of temsirolimus) and should be avoided. If patients must be co-administered a strong CYP3A4 inhibitor, based on pharmacokinetic studies, a temsirolimus dose reduction to 12.5 mg/week should be considered. The use of concomitant strong CYP3A4 inducers should be avoided (e.g. dexamethasone, phenytoin, carbamazepine, rifampin, rifabutin, rifampacin, phenobarbital). If patients must be co-administered a strong CYP3A4 inducer, based on pharmacokinetic studies, a temsirolimus dose increase from 25 mg/week up to 50 mg/week should be considered. Patients should be monitored for proteinuria and nephrotic syndrome.

In embodiments, the VEGF-pathway inhibitor is interferon alfa. Interferon alfa (interferon alfa-2B, interferon alfa-N3, peginterferon alfa-2B, and peginterferon alfa-2A) is marketed as INTRON A, PEGASYS, PEGINTRON, ALFERON N, and SYLATRON. INTRON A is indicated for treatment with hairy cell leukemia (2 million $IU/m^2$ administered intramuscularly or subcutaneously 3 times per week for up to 6 months), malignant melanoma (20 million $IU/m^2$ as an intravenous infusion 5 consecutive days per week, for 4 weeks, with maintenance of treatment of 10 million $IU/m^2$ as a subcutaneous injection three times per week for 48 weeks), follicular lymphoma (5 million IU subcutaneously three times per week for up to 18 months in conjunction with anthracycline-containing chemotherapy regimen and following completion of the chemotherapy regimen), condylomata acuminate 1.0 million IU per lesion in a maximum of 5 lesions in a single course; lesions are injected three times weekly on alternate days for 3 weeks), AIDS-related Kaposi's sarcoma (30 million $IU/m^2$/dose administered subcutaneously or intramuscularly three times per week until disease progression or maximal response has been achieved after 16 weeks of treatment), chronic hepatitis C (3 million IU three times per week subcutaneously or intramuscularly), and chronic hepatitis B (in adults, 30 to 35 million IU per week, administered subcutaneously or intramuscularly, either as 5 million IU daily or as 10 million IU three times per week for 16 weeks; and in pediatrics, 3 million $IU/m^2$ three times per week for the first week followed by dose escalation to 6 million $IU/m^2$ three times per week subcutaneously, for a total duration of 16 to 24 weeks). PEGASYS is indicated for chronic hepatitis (180 mcg per week or 1.5 mcg/kg/week in adults; and 180 mcg/1.73 $m^2 \times BSA$ per week or 60 $mcg/m^2$ per week in pediatrics). Potential adverse events include cardiovascular disorders and ischemic and hemorrhagic cerebrovascular events.

In embodiments, the VEGF-pathway inhibitor is rhEndostatin, rhEndostatin (ENDOSTAR) is indicated for HCC, NSCLC (squamous or non-squamous), postoperative NSCLC, advanced NSCLC with EGFR mutations, solid tumors in pediatric patients, and metastatic melanoma. For HCC, dosing is 30 mg/d, from 5 days before radiotherapy, for 7 days, 21 per cycle, with concurrent standard radiotherapy for HCC. For squamous NSCLC, dosing is 15 mg/m^2 for 5 days and 200 mg of pembrolizumab at day 1 in each cycle, repeating every 3 weeks till PD or unacceptable toxicities. Squamous NSCLC patients also receive carboplatin (5 U/AUC) or cisplatin (75 $mg/m^2$) and [nab]-paclitaxel (100 $mg/m^2$) for the first 4 cycles. For non-squamous NSCLC, dosing is 15 $mg/m^2$ for 5 days, 200 mg of pembrolizumab at day 1 and pemetrexed (500 $mg/m^2$ day 1) are given in each cycle, repeating every 3 weeks till to PD or unacceptable toxicities. Squamous and non-squamous NSCLC also receive carboplatin (5 U/AUC) or cisplatin (75 $mg/m^2$) and [nab]-paclitaxel (100 $mg/m^2$) (squamous) or pemetrexed (500 $mg/m^2$ day 1) (non-squamous) for the first 4 cycles. For untreated stage IIIB/IV NSCLC, dosing is continuous intravenous infusion rh-endostatin at 7.5 $mg/m^2$ for 14 days each cycle, 21 days as one cycle, 4 cycles in total, with docetaxel or pemetrexed. For advanced NSCLC with EGFR mutations, dosing is 15 mg CIV days 1-9, Q3W with icotinib. For postoperative NSCLC, dosing is rh-Endostatin 7.5 $mg/m^2$ days 1-14; 21 d as a cycle with pemetrexed and cis-platinum or with docetaxel and cis-platinum. For phase III B/IV squamous lung cancer with GP, dosing is rh-Endostatin at 7.5 $mg/m^2$, continuous intravenous infusion for 14 days each cycle, 21 days as one cycle, 4 cycles in total with gemcitabine, cisplatin. For advanced NSCLC with docetaxel, dosing is rh-endostatin at 7.5 $mg/m^2$, IV on day 1-14 of each 21-28 day cycle with docetaxel. For metastatic melanoma, dosing is based on body surface area as 15 $mg/m^2$ rh-endostatin with cisplatin and dacarbazine.

In embodiments, the VEGF-pathway inhibitor is cediranib. Cediranib (RECENTIN) is approved for use in cancer, including ovarian, breast, colorectal, metastatic colorectal, renal, lung, non-small cell lung cancer, sarcoma, glioblastoma, fallopian tube, peritoneal cancer and triple-negative breast cancer. Dosing is as follows. For metastatic colorectal cancer: 20 mg cediranib once a day in combination with FOLFOX or XELOX chemotherapy. For recurrent glioblastoma: 30 mg as monotherapy once daily; 20 mg once daily in combination with lomustine (110 $mg/m^2$) every 6 weeks. For recurrent, platinum chemotherapy-sensitive disease or ovarian cancer related to mutations in BRCA genes: 30 mg once a day with 200 mg olaparib twice a day. For recurrent ovarian, fallopian tube, peritoneal, or triple-negative breast cancer: (1) 20 mg daily and olaparib 100 mg twice daily (BID) (2) cediranib 20 mg daily, olaparib 200 mg BID; (3) cediranib 30 mg daily, olaparib 200 mg BID; (4) cediranib 30 mg daily, olaparib 400 mg BID. For advanced non-small cell lung cancer: cisplatin 80 $mg/m^2$ on day 1 and gemcitabine 1250 $mg/m^2$ on days 1 and 8 of a 3-week cycle, and daily oral cediranib at either 30 mg or 45 mg.

In embodiments, the VEGF-pathway inhibitor is semaxanib. Semaxanib is a tyrosine kinase inhibitor indicated for colorectal cancer, solid tumors, brain tumors, kidney cancer, melanoma, head and neck cancer, hematologic cancers, mesothelioma, soft tissue sarcomas, breast cancer, AIDS-Related Kaposi's Sarcoma, multiple myeloma, cervical cancer, prostate cancer, and ovarian cancer. For metastatic melanoma, 145 $mg/m^2$ semaxanib is administered intravenously twice-weekly in combination with thalidomide, commencing at 200 mg daily with intrapatient dose escalation as tolerated; or 85 or 145 $mg/m^2$ in combination with standard irinotecan/bolus 5-fluorouracil/leucovorin (IFL) for 4 weeks on/2 weeks off. For solid tumors, semaxanib is administered at a dose of 145 $mg/m^2$ twice weekly. For metastatic colon cancer, semaxanib is administered at a dose of 85 or 145 $mg/m^2$ twice weekly in combination with fluorouracil and leucovorin (given either weekly or daily for 5 days every 4 weeks). For Kaposi's sarcoma, semaxanib is administered at a dose of 65-145 $mg/m^2$ i.v. biw for six cycles (of 29 days).

In embodiments, the VEGF-pathway inhibitor is pomalidomide. Pomalidomide (POMALYST) is a thalidomide analogue indicated for the treatment of adult patients with multiple myeloma (MM) who have received at least two prior therapies including lenalidomide and a proteasome inhibitor and have demonstrated disease progression on or within 60 days of completion of the last therapy; in combination with dexamethasone. POMALYST is also indicated for adult patients with AIDS-related Kaposi sarcoma (KS) after failure of highly active antiretroviral therapy (HAART) or in patients with KS who are HIV negative. For MM, pomalidomide is administered at a dose of 4 mg per day orally on days 1 through 21 of repeated 28-day cycles in combination with dexamethasone until disease progression. For KS, pomalidomide is administered at a dose of 5 mg per day taken orally on Days 1 through 21 of repeated 28-day cycles until disease progression or unacceptable toxicity. Coadministration with strong CYP1A2 Inhibitors should be avoided, but if unavoidable, pomalidomide dosing should be reduced to 2 mg. The dosage form of pomalidomide is 1 mg, 2 mg, 3 mg, or 4 mg capsules. Deep venous thrombosis (DVT), pulmonary embolism (PE), myocardial infarction, and stroke may occur in patients with multiple myeloma treated with POMALYST.

In embodiments, the VEGF-pathway inhibitor is alitretinoin. Alitretinoin (PANRETIN) is a gel indicated for topical treatment of cutaneous lesions in patients with AIDS-related Kaposi's sarcoma. Panretin gel is not indicated when systemic anti-KS therapy is required (e.g., more than 10 new KS lesions in the prior month, symptomatic lymphedema, symptomatic pulmonary KS, or symptomatic visceral involvement). Panretin gel should initially be applied two (2) times a day to cutaneous KS lesions. The application frequency can be gradually increased to three (3) or four (4) times a day according to individual lesion tolerance. Panretin gel is available in tubes containing 60 grams.

In embodiments, the VEGF-pathway inhibitor is imiquimod. Imiquimod is marketed as ALDARA and ZYCLARA. ALDARA is a 5% cream supplied in single-use packets (24 per box), each of which contains 250 mg of the cream, equivalent to 12.5 mg of imiquimod. ZYCLARA is provided as a 2.5% or 3.75% cream in packets or a pump. Imiquimod is indicated for the topical treatment of clinically typical, nonhyperkeratotic, nonhypertrophic actinic keratoses (AK) on the face or scalp in immunocompetent adults; biopsy-confirmed, primary superficial basal cell carcinoma (sBCC) in immunocompetent adults; maximum tumor diameter of 2.0 cm on trunk, neck, or extremities (excluding hands and feet), only when surgical methods are medically less appropriate and patient follow-up can be reasonably assured; and external genital and perianal warts/condyloma *acuminata* in patients 12 years old or older.

In embodiments, the VEGF-pathway inhibitor is sinecatechins. Sinecatechins (VEREGEN) is a 15% topical ointment indicated for the treatment of external genital and perianal warts (*Condylomata acuminata*) in immunocompetent patients 18 years and older. VEREGEN is to be applied three times per day to all external genital and perianal warts.

In embodiments, the VEGF-pathway inhibitor is vismodegib. Vismodegib (ERIVEDGE) is a hedgehog pathway inhibitor indicated for the treatment of adults with metastatic basal cell carcinoma, or with locally advanced basal cell carcinoma that has recurred following surgery or who are not candidates for surgery and who are not candidates for radiation. The recommended dosage is 150 mg orally once daily. The dosage form is 150 mg capsules.

In embodiments, the VEGF-pathway inhibitor is sonidegib. Sonidegib (ODOMZO) is a hedgehog pathway inhibitor indicated for the treatment of adult patients with locally advanced basal cell carcinoma (BCC) that has recurred following surgery or radiation therapy, or those who are not candidates for surgery or radiation therapy. The recommended dosage is 200 mg orally once daily taken on an empty stomach, at least 1 hour before or 2 hours after a meal. Serum creatine kinase (CK) levels and renal function tests are prior to initiating ODOMZO treatment. The dosage form is 200 mg capsules.

In embodiments, the VEGF-pathway inhibitor is pegaptanib sodium. Pegaptanib sodium (MACUGEN) is indicated for the treatment of neovascular (wet) age-related macular degeneration. MACUGEN is administered in a dose of 0.3 mg once every six weeks by intravitreous injection into the eye. The dosage form is a 0.3 mg/90 µL solution in a single-use syringe for intravitreal injection.

In embodiments, the VEGF-pathway inhibitor is dexamethasone. Dexamethasone intravitreal implant (OZURDEX) is a corticosteroid indicated for the treatment of macular edema following branch retinal vein occlusion (BRVO) or central retinal vein occlusion (CRVO), the treatment of non-infectious uveitis affecting the posterior segment of the eye, or the treatment of diabetic macular edema. The dosage form is an intravitreal implant containing 0.7 mg dexamethasone in the NOVADUR solid polymer drug delivery system.

In embodiments, the VEGF-pathway inhibitor is fluocinolone acetonide. Fluocinolone acetonide (ILUVIEN) contains a corticosteroid and is indicated for the treatment of diabetic macular edema (DME) in patients who have been previously treated with a course of corticosteroids and did not have a clinically significant rise in intraocular pressure. The dosage form is a non-bioerodable intravitreal implant containing 0.19 mg fluocinolone acetonide in a drug delivery system, and is intended for intravitreal injection.

In embodiments, the VEGF-pathway inhibitor is conbercept. Conbercept (COMPAQ SIQQ) is indicated for treatment of age-related macular degeneration (AMD) and other macular diseases, Idiopathic Choroidal Neovascularization, Diabetic Retinopathy, Macular Edema, Central Retinal Vein Occlusion, Tractional Retinal Detachment, Circumscribed Choroidal Haemangioma, uveitis, Polypoidal Choroidal Vasculopathy, and Corneal Neovascularization. For AMD and other retinal vascular disorders, conbercept may be administered at a dose of 0.5 mg/eye monthly for 3 months followed by 0.5 mg/eye every 3 months; or just 0.5 mg/eye every 3 months without the 3 month loading period; or 0.5 mg or 2.0 mg for 3 consecutive monthly doses, after which either monthly or as-needed (PRN) therapy is administered at the same previous dose; or 0.5 mg every 8 weeks and 1.0 mg every 12 weeks after 3 monthly injections as a loading phase.

In embodiments, the VEGF-pathway inhibitor is brolucizumab. Brolucizumab-dbll (BEOVU) is a human vascular endothelial growth factor (VEGF) inhibitor indicated for the treatment of AMD. BEOVU is administered by intravitreal injection. The recommended dose for BEOVU is 6 mg (0.05 mL of 120 mg/mL solution) monthly (approximately every 25-31 days) for the first three doses, followed by one dose of 6 mg (0.05 mL) every 8-12 weeks. The dosage form is a 6 mg/0.05 mL solution for intravitreal injection in a single-dose vial. There is a potential risk of arterial thromboembolic events (ATE) following intravitreal use of VEGF inhibitors In embodiments, the VEGF-pathway inhibitor is selpercatinib. Selpercatinib (RETEVMO) is a kinase inhibitor indicated for the treatment of adult patients with metastatic RET fusion-positive NSCLC, adult and pediatric patients 12 years of age and older with advanced or metastatic RET-mutant medullary thyroid cancer (MTC) who require systemic therapy, and adult and pediatric patients 12 years of age and older with advanced or metastatic RET fusion-positive thyroid cancer who require systemic therapy and who are radioactive iodine-refractory (if radioactive iodine is appropriate). Patients are selected for treatment with RETEVMO based on the presence of a RET gene fusion (NSCLC or thyroid) or specific RET gene mutation (MTC). The recommended dosage in adults and pediatric patients 12 years of age or older is based on weight as follows. Less than 50 kg: 120 mg orally twice daily; 50 kg or greater: 160 mg orally twice daily. RETEVMO may be administered orally twice daily (approximately every 12 hours) until disease progression or unacceptable toxicity. Concomitant use of strong and moderate CYP3A inhibitors should be avoided, but if it cannot be avoided, the RETEVMO dose may be reduced as follows. If taking 120 mg twice daily: reduce to 80 mg twice daily with a moderate inhibitor and 40 mg twice daily with a strong inhibitor; if taking 160 mg twice daily: reduce to 120 mg twice daily with a moderate inhibitor and 80 mg twice daily with a strong inhibitor. Concomitant use of a PPI, a histamine-2 (H2) receptor antagonist, or a locally-acting antacid with RETEVMO should be avoided, but if it cannot be avoided, RETEVMO may be administered with food and/or 2 hours before or 10 hours after an H2 receptor antagonist; or 2 hours before or 2 hours after a locally-acting antacid. Dosing may also be reduced for severe hepatic impairment. The dosage form is 40 mg and 80 mg capsules. RETEVMO should not be initiated in patients with uncontrolled hypertension. Blood pressure should be monitored and RETEVMO should be withheld, reduced in dose, or permanently halted based on severity.

In embodiments, the VEGF-pathway inhibitor is nintedanib (OFEV). Nintedanib is a kinase inhibitor indicated for treatment of idiopathic pulmonary fibrosis (IPF), treatment of chronic fibrosing interstitial lung diseases (ILDs) with a progressive phenotype, and for slowing the rate of decline in pulmonary function in patients with systemic sclerosis-associated interstitial lung disease. Nintedanib is administered at a dose of 150 mg twice daily, about 12 hours apart. The dosage form is 150 mg or 100 mg capsules. Arterial thromboembolic events have been reported. Caution should be taken when treating patients at higher cardiovascular risk including known coronary artery disease. Treatment may be interrupted in patients who develop signs or symptoms of acute myocardial ischemia. For patients with mild hepatic impairment, the dose may be modified to 100 mg twice daily approximately 12 hours apart. In addition to symptomatic treatment, if applicable, dose reduction or temporary interruption may be indicated for the management of adverse reactions, until the specific adverse reaction resolves to levels that allow continuation of therapy. Treatment may be resumed at the full dosage (150 mg twice daily), or at the reduced dosage (100 mg twice daily), which subsequently may be increased to the full dosage. If a patient does not tolerate 100 mg twice daily, treatment with nintedanib may be discontinued. Dose modifications or interruptions may be necessary for liver enzyme elevations. Liver function tests (aspartate aminotransferase (AST), alanine aminotransferase (ALT), and bilirubin) may be conducted prior to initiation of treatment with nintedanib, at regular intervals during the first three months of treatment, and periodically thereafter or as clinically indicated. In patients who report symptoms that may indicate liver injury, including fatigue, anorexia, right upper abdominal discomfort, dark urine or jaundice, liver tests may be measured promptly. In patients with AST or ALT greater than 3 times the upper limit of normal (ULN) with signs or symptoms of liver injury and for AST or ALT elevations greater than 5 times the upper limit of normal, treatment may be discontinued. For AST or ALT greater than 3 times to less than 5 times the ULN without signs of liver damage, treatment may be interrupted or reduced to 100 mg twice daily. Once liver enzymes have returned to baseline values, treatment may be reintroduced at a reduced dosage (100 mg twice daily), which subsequently may be increased to the full dosage (150 mg twice daily).

In embodiments, the VEGF-pathway inhibitor is apatinib. Apatinib is indicated for treatment of advanced or metastatic gastric carcinoma, metastatic breast cancer, advanced hepatocellular carcinoma, metastatic colorectal cancer, esophageal cancer (advanced esophageal squamous cell carcinoma), and glioblastoma. Apatinib generally may be administered at a dose of 750 mg once daily. Other possible doses include 250, 500, 750, 850, and 1000 mg once daily. For advanced or metastatic gastric carcinoma, apatinib may be administered at a dose of 850 mg once daily or 425 mg twice daily. For advanced progressed lung adenocarcinoma patients with EGFR-TKI resistance, apatinib may be administered at a dose of 500 $mg/m^2$ per day for 21 consecutive days alone or in combination with traditional chemotherapy drugs pemetrexed (50 $mg/m^2$, once every 21 days) and docetaxel (75 $mg/m^2$, once every 21 days). For metastatic colorectal cancer, apatinib may be administered at a dose of 125 mg, 250 mg, 500 mg, 850 mg once per day, alone or in combination with other agents in either 21 or 28 day cycles. For advanced esophageal squamous cell carcinoma, apatinib may be administered at a dose of 500 mg daily in a 28 day cycle, which may be reduced to 250 mg.

In embodiments, the VEGF-pathway inhibitor is motesanib. Motesanib is indicated for thyroid cancer (progressive or symptomatic, advanced or metastatic medullary thyroid cancer: progressive differentiated thyroid cancer), non-small cell lung cancer (advanced nonsquamous), gastrointestinal stromal cancer, colorectal cancer, breast cancer (HER2-negative locally recurrent or metastatic breast cancer), persistent or recurrent ovarian cancer, fallopian tube and primary peritoneal carcinomas, advanced solid tumors, and low-grade neuroendocrine tumors. For advanced nonsquamous non-small-cell lung cancer (NSCLC), motesanib may be administered at a dose of 125 mg once daily, or 75 mg twice daily (5 days on/2 days off), both with carboplatin (AUC, 6 mg/ml min) and paclitaxel (200 $mg/m^2$) for up to six 3-week cycles. For HER2-negative locally recurrent or metastatic breast cancer: motesanib 125 mg orally once per day with paclitaxel (90 mg/m 2 on days 1, 8, and 15 every 3 weeks). For progressive or symptomatic, advanced or metastatic medullary thyroid cancer, progressive differentiated thyroid cancer, advanced solid tumors, and for persistent or recurrent ovarian, fallopian tube, and primary peritoneal carcinomas, motesanib may be administered at a dose of 125 mg daily. For ow-grade neuroendocrine tumors, motesanib may be administered at a dose of 125 mg once daily in combination with octreotide-LAR (30 mg administered on day 1 of each cycle 28-day cycle).

VEGF-pathway inhibitors may be administered in combination with one or more additional anti-cancer therapies. For example, VEGF-pathway inhibitors may be administered in combination with surgical therapy, radiation therapy, chemotherapy, immunotherapies (e.g. checkpoint inhibitors, adoptive cell transfer, antibodies, vaccines, cytokines, etc.), targeted therapies (e.g. small-molecule drugs, antibodies), hormone therapy, stem-cell transplant, and the like. The subject may be a candidate for or currently provided with any suitable combination of therapies prior to determination of risk of VEGF-inhibitor toxicities in the subject. Any suitable combination of therapies (e.g. VEGF-inhibitors, other anti-cancer therapies, supportive therapies, or any combination thereof) may be provided to the subject following determination of risk in the subject.

Any of the therapies described herein (e.g. VEGF-pathway inhibitors, supportive therapies, other anti-cancer therapies) may be provided by any suitable route. For example, the therapy may be provided orally. Alternatively, the therapy may be provided parenterally. Suitable doses and modes of administration may be determined based upon various factors, including the age, sex, weight, health of the subject, other medications being administered to the subject, and the like, using routine techniques known in the art.

By way of example and not of limitation, examples of the present disclosure will now be provided.

EXPERIMENTAL EXAMPLES

Example 1

The objective of the current study was to perform a GWAS of four randomized phase III clinical trials from the Cancer and Leukemia Group B (CALGB, now Alliance for Clinical Trials in Oncology. Alliance) to identify novel genes and genetic variants that showed a consistent risk of toxicity across the different studies.

Methods

Patients and Randomized, Phase III Clinical Trials

CALGB 80303 was conducted in advanced pancreatic cancer patients treated with gemcitabine and either 10 mg/kg bevacizumab or placebo. CALGB 40503 was conducted in hormone receptor-positive advanced-stage breast cancer patients treated with letrozole and either 15 mg/kg bevacizumab or placebo. CALGB 90401 was conducted in metastatic castration-resistant prostate cancer patients treated with docetaxel/prednisone with either 15 mg/kg bevacizumab or placebo. CALGB 40502 was conducted in locally recurrent or metastatic breast cancer patients treated with either nab-paclitaxel, ixabepilone, or paclitaxel, all administered in combination with 10 mg/kg bevacizumab. Patient eligibility, characteristics, stratifications, treatments, and the methods to detect progression of disease have been previously described.

Toxicity

Proteinuria and hypertension were recorded according to Common Toxicity Criteria for Adverse Events (CTCAE) version 3.0 (Table 1), per protocol. The composite toxicity is defined as the occurrence of either proteinuria or hypertension or both. For CALGB 40502, data on proteinuria and composite toxicity were not available. Urine protein levels were measured on day 1 and every four weeks after starting treatment in CALGB 80303; on day 1 of the $1^{st}$ cycle and up to 5 days before or on the day of treatment for subsequent cycles in CALGB 40503; and within 48 hours prior to every treatment cycle in CALGB 90401. Blood pressure was obtained on day 1 of each cycle in all trials, and plus on day 15 in CALGB 80303.

TABLE 1

Hypertension and proteinuria grades of toxicity according to Common Toxicity Criteria of Adverse Events (CTCAE) v3.0.
Urine dipstick test result: 1+ (15-30 mg/dL), 2+ (100-300 mg/dL), 3+ (300-1000 mg/dL), and 4+ (>1000 mg/dL). WNL within normal limits.

| Toxicity | Grade 1 | Grade 2 | Grade 3 | Grade 4 | Grade 5 |
|---|---|---|---|---|---|
| Proteinuria | 1+ or 0.15-1.0 g/24 hrs | 2+ to 3+ or >1.0-3.5 g/24 hrs | 4+ or >3.5 g/24 hrs | Nephrotic syndrome | Death |
| Hypertension | Asymptomatic, transient (<24 hrs) increase by >20 mmHg (diastolic) or to >150/100 if previously WNL; intervention not indicated | Recurrent or persistent (≥24 hrs) or symptomatic increase by >20 mmHg (diastolic) or to >150/100 if previously WNL; monotherapy may be indicated | Requiring more than one drug or more intensive therapy than previously | Life-threatening consequences (e.g., hypertensive crisis) | Death |

Bevacizumab-related toxicity was defined as the occurrence of toxicity (grade ≥2 or grade ≥3 of hypertension, proteinuria, or either proteinuria or hypertension-composite toxicity) after the start of treatment. Only toxicities with attribution of "possibly related" or higher were included. The occurrence of treatment-terminating events was used for censoring, as they determined the exit of the patients from the trial. Treatment-terminating events included death, disease progression, other toxicities defined per protocol, withdrawal of consent, loss to follow up, or unknown recorded events. The time to event was reconstructed manually for each patient in each study, as performed previously. The time to event was calculated as the time from the first administration of bevacizumab to the first date of experiencing the toxicity of interest, or other treatment-terminating events, whichever occurred first.

Genotyping and Quality Control

DNA for genotyping was obtained from peripheral blood. The genotyping platforms used in each study are described in Table 2, and the number of SNPs used for analysis after quality control (QC) are described in FIG. 1. Additional information on the quality control procedures can be found in the individual publications of the GWAS data.

TABLE 2

Patients of European ancestry treated with bevacizumab used in the GWAS data.
CALGB Cancer and Leukemia Group B, SD standard deviation, composite toxicity is defined as the occurrence of either proteinuria or hypertension or both.

| | CALGB trial | 80303 n = 154 | 40503 n = 105 | 90401 n = 316 | 40502 n = 466 |
|---|---|---|---|---|---|
| Age | Mean (SD) | 64.1 (10.2) | 68.4 (8.3) | 56.9 (11.7) | 57.2 (10.7) |
| Gender | Male | 90 | 0 | 316 | 0 |
| | Female | 64 | 105 | 0 | 466 |
| Cancer type | | Advanced pancreatic cancer | Hormone receptor-positive advanced-stage breast cancer | Metastatic castration-resistant prostate cancer | Recurrent or metastatic breast cancer |

TABLE 2-continued

Patients of European ancestry treated with bevacizumab used in the GWAS data.
CALGB Cancer and Leukemia Group B, SD standard deviation, composite toxicity is defined
as the occurrence of either proteinuria or hypertension or both.

| Treatment | Gemcitabine 1,000 mg/m² on days 1, 8, and 15 plus either placebo or bevacizumab 10 mg/kg on days 1 and 15 | | Letrozole 2.5 mg orally/day plus either placebo or bevacizumab 15 mg/kg every 21 days | | Docetaxel 75 mg/m² in combination with prednisone 5 mg orally on day 1 plus either placebo or bevacizumab 15 mg/kg every 21 days | | Paclitaxel 90 mg/m² or nab-paclitaxed 150 mg/m2 or ixabepilone 16 mg/m² on days 1, 8, and 15 plus bevacizumab 10 mg/kg on days 1 and 15 | |
|---|---|---|---|---|---|---|---|---|
| Genotype platform | Illumina HumanHap550-Quad | | Illumina Human OmniExpressExome-8 | | Illumina HumanHap610-Quad | | Illumina Human OmniExpressExome-8 | |
| | Grade≥2 | Grade≥3 | Grade≥2 | Grade ≥3 | Grade≥2 | Grade≥3 | Grade ≥2 | Grade≥3 |
| Hypertension (n, %) | 26 (16.9) | 19 (12.3) | 53 (50.5) | 29 (27.6) | 47 (15.0) | 22 (7.0) | 143 (30.7) | 50 (10.7) |
| Proteinuria (n, %) | 26 (16.9) | 9 (5.8) | 32 (30.5) | 10 (9.5) | 20 (6.4) | 5 (1.6) | — | — |
| Composite toxicity (n, %) | 43 (27.9) | 26 (16.9) | 73 (69.5) | 34 (32.4) | 61 (19.4) | 26 (8.2) | — | — |

Statistical Analysis
SNP-Based Association Testing

The association between SNPs and toxicities (grade ≥2 or grade ≥3) was tested in genetic European patients in the bevacizumab arm. Ethnicity information was determined by estimating the genetic ancestral origin of patients using the principal components analysis software implemented in Eigenstrat. A cause-specific Cox model, where the outcome is defined as the pair of time event and the censoring indicator, was fitted to obtain the estimate of the SNP effect (and the corresponding standard error estimate) on toxicity in each individual study. The analyses were powered against an additive genetic model. The inverse variance formula was used to combine the SNP effect in each study to obtain the estimate ($\beta$) of the SNP-toxicity association and its standard error. The heterogeneity across studies was examined by the Cochran's test (no heterogeneity was detected). Cox analyses for each variant, adjusting for age and gender, were performed by adding those variables as covariates in the model. The reported results are unadjusted, unless stated otherwise. The reported p values are not corrected for multiple comparisons. Quantile-quantile (Q-Q) plots were generated.

Gene-Based Association Testing

Under the same model described above, a gene-based analysis was also performed. First, all the human protein-coding genes were mapped to SNPs according to the location of SNPs with a margin equaling 50 by using the R package "snplist". Next, the cause-specific Cox model was fitted to obtain the score statistics for SNP by toxicity association in each study. Last, the Sequence Kernel Association Test (SKAT) was used to combine the SNP-level test statistics. This method allowed for different directions of the SNP effect in a gene and could accommodate also common alleles. From the SKAT test, the weighted quadratic statistics were computed using the MASS software, with p-values determined by the re-sampling method. The reported results are unadjusted, unless stated otherwise. The reported p values are not corrected for multiple comparisons. Q-Q plots were also generated for this analysis.

Functional Annotation of Variants

Functional annotation of SNPs and genes was performed using the SCAN database.

Variants were analyzed by the LDlink web-based application for analyses of linkage disequilibrium (LD). UCSC Genome Browser (http://genome.ucsc.edu/), RegulomeDB and Haploreg v4 were used for functional inference. The Genotype-Tissue Expression project (GTEx v7) and Neph-QTL were used for expression quantitative trait loci (eQTL) analyses.

Results

A total of 1,041 cancer patients of European ancestry treated with bevacizumab with available genotyping information were included in the study. The characteristics of patients from each trial, as well as the prevalence of toxicities, are shown in Table 2. Grade ≥2 hypertension (15.0%-50.5%) was more prevalent than grade ≥2 proteinuria (5.4-30.5%). The prevalence of either grade ≥2 proteinuria or grade ≥2 hypertension (composite toxicity) was 19.4-69.5%. Considering only the patients who had both toxicities, the prevalence was 1.9%-11.4%. The prevalence of these toxicities was higher in female patients in the breast cancer studies (CALGB 40502 and 40503) than in male patients in the prostate cancer study (CALGB 90401). A higher prevalence was also observed in females compared to males in the pancreatic cancer study (CALGB 80303) (Table 3).

TABLE 3

Prevalence of hypertension and proteinuria in CALGB 80303 by gender.
Composite toxicity is defined as the occurrence of
either proteinuria or hypertension or both.

| | Grade ≥ 2 | | Grade 3 | |
|---|---|---|---|---|
| | Female (n = 64) | Male (n = 90) | Female (n = 64) | Male (n = 90) |
| Hypertension (n, %) | 14 (21.9) | 12 (13.3) | 9 (14.1) | 10 (11.1) |
| Proteinuria (n, %) | 11 (17.2) | 15 (16.7) | 6 (9.4) | 3 (3.3) |
| Composite toxicity (n, %) | 20 (31.2) | 23 (25.6) | 14 (21.9) | 12 (13.3) |

Variants and Genes Associated with
Bevacizumab-Induced Proteinuria

Figure 2:
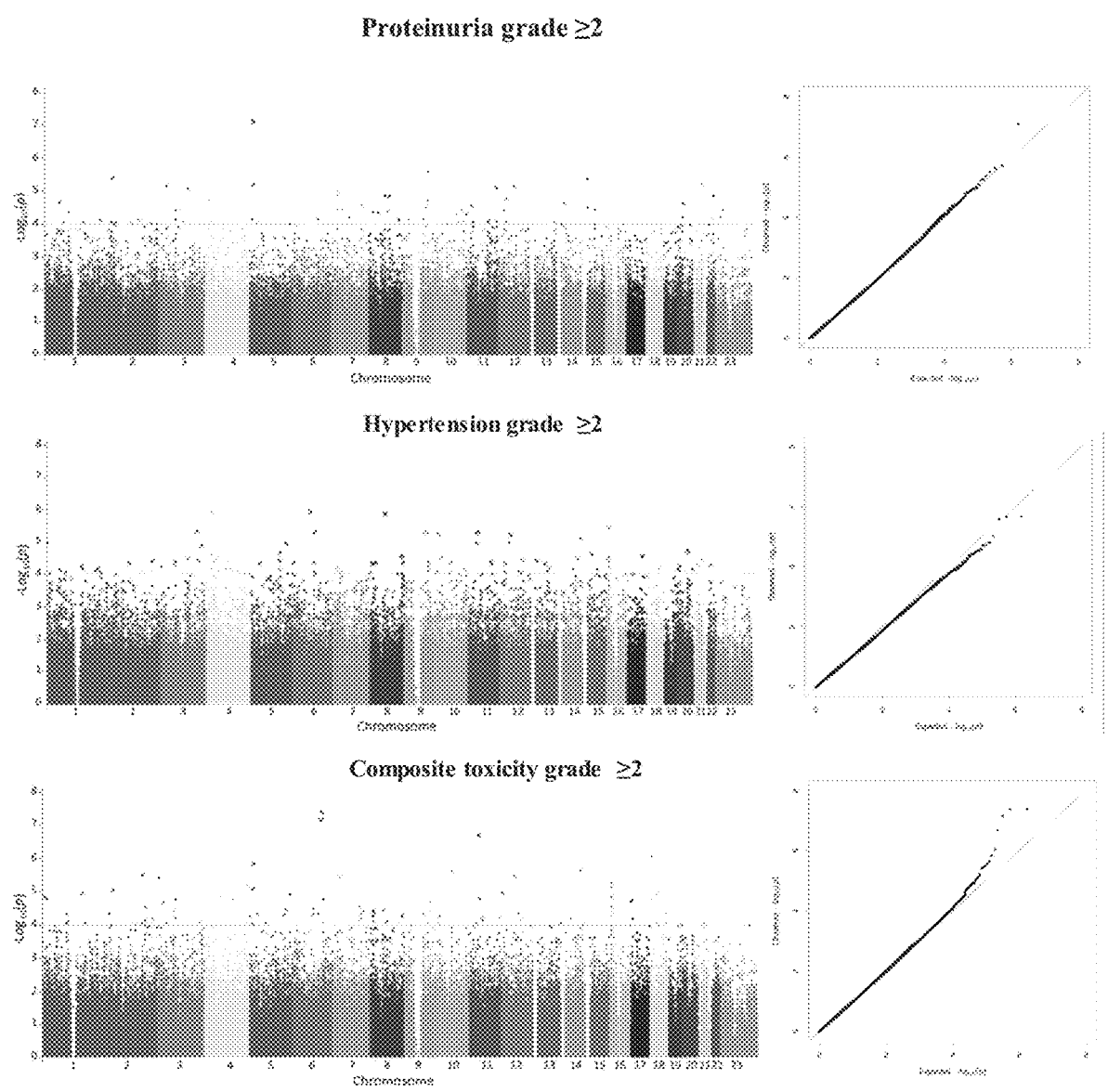
FIG. 2 shows Manhattan plots (left) and quantile-quantile (Q-Q) plots (right) from the SNP-based association results for proteinuria hypertension, and composite toxicity grade ≥2. Composite toxicity is defined as the occurrence of either proteinuria or hypertension or both.

For the SNP-based analysis of grade 22, the Manhattan and Q-Q plots are shown in FIG. 2. 90 variants were identified as associated with bevacizumab-induced proteinuria (Table 4).

TABLE 4

SNP's associated with Proteinuria (grade ≥2)

| SNP | CH | BP | effect allele | reference allele | MAF 80303 | MAF 40503 | MAF 90401 | gene | feature | Flanking gene | Flanking gene | p-value unadjusted | effect (β) unadjusted | p-value adjusted | effect (β) adjusted |
|---|---|---|---|---|---|---|---|---|---|---|---|---|---|---|---|
| rs339947 | 5 | 14071067 | A | C | 0.12 | . | 0.14 | NA | NA | DNAH5 | TRIO | 7.66E-08 | 1.27 | 1.58E-07 | 1.26 |
| rs13293961 | 9 | 104807170 | A | C | . | . | 0.08 | CYLC2 | missense | LOC100131879 | SMC2 | 2.39E-06 | 1.56 | 2.60E-06 | 1.61 |
| rs12612153 | 2 | 44755864 | C | A | 0.11 | . | 0.11 | C2orf34 | intron | PREPL | LOC100130502 | 3.89E-06 | 1.16 | 6.93E-06 | 1.15 |
| rs71803310 | 15 | 22890430 | A | C | 0.06 | 0.05 | . | NA | NA | SNORD116-24 | SNORD116-25 | 4.10E-06 | 1.54 | 4.19E-06 | 1.55 |
| rs12482855 | 21 | 42065030 | A | G | 0.06 | 0.06 | 0.06 | NA | NA | RIPK4 | PRDM15 | 6.28E-06 | 1.20 | 1.09E-05 | 1.20 |
| rs408130 | 5 | 14059289 | A | G | 0.21 | . | 0.28 | NA | NA | DNAH5 | TRIO | 6.33E-06 | 1.07 | 6.94E-06 | 1.09 |
| rs418173 | 5 | 14058033 | A | G | 0.21 | . | 0.28 | NA | NA | DNAH5 | TRIO | 6.33E-06 | 1.07 | 6.94E-06 | 1.09 |
| rs11716628 | 3 | 35851495 | G | A | . | 0.18 | . | NA | NA | ARPP-21 | LOC100131711 | 6.87E-06 | 1.39 | 1.04E-05 | 1.39 |
| rs7959783 | 12 | 67109382 | G | A | 0.31 | 0.26 | 0.33 | NA | NA | MDM1 | LOC729376 | 7.01E-06 | 0.72 | 6.56E-06 | 0.73 |
| rs627761 | 11 | 125330918 | G | A | 0.10 | 0.14 | 0.09 | LOC338667 | intron | DDX25 | CDON | 7.49E-06 | 1.19 | 1.34E-05 | 1.18 |
| rs2688994 | 3 | 126300783 | G | A | 0.13 | 0.35 | 0.14 | SLC12A8 | intron | HEG1 | ZNE148 | 8.13E-06 | 0.92 | 4.38E-06 | 0.98 |
| rs10486445 | 8 | 24980507 | G | A | 0.42 | . | 0.39 | OSBPL3 | intron | DFNA5 | CYCS | 1.17E-05 | 0.75 | 1.11E-05 | 0.78 |
| rs17345945 | 8 | 68674808 | A | G | 0.09 | . | 0.08 | CPA6 | intron | LOC100132812 | PREX2 | 1.36E-05 | 1.15 | 1.30E-05 | 1.19 |
| rs13276511 | 8 | 86959167 | G | A | 0.06 | . | . | NA | NA | REXO1L7P | LOC642137 | 1.39E-05 | 1.40 | 4.01E-05 | 1.37 |
| rs17624773 | 12 | 33136580 | G | A | 0.10 | 0.06 | 0.14 | NA | NA | ASSP14 | SYT10 | 1.79E-05 | 0.96 | 1.59E-05 | 0.97 |
| rs1509247 | 4 | 22952896 | G | A | 0.43 | 0.43 | 0.52 | LOC643751 | intron | GBA3 | PPARGC1A | 1.83E-05 | 0.70 | 1.09E-05 | 0.72 |
| rs12345440 | 9 | 102993955 | G | A | 0.09 | . | 0.10 | RP11-35N6.1 | intron | LOC392374 | LOC347275 | 1.89E-05 | 1.23 | 1.45E-05 | 1.28 |
| rs4916009 | 1 | 65144006 | A | G | 0.08 | . | 0.09 | JAK1 | intron | RAVER2 | LOC100130270 | 2.10E-05 | 1.17 | 8.86E-06 | 1.24 |
| rs2378865 | 14 | 30952224 | G | A | . | 0.42 | . | NA | NA | HEATR5A | C14orf126 | 2.35E-05 | 1.11 | 2.10E-05 | 1.14 |
| rs2064949 | 20 | 19756654 | G | A | . | 0.19 | . | NA | NA | RPL12L3 | RIN2 | 2.38E-05 | 1.07 | 6.46E-06 | 1.07 |
| rs12536799 | 7 | 133378576 | C | A | 0.11 | . | 0.08 | EXOC4 | intron | FAM10A7 | LRGUK | 2.82E-05 | 1.24 | 6.20E-06 | 1.25 |
| rs6483735 | 11 | 208444275 | G | A | 0.19 | 0.20 | 0.17 | NELL1 | intron | LOC100132634 | LOC347275 | 2.92E-05 | 0.80 | 1.61E-06 | 0.83 |
| rs123522151 | 9 | 102995858 | G | A | 0.10 | . | 0.10 | RP11-35N6.1 | intron | LOC392374 | LOC347275 | 3.07E-05 | 1.20 | 2.60E-06 | 1.22 |
| rs1431477 | 9 | 102994274 | C | A | 0.10 | . | 0.10 | RP11-35N6.1 | intron | LOC392374 | LOC347275 | 3.07E-05 | 1.20 | 4.19E-06 | 1.22 |
| rs11662763 | 18 | 5847091 | A | G | 0.14 | 0.11 | 0.13 | NA | NA | LOC645355 | TTMA | 3.11E-05 | 0.78 | 1.87E-05 | 0.79 |
| rs4780054 | 9 | 27387295 | A | G | 0.38 | 0.40 | 0.40 | NA | NA | NDNL2 | LOC100130736 | 3.16E-05 | 0.72 | 1.11E-05 | 0.70 |
| rs17725486 | 7 | 25037388 | G | A | . | 0.30 | . | NA | NA | OSBPL3 | CYCS | 3.26E-05 | 1.00 | 4.38E-06 | 1.03 |
| rs2391081 | 7 | 25034923 | G | A | . | 0.30 | . | NA | NA | OSBPL3 | CYCS | 3.26E-05 | 1.00 | 6.18E-06 | 1.03 |
| rs879965 | 11 | 46015867 | G | A | 0.46 | 0.47 | 0.44 | NA | NA | LOC222052 | LOC730338 | 3.29E-05 | 0.71 | 5.05E-05 | 0.68 |
| rs5927577 | X | 30558644 | A | G | . | 0.38 | . | NA | NA | LOC652904 | GK | 3.53E-05 | 1.13 | 1.34E-05 | 1.12 |
| rs12910488 | 15 | 59578470 | C | T | . | 0.42 | . | NA | NA | RORA | VPS13C | 3.60E-05 | -1.32 | 6.94E-06 | -1.33 |
| rs7616936 | 3 | 85886475 | C | A | 0.08 | . | 0.12 | CADM2 | intron | LOC440970 | LOC728144 | 3.71E-05 | 1.04 | 3.43E-05 | 1.01 |
| rs13255802 | 8 | 80730920 | A | G | . | 0.23 | . | STMN2 | intron | LOC/00128963 | HEY1 | 3.85E-05 | 1.16 | 3.15E-05 | 1.15 |
| rs11532247 | 12 | 19614829 | A | G | 0.50 | . | 0.49 | NA | NA | AEBP2 | LOC400013 | 3.90E-05 | 0.91 | 2.09E-05 | 0.95 |
| rs7614155 | 3 | 74196658 | G | A | 0.25 | . | 0.27 | NA | NA | LOC100129282 | HSP90AB5P | 3.95E-05 | 0.90 | 8.86E-06 | 0.90 |
| rs11196791 | 10 | 116323964 | G | A | . | 0.23 | . | ABLIM1 | intron | AFAP1L2 | PPLAP19 | 3.97E-05 | 1.16 | 1.61E-05 | 1.15 |
| rs2901044 | 10 | 116317439 | G | A | . | 0.23 | . | ABLIM1 | intron | AFAP1L2 | PPLAP19 | 3.97E-05 | 1.16 | 1.73E-05 | 1.15 |
| rs6996073 | 8 | 18594558 | C | T | . | 0.06 | . | PSD3 | intron | NAT2 | NSAF11 | 4.21E-05 | 1.36 | 1.72E-04 | 1.39 |
| rs972433 | 8 | 18599078 | C | T | . | 0.06 | . | PSD3 | intron | NAT2 | NSAF11 | 4.30E-05 | 1.35 | 1.77E-04 | 1.38 |
| rs2491608 | 1 | 105673803 | A | G | 0.44 | . | 0.46 | NA | NA | LOC642337 | LOC100130867 | 4.32E-05 | 0.94 | 3.25E-05 | 0.92 |
| rs13275710 | 8 | 41514221 | G | A | 0.17 | . | 0.13 | GINS4 | intron | KRT18P37 | AGPAT6 | 4.57E-05 | 1.05 | 1.45E-05 | 1.06 |
| rs12777350 | 10 | 90351816 | A | G | 0.06 | 0.07 | 0.06 | LIPJ | intron | C10orf59 | LOC389992 | 4.69E-05 | 1.10 | 3.74E-05 | 1.10 |
| rs6597976 | 11 | 1101474 | A | G | 0.06 | 0.06 | 0.07 | NA | NA | MUC2 | LOC100132635 | 5.03E-05 | 0.99 | 3.87E-05 | 1.01 |
| rs5904577 | X | 21604594 | A | G | . | 0.05 | . | KLHL34 | NA | SMPX | SMPX | 6.06E-05 | 1.68 | 2.10E-05 | 1.71 |
| rs2328452 | 20 | 19713174 | G | A | 0.17 | 0.17 | . | LOC100130408 | intron | SLC24A3 | RPL12L3 | 6.46E-05 | 0.98 | 5.10E-05 | 0.97 |
| rs6112574 | 20 | 19710695 | G | A | 0.17 | 0.17 | . | LOC100130408 | intron | SLC24A3 | RPL12L3 | 6.46E-05 | 0.98 | 5.31E-05 | 0.97 |

TABLE 4-continued

SNP's associated with Proteinuria (grade ≥2)

| SNP | CH | BP | effect allele | reference allele | MAF 80303 | MAF 40503 | MAF 90401 | gene | feature | Flanking gene | Flanking gene | p-value unadjusted | effect (β) unadjusted | p-value adjusted | effect (β) adjusted |
|---|---|---|---|---|---|---|---|---|---|---|---|---|---|---|---|
| rs7804806 | 7 | 75433618 | A | G | 0.32 | 0.29 | . | POR | intron | SNORA14A | TMEM120A | 6.67E-05 | 0.74 | 7.41E-05 | 0.73 |
| rs4579610 | 9 | 89230980 | G | A | 0.25 | 0.26 | . | NA | NA | LOC100132348 | DAPK1 | 6.82E-05 | 0.76 | 1.25E-04 | 0.74 |
| rs546913 | 6 | 112396275 | A | G | 0.05 | . | 0.05 | NA | NA | FYN | WISP3 | 6.84E-05 | 1.41 | 2.61E-05 | 1.51 |
| rs689328 | 6 | 112393380 | A | G | 0.05 | . | 0.05 | NA | NA | FYN | WISP3 | 6.84E-05 | 1.41 | 2.61E-05 | 1.51 |
| rs1358206 | 3 | 74198360 | G | A | 0.30 | . | 0.31 | NA | NA | LOC100129282 | HSP90AB5P | 7.03E-05 | 0.86 | 3.29E-05 | 0.87 |
| rs2980872 | 8 | 126486102 | A | G | 0.47 | 0.44 | 0.49 | NA | NA | NSMCE2 | TRIB1 | 7.11E-05 | -0.70 | 4.93E-05 | -0.70 |
| rs2899258 | 3 | 34685304 | C | A | 0.10 | . | 0.09 | RBM9 | intron | LOC100131802 | APOL3 | 7.11E-05 | 1.16 | 1.02E-04 | 1.14 |
| rs5750200 | 22 | 34641716 | C | A | 0.10 | . | 0.09 | RBM9 | utr-3 | NDUFA9P1 | LOC100131802 | 7.11E-05 | 1.16 | 1.02E-04 | 1.14 |
| rs339429 | 5 | 14032101 | A | T | 0.14 | 0.13 | 0.16 | NA | NA | DNAH5 | TRIO | 7.34E-05 | 0.85 | 1.20E-04 | 0.84 |
| rs11794832 | 9 | 18900581 | C | T | . | 0.22 | . | ADAMTSL1 | intron | LOC100129109 | FAM154A | 7.41E-05 | 1.24 | 3.15E-05 | 1.24 |
| rs6737965 | 2 | 159744839 | C | A | 0.08 | . | 0.10 | TANC1 | intron | BTF3L4P | WDSUB1 | 7.49E-05 | 1.00 | 1.82E-04 | -0.96 |
| rs4676847 | 3 | 72081959 | A | G | . | 0.15 | . | NA | NA | PROK2 | CCDC137P | 7.66E-05 | 1.15 | 4.62E-05 | 1.21 |
| rs2184352 | 10 | 121762442 | G | A | 0.10 | 0.07 | 0.07 | NA | NA | LOC651144 | LOC729402 | 7.74E-05 | 0.89 | 4.98E-05 | 0.89 |
| rs7552510 | 1 | 243234661 | A | C | 0.09 | 0.08 | 0.10 | EFCAB2 | intron | LOC100129656 | LOC100128825 | 7.93E-05 | 0.93 | 3.63E-05 | 0.95 |
| rs17262815 | 8 | 130560347 | C | T | . | 0.14 | . | NA | NA | LOC100129525 | LOC100130376 | 8.10E-05 | 1.25 | 5.66E-05 | 1.24 |
| rs11020388 | 11 | 92880495 | A | G | 0.18 | 0.17 | 0.17 | C11orf75 | intron | CCDC67 | L00729466 | 8.12E-05 | 0.75 | 4.98E-05 | 0.77 |
| rs555397 | 11 | 125341540 | G | A | 0.11 | 0.07 | 0.09 | CDON | intron | LOC338667 | LOC729561 | 8.22E-05 | 0.97 | 1.66E-04 | -0.95 |
| rs1874797 | 12 | 30027638 | G | A | 0.14 | 0.15 | 0.16 | NA | NA | TMTC1 | IPO8 | 8.35E-05 | 0.80 | 2.16E-04 | 0.76 |
| rs11919628 | 3 | 111812972 | T | A | . | 0.08 | . | NA | NA | LOC440973 | LOC389141 | 8.48E-05 | 1.48 | 1.53E-04 | -1.47 |
| rs17298333 | 7 | 25010467 | A | C | . | 0.31 | . | NA | NA | OSBPL3 | CYCS | 8.52E-05 | 0.97 | 7.04E-05 | 0.99 |
| rs1563591 | 4 | 180515297 | G | A | 0.10 | . | 0.10 | NA | NA | LOC391719 | hCG_2025798 | 8.71E-05 | 1.25 | 7.35E-05 | 1.27 |
| rs294027 | 11 | 26485638 | A | G | 0.15 | . | 0.19 | TMEA416C | NA | LOC645705 | MUC15 | 8.77E-05 | 1.00 | 3.92E-05 | 1.02 |
| rs17017895 | 2 | 36029204 | A | G | 0.10 | 0.09 | 0.11 | NA | NA | MRPL50P1 | CRIM1 | 8.78E-05 | 0.88 | 1.04E-05 | 0.93 |
| rs6884748 | 5 | 31527072 | G | A | 0.06 | . | 0.07 | RNASEN | intron | CDH6 | C5orf22 | 8.82E-05 | 1.13 | 2.61E-05 | 1.19 |
| rs6884823 | 5 | 31526878 | A | G | 0.06 | . | 0.07 | RNASEN | intron | CDH6 | C5orf22 | 8.82E-05 | 1.13 | 2.61E-05 | 1.19 |
| rs2757491 | 1 | 170533424 | G | A | 0.06 | . | 0.06 | DNM3 | intron | LOC100128178 | LOC100131486 | 8.85E-05 | 1.10 | 1.17E-04 | -1.08 |
| rs2757500 | 1 | 170545644 | A | G | 0.06 | . | 0.06 | DNM3 | intron | LOC100128178 | LOC100131486 | 8.85E-05 | 1.10 | 1.17E-04 | -1.08 |
| rs12777191 | 10 | 95052323 | G | A | 0.14 | 0.14 | 0.14 | NA | NA | LOC643863 | FER1L3 | 9.06E-05 | 0.77 | 1.10E-04 | 0.76 |
| rs957615 | 4 | 23518663 | T | C | . | 0.10 | . | NA | NA | PPARGC1A | LOC729175 | 9.22E-05 | 1.33 | 5.67E-05 | 1.36 |
| rs11898024 | 2 | 58115520 | C | A | 0.08 | . | 0.10 | NA | NA | LOC100131953 | VRK2 | 9.24E-05 | 1.15 | 6.94E-06 | 1.25 |
| rs10169411 | 2 | 42491253 | A | G | . | 0.13 | . | NA | NA | COX7A2L | KCNG3 | 9.25E-05 | 1.16 | 1.22E-04 | -1.14 |
| rs11693549 | 2 | 42543983 | 1 | C | . | 0.13 | . | KCNG3 | NA | COX7A2L | LOC100129718 | 9.25E-05 | 1.16 | 1.22E-04 | -1.14 |
| rs222468 | 2 | 42496035 | A | G | . | 0.13 | . | NA | NA | COX7A2L | KCNG3 | 9.25E-05 | 1.16 | 1.22E-04 | -1.14 |
| rs222471 | 2 | 42491561 | G | A | . | 0.13 | . | NA | NA | COX7A2L | KCNG3 | 9.25E-05 | 1.16 | 1.22E-04 | 1.14 |
| rs3794002 | 11 | 92892707 | A | G | 0.18 | . | 0.16 | C11orf75 | intron | CCDC67 | LOC729466 | 9.29E-05 | 0.91 | 6.50E-05 | 0.95 |
| rs11028782 | 11 | 25574425 | A | G | 0.24 | . | 0.18 | NA | NA | LOC554234 | LOC645705 | 9.40E-05 | 0.86 | 1.26E-04 | -0.85 |
| rs2076766 | 13 | 106979661 | G | A | 0.18 | 0.16 | 0.16 | FAM155A | intron | RP11-282A11.1 | LIG4 | 9.43E-05 | 0.71 | 1.65E-04 | -0.70 |
| rs1871072 | 10 | 54571008 | A | G | . | 0.31 | . | NA | NA | MBL2 | PCDH15 | 9.49E-05 | 1.21 | 1.42E-04 | -1.07 |
| rs6750890 | 2 | 208719259 | T | G | . | 0.10 | . | CRYGB | near-gene-5 | CRYGB | CRYGA | 9.49E-05 | 1.08 | 1.93E-04 | -1.20 |
| rs6712962 | 2 | 234577772 | G | A | 0.49 | 0.42 | 0.45 | TRPM8 | intron | LOC100130859 | SPP2 | 9.60E-05 | -0.70 | 1.39E-04 | -0.69 |
| rs318422 | 1 | 82792064 | A | G | 0.44 | 0.40 | 0.41 | NA | NA | LPHN2 | TTLL7 | 9.70E-05 | 0.64 | 1.21E-04 | -0.63 |
| rs17182641 | 14 | 21146287 | A | G | 0.11 | 0.08 | 0.13 | NA | NA | OR10G1P | TRA@ | 9.71E-05 | 0.92 | 1.09E-05 | 0.97 |
| rs10179237 | 2 | 42369005 | T | C | . | 0.12 | . | EML4 | intron | SGK493 | COX7A2L | 9.81E-05 | 1.19 | 1.35E-04 | -1.18 |
| rs2053349 | 2 | 42369709 | A | G | . | 0.12 | . | EML4 | intron | SGK493 | COX7A2L | 9.81E-05 | 1.19 | 1.35E-04 | -1.18 |

Fifty-nine out of 90 variants had the same direction of effect (either reduced or increased risk) in at least two out of the three studies (cutoff $p<1\times10^{-4}$). The top ten most statistically significant variants of that list are shown in Table 5.

TABLE 5

Ten most statistically significant variants, according to unadjusted p values, associated with grade ≥2 proteinuria, hypertension and composite toxicity with the same direction of effect (either reduced or increased risk) in at least two out of three trials for proteinuria and composite toxicity, and three out of four trials for hypertension. Ch chromosome, NA Intergenic SNP, MAF minor allele frequencies in CALGB 80303, 40503, 90401, and 40502 respectively, "_" SNP not present in the genotype platform of the trial, "." data on protein uria were not available. Composite toxicity is defined as the occurrence of either proteinuria or hypertension or both.

Figure 3:
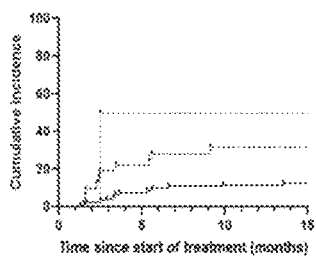
FIG. 3 shows effect of genotypes of rs339947 and rs12482855 associated with proteinuria grade ≥2, rs13135230 and rs2350620 associated with hypertension grade 2, and rs11662763 associated with composite toxicity grade ≥2. Composite toxicity is defined as the occurrence of either proteinuria or hypertension or both.
Figure 3:
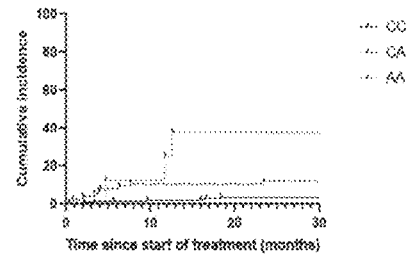
Figure 3:
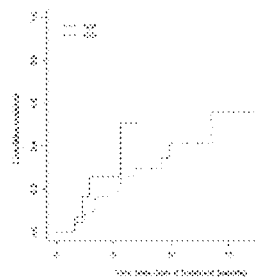
Figure 3:
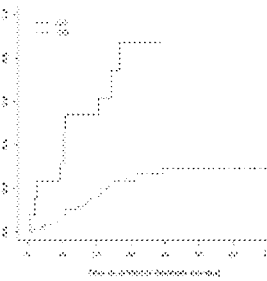
Figure 3:
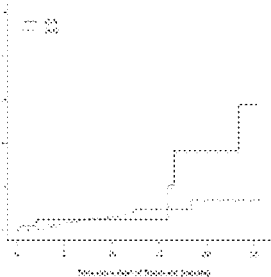
Figure 3:
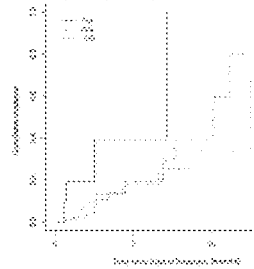
Figure 3:
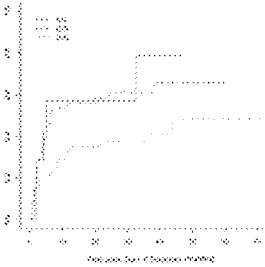
Figure 3:
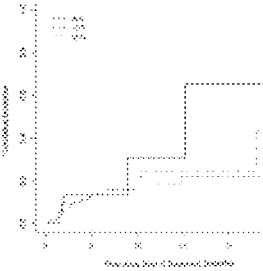
Figure 3:
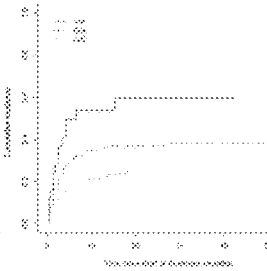
Figure 3:
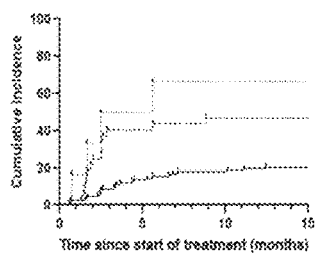
Figure 3:
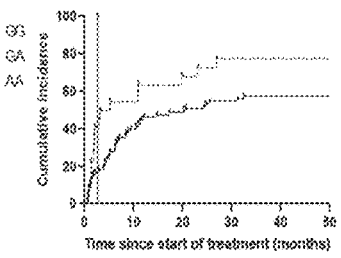
Figure 3:
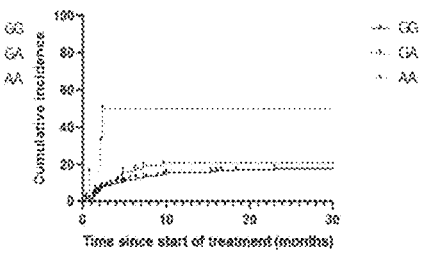
Figure 4A:
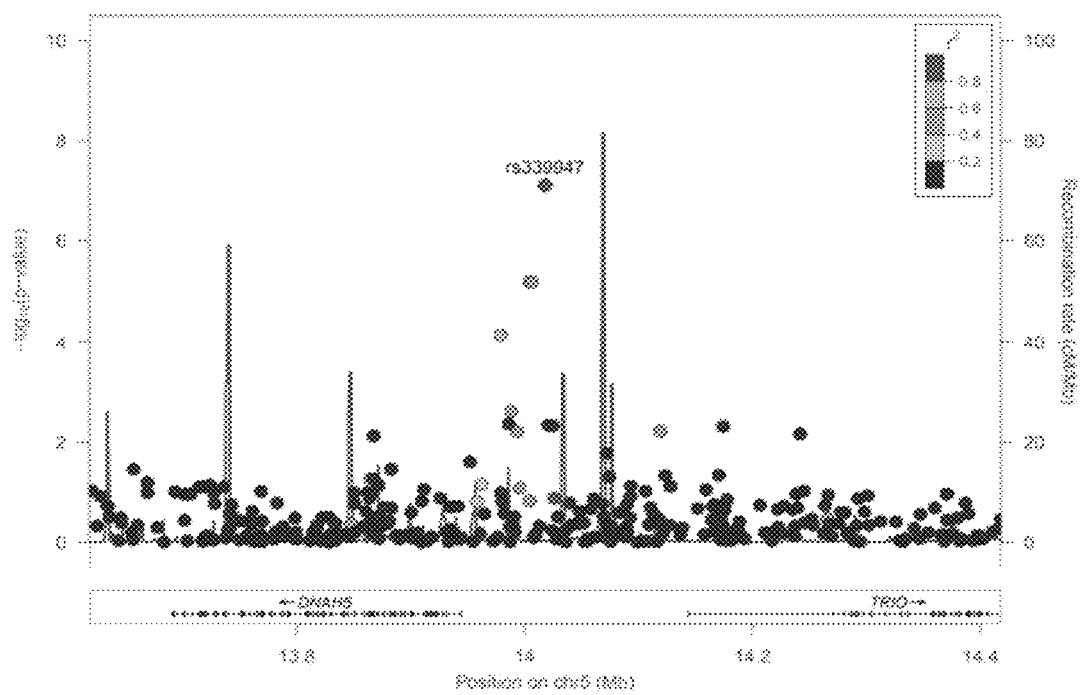
FIG. 4A-4C shows LocusZoom plots using 400 kb window left and right from the variant limits associated with bevacizumab-induced grade ≥2 proteinuria (FIG. 4A, top panel and FIG. 4C, top panel), composite toxicity (FIG. 4A, bottom panel), and hypertension (FIGS. 4B and 4C, bottom panel) in SNP-based analysis. Each circle represents the p-value for one SNP, with the top SNP shown in purple and the SNPs in the region colored depending on their degree of linkage disequilibrium (LD)($R^2$). X-axis denotes the position of the SNP in the region on chromosome; Y-axis denotes the p-value of the association.
Figure 4A:
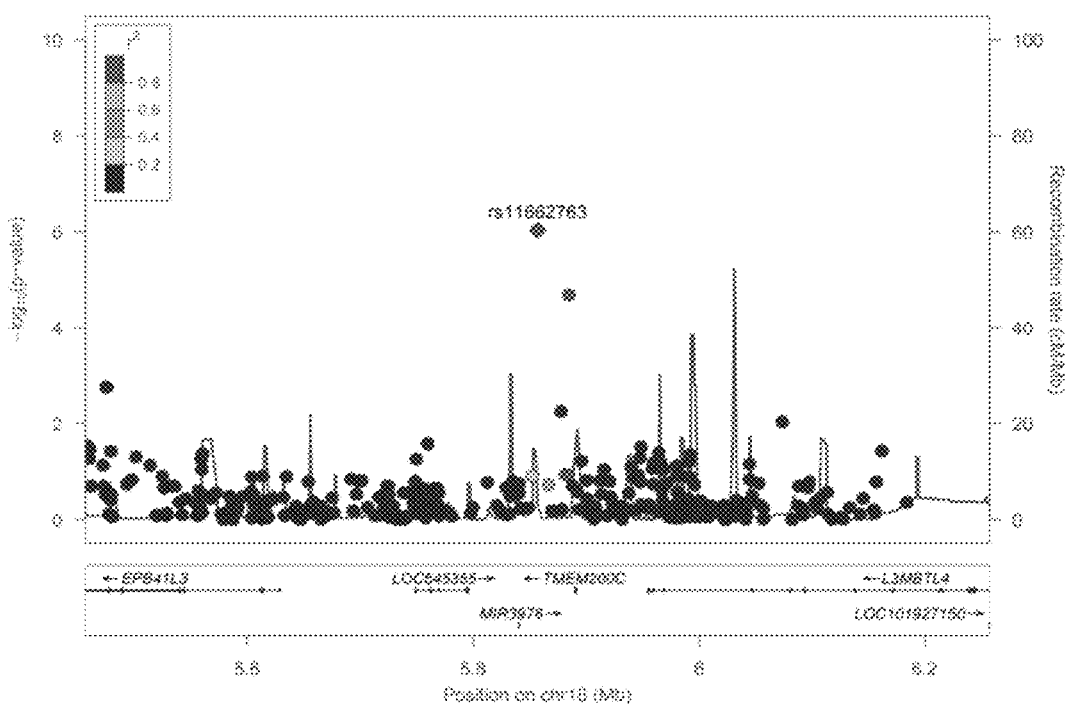
Figure 4B:
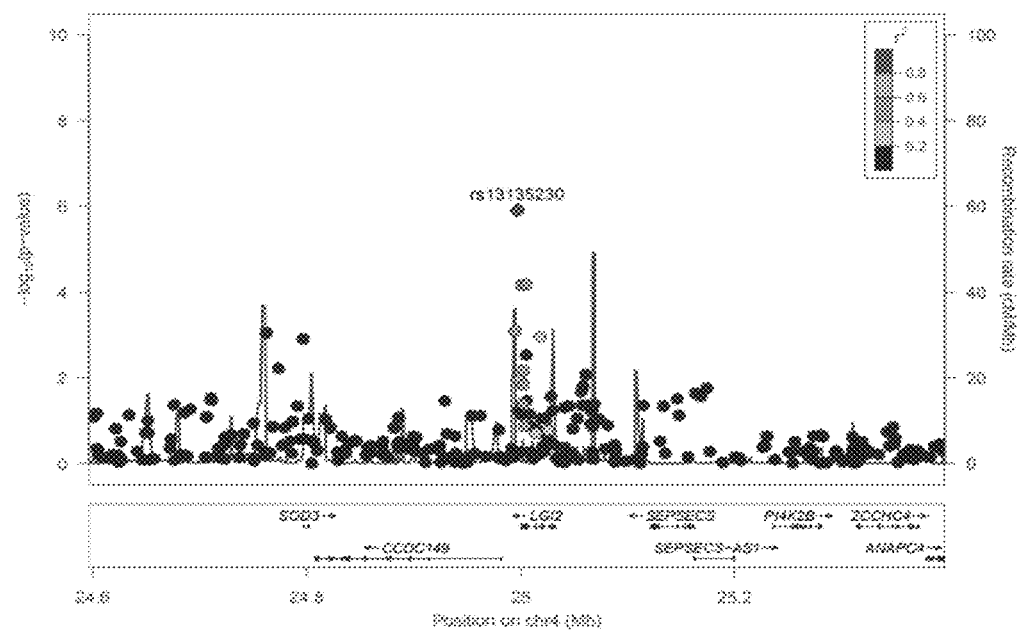
Figure 4B:
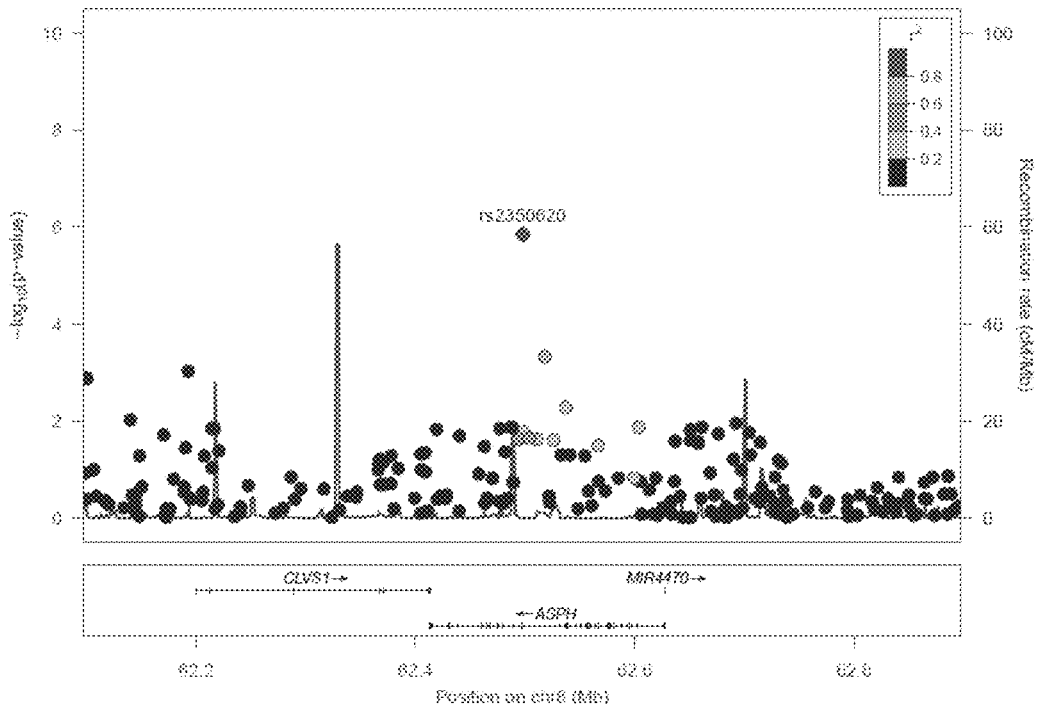
Figure 4C:
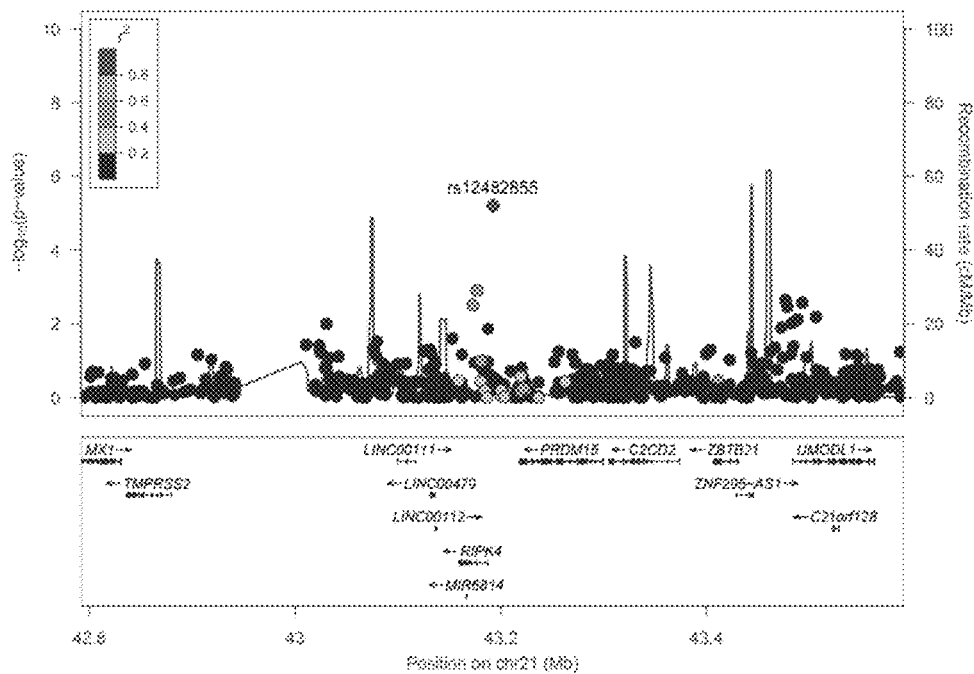
Figure 4C:
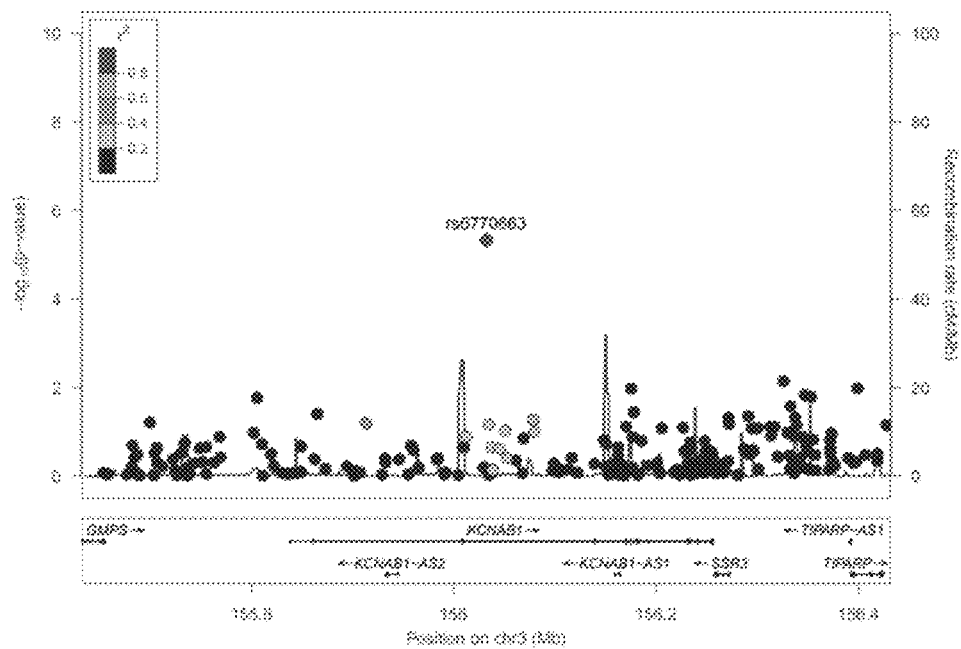

| SNP | Ch | Gene | Feature | Flanking gene | Flanking gene | Base change | MAF | Effect size (β) | p-value |
|---|---|---|---|---|---|---|---|---|---|
| Proteinuria | | | | | | | | | |
| rs339947 | 5 | NA | NA | DNAH5 | TRIO | C > A | 0.12/_/0.14/. | 1.27 | $7.66 \times 10^{-8}$ |
| rs12612153 | 2 | C2crf34 | Intron | PREPL | LOC100130502 | A > C | 0.11/_/0.11/. | 1.16 | $3.89 \times 10^{-6}$ |
| rs7180310 | 15 | NA | NA | SNORD116-24 | SNORD116-25 | C > A | 0.06/0.05/_/. | 1.54 | $4.10 \times 10^{-6}$ |
| rs12482855 | 21 | NA | NA | RIPK4 | PRDM15 | G > A | 0.06/0.06/0.06/. | 1.20 | $6.28 \times 10^{-6}$ |
| rs408130 | 5 | NA | NA | DNAH5 | TRIO | G > A | 0.21/_/0.28/. | 1.07 | $6.33 \times 10^{-6}$ |
| rs418173 | 5 | NA | NA | DNAH5 | TRIO | G > A | 0.21/_/0.28/. | 1.07 | $6.33 \times 10^{-6}$ |
| rs7959783 | 12 | NA | NA | MDM1 | LOC729376 | A > G | 0.31/0.26/0.33/. | 0.72 | $7.01 \times 10^{-6}$ |
| rs627761 | 11 | LOC338667 | Intron | DDX25 | CDON | A > G | 0.10/_/0.09/. | 1.19 | $7.49 \times 10^{-6}$ |
| rs2688994 | 3 | SLC12A8 | Intron | HEG1 | ZNF148 | G > A | 0.13/0.14/0.14/. | 0.92 | $8.13 \times 10^{-6}$ |
| rs20486445 | 7 | OSBPL3 | Intron | DFNA5 | CYCS | A > G | 0.42/0.35/0.39/. | 0.75 | $1.17 \times 10^{-5}$ |
| Hypertension | | | | | | | | | |
| rs13135230 | 4 | NA | NA | CCDC149 | LGI2 | G > A | 0.27/0.28/0.25/0.28 | 0.46 | $1.26 \times 10^{-6}$ |
| rs2350620 | 8 | ASPH | Intron | hCG_1988300 | LOC645551 | A > G | 0.32/0.26/0.32/0.32 | −0.49 | $1.44 \times 10^{-6}$ |
| rs6770663 | 3 | KCNAB1 | Intron | LOC751837 | SSR3 | A > G | 0.09/0.09/0.08/0.09 | 0.57 | $4.79 \times 10^{-6}$ |
| rs1145786 | 6 | NA | NA | MAP3K7 | LOC1001 29847 | A > G | 0.33/0.32/0.34/0.33 | 0.39 | $5.10 \times 10^{-6}$ |
| rs7130734 | 11 | NA | NA | LRRC4C | LOC100131020 | C > A | 0.35/0.30/_/0.33 | 0.42 | $1.17 \times 10^{-5}$ |
| rs2179218 | 20 | PTPRT | Intron | LOC643172 | PPIAL | G > A | 0.13/0.15/0.14/0.13 | 0.49 | $1.99 \times 10^{-5}$ |
| rs10519829 | 5 | NA | NA | LOC644659 | LOC100130551 | G > A | 0.44/0.46/0.47/0.47 | 0.36 | $2.28 \times 10^{-5}$ |
| rs1530837 | 15 | PLA2G4E | Intron | EHD4 | PLA2G4D | A > G | 0.23/0.19/0.18/0.17 | 0.43 | $2.59 \times 10^{-5}$ |
| rs2000611 | 14 | KCNK10 | Intron | KCNK10 | SPATA7 | A > G | 0.44/0.43/0.50/0.48 | −0.37 | $3.49 \times 10^{-5}$ |
| rs4611262 | 12 | NUP37 | Intron | CCDC53 | C12or148 | G > A | 0.20/0.25/0.23/0.23 | 0.39 | $3.74 \times 10^{-5}$ |
| Composite toxicity | | | | | | | | | |
| rsl1662763 | 18 | NA | NA | LOC645355 | TTMA | G > A | 0.14/0.11/0.13/. | 0.67 | $9.19 \times 10^{-7}$ |
| rs8006648 | 14 | NA | NA | LOC730121 | GALC | G > A | 0.27/0.28/0.26/. | 0.58 | $2.33 \times 10^{-6}$ |
| rs2456761 | 10 | NA | NA | LOC729184 | CDC2 | C > A | 0.35/_/0.34/. | 0.72 | $2.80 \times 10^{-6}$ |
| rs1000032 | 2 | NA | NA | KIAA1715 | EVX2 | C > A | 0.13/0.18/0.19/. | 0.62 | $3.21 \times 10^{-6}$ |
| rs2687640 | 7 | CPVL | Intron | KIAA0644 | LOC100131724 | G > A | 0.06/_/0.06/. | 1.03 | $3.55 \times 10^{-6}$ |
| rs9310707 | 3 | CNTA4 | Intron | LOC727610 | LOC100130346 | G > A | 0.37/0.37/0.36/. | 0.53 | $4.03 \times 10^{-6}$ |
| rs13156044 | 5 | DNAH5 | Intron | LOC391736 | TRIO | G > A | 0.15/0.11/011/. | 0.60 | $8.51 \times 10^{-6}$ |
| rs12328055 | 2 | NA | NA | FSHR | LOC130728 | G > A | 0.06/_/0.05/. | 0.99 | $9.19 \times 10^{-6}$ |
| rs4799369 | 18 | DTNA | Intron | LOC646842 | MAPRE2 | A > G | 0.20/0.20/0.18/. | 0.59 | $1.14 \times 10^{-5}$ |
| rs2757491 | 1 | DNM3 | Intron | LOC100128178 | LOC100131486 | G > A | 0.06/_/0.06/. | 0.90 | $1.21 \times 10^{-5}$ | rs339947 (C>A, minor allele frequency, MAF 0.12-0.14) was the most statistically significant ($p=7.66\times10^{-8}$, $\beta=1.27$), with the A allele increasing the risk of proteinuria (FIG. 3). rs339947 is an intergenic variant located 73 kb 5' from DNAH5 and 130 kb 5' from TRIO (FIG. 4A). rs408130 and rs418173 (G>A and MAF 0.21-0.28 for both) are among the ten most statistically significant variants and in complete LD with each other ($R^2=1.00$) and in moderate LD with rs339947 ($R^2=0.51$). rs12482855 (G>A, MAF 0.06) had the same direction of effect in all three trials ($p=6.28\times10^{-6}$, $\beta=1.20$), with the A allele increasing the risk of proteinuria (FIG. 3). rs12482855 is 4.7 kb 5' from RIPK4, an intergenic variant and does not have any variant in high LD ($r^2>0.8$) with it (FIG. 4C).

Figure 5:
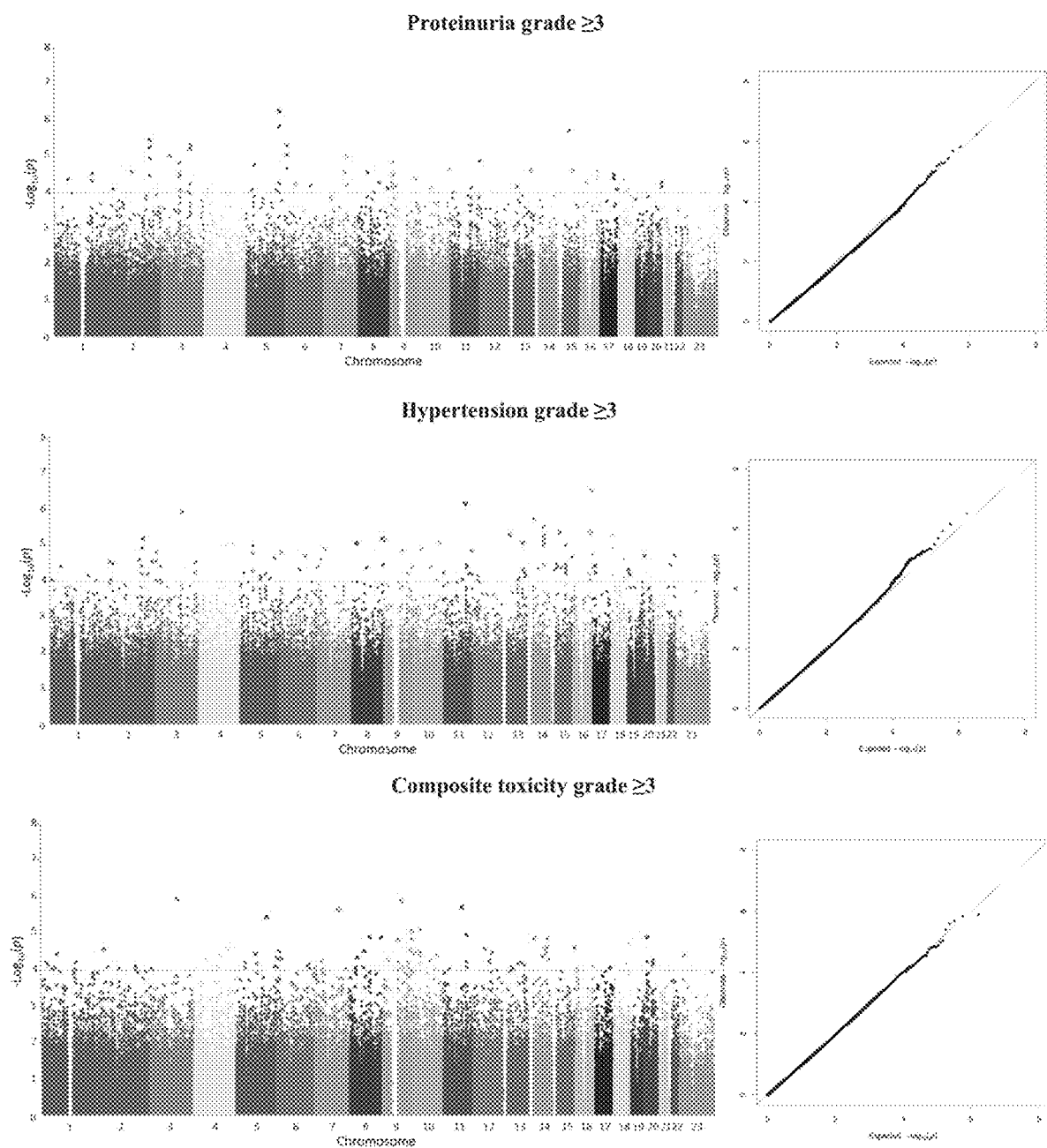
FIG. 5 shows Manhattan plots (left) and quantile-quantile (Q-Q) plots (right) from the SNP-based association results for proteinuria, hypertension, and composite toxicity grade ≥3. Composite toxicity is defined as the occurrence of either proteinuria or hypertension or both.

For the SNP-based analysis of grade ≥3, the Manhattan and Q-Q plots are shown in FIG. 5. 67 variants were identified as associated with proteinuria. Results are shown in Table 6.

TABLE 6

SNPs associated with proteinuria (grade ≥3)

| SNP | CH | BP | effect allele | reference allele | MAF 80303 | MAF 40503 | MAF 90401 | gene | feature | Flanking gene | Flanking gene | p-value | effect (β) |
|---|---|---|---|---|---|---|---|---|---|---|---|---|---|
| rs2303028 | 5 | 150485987 | A | G | 0.19 | 0.20 | 0.16 | ANXA6 | intron | TNIP1 | CCDC69 | 5.75E-07 | 1.57 |
| rs3792775 | 5 | 150483530 | A | G | 0.25 | 0.24 | 0.21 | ANXA6 | intron | TNIP1 | CCDC69 | 1.56E-06 | 1.49 |
| rs17525472 | 15 | 49756960 | G | A | 0.14 | . | 0.12 | NA | NA | DMXL2 | SCG3 | 2.05E-06 | 1.98 |
| rs7579312 | 2 | 189590930 | A | G | . | 0.06 | . | NA | NA | COL3A1 | COL5A2 | 3.65E-06 | 2.49 |
| rs7761644 | 6 | 6933004 | G | A | . | 0.08 | . | NA | NA | RP11-320C15.1 | LOC643936 | 5.28E-06 | 1.96 |

TABLE 6-continued

SNPs associated with proteinuria (grade ≥3)

| SNP | CH | BP | effect allele | reference allele | MAF 80303 | MAF 40503 | MAF 90401 | gene | feature | Flanking gene | Flanking gene | p-value | effect (β) |
|---|---|---|---|---|---|---|---|---|---|---|---|---|---|
| rs6772933 | 3 | 136335379 | G | A | 0.05 | 0.10 | 0.07 | EPHB1 | intron | LOC645218 | PPP2R3A | 5.31E-06 | 1.85 |
| rs10188246 | 2 | 189879253 | G | A | . | 0.06 | 0.06 | NA | NA | COL5A2 | KRT18P19 | 5.86E-06 | 1.68 |
| rs12636883 | 3 | 133912212 | A | C | 0.13 | 0.13 | 0.15 | NPHP3 | intron | UBA5 | NCRNA00119 | 6.57E-06 | 1.49 |
| rs9502527 | 6 | 6930995 | G | A | . | 0.08 | . | NA | NA | RP11-320C15.1 | LOC643936 | 9.56E-06 | 1.94 |
| rs2070492 | 3 | 38332821 | A | G | 0.09 | 0.10 | 0.10 | SLC22A14 | missense | SLC22A13 | XYLB | 1.04E-05 | 1.77 |
| rs7341475 | 7 | 103192051 | A | G | 0.16 | 0.11 | 0.15 | RELN | intron | SLC26A5 | ORC5L | 1.07E-05 | 1.66 |
| rs6434309 | 2 | 189591411 | A | C | 0.08 | 0.08 | 0.10 | NA | NA | COL3A1 | COL5A2 | 1.22E-05 | 1.47 |
| rs2105632 | 11 | 131842137 | G | A | 0.14 | 0.14 | 0.13 | OPCWL | intron | HNT | LOC100128095 | 1.36E-05 | 1.61 |
| rs1590347 | 9 | 10325382 | A | G | . | 0.12 | . | PTPRD | intron | RN7SLP2 | LOC646087 | 1.48E-05 | 1.90 |
| rs17460569 | 3 | 85702141 | G | A | 0.08 | . | 0.13 | NA | NA | LOC440970 | CADM2 | 1.55E-05 | 2.33 |
| rs10061011 | 5 | 36478917 | G | A | . | 0.07 | 0.05 | NA | NA | RANBP3L | SLC1A3 | 1.77E-05 | 2.57 |
| rs7341301 | 6 | 6930714 | A | G | 0.11 | 0.08 | 0.09 | NA | NA | RP11-320C15.1 | LOC643936 | 2.20E-05 | 1.28 |
| rs12248682 | 10 | 131200410 | A | G | 0.09 | 0.07 | 0.10 | MGMT | intron | hCG_1795091 | LOC100129103 | 2.36E-05 | 1.65 |
| rs12864893 | 13 | 97867240 | A | C | 0.06 | . | 0.08 | FARP1 | intron | RNF113B | STK24 | 2.56E-05 | 1.87 |
| rs893911 | 15 | 64715542 | A | G | 0.19 | 0.14 | 0.18 | NA | NA | LCTL | SMAD6 | 2.56E-05 | 1.28 |
| rs280877 | 16 | 76215748 | G | A | 0.19 | 0.14 | 0.16 | NA | NA | ADAMTS18 | NUDT7 | 2.70E-05 | 1.22 |
| rs7581769 | 2 | 105053248 | A | G | 0.11 | . | 0.09 | MRPS9 | intron | LOC100128684 | LOC100133048 | 2.82E-05 | 1.62 |
| rs2974319 | 8 | 42594234 | G | A | 0.06 | 0.08 | 0.08 | NA | NA | C8orf40 | CHRNB3 | 2.88E-05 | 1.92 |
| rs61737465 | 7 | 94378463 | A | G | . | 0.06 | . | NA | NA | ARF1P1 | PON1 | 2.89E-05 | 1.84 |
| rs551112 | 9 | 14433468 | A | C | 0.05 | 0.09 | 0.07 | NA | NA | NFIB | ZDHHC21 | 2.92E-05 | 1.61 |
| rs6781294 | 3 | 86413784 | G | A | 0.07 | 0.12 | 0.12 | NA | NA | CADM2 | VGLL3 | 2.93E-05 | 1.48 |
| rs1999184 | 1 | 176940266 | G | A | 0.09 | . | 0.07 | NA | NA | C1orf220 | LOC646976 | 3.03E-05 | 2.29 |
| rs9860570 | 3 | 86372146 | G | A | 0.07 | 0.12 | 0.12 | NA | NA | CADM2 | VGLL3 | 3.15E-05 | 1.48 |
| rs9899787 | 17 | 62161091 | G | A | . | 0.10 | . | PRKCA | intron | APOH | CACNG5 | 3.34E-05 | 2.46 |
| rs7875861 | 9 | 10275562 | G | A | . | 0.08 | . | PTPRD | intron | RN7SLP2 | LOC646087 | 3.47E-05 | 2.87 |
| rs10184895 | 2 | 189788608 | A | T | . | 0.06 | . | NA | NA | COL5A2 | KRT18P19 | 3.53E-05 | 1.67 |
| rs9864170 | 3 | 85693598 | A | G | 0.13 | . | 0.18 | NA | NA | LOC440970 | CADM2 | 3.77E-05 | 1.68 |
| rs280866 | 16 | 76211348 | A | G | 0.07 | 0.07 | 0.07 | NA | NA | ADAMTS18 | NLIDT7 | 3.87E-05 | 1.59 |
| rs282999 | 16 | 76151802 | G | A | 0.22 | 0.17 | 0.19 | NA | NA | ADAMTS18 | NUDT7 | 4.13E-05 | 1.29 |
| rs9912154 | 17 | 62159169 | A | G | . | 0.11 | . | PRKCA | intron | APOH | CACNG5 | 4.21E-05 | 2.44 |
| rs4979476 | 9 | 116740531 | G | A | 0.09 | 0.09 | 0.08 | NA | NA | TNFSF8 | TNC | 4.26E-05 | 1.50 |
| rs4916009 | 1 | 65144006 | A | G | 0.08 | . | 0.09 | JAK1 | intron | RAVER2 | LOC100130270 | 4.39E-05 | 1.96 |
| rs1583609 | 18 | 26882002 | A | G | 0.10 | 0.10 | 0.11 | NA | NA | DSC3 | DSC2 | 4.46E-05 | 1.72 |
| rs10798628 | 1 | 176918995 | A | G | 0.10 | . | 0.08 | NA | NA | C1corf220 | LOC646976 | 4.76E-05 | 2.29 |
| rs7826830 | 8 | 95723804 | A | G | 0.17 | 0.13 | 0.14 | RBiv135A | intron | KIAA1429 | DPY19L4 | 5.25E-05 | 1.36 |
| rs8116164 | 20 | 61083073 | A | G | 0.13 | 0.08 | 0.12 | NA | NA | LOC100128172 | BHLHB4 | 5.38E-05 | 1.49 |
| rs12486323 | 3 | 133913494 | G | A | . | 0.16 | . | NPHP3 | intron | UBA5 | NCRNA00119 | 5.56E-05 | 1.84 |
| rs9922975 | 16 | 26847848 | G | A | 0.13 | 0.11 | 0.12 | NA | NA | HS3ST4 | C16orf82 | 5.57E-05 | 1.27 |
| rs661198 | 9 | 10289084 | A | G | 0.10 | 0.10 | 0.09 | PTPRD | intron | RN7SLP2 | LOC646087 | 5.61E-05 | 1.33 |
| rs17717970 | 5 | 150954894 | G | A | . | 0.11 | . | NA | NA | FAT2 | SPARC | 5.79E-05 | 1.71 |
| rs11965083 | 6 | 45935458 | G | A | . | 0.18 | . | NA | NA | RLJNX2 | CLIC5 | 5.96E-05 | 1.80 |
| rs7637944 | 3 | 132912301 | A | C | 0.15 | 0.14 | 0.13 | CPNE4 | intron | MRPL3 | LOC729674 | 5.98E-05 | 1.26 |
| rs12533538 | 7 | 105218549 | A | C | 0.06 | 0.06 | 0.07 | ATXN7L1 | intron | LOC100131028 | LOC100129553 | 6.14E-05 | 1.47 |
| rs546913 | 6 | 112396275 | A | G | 0.05 | . | 0.05 | NA | NA | FYN | WISP3 | 6.73E-05 | 2.19 |
| rs689328 | 6 | 112393380 | A | G | 0.05 | . | 0.05 | NA | NA | FYN | WISP3 | 6.73E-05 | 2.19 |
| rs1332175 | 9 | 25493034 | G | A | 0.07 | 0.06 | 0.06 | NA | NA | C9orf134 | TUSC1 | 6.78E-05 | 1.65 |
| rs4479482 | 20 | 59037337 | A | G | 0.11 | 0.10 | 0.09 | NA | NA | MTCO2L | CDH4 | 6.98E-05 | 1.53 |
| rs445775 | 13 | 32422448 | A | G | . | 0.06 | 0.06 | NA | NA | PDS5B | hCG_1643176 | 7.14E-05 | 1.84 |
| rs10959051 | 9 | 10320850 | G | A | 0.24 | 0.30 | 0,22 | PTPRD | intron | RN7SLP2 | L0C:646087 | 7.23E-05 | 1.17 |
| rs10516313 | 4 | 17028411 | A | G | 0.14 | . | 0.16 | NA | NA | LOC729006 | LOC645097 | 7.55E-05 | 1.78 |
| rs7948079 | 11 | 96725167 | A | G | 0.10 | 0.09 | 0.08 | NA | NA | LOC100131233 | LOC643381 | 7.74E-05 | 1.29 |
| rs2167171 | 8 | 133556707 | C | A | 0.08 | 0.09 | 0.07 | KCNC23 | intron | HHLA1 | LRRC6 | 7.77E-05 | 1.39 |
| rs2277719 | 18 | 54350509 | A | C | 0.06 | . | 0.07 | ALPK2 | intron | NEDD4L | LOC100128163 | 7.79E-05 | 1.77 |
| rs3844600 | 10 | 49353903 | A | G | 0.22 | 0.20 | 0.22 | ARHGAP22 | intron | MAPK8 | WDEY4 | 7.90E-05 | 1.23 |
| rs1285295 | 17 | 75513707 | A | C | . | 0.09 | . | NA | NA | CBX4 | TBC1D16 | 8,12E-05 | 1.71 |
| rs2723129 | 2 | 23438312 | G | A | 0.09 | 0.07 | 0.09 | NA | NA | LOC100130841 | KLHL29 | 8.33E-05 | 1.33 |
| rs1330656 | 5 | 26084219 | A | C | 0.17 | 0.17 | 0.13 | NA | NA | MSNL1 | LOC100132866 | 8.68E-05 | 1.50 |
| rs10065544 | 5 | 136592476 | G | A | 0.20 | 0.19 | 0.21 | SPOCK1 | intron | LOC391834 | KLHL3 | 8.78E-05 | 1.19 |
| rs992803 | 3 | 86325620 | A | C | 0.14 | 0.16 | 0.19 | NA | NA | CADM2 | VGLL3 | 8.83E-05 | 1.20 |
| rs9825532 | 3 | 89169850 | A | G | . | 0.27 | . | NA | NA | LOC728432 | EPHA3 | 9,32E-05 | 2.36 |
| rs2302840 | 18 | 41326985 | A | G | 0.13 | . | 0.11 | NA | NA | LOC100131669 | SLC14A2 | 9.40E-05 | 1.93 |
| rs17237607 | 3 | 126170122 | A | G | 0.08 | 0.10 | 0.08 | HEG1 | utr-3 | MUC13 | SLC12A8 | 9.87E-05 | 1.36 |

Figure 6:
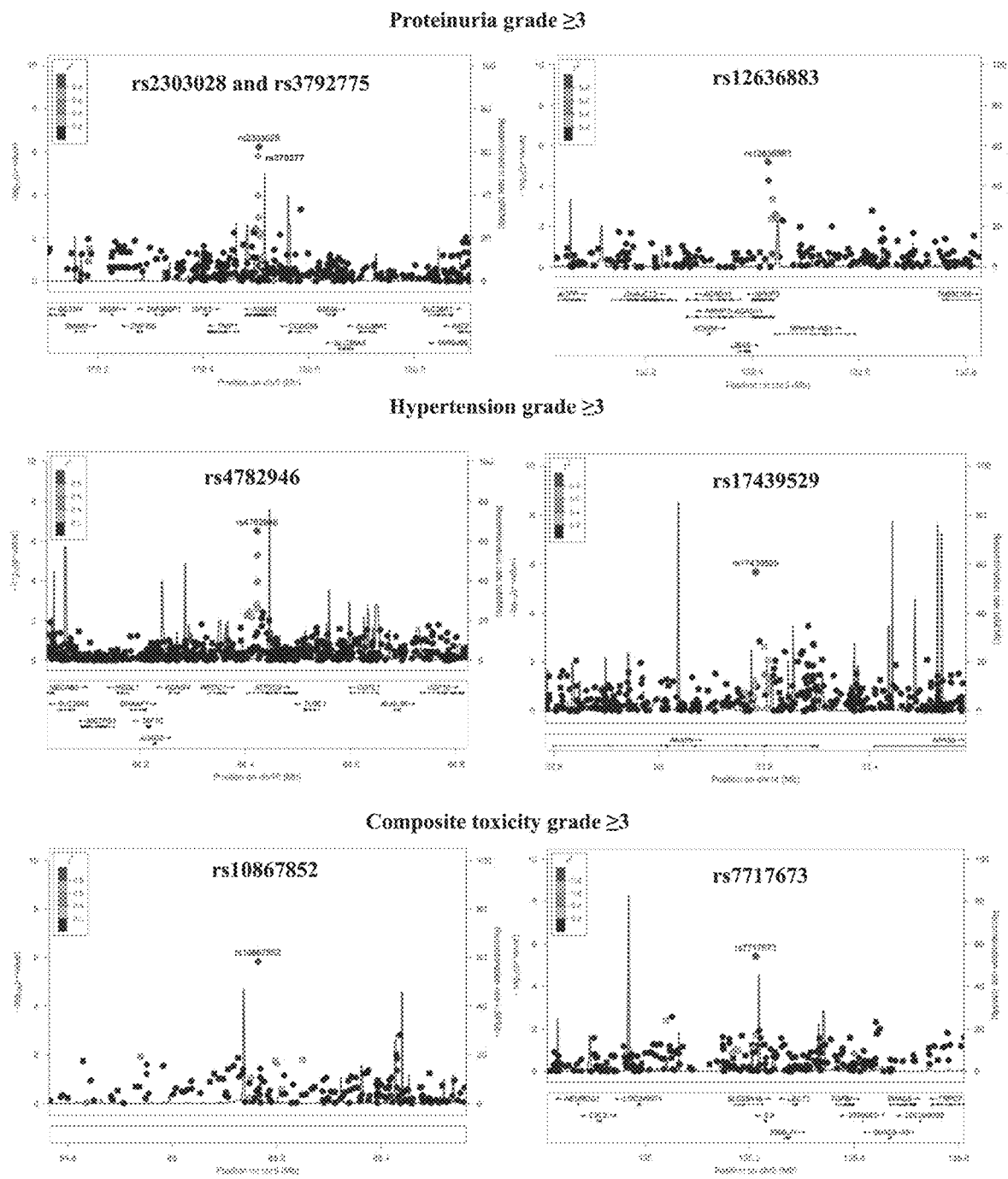
FIG. 6 shows LocusZoom plots using 400 kb window left and right from the variant limits associated with bevacizumab-induced grade ≥3 proteinuria, hypertension, and composite toxicity in SNP-based analysis. Each circle represents the p-value for one SNP, with the top SNP shown in purple and the SNPs in the region colored depending on their degree of linkage disequilibrium (LD)($R^2$). X-axis denotes the position of the SNP in the region on chromosome: Y-axis denotes the p-value of the association.

Forty-nine out of 67 variants had the same direction of effect (either reduced or increased risk) in at least two out of the three studies (cutoff $p<1\times10^{-1}$). The top ten most statistically significant variants of that list are shown in Table 7. rs2303028 (G>A MAF 0.16-0.20) was the most statistically significant ($p=5.75\times10^{7}$, $\beta=1.57$), with the A allele increasing the risk of proteinuria. rs2303028 is an intronic variant in ANXA6 (FIG. 6). rs3792775 (G>A and MAF 0.21-0.25) was the next most statistically significant variant ($p=1.56\times10-6$, $\beta=1.49$), also located in intron of ANX46 and in moderate LD with rs2303028 ($R^2=0.77$) (FIG. 6), with the A allele increasing the risk of proteinuria. rs12636883 (A>G, MAF 0.05-0.10) also had the same direction of effect in all three trials ($p=5.57\times10^{-6}$, $\beta=1.49$), with the A allele increasing the risk of proteinuria. rs12636883 is an intronic variant in NPHP3 (FIG. 6).

TABLE 7

Ten most statistically significant variants, according to unadjusted p values grade ≥3, associated with proteinuria, hypertension and composite toxicity with the same direction of effect (either reduced or increased risk) in at least two out of three trials for proteinuria and composite toxicity, and three out of four trials for hypertension. Ch chromosome, NA Intergenic SNP, MAF minor allele frequencies in CALGB 80303, 40503, 90401, and 40502 respectively, "_" SNP not present in the genotype platform of the trial, "." data on protein uria were not available. Composite toxicity is defined as the occurrence of either proteinuria or hypertension or both.

| SNP | Ch | Gene | Feature | Flanking gene | Flanking gene | Base change | MAF | Effect size ($\beta$) | p-value |
|---|---|---|---|---|---|---|---|---|---|
| Proteinuria | | | | | | | | | |
| rs2303028 | 5 | ANX.46 | Intron | TNIP1 | CCDC69 | G > A | 0.19/0.20/0.16/. | 1.57 | $5.75 \times 10^{-7}$ |
| rs3792775 | 5 | ANXA6 | Intron | TNIP1 | CCDC69 | G > A | 0.25/0.24/0.21/. | 1.49 | $1.56 \times 10^{-6}$ |
| rs17525472 | 15 | NA | NA | DMXL2 | SCG3 | A > G | 0.14/_/0.12/. | 1.93 | $2.05 \times 10^{-6}$ |
| rs6772933 | 3 | EPHB1 | Intron | LOC645218 | PPP2R3A | A > G | 0.05/0.10/0.07/. | 1.85 | $5.31 \times 10^{-6}$ |
| rs10188246 | 2 | NA | NA | COL5A2 | KRT18P19 | A > G | _/0.06/0.06/. | 1.68 | $5.86 \times 10^{-6}$ |
| rs12636883 | 3 | NPHP3 | Intron | UBA5 | NCRNA00119 | C > A | 0.13/0.13/0.15/. | 1.49 | $5.57 \times 10^{-6}$ |
| rs2070492 | 3 | SLC22A14 | Missense | SLC22A13 | XYLB | G > A | 0.09/0.10/0.10/. | 1.77 | $1.04 \times 10^{-5}$ |
| rs7341475 | 7 | RELN | Intron | SLC26A5 | ORC5L | G > A | 0.16/0.11/0.15/. | 1.66 | $1.07 \times 10^{-5}$ |
| rs6434309 | 2 | NA | NA | COL3A1 | COL5A2 | C > A | 0.08/0.08/0.10/. | 1.47 | $1.22 \times 10^{-5}$ |
| rs2105632 | 11 | OPCML | Intron | HNT | LOC100128095 | A > G | 0.14/0.14/0.13/. | 1.61 | $1.36 \times 10^{-5}$ |
| Hypertension | | | | | | | | | |
| rs4782946 | 16 | ATP2C2 | Intron | WFDC1 | KIAA1609 | G > A | 0.37/0.38/0.37/0.43 | 0.66 | $3.09 \times 10^{-7}$ |
| rs17439529 | 14 | AKAP6 | Intron | MTCO1P2 | NPAS3 | G > A | 0.36/0.40/0.38/0.40 | -0.72 | $2.08 \times 10^{-6}$ |
| rs1530837 | 15 | PLA2G4E | Intron | EHD4 | PLA2G4D | A > G | 0.23/0.19/0.18/0.17 | 0.66 | $4.87 \times 10^{-6}$ |
| rs11863271 | 16 | ATP2C2 | Intron | WFDC1 | KIAA1609 | G > A | 0.20/0.17/0.19/0.22 | 0.63 | $5.23 \times 10^{-6}$ |
| rs1171065 | 13 | DCLK1 | Intron | NBEA | SOHLH2 | A > C | 0.19/0.26/0.19/0.21 | 0.62 | $5.73 \times 10^{-6}$ |
| rs670362 | 18 | NA | NA | VAPA | APCDD1 | G > A | 0.18/0.14/0.11/0.12 | 0.67 | $6.10 \times 10^{-6}$ |
| rs2665917 | 8 | NIBP | Intron | C8orf17 | LOC100131910 | G > A | 0.44/0.48/0.47/0.47 | 0.63 | $7.13 \times 10^{-6}$ |
| rs10967306 | 9 | VLDLR | Intron | FLJ35024 | KCNV2 | G > A | 0.07/0.07/0.09/0.03 | 0.87 | $8.16 \times 10^{-6}$ |
| rs1320881 | 3 | NA | NA | LOC100132107 | ADAN128 | G > A | 0.24/0.18/0.21/0.24 | 0.61 | $9.86 \times 10^{-6}$ |
| rs4691370 | 4 | NA | NA | hCG_1814936 | PDGFC | A > G | 0.06/0.09/_/0.07 | 0.82 | $1.00 \times 10^{-5}$ |
| Composite toxicity | | | | | | | | | |
| rs10867852 | 9 | NA | NA | LOC442427 | RASEF | G > A | 0.08/0.07/0.06/. | 1.16 | $1.46 \times 10^{-6}$ |
| rs7717673 | 5 | SLC25A48 | Intron | LOC153328 | IL9 | G > A | 0.11/0.12/0.12/. | 0.94 | $3.93 \times 10^{-6}$ |
| rs2454331 | 8 | NA | NA | LOC100129100 | RIPK2 | A > G | 0.43/0.40/0.43/. | -0.77 | $1.43 \times 10^{-6}$ |
| rs873224 | 8 | NA | NA | FLJ4.3860 | LOC100131146 | A > G | 0.11/0.10/0.08/. | 0.86 | $1.48 \times 10^{-6}$ |
| rs966439 | 14 | NA | NA | LOC283584 | LOC283585 | A > G | 0.21/0.17/0.16/. | 0.70 | $1.52 \times 10^{-6}$ |
| rs7849777 | 9 | COL5A1 | Intron | RXRA | LOC100130622 | G > A | 0.09/0.05/0.06/. | 1.31 | $1.56 \times 10^{-6}$ |
| rs10869538 | 9 | PIP5K1B | Intron | LOC100131240 | PRKACG | A > G | 0.15/0.16/0.15/. | 0.74 | $1.74 \times 10^{-6}$ |
| rs11664759 | 18 | NA | NA | LOC400655 | FBXO15 | G > A | 0.11/0,15/0.15/. | 0.83 | $2.21 \times 10^{-6}$ |
| rs1978259 | 14 | NA | NA | LOC283584 | LOC283585 | C > A | 0.20/_/0.16/. | 0.81 | $2.63 \times 10^{-6}$ |
| rs17109031 | 12 | NA | NA | SMUG1 | LOC100132010 | G > A | 0.13/0.08/0.10/. | 0.85 | $2.93 \times 10^{-6}$ |

Figure 7:
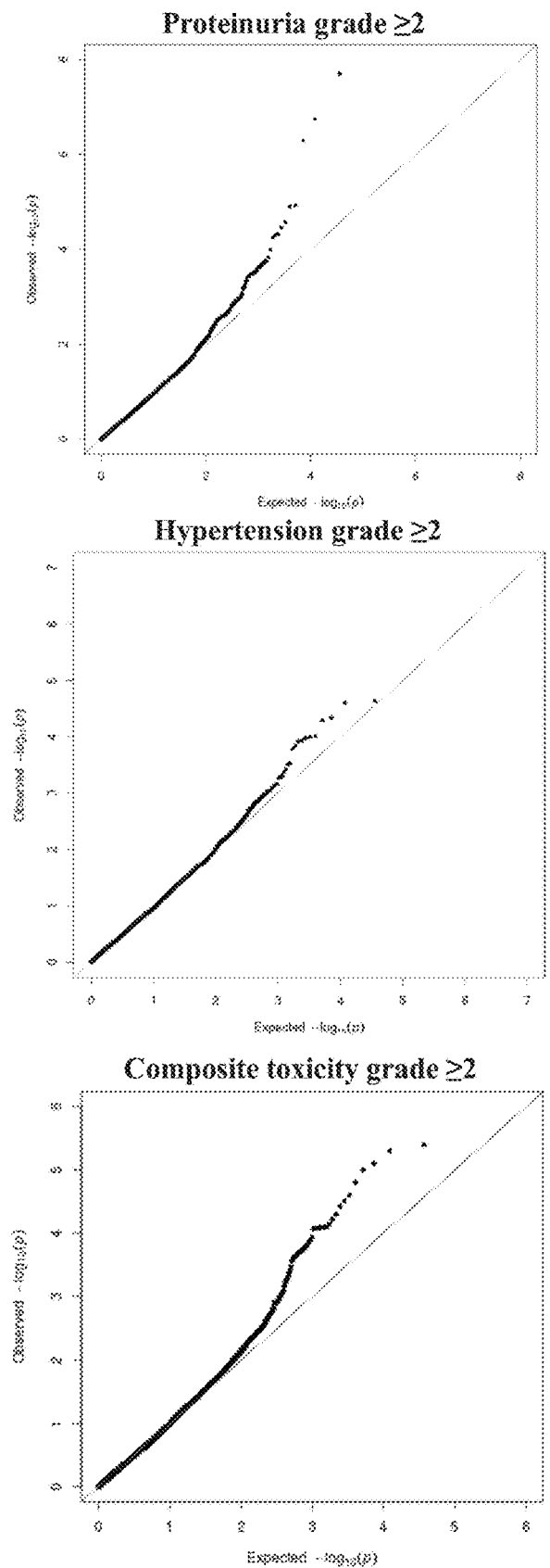
FIG. 7 shows quantile-quantile (Q-Q) plot from gene-based association results for grade ≥3 proteinuria, hypertension, and composite toxicity. Composite toxicity is defined as the occurrence of either proteinuria or hypertension or both.

For the gene-based analysis of grade ≥2, the Q-Q plot is shown in FIG. 7. Identified genes associated with proteinuria, hypertension, and composite toxicity are shown in Table 8.

TABLE 8

Genes associated with proteinuria, hypertension, or composite toxicity (grade ≥2)

| Proteinuria | | | Hypertension | | | Composite toxicity | | |
|---|---|---|---|---|---|---|---|---|
| Gene | p-value unadjusted | p-value adjusted | Gene | p-value unadjusted | p-value adjusted | Gene | p-value unadjusted | p-value adjusted |
| C1D | 2.00E-08 | 2.00E-08 | UNC50 | 2.30E-05 | 3.20E-05 | SLC25A24 | 4.00E-06 | 3.00E-06 |
| IL17F | 1.80E-07 | 5.90E-07 | KATNB1 | 2.50E-05 | 7.30E-05 | SMS | 5.00E-06 | 5.00E-06 |
| MCM3 | 5.10E-07 | 1.15E-06 | MGAT4A | 4.60E-05 | 6.10E-05 | CEP295 | 1.00E-06 | 7.00E-06 |
| SMPX | 1.20E-05 | 8.91E-06 | FBXO9 | 5.10E-05 | 3.60E-05 | YWHAE | 1.60E-05 | 1.30E-05 |

TABLE 8-continued

Genes associated with proteinuria, hypertension, or composite toxicity (grade ≥2)

| | Proteinuria | | | Hypertension | | | Composite toxicity | |
|---|---|---|---|---|---|---|---|---|
| Gene | p-value unadjusted | p-value adjusted | Gene | p-value unadjusted | p-value adjusted | Gene | p-value unadjusted | p-value adjusted |
| KLHL34 | 1.26E−05 | 1.50E−05 | STRIP1 | 9.80E−05 | 1.05E−04 | PTPN3 | 4.00E−05 | 7.10E−05 |
| EAPP | 2.70E−05 | 2.70E−05 | CCDC54 | 1.01E−04 | 7.70E−05 | KLHL35 | 4.50E−05 | 3.50E−05 |
| CNKSR2 | 3.50E−05 | 2.70E−05 | COA5 | 1.06E−04 | 1.46E−04 | H6PD | 5.10E−05 | 4.00E−05 |
| LIPJ | 4.80E−05 | 7.10E−05 | KIFC3 | 1.18E−04 | 2.76E−04 | MBTPS2 | 7.50E−05 | 7.10E−05 |
| ITGB6 | 5.00E−05 | 5.50E−05 | ICK | 1.21E−04 | 7.70E−05 | CRK | 1.37E−04 | 1.51E−04 |
| XCR1 | 5.70E−05 | 1.86E−04 | AHCYL1 | 1.45E−04 | 1.75E−04 | SLC17A6 | 1.50E−04 | 1.44E−04 |
| RFPL4AL1 | 1.03E−04 | 1.42E−04 | CAPZA2 | 1.63E−04 | 1.36E−04 | ALDH4A1 | 2.13E−04 | 2.42E−04 |
| PDE3A | 1.48E−04 | 7.86E−04 | A4GALT | 2.96E−04 | 1.93E−04 | HSD3B2 | 2.43E−04 | 2.37E−04 |
| SNX6 | 1.81E−04 | 1.11E−04 | LUZP4 | 3.10E−04 | 2.59E−04 | ZNF217 | 2.74E−04 | 3.05E−04 |
| PWWP2A | 1.82E−04 | 3.60E−04 | CFAP69 | 3.80E−04 | 3.21E−04 | STAT4 | 3.44E−04 | 1.97E−04 |
| NDHP2 | 2.01E−04 | 6.17E−04 | STK10 | 4.30E−04 | 4.79E−04 | TAS1R2 | 3.46E−04 | 3.42E−04 |
| VCP | 2.09E−04 | 2.13E−03 | TMPRSS12 | 5.03E−04 | 4.01E−04 | HDAC11 | 3.55E−04 | 4.02E−04 |
| CRYBB2 | 2.34E−04 | 9.40E−05 | AQP12A | 5.12E−04 | 5.00E−04 | AZI2 | 4.00E−04 | 4.26E−04 |
| RFPL4A | 2.38E−04 | 2.24E−04 | CYSLTR2 | 5.38E−04 | 3.81E−04 | CMC1 | 4.26E−04 | 4.35E−04 |
| CRYBB3 | 2.47E−04 | 9.00E−05 | DTD1 | 6.85E−04 | 5.41E−04 | FAM155B | 4.36E−04 | 2.96E−04 |
| ALDH6A1 | 2.87E−04 | 3.69E−04 | BRD1 | 6.94E−04 | 9.23E−04 | TGM3 | 6.14E−04 | 4.83E−04 |
| CTRB2 | 3.03E−04 | 5.53E−04 | CSRP2 | 7.46E−04 | 7.00E−04 | N1C3R | 6.37E−04 | 1.07E−03 |
| FANCG | 3.12E−04 | 3.94E−03 | FUK | 7.74E−04 | 6.71E−04 | IL17F | 6.75E−04 | 5.61E−04 |
| PIGO | 3.21E−04 | 4.29E−03 | ST3GAL2 | 8.16E−04 | 5.12E−04 | HSD3B1 | 6.93E−04 | 6.49E−04 |
| KIAA1671 | 3.29E−04 | 1.14E−04 | CDK14 | 8.68E−04 | 8.26E−04 | RGPD6 | 7.04E−04 | 6.84E−04 |
| DDB2 | 3.33E−04 | 1.75E−04 | SEPT2 | 9.21E−04 | 1.14E−03 | RPS3 | 9.49E−04 | 1.01E−03 |
| ACP2 | 3.38E−04 | 1.99E−04 | SF3B3 | 9.23E−04 | 6.91E−04 | MALL | 1.09E−03 | 7.92E−04 |
| MSANTD1 | 3.61E−04 | 4.62E−04 | RDH14 | 9.27E−04 | 9.37E−04 | SPAG4 | 1.10E−03 | 1.32E−03 |
| TGFA | 3.78E−04 | 4.88E−04 | CCDC58 | 1.03E−03 | 7.33E−04 | MYH11 | 1.16E−03 | 1.47E−03 |
| CTRB1 | 3.81E−04 | 6.26E−04 | COLGALT2 | 1.05E−03 | 8.33E−04 | RBL1 | 1.16E−03 | 1.43E−03 |
| C9orf131 | 3.85E−04 | 1.73E−03 | ZDHHC22 | 1.05E−03 | 7.83E−04 | MRPL9 | 1.22E−03 | 1.30E−03 |
| SPRY4 | 4.63E−04 | 1.02E−03 | NT5C1B | 1.10E−03 | 1.02E−03 | SKAP1 | 1.24E−03 | 1.58E−03 |
| DIRC2 | 5.26E−04 | 2.13E−04 | CSTA | 1.14E−03 | 9.29E−04 | IFFO2 | 1.25E−03 | 1.21E−03 |
| PTGR2 | 5.43E−04 | 8.58E−04 | IL33 | 1.16E−03 | 1.06E−03 | C1QTNF7 | 1.26E−03 | 7.18E−04 |
| GPX5 | 6.26E−04 | 3.13E−03 | RYR2 | 1.20E−03 | 1.97E−03 | GDPD5 | 1.32E−03 | 1.11E−03 |
| DNAJB5 | 6.38E−04 | 4.62E−04 | ACKR3 | 1.27E−03 | 8.26E−04 | PIK3C2B | 1.32E−03 | 1.03E−03 |
| RGS12 | 6.72E−04 | 1.02E−03 | EPB41L4B | 1.28E−03 | 1.68E−03 | RASGRF1 | 1.34E−03 | 1.07E−03 |
| URB2 | 8.40E−04 | 4.09E−04 | CTSK | 1.35E−03 | 2.17E−03 | CCDC172 | 1.54E−03 | 1.46E−03 |
| MLH1 | 8.86E−04 | 1.38E−03 | MFSD2A | 1.39E−03 | 1.48E−03 | TMEM182 | 1.59E−03 | 1.08E−03 |
| RAN | 1.02E−03 | 1.91E−04 | S100P | 1.44E−03 | 1.28E−03 | GLRA3 | 1.76E−03 | 1.72E−03 |
| FZD6 | 1.02E−03 | 1.07E−03 | COG4 | 1.45E−03 | 1.49E−03 | HOMER1 | 1.88E−03 | 1.98E−03 |
| TTC1 | 1.03E−03 | 9.29E−04 | CASR | 1.46E−03 | 1.02E−03 | NEFM | 1.90E−03 | 1.60E−03 |
| GNG7 | 1.04E−03 | 5.33E−04 | CNBD2 | 1.48E−03 | 1.19E−03 | TET1 | 2.01E−03 | 2.22E−03 |
| TAF5L | 1.08E−03 | 5.84E−04 | PDE4DIP | 1.48E−03 | 9.00E−04 | SLC25A16 | 2.02E−03 | 2.01E−03 |
| ZBTB3 | 1.14E−03 | 1.75E−03 | TIAL1 | 1.60E−03 | 1.47E−03 | MCM3 | 2.03E−03 | 1.87E−03 |
| PITPNM2 | 1.15E−03 | 1.39E−03 | LIBE4B | 1.62E−03 | 1.22E−03 | PLCL1 | 2.03E−03 | 2.18E−03 |
| CALCR | 1.16E−03 | 1.82E−03 | ARNT | 1.75E−03 | 2.47E−03 | GABRA3 | 2.10E−03 | 2.09E−03 |
| POLR2G | 1.18E−03 | 2.76E−04 | ARHGAP42 | 1.81E−03 | 1.61E−03 | MPP3 | 2.10E−03 | 1.93E−03 |
| SLC25A24 | 1.21E−03 | 1.21E−03 | LRRC3B | 1.83E−03 | 1.42E−03 | NPTX2 | 2.10E−03 | 2.27E−03 |
| RWDD2B | 1.22E−03 | 6.29E−04 | NYAP2 | 1.86E−03 | 1.84E−03 | NFS1 | 2.11E−03 | 2.48E−03 |
| CCT8 | 1.24E−03 | 7.50E−04 | SSX5 | 1.89E−03 | 2.53E−03 | RBM12 | 2.15E−03 | 2.09E−03 |
| STOML2 | 1.32E−03 | 1.85E−02 | PAQR4 | 1.93E−03 | 2.15E−03 | SEMA5B | 2.26E−03 | 2.36E−03 |
| KRTAP12-4 | 1.35E−03 | 1.60E−03 | KREMEN2 | 2.02E−03 | 2.20E−03 | GPATCH2 | 2.28E−03 | 1.33E−03 |
| STX2 | 1.35E−03 | 2.65E−04 | SNX11 | 2.06E−03 | 3.48E−03 | CPNE1 | 2.29E−03 | 2.39E−03 |
| PRB3 | 1.40E−03 | 2.34E−03 | FLYWCH1 | 2.07E−03 | 2.31E−03 | PEX11G | 2.32E−03 | 1.93E−03 |
| FER1L6 | 1.41E−03 | 2.01E−03 | PKMYT1 | 2.10E−03 | 2.48E−03 | XYLB | 2.40E−03 | 2.87E−03 |
| PRB4 | 1.45E−03 | 7.21E−02 | PACSIN2 | 2.28E−03 | 1.79E−03 | ADAM12 | 2.43E−03 | 1.92E−03 |
| MPP3 | 1.48E−03 | 1.08E−03 | GP1BA | 2.32E−03 | 1.98E−03 | SCYL2 | 2.43E−03 | 2.67E−03 |
| OR4N5 | 1.54E−03 | 1.82E−03 | KIF1A | 2.38E−03 | 1.39E−03 | YY2 | 2.52E−03 | 2.09E−03 |
| PLEKHB1 | 1.61E−03 | 1.06E−03 | NBPF9 | 2.45E−03 | 1.79E−03 | TMEM165 | 2.56E−03 | 2.11E−03 |
| RBM7 | 1.62E−03 | 1.51E−03 | SKAP1 | 2.50E−03 | 3.75E−03 | RHAG | 2.58E−03 | 2.42E−03 |
| KRTAP12-3 | 1.63E−03 | 2.14E−03 | STEAP2 | 2.50E−03 | 2.45E−03 | ANAPC5 | 2.61E−03 | 2.70E−03 |
| FAM214B | 1.64E−03 | 1.83E−03 | RBM42 | 2.52E−03 | 3.81E−03 | CHRNG | 2.66E−03 | 2.17E−03 |
| TMEM223 | 1.74E−03 | 5.45E−04 | TMEM115 | 2.69E−03 | 2.31E−03 | BIVM | 2.73E−03 | 3.12E−03 |
| PHOSPHO2 | 1.79E−03 | 2.85E−02 | CIPC | 2.70E−03 | 2.17E−03 | CAMKK2 | 2.78E−03 | 2.43E−03 |
| NXF1 | 1.88E−03 | 5.13E−04 | ARFGAP3 | 2.80E−03 | 2.01E−03 | LMTK3 | 2.83E−03 | 2.37E−03 |
| TMEM179B | 1.90E−03 | 5.93E−04 | C10orf142 | 2.83E−03 | 2.07E−03 | C1D | 2.92E−03 | 2.62E−03 |
| OR4M1 | 1.94E−03 | 3.15E−03 | TTLL5 | 2.91E−03 | 1.63E−03 | DLL3 | 2.92E−03 | 2.65E−03 |
| TAF6L | 1.99E−03 | 5.44E−04 | PRDM2 | 2.93E−03 | 3.37E−03 | ERCC5 | 2.94E−03 | 3.90E−03 |
| SCYL2 | 2.02E−03 | 1.99E−03 | ZC2HC1B | 3.04E−03 | 3.48E−03 | RBM39 | 2.97E−03 | 3.34E−03 |
| GRHL2 | 2.04E−03 | 1.01E−02 | LTV1 | 3.10E−03 | 3.23E−03 | TNKS | 2.98E−03 | 3.51E−03 |
| TTC9C | 2.04E−03 | 3.82E−04 | CCN1 | 3.29E−03 | 3.61E−03 | ZNF835 | 3.07E−03 | 2.27E−03 |
| DLG5 | 2.13E−03 | 1.62E−03 | IL23R | 3.30E−03 | 3.29E−03 | EIF4E2 | 3.10E−03 | 1.94E−03 |
| OR4Q3 | 2.19E−03 | 3.31E−03 | MRFAP1L1 | 3.33E−03 | 3.55E−03 | PRPF38A | 3.16E−03 | 2.94E−03 |
| PPP1R16A | 2.26E−03 | 3.27E−03 | CLDN9 | 3.38E−03 | 4.11E−03 | TLK1 | 3.17E−03 | 3.19E−03 |
| GCNT2 | 2.29E−03 | 1.51E−02 | ZBED4 | 3.45E−03 | 3.96E−03 | TMC1 | 3.24E−03 | 2.78E−03 |
| GPT | 2.29E−03 | 3.28E−03 | ENO3 | 3.52E−03 | 2.97E−03 | TRAPPC4 | 3.28E−03 | 3.96E−03 |
| MFSD3 | 2.29E−03 | 3.23E−03 | ZNF774 | 3.55E−03 | 3.04E−03 | PPP1R15B | 3.31E−03 | 2.80E−03 |

TABLE 8-continued

Genes associated with proteinuria, hypertension, or composite toxicity (grade ≥2)

| | Proteinuria | | | Hypertension | | | Composite toxicity | |
|---|---|---|---|---|---|---|---|---|
| Gene | p-value unadjusted | p-value adjusted | Gene | p-value unadjusted | p-value adjusted | Gene | p-value unadjusted | p-value adjusted |
| LRRC24 | 2.32E−03 | 3.41E−03 | SEL1L | 3.59E−03 | 3.43E−03 | CCDC84 | 3.35E−03 | 3.88E−03 |
| FOXH1 | 2.33E−03 | 3.27E−03 | NDNF | 3.64E−03 | 2.61E−03 | RPS25 | 3.35E−03 | 3.69E−03 |
| C11orf71 | 2.39E−03 | 1.97E−03 | AP2B1 | 3.76E−03 | 3.88E−03 | KCTD12 | 3.43E−03 | 3.24E−03 |
| SLC40A1 | 2.40E−03 | 3.24E−03 | COX6B1 | 3.83E−03 | 4.82E−03 | TCOF1 | 3.45E−03 | 2.60E−03 |
| RFC3 | 2.42E−03 | 3.46E−03 | CLDN6 | 3.97E−03 | 3.87E−03 | SLC37A4 | 3.49E−03 | 4.14E−03 |
| RECQL4 | 2.45E−03 | 3.25E−03 | ETV2 | 3.97E−03 | 5.02E−03 | TIMM50 | 3.63E−03 | 3.14E−03 |
| NCOA3 | 2.46E−03 | 1.42E−03 | PFN1 | 3.98E−03 | 3.33E−03 | TIGD1 | 3.76E−03 | 2.34E−03 |
| STX5 | 2.47E−03 | 6.63E−04 | DGKE | 4.11E−03 | 4.43E−03 | TRIM28 | 3.84E−03 | 3.09E−03 |
| WDR37 | 2.47E−03 | 1.75E−03 | SLC25A11 | 4.23E−03 | 3.71E−03 | PDZRN3 | 3.91E−03 | 3.97E−03 |
| LGALS2 | 2.51E−03 | 9.13E−04 | ZNF485 | 4.23E−03 | 3.78E−03 | KATNB1 | 3.92E−03 | 3.13E−03 |
| CYHR1 | 2.53E−03 | 3.66E−03 | TSPAN33 | 4.41E−03 | 3.42E−03 | RIIAD1 | 3.99E−03 | 4.39E−03 |
| DSG1 | 2.54E−03 | 3.00E−03 | FBXW11 | 4.52E−03 | 6.35E−03 | CHMP2A | 4.02E−03 | 2.98E−03 |
| KIFC2 | 2.54E−03 | 3.64E−03 | IL2 | 4.52E−03 | 5.88E−03 | MZF1 | 4.04E−03 | 3.34E−03 |
| BBS5 | 2.55E−03 | 5.94E−03 | TBX5 | 4.54E−03 | 3.19E−03 | UBE2M | 4.04E−03 | 3.17E−03 |
| TONSL | 2.56E−03 | 3.72E−03 | C17orf100 | 4.57E−03 | 6.94E−03 | FBXO47 | 4.27E−03 | 4.89E−03 |
| LRRC14 | 2.58E−03 | 3.01E−03 | XAGE2 | 4.60E−03 | 5.24E−03 | PGLS | 4.49E−03 | 5.44E−03 |
| REXO2 | 2.62E−03 | 3.09E−03 | HNMT | 4.68E−03 | 4.21E−03 | RALY | 4.49E−03 | 4.18E−03 |
| CCDC173 | 2.74E−03 | 2.83E−03 | ASPH | 4.69E−03 | 5.83E−03 | ZBTB45 | 4.51E−03 | 3.64E−03 |
| CYLC1 | 2.75E−03 | 2.05E−03 | RN17167 | 4.73E−03 | 3.72E−03 | CTNNB1 | 4.60E−03 | 4.57E−03 |
| PCBP2 | 2.75E−03 | 5.19E−03 | DAB2IP | 4.84E−03 | 4.68E−03 | NAMPT | 4.73E−03 | 2.83E−03 |
| SOST | 2.79E−03 | 1.74E−03 | KIF1B | 4.86E−03 | 4.48E−03 | STAT1 | 4.77E−03 | 3.79E−03 |
| DLGAP1 | 2.82E−03 | 6.77E−03 | CENPL | 4.88E−03 | 2.88E−03 | CRISP3 | 4.81E−03 | 4.96E−03 |
| SMIM18 | 2.83E−03 | 6.26E−04 | NUP155 | 4.88E−03 | 2.56E−03 | PLEKHA6 | 4.89E−03 | 4.08E−03 |
| SNRPA | 2.84E−03 | 2.93E−03 | ATP10A | 4.97E−03 | 1.06E−02 | SLC22A14 | 4.93E−03 | 5.34E−03 |
| KLHL41 | 2.88E−03 | 6.49E−03 | FOXG1 | 5.02E−03 | 4.55E−03 | CGB8 | 5.05E−03 | 4.18E−03 |
| RNF19A | 2.89E−03 | 2.69E−03 | CRHR2 | 5.16E−03 | 5.36E−03 | ZNF446 | 5.08E−03 | 3.84E−03 |
| EFNA5 | 2.90E−03 | 3.64E−03 | ZNF707 | 5.17E−03 | 4.53E−03 | UBC | 5.18E−03 | 3.48E−03 |
| RC3H1 | 2.94E−03 | 2.07E−03 | HOMER1 | 5.18E−03 | 4.44E−03 | PTAR1 | 5.20E−03 | 2.76E−03 |
| SP1 | 2.94E−03 | 1.57E−03 | PIM2 | 5.18E−03 | 5.38E−03 | NPHP1 | 5.24E−03 | 5.06E−03 |
| FASTKD1 | 2.95E−03 | 6.60E−03 | GPAT2 | 5.32E−03 | 4.94E−03 | TEX13B | 5.24E−03 | 5.56E−03 |
| NUMBL | 3.02E−03 | 2.90E−03 | AQP128 | 5.38E−03 | 5.56E−03 | IGF1R | 5.25E−03 | 4.61E−03 |
| ZNF256 | 3.05E−03 | 2.69E−03 | TNERSF12A | 5.48E−03 | 6.02E−03 | LHB | 5.31E−03 | 3.58E−03 |
| ITPKC | 3.12E−03 | 3.79E−03 | CPNE6 | 5.50E−03 | 1.24E−02 | CD74 | 5.36E−03 | 3.92E−03 |
| ACCSL | 3.15E−03 | 7.81E−02 | HS6ST1 | 5.61E−03 | 1.29E−02 | DNAJ35 | 5.38E−03 | 6.12E−03 |
| VWA5B1 | 3.15E−03 | 3.67E−03 | HERC5 | 5.66E−03 | 5.20E−03 | CITED1 | 5.39E−03 | 3.93E−03 |
| DUSP3 | 3.18E−03 | 1.79E−03 | GPR139 | 5.69E−03 | 7.03E−03 | KLHL26 | 5.39E−03 | 4.53E−03 |
| SERPINC1 | 3.25E−03 | 2.56E−03 | FLYWCH2 | 5.73E−03 | 6.61E−03 | C9orf135 | 5.42E−03 | 4.63E−03 |
| RNLS | 3.26E−03 | 3.51E−03 | TXNDC2 | 5.76E−03 | 5.92E−03 | ROMO1 | 5.51E−03 | 5.81E−03 |
| C19orf54 | 3.30E−03 | 3.12E−03 | HCFC1R1 | 5.77E−03 | 6.77E−03 | ZCCHC11 | 5.55E−03 | 4.16E−03 |
| ZNF429 | 3.36E−03 | 2.88E−03 | ZXDA | 5.84E−03 | 7.91E−03 | DIRC2 | 5.59E−03 | 4.89E−03 |
| C2orf88 | 3.45E−03 | 4.75E−03 | THOC6 | 5.85E−03 | 6.99E−03 | DIRAS2 | 5.62E−03 | 5.21E−03 |
| KRT25 | 3.45E−03 | 3.73E−03 | GSTA2 | 5.94E−03 | 6.16E−03 | AKAP1 | 5.63E−03 | 5.12E−03 |
| SHMT1 | 3.60E−03 | 2.50E−05 | CETP | 5.95E−03 | 5.20E−03 | KCNJ14 | 5.63E−03 | 5.16E−03 |
| HERC6 | 3.71E−03 | 2.85E−03 | RIMBP2 | 5.95E−03 | 4.68E−03 | TXNL1 | 5.86E−03 | 3.61E−03 |
| KRTAP10-10 | 3.74E−03 | 5.55E−03 | C1QTNF7 | 6.15E−03 | 5.50E−03 | ELOVL2 | 5.91E−03 | 8.74E−03 |
| MIA | 3.74E−03 | 4.27E−03 | ZNF592 | 6.21E−03 | 1.16E−02 | ZDHHC7 | 5.94E−03 | 3.65E−03 |
| SMCR8 | 3.81E−03 | 2.06E−03 | GIPC2 | 6.22E−03 | 5.12E−03 | DUSP3 | 6.01E−03 | 6.00E−03 |
| RAB6A | 3.82E−03 | 1.96E−03 | ARHGAP15 | 6.34E−03 | 5.07E−03 | SOST | 6.04E−03 | 6.47E−03 |
| TAS2R42 | 3.82E−03 | 5.90E−03 | PLAGL1 | 6.43E−03 | 6.22E−03 | MPZ | 6.06E−03 | 6.28E−03 |
| RBPMS | 3.84E−03 | 1.33E−03 | ZNF787 | 6.44E−03 | 7.05E−03 | COPG2 | 6.08E−03 | 5.69E−03 |
| EVPLL | 3.88E−03 | 3.10E−03 | ZNF835 | 6.45E−03 | 8.13E−03 | ETAA1 | 6.09E−03 | 7.90E−03 |
| ST6GALNAC3 | 3.93E−03 | 1.03E−02 | NAPEPLD | 6.46E−03 | 1.10E−02 | NF2 | 6.11E−03 | 6.26E−03 |
| RAB4B | 4.00E−03 | 4.65E−03 | FAM83H | 6.49E−03 | 5.92E−03 | SLC27A5 | 6.13E−03 | 5.15E−03 |
| KRTAP10-11 | 4.06E−03 | 4.98E−03 | CNTF | 6.52E−03 | 7.36E−03 | GRWD1 | 6.23E−03 | 5.43E−03 |
| OVOL2 | 4.06E−03 | 6.26E−03 | MAPK15 | 6.55E−03 | 5.72E−03 | COLGALT1 | 6.28E−03 | 7.51E−03 |
| SLC25A33 | 4.10E−03 | 2.97E−03 | SMO | 6.55E−03 | 6.00E−03 | CTSH | 6.32E−03 | 4.97E−03 |
| WDR1 | 4.24E−03 | 5.07E−03 | CC'DC166 | 6.68E−03 | 5.83E−03 | CELF3 | 6.34E−03 | 5.66E−03 |
| RPUSD2 | 4.26E−03 | 7.35E−04 | GOLGA7B | 6.69E−03 | 7.37E−03 | FAM129C | 6.38E−03 | 7.67E−03 |
| BOD1L1 | 4.39E−03 | 4.92E−03 | GATAD1 | 6.73E−03 | 8.39E−03 | DRC7 | 6.40E−03 | 5.35E−03 |
| ID12 | 4.56E−03 | 3.28E−03 | C3orf38 | 6.75E−03 | 6.86E−03 | MAP9 | 6.56E−03 | 2.67E−03 |
| WDR74 | 4.59E−03 | 1.58E−03 | ATP1B2 | 6.79E−03 | 6.32E−03 | VCX2 | 6.56E−03 | 5.70E−03 |
| EGLN2 | 4.66E−03 | 5.51E−03 | MED12 | 6.83E−03 | 2.72E−02 | YTHDF2 | 6.60E−03 | 6.20E−03 |
| IDI1 | 4.68E−03 | 4.16E−03 | URB2 | 6.83E−03 | 8.02E−03 | OR4M1 | 6.68E−03 | 1.16E−02 |
| MED1 | 4.73E−03 | 1.80E−03 | PCED1B | 6.88E−03 | 9.27E−03 | MACROD2 | 6.70E−03 | 4.69E−03 |
| MAGEA1 | 4.82E−03 | 7.16E−03 | MOAP1 | 6.89E−03 | 7.75E−03 | MAPK15 | 6.71E−03 | 5.51E−03 |
| KLHL35 | 4.83E−03 | 5.01E−03 | NLGN3 | 6.90E−03 | 2.77E−02 | UGGT1 | 6.72E−03 | 1.89E−02 |
| MSTN | 4.93E−03 | 3.60E−03 | HAUS5 | 6.91E−03 | 8.60E−03 | CGB5 | 6.74E−03 | 4.91E−03 |
| CLIC4 | 4.96E−03 | 9.75E−03 | OTOP1 | 6.97E−03 | 7.63E−03 | PIM3 | 6.81E−03 | 6.29E−03 |
| SLC3A2 | 4.96E−03 | 1.95E−03 | TMEM251 | 7.05E−03 | 7.71E−03 | GUCD1 | 6.87E−03 | 7.38E−03 |
| CYP7B1 | 5.25E−03 | 6.55E−03 | DARS2 | 7.08E−03 | 4.44E−03 | KANSL1 | 6.95E−03 | 7.57E−03 |
| PTGIS | 5.40E−03 | 6.26E−03 | WASF3 | 7.08E−03 | 1.10E−02 | OR4Q3 | 6.97E−03 | 1.12E−02 |
| VPS28 | 5.43E−03 | 6.67E−03 | RGPD6 | 7.13E−03 | 7.15E−03 | FAM83H | 6.99E−03 | 5.87E−03 |
| ZNF138 | 5.47E−03 | 6.10E−03 | MAPK81P3 | 7.19E−03 | 8.33E−03 | RNF103 | 7.08E−03 | 5.69E−03 |

TABLE 8-continued

Genes associated with proteinuria, hypertension, or composite toxicity (grade ≥2)

| | Proteinuria | | | Hypertension | | | Composite toxicity | |
|---|---|---|---|---|---|---|---|---|
| Gene | p-value unadjusted | p-value adjusted | Gene | p-value unadjusted | p-value adjusted | Gene | p-value unadjusted | p-value adjusted |
| RPS10 | 5.53E−03 | 4.86E−03 | UACA | 7.23E−03 | 9.30E−03 | UBXN11 | 7.16E−03 | 6.68E−03 |
| SLC30A1 | 5.61E−03 | 4:78E−03 | GRIPAP1 | 7.25E−03 | 7.16E−03 | CREB3L3 | 7.19E−03 | 9.51E−03 |
| CDC42EP1 | 5.69E−03 | 4.23E−03 | MEF2D | 7.33E−03 | 6.78E−03 | LIPJ | 7.30E−03 | 8.04E−03 |
| HSPA13 | 5.83E−03 | 7.30E−03 | CRTAC1 | 7.40E−03 | 9.06E−03 | EFHD1 | 7.34E−03 | 5.26E−03 |
| SMIM10L1 | 5.90E−03 | 4.24E−03 | OR5M1 | 7.59E−03 | 5.59E−03 | SATL1 | 7.34E−03 | 5.24E−03 |
| BANP | 6.22E−03 | 8.91E−03 | ZFP91 | 7.61E−03 | 5.47E−03 | IZUMO2 | 7.43E−03 | 7.49E−03 |
| CDK2AP1 | 6.28E−03 | 7.38E−03 | TUBGCP3 | 7.62E−03 | 9.74E−03 | CGB1 | 7.49E−03 | 5.21E−03 |
| IRF5 | 6.31E−03 | 7.71E−03 | CERS5 | 7.70E−03 | 9.45E−03 | LARP1B | 7.49E−03 | 6.48E−03 |
| NXPH3 | 6.32E−03 | 8.94E−03 | GSTP1 | 7.74E−03 | 8.33E−03 | CGB2 | 7.56E−03 | 5.27E−03 |
| SULT1C2 | 6.40E−03 | 6.67E−03 | HEY1 | 7.93E−03 | 1.00E−02 | KLF14 | 7.65E−03 | 5.81E−03 |
| BIRC7 | 6.45E−03 | 1.08E−02 | BLOC1S4 | 8.04E−03 | 7.91E−03 | CYTH2 | 7.67E−03 | 7.05E−03 |
| KPNA3 | 6.51E−03 | 172E−03 | CLIC6 | 8.06E−03 | 7.77E−03 | MAP3K7 | 7.68E−03 | 8.11E−03 |
| FGER1OP | 6.57E−03 | 1.86E−03 | RGL4 | 8.22E−03 | 1.89E−02 | TTLL10 | 7.71E−03 | 6.72E−03 |
| PASD1 | 6.58E−03 | 7.01E−03 | WFIKKN2 | 8.30E−03 | 6.80E−03 | ZNF707 | 7.71E−03 | 6.07E−03 |
| ABCB10 | 6.64E−03 | 5.38E−03 | HSD3B1 | 8.45E−03 | 9.51E−03 | PPP2R1A | 7.73E−03 | 5.78E−03 |
| NKAIN4 | 6.65E−03 | 1.10E−02 | SPAG4 | 8.49E−03 | 7.10E−03 | HSPA13 | 7.77E−03 | 8.48E−03 |
| DSG4 | 6.81E−03 | 9.69E−03 | 11-Sep | 8.62E−03 | 9.72E−03 | NBPF4 | 7.77E−03 | 7.72E−03 |
| NKX3-2 | 6.82E−03 | 4.65E−03 | SST | 8.64E−03 | 1.15E−02 | PAIP2 | 7.86E−03 | 8.55E−03 |
| AA4HR2 | 6.86E−03 | 4.81E−03 | UPK1A | 8.86E−03 | 8.32E−03 | SCAND1 | 7.91E−03 | 8.12E−03 |
| PRR13 | 6.90E−03 | 5.07E−03 | ADAMTS20 | 8.93E−03 | 8.28E−03 | DHRS7 | 7.99E−03 | 7.25E−03 |
| OGT | 6.93E−03 | 7.99E−03 | CXCL3 | 8.94E−03 | 9.32E−03 | NCL | 8.02E−03 | 7.61E−03 |
| MROH9 | 6.95E−03 | 9.50E−03 | C17orf67 | 8.98E−03 | 1.07E−02 | KRT25 | 8.05E−03 | 8.57E−03 |
| A1CF | 7.00E−03 | 6.01E−03 | WDR87 | 8.99E−03 | 9.91E−03 | GPR63 | 8.08E−03 | 8.11E−03 |
| MAPT | 7.12E−03 | 7.20E−03 | TOB1 | 9.37E−03 | 5.88E−03 | ALPK2 | 8.21E−03 | 7.95E−03 |
| MFHAS1 | 7.12E−03 | 1.86E−02 | BCAR1 | 9.47E−03 | 7.97E−03 | CABP5 | 8.23E−03 | 9.68E−03 |
| TAF1 | 7.13E−03 | 8.69E−03 | CPNE4 | 9.48E−03 | 1.34E−02 | HES7 | 8.23E−03 | 9.19E−03 |
| ATG101 | 7.28E−03 | 6.35E−03 | MGARP | 9.55E−03 | 1.06E−02 | DEFB112 | 8.24E−03 | 9.00E−03 |
| TOP3A | 7.37E−03 | 4.99E−03 | TERT | 9.55E−03 | 6.65E−03 | PCGF6 | 8.26E−03 | 7.65E−03 |
| EFHB | 7.44E−03 | 6.63E−03 | FMOD | 9.67E−03 | 5.49E−03 | ORC1 | 8.32E−03 | 7.96E−03 |
| NR1H3 | 7.46E−03 | 5.63E−03 | LYPD3 | 9.68E−03 | 9.51E−03 | CD300LG | 8.52E−03 | 8.06E−03 |
| PET117 | 7.52E−03 | 7.36E−03 | SUCLA2 | 9.71E−03 | 8.49E−03 | NEFL | 8.60E−03 | 7.96E−03 |
| PPIG | 7.57E−03 | 1.95E−02 | TNMD | 9.72E−03 | 9.27E−03 | HNRNPD | 8.61E−03 | 8.20E−03 |
| DAZ4P2 | 7.66E−03 | 4.69E−03 | NREP | 9.86E−03 | 8.78E−03 | STAG2 | 8.64E−03 | 7.66E−03 |
| PPP1R14D | 7.78E−03 | 3.53E−03 | FBXO3 | 9.91E−03 | 6.76E−03 | FBRS | 8.82E−03 | 8.84E−03 |
| ZFYVE19 | 7.85E−03 | 3.07E−03 | STON1 | 9.97E−03 | 9.49E−03 | CC2D2A | 8.88E−03 | 7.08E−03 |
| SNTG1 | 7.89E−03 | 8.43E−03 | HTRA3 | 9.99E−03 | 1.03E−02 | CCDC166 | 8.94E−03 | 7.44E−03 |
| PRPS1 | 7.94E−03 | 8.51E−03 | | | | CFAP69 | 8.98E−03 | 8.17E−03 |
| SLC36A4 | 7.95E−03 | 5.05E−03 | | | | TFB1M | 9.12E−03 | 1.16E−02 |
| SMAGP | 8.02E−03 | 4.61E−03 | | | | C14orf177 | 9.17E−03 | 8.13E−03 |
| CD300LG | 8.10E−03 | 7.00E−03 | | | | IQCA1 | 9.17E−03 | 8.03E−03 |
| CTXN2 | 8.11E−03 | 1.02E−02 | | | | MROH8 | 9.20E−03 | 8.00E−03 |
| ZSWIM16 | 8.17E−03 | 1.52E−03 | | | | AUTS2 | 9.21E−03 | 7.21E−03 |
| KRTAP10-12 | 8.24E−03 | 1.05E−02 | | | | SMG1 | 9.26E−03 | 1.06E−02 |
| PRRG3 | 8.26E−03 | 7.78E−03 | | | | NSUN3 | 9.32E−03 | 9.80E−03 |
| DEPDC4 | 8.30E−03 | 6.83E−03 | | | | SSBP3 | 9.38E−03 | 1.02E−02 |
| CTHRC1 | 8.34E−03 | 1.36E−02 | | | | ING3 | 9.47E−03 | 1.18E−02 |
| C19orf18 | 8.39E−03 | 7.28E−03 | | | | SND1 | 9.50E−03 | 7.05E−03 |
| KRTAP12-1 | 8.42E−03 | 1.04E−02 | | | | KPNA3 | 9.51E−03 | 5.29E−03 |
| SOCS4 | 8.44E−03 | 5.01E−03 | | | | NCALD | 9.55E−03 | 1.10E−02 |
| PLSCR5 | 8.48E−03 | 1.18E−02 | | | | TERT | 9.55E−03 | 7.97E−03 |
| AVP | 8.58E−03 | 5.39E−03 | | | | KLF3 | 9.56E−03 | 1.09E−02 |
| NR2E1 | 8.69E−03 | 2.43E−02 | | | | UBN2 | 9.74E−03 | 9.79E−03 |
| C4orf36 | 8.79E−03 | 7.50E−03 | | | | ZFP37 | 9.76E−03 | 6.02E−03 |
| GNGT1 | 8.83E−03 | 1.04E−01 | | | | GPI | 9.80E−03 | 1.03E−02 |
| MANSC1 | 8.83E−03 | 1.10E−02 | | | | ODF1 | 9.84E−03 | 8.11E−03 |
| YTHDF1 | 8.91E−03 | 1.08E−02 | | | | HIST2H2BF | 9.98E−03 | 9.42E−03 |
| MUC5AC | 9.02E−03 | 2.03E−02 | | | | | | |
| GTPBP4 | 9.10E−03 | 6.79E−03 | | | | | | |
| SEMA5B | 9.11E−03 | 6.34E−03 | | | | | | |
| ZNF410 | 9.13E−03 | 1.16E−02 | | | | | | |
| MADD | 9.28E−03 | 6.45E−03 | | | | | | |
| ETNPPL | 9.30E−03 | 5.88E−03 | | | | | | |
| ATP1A1 | 9.31E−03 | 2.53E−02 | | | | | | |
| FREM3 | 9.35E−03 | 6.61E−03 | | | | | | |
| SLC22A2 | 9.40E−03 | 1.04E−02 | | | | | | |
| SLC25A26 | 9.41E−03 | 2.16E−02 | | | | | | |
| KRTAP12-2 | 9.42E−03 | 1.21E−02 | | | | | | |
| FBN1 | 9.43E−03 | 1.05E−02 | | | | | | |
| OXT | 9.44E−03 | 6.54E−03 | | | | | | |
| 7RAF5 | 9.48E−03 | 3.38E−03 | | | | | | |
| GDPD5 | 9.52E−03 | 1.07E−02 | | | | | | |
| B1N2 | 9.58E−03 | 5.65E−03 | | | | | | |
| C9orf47 | 9.64E−03 | 6.01E−03 | | | | | | |

TABLE 8-continued

Genes associated with proteinuria, hypertension, or composite toxicity (grade ≥2)

| | Proteinuria | | | Hypertension | | | Composite toxicity | |
|---|---|---|---|---|---|---|---|---|
| Gene | p-value unadjusted | p-value adjusted | Gene | p-value unadjusted | p-value adjusted | Gene | p-value unadjusted | p-value adjusted |
| PTCHD4 | 9.71E−03 | 1.31E−02 | | | | | | |
| SNCA1P | 9.79E−03 | 3.00E−02 | | | | | | |

The ten most statistically significant genes are shown in Table 9. C1D ($p=2.00 \times 10^{-8}$) was the most significant, followed by IL17F ($p=1.80 \times 10^{-7}$).

TABLE 9

Ten most statistically significant genes, according to unadjusted p values, associated with proteinuria, hypertension, and composite toxicity from the gene-based association analysis grade ≥ 2. Composite toxicity is defined as the occurrence of either proteinuria or hypertension or both.

| Proteinuria | | Hypertension | | Composite toxicity | |
|---|---|---|---|---|---|
| Gene | p-value | Gene | p-value | Gene | p-value |
| C1D | $2.00 \times 10^{-8}$ | UNC50 | $2.30 \times 10^{-5}$ | SLC25A24 | $4.00 \times 10^{-6}$ |
| IL17F | $1.80 \times 10^{-7}$ | KATNB1 | $2.50 \times 10^{-5}$ | SMS | $5.00 \times 10^{-6}$ |
| MCM3 | $5.10 \times 10^{-7}$ | MGAT4A | $4.60 \times 10^{-5}$ | CEP295 | $1.00 \times 10^{-5}$ |
| SMPX | $1.20 \times 10^{-5}$ | FBXO9 | $5.10 \times 10^{-5}$ | YWHAE | $1.60 \times 10^{-5}$ |
| KLHL34 | $1.26 \times 10^{-5}$ | STRIP1 | $9.80 \times 10^{-5}$ | PTPN3 | $4.00 \times 10^{-5}$ |
| EAPP | $2.70 \times 10^{-5}$ | CCDC54 | $1.01 \times 10^{-4}$ | KLHL35 | $4.50 \times 10^{-5}$ |
| CNKSR2 | $3.50 \times 10^{-5}$ | COA5 | $1.06 \times 10^{-4}$ | H6PD | $5.10 \times 10^{-5}$ |
| LIPJ | $4.80 \times 10^{-5}$ | KIFC3 | $1.18 \times 10^{-4}$ | MBTPS2 | $7.50 \times 10^{-5}$ |
| ITGB6 | $5.00 \times 10^{-5}$ | ICK | $1.21 \times 10^{-4}$ | CRK | $1.37 \times 10^{-4}$ |
| XCR1 | $5.70 \times 10^{-5}$ | AHCYL1 | $1.45 \times 10^{-4}$ | SLC17A6 | $1.50 \times 10^{-4}$ |

Variants and Genes Associated with Bevacizumab-Induced Hypertension

For the SNP-based analysis of grade ≥2 hypertension, the Manhattan and Q-Q plots are shown in FIG. 2. 104 variants associated with hypertension were identified (Table 10).

TABLE 10

SNPs associated with hypertension (grade ≥2).

| SNP | CH | BP | effect allele | reference allele | MAF 80303 | MAF 40503 | MAF 90401 | MAF 40502 | gene | feature | Flanking gene | Flanking gene | p-value unadjusted | effect (β) unadjusted | p-value adjusted | effect (β) adjusted |
|---|---|---|---|---|---|---|---|---|---|---|---|---|---|---|---|---|
| rs3393027 | 6 | 70727823 | G | A | 0.09 | | | | COL19A1 | intron | LMBRD1 | COL9A1 | 1.21E-06 | 1.87 | 4.12E-06 | 2.00 |
| rs13135230 | 4 | 24605796 | A | G | 0.27 | 0.28 | 0.25 | 0.28 | NA | NA | CCDC149 | LGI2 | 1.26E-06 | 0.46 | 1.36E-06 | 0.47 |
| rs2350620 | 8 | 62660161 | G | A | 0.32 | 0.26 | 0.32 | 0.32 | ASPH | intron | hCG_1988300 | LOC645551 | 1.44E-06 | -0.49 | 1.23E-06 | -0.50 |
| rs7204266 | 19 | 8760046 | G | A | 0.28 | | 0.28 | | GRIN2A | intron | LOC653737 | LOC727844 | 3.61E-06 | 0.76 | 2.58E-06 | 0.79 |
| rs6770663 | 3 | 157514872 | G | A | 0.09 | 0.09 | 0.08 | 0.09 | KCNAB1 | intron | LOC751837 | SSR3 | 4.79E-06 | 0.57 | 4.16E-06 | 0.58 |
| rs1145786 | 6 | 91678597 | G | A | 0.33 | 0.32 | 0.34 | 0.33 | NA | NA | MAP3K7 | LOC100129847 | 5.10E-06 | 0.39 | 7.18E-06 | 0.39 |
| rs7038808 | 9 | 91931116 | A | G | 0.13 | | 0.15 | | NA | NA | IL6RL1 | OR7E31P | 5.20E-06 | 0.91 | 9.36E-06 | 0.90 |
| rs11036390 | 11 | 41387322 | C | A | | 0.27 | | 0.31 | LRRC4C | NA | LRRC4C | LOC100131020 | 5.23E-06 | 0.46 | 5.57E-06 | 0.47 |
| rs10905087 | 10 | 70822760 | A | G | | 0.25 | | 0.23 | LOC439949 | NA | LOC439949 | SFMBT2 | 6.01E-06 | -0.64 | 5.30E-06 | -0.65 |
| rs12316952 | 12 | 46238282 | G | A | 0.06 | | 0.08 | | LOC100127978 | NA | LOC100127978 | RPAP3 | 6.17E-06 | 1.14 | 8.30E-06 | 1.14 |
| rs17097718 | 14 | 98252288 | T | C | | 0.06 | | | LOC100132612 | missense | LOC100127978 | RPL3P4 | 8.56E-06 | 1.48 | 8.45E-06 | -0.54 |
| rs757354 | 12 | 46233818 | C | A | 0.06 | | 0.08 | | C14orf177 | NA | LOC100127978 | RPAP3 | 1.11E-05 | 1.11 | 1.42E-05 | 1.11 |
| rs7553399 | 1 | 3406309 | A | C | | 0.25 | | | NA | missense | ARHGEF16 | TPRG1L | 1.14E-05 | 1.06 | 1.34E-05 | 1.06 |
| rs7130734 | 11 | 41385931 | A | C | 0.35 | 0.30 | | 0.33 | MEGF6 | NA | LRRC4C | LOC100131020 | 1.17E-05 | 0.42 | 8.77E-06 | 0.43 |
| rs13176984 | 5 | 151653739 | C | T | | 0.11 | | 0.18 | NA | NA | GLRA1 | NMLIR2 | 1.20E-05 | 0.55 | 6.10E-06 | 0.57 |
| rs1714367 | 3 | 76714180 | A | G | 0.14 | | 0.17 | | NAALADL2 | intron | LOC647212 | LOC100128870 | 1.40E-05 | 0.83 | 1.49E-05 | 0.82 |
| rs2179121 | 20 | 40502874 | A | G | 0.13 | 0.15 | 0.14 | 0.13 | PTPRT | intron | LOC643172 | PPIAL | 1.99E-05 | 0.49 | 3.00E-05 | 0.48 |
| rs16986558 | 20 | 40207824 | A | G | 0.06 | | 0.06 | | PTPRT | intron | LOC643172 | PPIAL | 2.18E-05 | 0.93 | 1.02E-05 | 0.99 |
| rs10519829 | 5 | 25045325 | A | G | 0.44 | 0.46 | 0.47 | 0.47 | PLA2G4E | intron | LOC644659 | PLA2G4D | 2.28E-05 | 0.36 | 1.84E-05 | 0.37 |
| rs4697273 | 4 | 21844894 | G | A | 0.23 | 0.19 | 0.18 | 0.17 | PITPNC1 | NA | EHD4 | GPR125 | 2.59E-05 | 0.43 | 2.28E-05 | 0.44 |
| rs2949929 | 17 | 62943076 | T | C | | 0.28 | | 0.20 | NA | NA | KCNIP4 | NOL11 | 2.60E-05 | 0.50 | 3.76E-05 | 0.49 |
| rs1564470 | 8 | 13629011 | A | C | | 0.27 | | 0.25 | NA | NA | LOC729822 | LOC286094 | 2.98E-05 | 0.48 | 3.75E-05 | 0.48 |
| rs7201930 | 19 | 8661566 | G | A | 0.30 | | 0.32 | | GRIN2A | intron | LOC653737 | LOC727844 | 3.10E-05 | 0.74 | 2.70E-05 | 0.75 |
| rs2125944 | 4 | 42421675 | A | G | 0.29 | 0.36 | 0.33 | 0.32 | NA | intron | ATP8A1 | GRXCR1 | 3.15E-05 | 0.72 | 2.35E-05 | 0.74 |
| rs10828545 | 10 | 18669609 | A | G | 0.08 | 0.43 | 0.10 | 0.48 | CACNB2 | intron | SLC39A12 | NSUN6 | 3.19E-05 | 0.86 | 5.09E-05 | 0.84 |
| rs4688081 | 3 | 19398144 | G | A | | 0.34 | | 0.37 | NA | NA | LOC728873 | IGSF11 | 3.21E-05 | -0.47 | 1.79E-05 | -0.49 |
| rs9921541 | 16 | 9899263 | A | G | | 0.41 | | 0.40 | GRIN2A | intron | LOC653737 | LOC727844 | 3.38E-05 | -0.44 | 4.05E-05 | -0.44 |
| rs4899947 | 14 | 0.88769467 | C | T | | | 0.24 | | KCNK10 | intron | KCNK10 | SPATA7 | 3.38E-05 | 0.71 | 3.17E-05 | 0.72 |
| rs2000611 | 14 | 87837079 | G | A | 0.23 | 0.36 | 0.50 | 0.32 | KCNK10 | intron | KCNK10 | SPATA7 | 3.48E-05 | 0.44 | 1.75E-05 | 0.45 |
| rs11732343 | 4 | 89722914 | C | G | 0.44 | 0.43 | | 0.48 | NA | intron | LOC100129137 | HERC3 | 3.49E-05 | -0.37 | 2.25E-05 | -0.38 |
| rs4611262 | 12 | 1026889 | A | G | 0.08 | 0.25 | 0.23 | 0.23 | NUP37 | NA | CCDC53 | C12orf48 | 3.62E-05 | 1.70 | 2.22E-05 | 1.78 |
| rs9512328 | 13 | 26149803 | A | G | 0.20 | 0.09 | 0.09 | 0.08 | WASF3 | intron | LOC646527 | GPR12 | 3.74E-05 | 0.39 | 1.59E-05 | 0.40 |
| rs996784 | 3 | 64707301 | T | G | 0.06 | | | 0.27 | NA | NA | LOC647107 | LOC730129 | 3.84E-05 | 0.54 | 8.30E-05 | 0.52 |
| rs13161952 | 5 | 25046494 | G | A | | 0.23 | | 0.21 | NA | NA | LOC644659 | LOC100130551 | 3.86E-05 | 0.45 | 5.91E-05 | 0.44 |
| rs1517527 | 20 | 6252547 | G | A | 0.41 | 0.30 | 0.42 | | DSCAM | intron | PARD3B | NRP2 | 3.96E-05 | 0.45 | 2.11E-05 | 0.46 |
| rs760122 | 21 | 40701616 | A | G | 0.23 | | 0.26 | | SYNPR | intron | PCP4 | BACE2 | 4.11E-05 | 0.69 | 7.39E-05 | 0.68 |
| rs11713383 | 3 | 6352390 | A | G | 0.38 | 0.36 | 0.35 | | GRIN2A | intron | LOC100129031 | S100A1L | 4.15E-05 | 0.69 | 7.05E-05 | 0.69 |
| rs9933832 | 16 | 9856135 | G | A | 0.29 | 0.43 | 0.32 | | NA | intron | LOC653737 | LOC727844 | 4.17E-05 | 0.71 | 7.36E-05 | 0.71 |
| rs1350117 | 4 | 34666752 | G | A | 0.40 | 0.33 | 0.38 | | NA | intron | LOC100131879 | LOC100132690 | 4.19E-05 | 0.70 | 3.09E-05 | 0.73 |
| rs2220706 | 9 | 04673784 | G | A | 0.05 | | 0.06 | 0.07 | NA | NA | FLJ32810 | CYLC2 | 4.32E-05 | -0.39 | 3.35E-05 | -0.40 |
| rs17648695 | 11 | 00363635 | C | T | | | | 0.11 | LOC100129602 | utr-3 | LOC100129602 | PGR | 4.40E-05 | 0.65 | 6.89E-05 | 0.64 |
| rs17654410 | 11 | 00369356 | T | C | | 0.14 | | 0.11 | TMEM133 | intron | LOC729184 | TMEM133 | 4.41E-05 | 0.54 | 3.70E-05 | 0.55 |
| rs2456761 | 10 | 62200548 | A | C | 0.35 | 0.14 | 0.34 | | NA | NA | EXOC2 | CDC2 | 4.57E-05 | 0.74 | 3.70E-05 | 0.55 |
| rs7738087 | 6 | 939790 | G | A | 0.42 | 0.40 | 0.37 | 0.37 | NA | NA | EXOC2 | FOXQ1 | 4.67E-05 | 0.36 | 6.59E-05 | 0.36 |

TABLE 10-continued

SNPs associated with hypertension (grade ≥2).

| SNP | CH | BP | effect allele | reference allele | MAF 80303 | MAF 40503 | MAF 90401 | MAF 40502 | gene | feature | Flanking gene | Flanking gene | p-value unadjusted | effect (β) unadjusted | p-value adjusted | effect (β) adjusted |
|---|---|---|---|---|---|---|---|---|---|---|---|---|---|---|---|---|
| rs17787479 | 8 | 140579876 | A | C | 0.21 | 0.26 | 0.20 | 0.20 | NA | NA | COL22A1 | KCNK9 | 4.68E-05 | 0.40 | 5.88E-05 | 0.40 |
| rs7618831 | 3 | 63531349 | A | G | 0.38 | . | 0.36 | . | SYNPR | intron | LOC100129031 | S100A1L | 4.69E-05 | 0.71 | 8.08E-05 | 0.70 |
| rs873766 | 2 | 106042957 | C | T | . | 0.12 | . | 0.10 | NA | NA | LOC100132455 | C2orf40 | 4.71E-05 | 0.57 | 5.40E-05 | 0.57 |
| rs2886725 | 5 | 37770836 | A | G | . | 0.14 | . | . | NA | NA | WDR70 | GDNF | 4.80E-05 | 1.02 | 6.25E-05 | 1.07 |
| rs10087981 | 8 | 23282409 | A | C | . | 0.32 | . | 0.28 | LOXL2 | intron | R3HCC1 | ENTPD4 | 4.84E-05 | -0.49 | 6.10E-05 | -0.49 |
| rs6302 | 6 | 87782302 | T | C | . | 0.10 | . | 0.08 | HTR1E | reference | LOC643971 | CGA | 4.85E-05 | 0.63 | 8.23E-05 | 0.61 |
| rs365277 | 13 | 61808609 | G | A | 0.47 | 0.46 | 0.41 | 0.45 | NA | NA | LOC100133193 | LOC647259 | 4.93E-05 | -0.37 | 6.04E-05 | -0.37 |
| rs3858416 | 11 | 100230559 | T | C | . | 0.06 | . | 0.05 | FLJ32810 | intron | LOC100128386 | LOC100129602 | 4.95E-05 | 0.66 | 3.14E-05 | 0.68 |
| rs7821773 | 8 | 9748866 | G | A | 0.08 | 0.05 | 0.08 | . | NA | NA | TNKS | MSRA | 4.97E-05 | 0.78 | 2.07E-05 | 0.46 |
| rs10842185 | 12 | 23625382 | G | A | 0.10 | 0.13 | 0.10 | 0.10 | SOX5 | intron | LOC100131418 | LOC100129937 | 4.97E-05 | 0.50 | 2.92E-05 | 0.52 |
| rs6445360 | 3 | 63523420 | A | G | 0.38 | . | 0.36 | . | SYNPR | intron | LOC100129031 | S100A1L | 5.26E-05 | 0.71 | 9.10E-05 | 0.70 |
| rs2825322 | 21 | 19343047 | G | A | 0.27 | 0.34 | 0.27 | 0.26 | NA | NA | PPIAL3 | SLC6A6P | 5.51E-05 | -0.43 | 5.98E-05 | -0.43 |
| rs805772 | 20 | 5619460 | T | G | . | 0.13 | . | 0.12 | NA | NA | RP5-1022P6.2 | C20orf196 | 5.58E-05 | 0.57 | 5.50E-05 | 0.58 |
| rs1352981 | 9 | 104625739 | A | G | 0.08 | . | 0.08 | . | NA | NA | LOC100131879 | CYLC2 | 5.74E-05 | 0.85 | 6.63E-05 | 0.85 |
| rs12170867 | 22 | 30292076 | A | G | . | 0.09 | . | 0.11 | SFI1 | intron | LOC100128535 | PISD | 5.76E-05 | 0.57 | 8.56E-05 | 0.56 |
| rs2278495 | 18 | 52838811 | A | G | 0.25 | . | 0.24 | . | WDR7 | intron | LOC100130858 | FAM44C | 6.11E-05 | 0.72 | 8.93E-05 | 0.71 |
| rs2729007 | 3 | 2132357 | A | G | 0.21 | 0.26 | 0.22 | 0.22 | CNTN4 | intron | LOC727810 | LOC100130346 | 6.14E-05 | 0.40 | 8.80E-05 | 0.39 |
| rs2991492 | 13 | 78625387 | A | G | . | 0.48 | . | 0.48 | NA | NA | LOC90415 | LOC100128339 | 6.15E-05 | -0.43 | 9.05E-05 | -0.42 |
| rs2267796 | 16 | 9884214 | G | A | 0.24 | . | 0.24 | . | GRIN2A | intron | LOC653737 | LOC727844 | 6.60E-05 | 0.69 | 5.78E-05 | 0.70 |
| rs22320 | 4 | 24614069 | C | A | 0.15 | 0.18 | 0.13 | 0.15 | LGI2 | utr-3 | CCDC149 | SEPSECS | 6.67E-05 | 0.46 | 7.23E-05 | 0.47 |
| rs7659172 | 4 | 24609653 | A | G | . | 0.18 | . | 0.15 | NA | NA | CCDC149 | LGI2 | 6.83E-05 | 0.53 | 9.37E-05 | 0.53 |
| rs1171566 | 1 | 154766593 | C | T | . | 0.28 | . | 0.32 | IQGAP3 | reference | MEF2D | TTC24 | 6.84E-05 | 0.41 | 7.42E-05 | 0.41 |
| rs1370215 | 1 | 52839937 | G | A | 0.25 | . | 0.24 | . | WDR7 | intron | LOC100130858 | FAM44C | 6.99E-05 | 0.72 | 1.02E-05 | 0.70 |
| rs540509 | 7 | 17071448 | G | A | . | 0.19 | . | 0.23 | NA | NA | LOC100131425 | LOC100131512 | 7.03E-05 | 0.45 | 4.91E-05 | 0.46 |
| rs1288934 | 1 | 224894661 | A | G | 0.24 | 0.27 | 0.24 | 0.26 | ITPKB | intron | C1orf95 | PSEN2 | 7.05E-05 | -0.43 | 7.60E-05 | -0.43 |
| rs3745539 | 19 | 56219853 | G | A | 0.08 | . | 0.06 | . | KLK11 | missense | KLK10 | KLK12 | 7.08E-05 | 0.93 | 7.94E-05 | 0.92 |
| rs2860529 | 4 | 105672170 | A | G | 0.22 | 0.20 | 0.23 | 0.23 | NA | NA | LOC728847 | LOC391679 | 7.11E-05 | 0.37 | 8.67E-05 | 0.37 |
| rs2172102 | 5 | 125024395 | G | A | . | 0.28 | . | 0.19 | NA | NA | LOC644659 | LOC100130551 | 7.12E-05 | 0.44 | 5.08E-05 | 0.45 |
| rs1219508 | 10 | 123451644 | A | G | 0.22 | 0.24 | 0.23 | 0.23 | NA | NA | LOC729426 | ATE1 | 7.14E-05 | -0.46 | 1.42E-05 | 0.44 |
| rs4580675 | 4 | 80827274 | G | A | 0.43 | 0.47 | 0.44 | 0.47 | NA | NA | OR7E94P | GDEP | 7.15E-05 | -0.36 | 8.47E-05 | -0.36 |
| rs12480201 | 20 | 59812166 | A | G | 0.14 | . | 0.15 | . | CDH4 | intron | LOC100131417 | TAF4 | 7.18E-05 | 0.85 | 4.39E-05 | 0.88 |
| rs1268663 | 14 | 6435834 | A | G | 0.20 | 0.22 | 0.20 | 0.21 | SPTB | intron | LOC100129913 | CHURC1 | 7.34E-05 | 0.41 | 5.26E-05 | 0.42 |
| rs4775610 | 15 | 61119110 | A | G | . | 0.31 | . | 0.28 | TLN2 | NA | TPM1 | TPM1 | 7.37E-05 | 0.42 | 7.35E-05 | 0.42 |
| rs11133274 | 4 | 53994137 | A | G | 0.21 | 0.20 | 0.21 | 0.20 | FIP1L1 | intron | LOC100130982 | LNX1 | 7.50E-05 | 0.38 | 2.46E-05 | 0.41 |

TABLE 10-continued

SNPs associated with hypertension (grade ≥2).

| SNP | CH | BP | effect allele | reference allele | MAF 80303 | MAF 40503 | MAF 90401 | MAF 40502 | gene | feature | Flanking gene | Flanking gene | p-value unadjusted | effect (β) unadjusted | p-value adjusted | effect (β) adjusted |
|---|---|---|---|---|---|---|---|---|---|---|---|---|---|---|---|---|
| rs4813886 | 20 | 912652 | G | A | 0.11 | 0.12 | 0.12 | 0.12 | RSPO4 | intron | ANGPT4 | PSMF1 | 7.61E-05 | 0.46 | 5.87E-05 | 0.47 |
| rs4743599 | 9 | 104651778 | G | A | 0.08 | . | 0.08 | . | NA | NA | LOC100131879 | CYLC2 | 7.73E-05 | 0.84 | 9.03E-05 | 0.84 |
| rs2713289 | 4 | 134759843 | A | G | 0.48 | 0.49 | 0.49 | 0.47 | NA | NA | PCDH10 | PABPC4L | 7.89E-05 | 0.34 | 8.57E-05 | 0.34 |
| rs1884114 | 20 | 914504 | T | G | . | 0.08 | 0.27 | 0.08 | RSPO4 | intron | ANGPT4 | PSMF1 | 7.90E-05 | 0.62 | 5.11E-05 | 0.64 |
| rs338248 | 1 | 58703893 | C | A | 0.29 | 0.24 | 0.38 | 0.29 | NA | NA | DAB1 | OMA1 | 7.90E-05 | 0.37 | 8.49E-05 | 0.37 |
| rs3767867 | 1 | 210624222 | G | G | 0.35 | . | 0.42 | . | TMEM206 | intron | PPP2R5A | NENF | 7.91E-05 | -0.81 | 1.00E-04 | -0.80 |
| rs9530488 | 13 | 75370156 | A | G | 0.36 | . | . | . | NA | NA | FLJ35379 | LOC100132423 | 8.04E-05 | 0.68 | 1.49E-04 | -0.66 |
| rs11251166 | 10 | 2357939 | C | A | . | . | . | 0.28 | NA | NA | LOC728209 | LOC727878 | 8.22E-05 | 0.50 | 7.30E-04 | 0.51 |
| rs1452232 | 12 | 83750362 | C | A | 0.37 | . | . | . | NA | NA | LOC100128335 | SLC6A15 | 8.38E-05 | 0.69 | 1.03E-04 | 0.69 |
| rs7667510 | 4 | 41913903 | G | A | . | 0.15 | . | 0.15 | NA | NA | BEND4 | SHISA3 | 8.39E-05 | 0.49 | 9.27E-05 | 0.49 |
| rs2687640 | 7 | 29138781 | A | G | 0.06 | . | 0.06 | 0.05 | CPVL | intron | KIAA0644 | LOC100131724 | 8.45E-05 | 0.66 | 9.57E-05 | 0.66 |
| rs711272 | 6 | 91667454 | G | A | 0.28 | 0.27 | 0.30 | 0.27 | NA | NA | MAP3K7 | LOC100129847 | 8.72E-05 | 0.35 | 8.10E-05 | 0.36 |
| rs16924767 | 12 | 22260834 | G | A | 0.13 | . | 0.16 | . | ST8SIA1 | intron | CMAS | KIAA0528 | 8.98E-05 | 0.89 | 9.26E-05 | 0.90 |
| rs12757197 | 1 | 233657182 | A | G | 0.07 | 0.17 | 0.10 | . | TBCE | intron | GGPS1 | B3GALNT2 | 9.19E-05 | 0.83 | 4.07E-05 | 0.91 |
| rs11164023 | 1 | 84861990 | G | A | 0.20 | 0.19 | 0.19 | 0.22 | NA | NA | CTBS | C1orf180 | 9.25E-05 | 0.40 | 5.75E-05 | 0.41 |
| rs4948291 | 10 | 59770095 | T | C | . | 0.33 | . | 0.36 | UBE2D1 | intron | CISD1 | TFAM | 9.30E-05 | 0.40 | 7.00E-05 | 0.41 |
| rs17156773 | 1 | 17407630 | A | G | . | 0.07 | . | 0.09 | ADARB2 | intron | C10orf109 | LOC100129465 | 9.42E-05 | 0.63 | 8.49E-05 | 0.64 |
| rs2288502 | 5 | 156582630 | G | A | 0.07 | 0.07 | 0.06 | 0.06 | ITK | intron | FAM71B | CITIP2 | 9.45E-05 | 0.61 | 1.04E-04 | -0.61 |
| rs1362972 | 12 | 94599424 | A | C | 0.12 | . | 0.18 | . | NTN4 | intron | LOC100132594 | SNRPF | 9.47E-05 | 0.79 | 1.73E-04 | -0.78 |
| rs1480802 | 8 | 136293393 | C | A | 0.37 | . | 0.38 | . | NA | NA | ZFAT | LOC286094 | 9.54E-05 | 0.71 | 6.70E-05 | 0.73 |
| rs6681946 | 1 | 17358138 | G | A | 0.20 | . | 0.21 | . | NA | NA | PADI2 | LOC400743 | 9.59E-05 | 0.73 | 1.18E-04 | 0.72 |
| rs4735993 | 8 | 1141126 | G | A | . | 0.27 | . | 0.26 | NA | NA | LOC401442 | DLGAP2 | 9.70E-05 | 0.42 | 4.38E-05 | 0.45 |
| rs2515034 | 8 | 119565108 | G | A | 0.06 | 0.09 | . | . | SAMD12 | intron | EXT1 | LOC441377 | 9.86E-05 | 1.68 | 7.67E-05 | 1.77 |
| rs4691370 | 4 | 157809201 | G | A | 0.06 | . | . | 0.07 | NA | NA | hCG_1814936 | PDGFC | 9.91E-05 | 0.59 | 1.02E-04 | 0.60 |
| rs2077923 | 16 | 9788282 | G | A | 0.29 | . | 0.32 | . | GRIN2A | intron | LOC653737 | LOC727844 | 9.95E-05 | 0.68 | 8.64E-05 | 0.69 |

Thirty-four out of the 104 variants had the same direction of effect in at least three out of the four studies (cutoff $p<1\times10^4$). The top ten most statistically significant variants of that list in shown in Table 5. rs13135230 (G>A, MAF 0.25-0.28) was the most statistically significant ($p=1.26\times 10^{-4}$, =0.46), with the A allele increasing the risk of hypertension (FIG. 3). rs13135230 is 3.8 kb 3' from LGI2 (FIG. 4). rs2350620 (A>G, MAF 0.26-0.32) is the next most statistically significant ($p=1.44\times10^{-6}$, $\beta=0.49$) with the G allele decreasing the risk of hypertension (FIG. 13). rs2350620 is located in the intron 14 of ASPH (FIG. 4B). rs6770663 (A>G, MAF 0.08-0.09) is the next most statistically significant ($p=4.79\times10^{-6}$, $\beta=0.57$) with the G allele increasing the risk of hypertension (FIG. 13). rs6770663 is located in the intron 1 of KCNAB1 (FIG. 4C) Among these ten variants, the only two with p-value <0.05 in three out of the four studies were rs2350620 and rs6770663 (Table 5).

Figure 13:
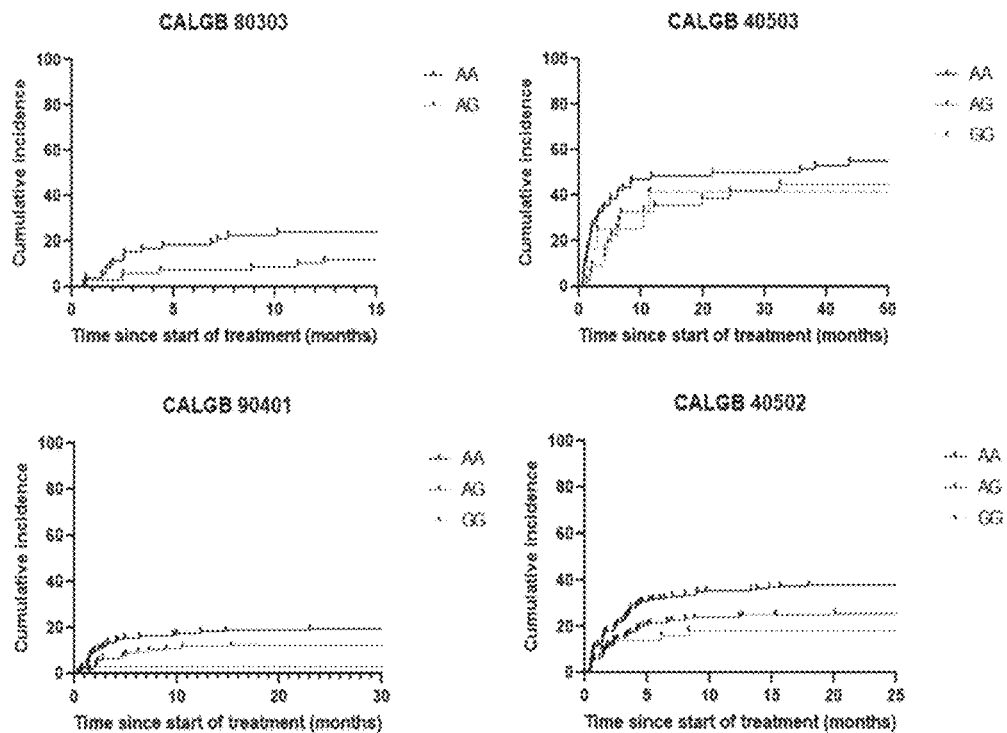
FIG. 13 shows the cumulative incidence of grade ≥2 hypertension for rs2350620 and rs6770663.
Figure 13:
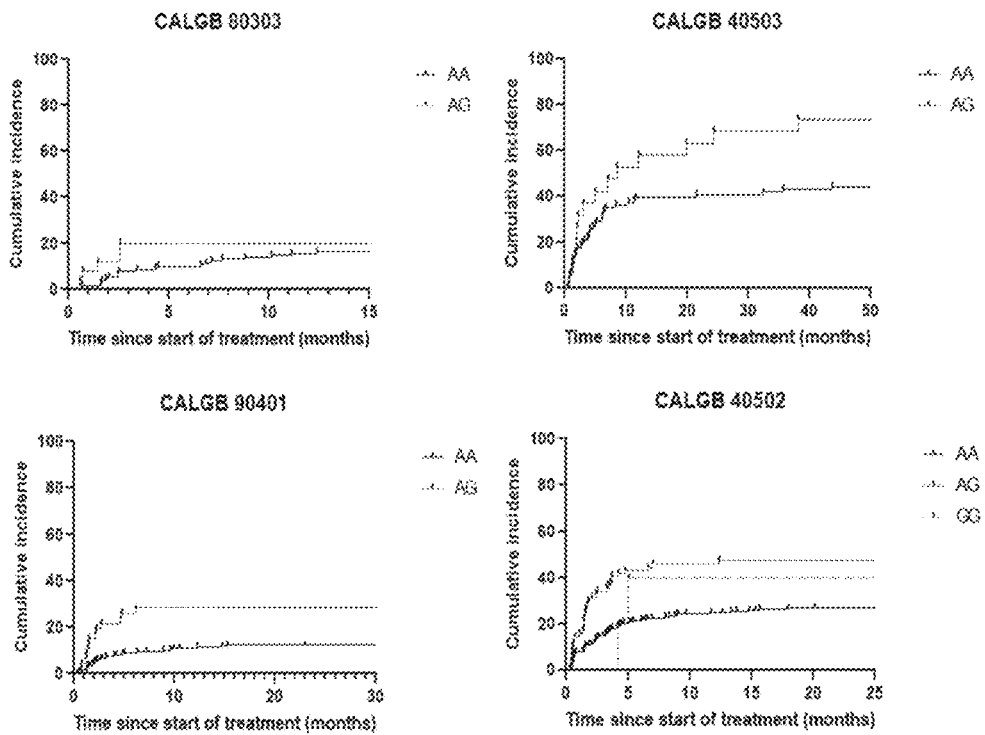

FIG. 13 shows the cumulative incidence of grade ≥2 hypertension for rs2350620 and rs6770663. For the SNP-based analysis of grade ≥3, the Manhattan and Q-Q plots are shown in FIG. 5. 106 variants were identified as associated with hypertension (Table 11).

Forty-seven out of 106 variants had the same direction of effect (either reduced or increased risk) in at least three out of the four studies (cutoff $p<1\times10^{-4}$). The top ten most statistically significant variants of that list are shown in Table 7. rs4782946 (G>A MAF 0.37-0.43) was the most statistically significant ($p=3.09\times10^{-7}$, $\beta=0.66$) with the A allele increasing the risk of hypertension. rs4782946 is an intronic variant in ATP2C2 (FIG. 6). rs17439529 (G>A, MAF 0.36-0.40) was the next most statistically significant ($p=2.08\times10{-6}$, $\beta=-0.72$) with the A allele decreasing the risk of hypertension. rs17439529 is located in the intron of AKAP6 (FIG. 6).

TABLE 11

| SNPs associated with hypertension (grade ≥3) | | | | | | | |
|---|---|---|---|---|---|---|---|
| SNP | CH | BP | effect allele | reference allele | MAF 80303 | MAF 40503 | MAF 90401 |
| rs4782946 | 16 | 82979663 | A | G | 0.37 | 0.38 | 0.37 |
| rs3858416 | 11 | 100230559 | A | G | . | 0.06 | . |
| rs6807110 | 3 | 120338347 | C | A | . | . | 0.06 |
| rs17439529 | 14 | 32253709 | A | G | 0.36 | 0.40 | 0.38 |
| rs10129969 | 14 | 77017051 | G | A | . | 0.06 | . |
| rs9933396 | 16 | 78434745 | G | A | 0.06 | . | 0.05 |
| rs1530837 | 15 | 40069082 | G | A | 0.23 | 0.19 | 0.18 |
| rs11863271 | 16 | 82980316 | A | G | 0.20 | 0.17 | 0.19 |
| rs1171065 | 13 | 35359822 | C | A | 0.19 | 0.26 | 0.19 |
| rs8010861 | 14 | 77018319 | G | A | . | 0.07 | . |
| rs670362 | 18 | 10056414 | A | G | 0.18 | 0.14 | 0.11 |
| rs17649232 | 2 | 182712983 | G | A | 0.07 | . | 0.06 |
| rs2665917 | 8 | 141032458 | A | G | 0.44 | 0.48 | 0.47 |
| rs1048147 | 14 | 77209741 | A | C | . | 0.18 | . |
| rs11624101 | 14 | 77207812 | A | G | . | 0.18 | . |
| rs176955 | 14 | 77250973 | G | A | . | 0.18 | . |
| rs10967306 | 9 | 2630805 | A | G | 0.07 | 0.07 | 0.09 |
| rs17091403 | 10 | 115923895 | A | G | 0.13 | . | 0.10 |
| rs732121 | 13 | 95897355 | G | A | 0.06 | . | 0.07 |
| rs12887282 | 14 | 77270338 | C | A | . | 0.18 | . |
| rs1320881 | 8 | 23934297 | A | G | 0.24 | 0.18 | 0.21 |
| rs10011590 | 4 | 124693385 | G | A | . | 0.16 | . |
| rs4691370 | 4 | 157809201 | G | A | 0.06 | 0.09 | . |
| rs1008988 | 14 | 77330548 | A | G | . | 0.18 | . |
| rs11852645 | 15 | 68821216 | C | A | . | 0.13 | . |
| rs4632066 | 14 | 77317035 | A | G | . | 0.18 | . |
| rs10073306 | 5 | 58097612 | A | G | 0.19 | 0.18 | 0.17 |
| rs8088993 | 18 | 10052583 | G | A | . | 0.10 | . |
| rs3821004 | 2 | 178188309 | A | G | 0.09 | 0.10 | 0.08 |
| rs2505083 | 10 | 30375128 | G | A | . | 0.40 | . |
| rs196584 | 7 | 36284221 | A | G | 0.07 | 0.13 | 0.09 |
| rs10867852 | 9 | 84353502 | A | G | 0.08 | 0.07 | 0.06 |
| rs1944142 | 11 | 130222650 | G | A | . | 0.45 | . |
| rs7765461 | 6 | 1657305 | C | A | . | 0.20 | . |
| rs17749328 | 3 | 5538371 | A | G | 0.12 | 0.15 | 0.09 |
| rs10051270 | 5 | 58106740 | A | C | 0.14 | 0.17 | 0.14 |
| rs464349 | 16 | 88183752 | A | G | 0.45 | 0.47 | 0.50 |
| rs2858536 | 22 | 48127214 | G | A | . | 0.20 | . |
| rs17078062 | 6 | 116992250 | C | A | 0.19 | 0.16 | 0.19 |
| rs7267054 | 20 | 17569201 | A | G | 0.08 | . | 0.08 |
| rs7174784 | 15 | 99119567 | G | A | . | . | 0.41 |
| rs2288502 | 5 | 156582630 | A | G | 0.07 | 0.07 | 0.06 |
| rs540509 | 7 | 17071448 | G | A | . | 0.19 | . |
| rs8084568 | 18 | 57190720 | A | G | 0.08 | 0.12 | 0.09 |
| rs4425091 | 2 | 165199471 | G | A | . | 0.26 | . |
| rs11129096 | 3 | 2330167 | A | G | . | 0.30 | 0.33 |
| rs7574859 | 2 | 29947713 | C | A | 0.11 | 0.15 | 0.17 |
| rs35969878 | 2 | 226443471 | G | A | . | 0.09 | . |
| rs2879464 | 3 | 182528567 | G | A | . | 0.45 | . |
| rs10206343 | 2 | 46019476 | G | A | 0.13 | 0.12 | 0.14 |
| rs511092 | 15 | 27520966 | G | A | 0.32 | 0.34 | 0.34 |
| rs6494889 | 15 | 68781337 | A | G | . | 0.13 | . |
| rs760628 | 22 | 27789732 | G | A | 0.22 | 0.22 | 0.24 |
| rs2267760 | 14 | 77217446 | A | G | . | 0.19 | . |

TABLE 11-continued

| | | | | | | | | |
|---|---|---|---|---|---|---|---|---|
| rs2233230 | 8 | 141012685 | G | A | 0.45 | 0.48 | 0.47 |
| rs4320922 | 11 | 104627661 | A | G | . | 0.49 | . |
| rs752280 | 2 | 174261681 | C | A | 0.13 | 0.11 | 0.14 |
| rs1990236 | 17 | 11806187 | A | G | 0.20 | 0.18 | 0.19 |
| rs13062101 | 3 | 23458540 | A | G | 0.40 | 0.40 | 0.43 |
| rs11206344 | 1 | 54625582 | C | A | . | 0.44 | . |
| rs6463224 | 7 | 1106944 | A | C | 0.19 | . | . |
| rs16954699 | 15 | 68789686 | G | A | . | 0.13 | . |
| rs2059322 | 15 | 68792114 | C | A | . | 0.13 | . |
| rs7075347 | 10 | 76203313 | A | G | 0.07 | . | 0.08 |
| rs10988111 | 9 | 130559781 | G | A | 0.45 | . | 0.46 |
| rs1364075 | 16 | 85631051 | C | A | 0.30 | 0.33 | 0.32 |
| rs11855184 | 15 | 49594756 | A | C | . | 0.14 | . |
| rs16933415 | 8 | 68660493 | G | A | . | . | . |
| rs1449047 | 11 | 104720707 | A | G | . | 0.15 | . |
| rs1514035 | 15 | 31357207 | G | A | 0.11 | 0.08 | 0.06 |
| rs9584088 | 13 | 92633700 | A | C | . | 0.20 | . |
| rs2585348 | 14 | 48194882 | A | 1 | 0.34 | 0.44 | 0.44 |
| rs17708487 | 6 | 90700670 | G | A | 0.23 | 0.22 | 0.25 |
| rs7173605 | 15 | 21400911 | G | A | . | 0.11 | . |
| rs11673509 | 19 | 5031647 | A | G | 0.09 | . | 0.08 |
| rs1078097 | 15 | 68795974 | A | G | . | 0.12 | . |
| rs406992 | 5 | 58117438 | A | 1 | 0.17 | 0.20 | 0.18 |
| rs6650294 | 13 | 102681443 | G | A | . | 0.10 | . |
| rs10852800 | 17 | 11825241 | A | G | 0.20 | 0.18 | 0.19 |
| rs6598035 | 11 | 335595 | A | G | 0.35 | 0.37 | 0.29 |
| rs6554770 | 5 | 13323090 | A | G | . | 0.17 | 0.17 |
| rs1011236 | 15 | 68818494 | A | G | . | 0.13 | . |
| rs12449769 | 17 | 11809087 | G | A | 0.21 | 0.18 | 0.19 |
| rs6778227 | 3 | 182516536 | G | A | 0.44 | 0.46 | 0.42 |
| rs2293473 | 2 | 178196274 | A | G | 0.07 | 0.08 | . |
| rs723079 | 11 | 112699658 | C | A | 0.15 | 0.12 | 0.12 |
| rs966697 | 9 | 111119949 | A | G | 0.39 | 0.37 | 0.35 |
| rs11221807 | 11 | 129067604 | G | A | . | 0.16 | . |
| rs1978368 | 2 | 205209582 | A | C | 0.09 | . | 0.08 |
| rs17365340 | 5 | 113989891 | A | C | 0.10 | 0.09 | 0.06 |
| rs16954789 | 15 | 68823323 | C | A | . | 0.13 | 0.10 |
| rs1292299 | 18 | 10055917 | G | A | 0.21 | 0.15 | 0.15 |
| rs10415904 | 19 | 9175135 | C | A | 0.14 | 0.16 | 0.18 |
| rs2386717 | 16 | 72370567 | A | C | 0.32 | . | 0.30 |
| rs7328957 | 13 | 103355842 | G | A | 0.12 | 0.11 | 0.11 |
| rs13374607 | 1 | 182693445 | G | A | 0.08 | . | 0.07 |
| rs16924767 | 12 | 22260834 | G | A | 0.13 | . | 0.16 |
| rs17543819 | 5 | 89989605 | A | G | 0.06 | . | 0.08 |
| rs17344132 | 13 | 103339702 | G | A | 0.10 | 0.11 | 0.09 |
| rs2503697 | 13 | 72567440 | A | G | . | 0.06 | . |
| rs17622455 | 5 | 90031559 | G | A | 0.06 | . | 0.08 |
| rs7717673 | 5 | 135239365 | A | G | 0.11 | 0.12 | 0.12 |
| rs4519437 | 18 | 63045205 | A | G | . | 0.10 | . |
| rs1213236 | 11 | 84849951 | A | G | 0.07 | . | . |
| rs17019472 | 2 | 36780787 | G | A | 0.13 | 0.11 | 0.14 |
| rs4506930 | 16 | 75154359 | G | A | 0.40 | . | 0.41 |

SNPs associated with hypertension (grade ≥3)

| SNP | MAF 40502 | gene | feature | Flanking gene | Flanking gene | p-value | effect (β) |
|---|---|---|---|---|---|---|---|
| rs4782946 | 0.43 | ATP2C2 | intron | WFDC1 | KIAA1609 | 3.09E−07 | 0.66 |
| rs3858416 | 0.05 | FLJ32810 | intron | LOC100128386 | LOC100129602 | 7.29E−07 | 1.06 |
| rs6807110 | . | IGSF11 | intron | LOC728873 | C3orf30 | 1.27E−06 | 1.70 |
| rs17439529 | 0.40 | AKAP6 | intron | MTCO1P2 | NPAS3 | 2.08E−06 | −0.72 |
| rs10129969 | 0.09 | THSD3 | intron | AHSA1 | SPTLC2 | 3.47E−06 | 1.04 |
| rs9933396 | . | NA | NA | LOC440389 | LOC729847 | 4.46E−06 | 1.44 |
| rs1530837 | 0.17 | PLA2G4E | intron | EHD4 | PLA2G4D | 4.87E−06 | 0.66 |
| rs11863271 | 0.22 | ATP2C2 | intron | WFDC1 | KIAA1609 | 5.23E−06 | 0.63 |
| rs1171065 | 0.21 | DCLK1 | intron | NBEA | SOHLH2 | 5.73E−06 | 0.62 |
| rs8010861 | 0.09 | THSD3 | intron | AHSA1 | SPTLC2 | 5.92E−06 | 1.01 |
| rs670362 | 0.12 | NA | NA | VAPA | APCDD1 | 6.10E−06 | 0.67 |
| rs17649232 | . | NA | NA | PPP1R1C | PDE1A | 7.08E−06 | 1.60 |
| rs2665917 | 0.47 | NIBP | intron | C8orf17 | LOC100131910 | 7.13E−06 | 0.63 |
| rs1048147 | 0.18 | ALKBH1 | utr-3 | SPTLC2 | RPL21P10 | 7.63E−06 | 0.78 |
| rs11624101 | 0.18 | ALKBH1 | near-gene-3 | SPTLC2 | ALKBH1 | 7.63E−06 | 0.78 |
| rs176955 | 0.18 | C14orf156 | intron | ALKBH1 | SNW1 | 7.63E−06 | 0.78 |
| rs10967306 | 0.08 | VLDLR | intron | FLJ35024 | KCNV2 | 8.16E−06 | 0.87 |
| rs17091403 | . | C10orf118 | utr-5 | ADRB1 | TDRD1 | 9.41E−06 | 1.17 |
| rs732121 | . | HS6ST3 | intron | UGCGL2 | HSP90AB6P | 9.44E−06 | 1.35 |
| rs12887282 | 0.18 | SNW1 | intron | C14orf156 | C14orf178 | 9.68E−06 | 0.77 |
| rs1320881 | 0.24 | NA | NA | LOC100132107 | ADAM28 | 9.86E−06 | 0.61 |
| rs10011590 | 0.17 | NA | NA | SPRY1 | LOC644624 | 1.00E−05 | 0.77 |
| rs4691370 | 0.07 | NA | NA | hCG_1814936 | PDGFC | 1.00E−05 | 0.82 |

TABLE 11-continued

| | | | | | | | |
|---|---|---|---|---|---|---|---|
| rs1008988 | 0.18 | NA | NA | C14orf178 | ADCK1 | 1.06E-05 | 0.77 |
| rs11852645 | 0.09 | UACA | intron | TLE3 | LOC729611 | 1.08E-05 | 0.93 |
| rs4632066 | 0.18 | NA | NA | C14orf178 | ADCK1 | 1.09E-05 | 0.77 |
| rs10073306 | 0.16 | RAB3C | intron | GAPT | PDE4D | 1.12E-05 | 0.64 |
| rs8088993 | 0.10 | NA | NA | VAPA | APCDD1 | 1.26E-05 | 0.84 |
| rs3821004 | 0.08 | TTC30A | utr-3 | TTC30B | PDE11A | 1.31E-05 | 0.83 |
| rs2505083 | . | KIAA1462 | intron | SVIL | LOC729663 | 1.33E-05 | 1.27 |
| rs196584 | 0.07 | EEPD1 | intron | LOC100131181 | KIAA0895 | 1.37E-05 | 0.75 |
| rs10867852 | 0.06 | NA | NA | LOC442427 | RASEF | 1.54E-05 | 1.01 |
| rs1944142 | 0.49 | NA | NA | C11orf44 | SNX19 | 1.54E-05 | 0.72 |
| rs7765461 | 0.15 | GMDS | intron | FLJ46552 | LOC100128372 | 1.68E-05 | 0.78 |
| rs17749328 | 0.12 | NA | NA | MRPS35P1 | MRPS36P1 | 1.72E-05 | 0.70 |
| rs10051270 | 0.13 | RAB3C | intron | GAPT | PDE4D | 1.76E-05 | 0.67 |
| rs464349 | 0.48 | CPNE7 | intron | RPL13 | DPEP1 | 1.86E-05 | 0.58 |
| rs2858536 | 0.19 | NA | NA | LOC643653 | FLJ44385 | 2.04E-05 | 0.75 |
| rs17078062 | 0.19 | NA | NA | FAM26D | RWDD1 | 2.09E-05 | 0.64 |
| rs7267054 | . | RRBP1 | intron | DSTN | BANF2 | 2.10E-05 | 1.30 |
| rs7174784 | . | NA | NA | ASB7 | LOC440313 | 2.27E-05 | 1.42 |
| rs2288502 | 0.06 | ITK | intron | FAM71B | CYFIP2 | 2.47E-05 | 0.89 |
| rs540509 | 0.23 | NA | NA | LOC100131425 | LOC100131512 | 2.64E-05 | 0.73 |
| rs8084568 | 0.09 | NA | NA | hCG_1659830 | LOC100129867 | 2.66E-05 | 0.77 |
| rs4425091 | 0.29 | NA | NA | GRB14 | COBLL1 | 2.77E-05 | 0.70 |
| rs11129096 | 0.34 | CNTN4 | intron | LOC727810 | LOC100130346 | 2.99E-05 | -0.75 |
| rs7574859 | 0.21 | ALK | intron | CLIP4 | YPEL5 | 3.06E-05 | 0.60 |
| rs35969878 | 0.11 | NA | NA | KIAA1486 | LOC646736 | 3.13E-05 | 0.88 |
| rs2879464 | 0.42 | NA | NA | DNAJC19 | SOX2OT | 3.21E-05 | 0.68 |
| rs10206343 | 0.12 | PRKCE | intron | SRBD1 | EPAS1 | 3.50E-05 | 0.70 |
| rs511092 | 0.35 | NA | NA | NDNL2 | LOC100130736 | 3.54E-05 | 0.55 |
| rs6494889 | 0.09 | UACA | intron | TLE3 | LOC729611 | 3.68E-05 | 0.89 |
| rs760628 | . | NA | NA | C22orf31 | KREMEN1 | 3.71E-05 | 0.73 |
| rs2267760 | 0.20 | ALKBH1 | intron | SPTLC2 | RPL21P10 | 3.76E-05 | 0.69 |
| rs2233230 | 0.48 | NIBP | intron | KCNK9 | LOC100131910 | 3.78E-05 | 0.58 |
| rs4320922 | 0.46 | NA | NA | OR2AL1P | GRIA4 | 3.85E-05 | -0.72 |
| rs752280 | 0.11 | NA | NA | LOC100129456 | LOC644056 | 4.04E-05 | 0.73 |
| rs1990236 | 0.18 | DNAH9 | missense | FLJ45455 | ZNF18 | 4.11E-05 | 0.59 |
| rs13062101 | 0.45 | UBE2E2 | intron | LOC100130785 | UBE2E1 | 4.17E-05 | 0.53 |
| rs11206344 | . | SSBP3 | intron | C1orf191 | LOC645436 | 4.18E-05 | -1.19 |
| rs6463224 | 0.21 | C7orf50 | intron | GPER | ZFAND2A | 4.18E-05 | 0.75 |
| rs16954699 | 0.09 | UACA | intron | TLE3 | LOC729611 | 4.32E-05 | 0.88 |
| rs2059322 | 0.09 | UACA | intron | TLE3 | LOC729611 | 4.32E-05 | 0.88 |
| rs7075347 | . | NA | NA | LOC645646 | MYST4 | 4.36E-05 | 1.10 |
| rs10988111 | . | ZER1 | intron | ZDHHC12 | TBC1D13 | 4.39E-05 | -1.09 |
| rs1364075 | 0.34 | NA | NA | LOC729979 | LOC730018 | 4.39E-05 | 0.52 |
| rs11855184 | 0.15 | DMXL2 | intron | GLDN | SCG3 | 4.48E-05 | 0.76 |
| rs16933415 | 0.11 | CPA6 | intron | LOC100132812 | PREX2 | 4.50E-05 | 1.02 |
| rs1449041 | 0.16 | NA | NA | OR2AL1P | GRIA4 | 4.52E-05 | 0.79 |
| rs1514035 | 0.08 | NA | NA | FMN1 | RYR3 | 4.64E-05 | 0.81 |
| rs9584088 | 0.20 | NA | NA | GPC5 | GPC6 | 4.88E-05 | 0.71 |
| rs2585348 | 0.41 | NA | NA | RPL18P1 | ATP5GP2 | 4.92E-05 | 0.54 |
| rs17708487 | 0.22 | BACH2 | intron | GJA10 | LOC100129711 | 5.03E-05 | 0.56 |
| rs7173605 | 0.13 | NA | NA | MKRN3 | MAGEL2 | 5.15E-05 | 0.83 |
| rs11673509 | . | JMJD2B | intron | UHRF1 | LOC100128439 | 5.26E-05 | 1.12 |
| rs1078097 | 0.09 | UACA | intron | TLE3 | LOC729611 | 5.32E-05 | 0.87 |
| rs406992 | 0.17 | RAB3C | intron | GAPT | PDE4D | 5.54E-05 | 0.61 |
| rs6650294 | 0.10 | NA | NA | SLC10A2 | LOC728183 | 6.04E-05 | 0.79 |
| rs10852800 | 0.18 | ZNF18 | intron | DNAH9 | MAP2K4 | 6.18E-05 | 0.58 |
| rs6598035 | 0.31 | NA | NA | IFITM3 | B4GALNT4 | 6.23E-05 | -0.62 |
| rs6554770 | 0.14 | NA | NA | CTNND2 | LOC391738 | 6.28E-05 | 0.66 |
| rs1011236 | 0.09 | UACA | intron | TLE3 | LOC729611 | 6.30E-05 | 0.88 |
| rs12449769 | 0.19 | DNAH9 | intron | FLJ45455 | ZNF18 | 6.34E-05 | 0.56 |
| rs6778227 | 0.43 | NA | NA | DNAJC19 | SOX2OT | 6.36E-05 | 0.53 |
| rs2293473 | 0.06 | PDE11A | utr-3 | TTC30A | LOC100131480 | 6.59E-05 | 0.87 |
| rs723079 | 0.11 | TTC12 | intron | NCAM1 | ANKK1 | 6.62E-05 | 0.62 |
| rs966697 | 0.36 | EPB41L4B | intron | C9orf4 | PTPN3 | 6.69E-05 | -0.60 |
| rs11221807 | 0.16 | NA | NA | BARX2 | LOC729717 | 6.74E-05 | 0.74 |
| rs1978368 | . | PARD39 | intron | LOC100132669 | NRP2 | 6.78E-05 | 1.12 |
| rs17365340 | 0.09 | NA | NA | KCNN2 | TRIM36 | 6.84E-05 | 0.76 |
| rs16954789 | 0.09 | UACA | intron | TLE3 | LOC729611 | 6.91E-05 | 0.83 |
| rs1292299 | 0.15 | NA | NA | VAPA | APCDD1 | 6.99E-05 | 0.57 |
| rs10415904 | 0.15 | NA | NA | OR7E16P | OR7E25P | 7.00E-05 | 0.59 |
| rs2386717 | . | NA | NA | C16orf47 | LOC441506 | 7.03E-05 | 0.89 |
| rs7328957 | 0.13 | NA | NA | LOC728183 | DAOA | 7.27E-05 | 0.69 |
| rs13374607 | 0.07 | C1orf21 | intron | TSEN15 | LOC100129573 | 7.57E-05 | 0.93 |
| rs16924767 | . | ST8SIA1 | intron | CMAS | KIAA0528 | 7.58E-05 | 1.17 |
| rs17543819 | . | GPR98 | synonymous | LYSMD3 | LOC729040 | 7.77E-05 | 1.12 |
| rs17344132 | 0.11 | NA | NA | LOC728183 | DAOA | 7.85E-05 | 0.67 |
| rs2503697 | 0.06 | NA | NA | KLF5 | FABP5L1 | 8.96E-05 | 0.90 |
| rs17622455 | . | GPR98 | intron | LYSMD3 | LOC729040 | 9.33E-05 | 1.11 |
| rs7717673 | 0.11 | NA | NA | LOC153328 | IL9 | 9.37E-05 | 0.68 |
| rs4519437 | 0.08 | NA | NA | CDH19 | DSEL | 9.42E-05 | 0.83 |

TABLE 11-continued

| | | | | | | | |
|---|---|---|---|---|---|---|---|
| rs1213236 | 0.07 | NA | NA | DLG2 | TMEM126B | 9.49E−05 | 0.94 |
| rs17019472 | 0.14 | VIT | intron | FEZ2 | STRN | 9.93E−05 | 0.6266 |
| rs4506930 | . | NA | NA | CNTNAP4 | LOC100128497 | 9.93E−05 | −1.0612 |

For the gene-based analysis of grade ≥2, the Q-Q plot is shown in FIG. 7. Table 9 shows the ten most statistically significant genes. UNC50 was the most statistically significant gene (p=2.30×10$^{-5}$).

Variants and Genes Associated with Bevacizumab-Induced Proteinuria and Hypertension (Composite Toxicity)

For the SNP-based analysis of grade ≥2, the Manhattan and Q-Q plots are shown in FIG. 2. 100 variants associated with composite toxicity were identified (Table 12).

TABLE 12

SNPs associated with composite toxicity (grade ≥2)

| SNP | CH | BP | effect allele | reference allele | MAF 80303 | MAF 40503 | MAF 90401 | gene |
|---|---|---|---|---|---|---|---|---|
| rs17084411 | 6 | 122692679 | A | G | . | 0.11 | . | NA |
| rs1927869 | 6 | 122627419 | T | C | . | 0.11 | . | NA |
| rs17084371 | 6 | 122612111 | G | A | . | 0.11 | . | NA |
| rs11036390 | 11 | 41387322 | C | A | . | 0.27 | . | NA |
| rs11662763 | 18 | 5847091 | A | G | 0.14 | 0.11 | 0.13 | NA |
| rs2937754 | 5 | 17308803 | G | A | . | 0.19 | . | BASP1 |
| rs8006648 | 14 | 87359052 | A | G | 0.27 | 0.28 | 0.26 | NA |
| rs2456761 | 10 | 62200548 | A | C | 0.35 | . | 0.34 | NA |
| rs1000032 | 2 | 176643771 | A | C | 0.13 | 0.18 | 0.19 | NA |
| rs2203208 | 12 | 57257435 | G | A | . | 0.20 | . | NA |
| rs2687640 | 7 | 29138781 | A | G | 0.06 | . | 0.06 | CPVL |
| rs9310707 | 3 | 2307104 | A | G | 0.37 | 0.37 | 0.36 | CNTN4 |
| rs7197696 | 16 | 6110274 | G | A | . | 0.14 | . | A2BP1 |
| rs9991738 | 4 | 182341049 | C | T | . | 0.49 | . | NA |
| rs12597709 | 16 | 6102147 | G | A | . | 0.13 | . | A2BP1 |
| rs13156044 | 5 | 13920851 | A | G | 0.15 | 0.11 | 0.11 | DNAH5 |
| rs12328055 | 2 | 49824743 | A | G | 0.06 | . | 0.05 | NA |
| rs4799369 | 18 | 30594128 | G | A | 0.20 | 0.20 | 0.18 | DTNA |
| rs11610946 | 12 | 3985117 | G | A | . | 0.14 | . | NA |
| rs750585 | 5 | 168644898 | G | A | . | 0.13 | . | SLIT3 |
| rs2757491 | 1 | 170533424 | A | G | 0.06 | . | 0.06 | DNM3 |
| rs2757500 | 1 | 170545644 | A | G | 0.06 | . | 0.06 | DNM3 |
| rs17752325 | 4 | 65927951 | A | G | 0.11 | . | 0.13 | EPHA5 |
| rs7204266 | 16 | 9876004 | G | A | 0.28 | . | 0.28 | GRIN2A |
| rs12754186 | 1 | 19638913 | T | G | . | 0.11 | . | CAPZB |
| rs7202526 | 16 | 6808380 | A | G | 0.30 | 0.30 | 0.29 | A2BP1 |
| rs1001952 | 11 | 41421246 | C | T | . | 0.26 | . | NA |
| rs11154658 | 6 | 132422252 | G | T | . | 0.13 | . | LOC100131774 |
| rs7553399 | 1 | 3406309 | C | A | . | 0.25 | . | MEGF6 |
| rs1358206 | 3 | 74198360 | G | A | 0.30 | . | 0.31 | NA |
| rs17867545 | 4 | 118873138 | T | C | . | 0.10 | . | NA |
| rs16945809 | 17 | 1241236 | G | A | 0.08 | 0.08 | 0.06 | YWHAE |
| rs7234672 | 18 | 5875157 | A | G | 0.15 | . | 0.14 | NA |
| rs13062101 | 3 | 23458540 | A | G | 0.40 | 0.40 | 0.43 | UBE2E2 |
| rs10820743 | 9 | 106711480 | G | A | 0.29 | 0.28 | 0.27 | ABCA1 |
| rs7201930 | 16 | 9866156 | G | A | 0.29 | . | 0.33 | GRIN2A |
| rs12706180 | 7 | 117784949 | A | G | 0.34 | . | . | NA |
| rs9933832 | 16 | 9856135 | A | G | 0.29 | . | 0.32 | GRIN2A |
| rs6706281 | 2 | 190160993 | C | A | . | 0.26 | . | NA |
| rs1437883 | 2 | 190167713 | C | T | . | 0.25 | . | NA |
| rs4407684 | 6 | 85500368 | A | G | 0.47 | . | 0.53 | TBX18 |
| rs4149265 | 9 | 106712319 | A | G | 0.29 | 0.28 | 0.27 | ABCA1 |
| rs17202944 | 8 | 13848320 | G | T | . | 0.33 | . | NA |
| rs4738274 | 8 | 56645881 | A | C | 0.29 | . | 0.27 | NA |
| rs277311 | 5 | 154473983 | A | G | 0.14 | 0.14 | 0.14 | NA |
| rs2866223 | 4 | 101744971 | G | A | 0.19 | 0.18 | 0.21 | NA |
| rs7614155 | 3 | 74196658 | G | A | 0.25 | . | 0.27 | NA |
| rs6966727 | 7 | 130025354 | G | A | 0.06 | . | . | NA |
| rs6982610 | 8 | 14557840 | C | A | . | 0.36 | . | SGCZ |
| rs924945 | 18 | 67586419 | A | G | 0.34 | 0.41 | 0.34 | NA |
| rs17021160 | 2 | 37717573 | T | G | . | 0.07 | . | NA |
| rs9921541 | 16 | 9899263 | A | C | 0.23 | . | 0.24 | GRIN2A |
| rs2250378 | 12 | 73914832 | C | T | . | 0.23 | . | LOC100130268 |
| rs351572 | 8 | 16065839 | G | A | 0.40 | 0.49 | 0.44 | MSR1 |
| rs11642239 | 16 | 9904081 | G | A | 0.25 | 0.28 | 0.25 | GRIN2A |
| rs1480802 | 8 | 136293393 | C | A | 0.37 | . | 0.38 | NA |

TABLE 12-continued

| SNP | | | | | | | | |
|---|---|---|---|---|---|---|---|---|
| rs2886725 | 5 | 37806593 | A | G | . | 0.14 | . | NA |
| rs1524145 | 2 | 35975892 | T | G | . | 0.43 | . | NA |
| rs12525751 | 6 | 109444416 | A | G | 0.24 | 0.19 | 0.22 | SESN1 |
| rs2077923 | 16 | 9788282 | G | A | 0.29 | . | 0.32 | GRIN2A |
| rs7853963 | 9 | 82908731 | A | G | 0.15 | . | 0.14 | NA |
| rs1410171 | 6 | 85459030 | A | G | 0.47 | . | 0.53 | NA |
| rs1904982 | 1 | 105061407 | T | C | . | 0.50 | . | NA |
| rs12706181 | 7 | 117789716 | A | G | 0.34 | . | . | NA |
| rs1345697 | 5 | 147922431 | G | A | 0.48 | 0.49 | 0.51 | HTR4 |
| rs11255686 | 10 | 8496013 | C | A | . | 0.46 | . | NA |
| rs181343 | 11 | 129070462 | A | G | 0.23 | 0.23 | 0.26 | NA |
| rs7724465 | 5 | 4723864 | A | G | . | 0.06 | . | NA |
| rs13258175 | 8 | 13873685 | A | G | . | 0.45 | . | NA |
| rs7821773 | 8 | 9748866 | G | A | 0.08 | 0.05 | 0.08 | NA |
| rs1564470 | 8 | 136290117 | A | C | 0.30 | . | 0.32 | NA |
| rs6763279 | 3 | 74195448 | G | A | 0.25 | 0.29 | 0.27 | NA |
| rs2243628 | 10 | 7553828 | A | G | 0.37 | . | 0.34 | NA |
| rs10792038 | 11 | 56079983 | G | A | 0.34 | . | 0.38 | NA |
| rs13024296 | 2 | 224298740 | A | G | 0.17 | . | 0.20 | NA |
| rs7968026 | 12 | 83754187 | A | G | 0.31 | . | 0.30 | NA |
| rs41958 | 7 | 117760681 | A | G | 0.35 | . | . | NA |
| rs2543540 | 17 | 7572396 | A | G | . | 0.40 | . | DNAH2 |
| rs17615862 | 14 | 43931394 | T | C | . | 0.25 | . | NA |
| rs693996 | 11 | 56046568 | A | G | 0.34 | . | 0.38 | NA |
| rs1123110 | 2 | 190152444 | C | T | . | 0.34 | . | SLC40A1 |
| rs7754913 | 6 | 132423548 | C | A | 0.11 | 0.13 | 0.13 | LOC100131774 |
| rs9863361 | 3 | 177769362 | G | A | . | . | 0.03 | NA |
| rs2940774 | 4 | 22958441 | A | G | 0.17 | . | 0.25 | LOC643751 |
| rs1219769 | 1 | 108340149 | A | G | 0.32 | . | 0.32 | NA |
| rs2977983 | 8 | 71233342 | A | G | 0.06 | . | . | NCOA2 |
| rs4831257 | 8 | 13878742 | A | G | . | 0.40 | . | NA |
| rs8049793 | 16 | 7401978 | C | A | 0.19 | 0.17 | 0.17 | A2BP1 |
| rs7725683 | 5 | 68255470 | G | A | . | 0.23 | . | NA |
| rs2206593 | 1 | 184909052 | A | G | 0.08 | . | . | PTGS2 |
| rs7038808 | 9 | 91931116 | A | G | 0.13 | . | 0.15 | NA |
| rs8098087 | 18 | 67662582 | A | G | 0.23 | 0.28 | 0.22 | NA |
| rs17252114 | 3 | 41187757 | A | G | 0.45 | 0.50 | 0.52 | NA |
| rs9805752 | 13 | 113894531 | A | G | . | . | 0.16 | RASA3 |
| rs12272563 | 11 | 32465808 | A | G | . | 0.20 | . | NA |
| rs222151 | 21 | 26692482 | A | G | 0.25 | 0.23 | 0.22 | NA |
| rs873930 | 10 | 7569980 | G | A | 0.46 | 0.47 | 0.43 | NA |
| rs10502634 | 18 | 30570172 | G | A | 0.11 | 0.09 | 0.10 | DTNA |
| rs1349498 | 2 | 173300852 | A | G | 0.17 | 0.22 | 0.19 | NA |
| rs2704783 | 2 | 146216429 | C | T | . | 0.28 | . | NA |

SNPs associated with composite toxicity (grade ≥2)

| SNP | feature | Flanking gene | Flanking gene | p-value unadjusted | effect (β) unadjusted | p-value adjusted | effect (β) adjusted |
|---|---|---|---|---|---|---|---|
| rs17084411 | NA | LOC644502 | HSF2 | 4.24E−08 | 1.52 | 4.74E−08 | 1.55 |
| rs1927869 | NA | LOC644502 | HSF2 | 4.24E−08 | 1.52 | 4.74E−08 | 1.55 |
| rs17084371 | NA | LOC644502 | HSF2 | 7.24E−08 | 1.47 | 8.05E−08 | 1.49 |
| rs11036390 | NA | LRRC4C | LOC100131020 | 2.15E−07 | 1.02 | 2.37E−07 | 1.02 |
| rs11662763 | NA | LOC645355 | TTMA | 9.19E−07 | 0.67 | 9.48E−05 | 0.61 |
| rs2937754 | intron | FLJ34047 | LOC646012 | 1.52E−06 | 0.95 | 1.52E−06 | 0.97 |
| rs8006648 | NA | LOC730121 | GALC | 2.33E−06 | 0.58 | 2.87E−05 | 0.55 |
| rs2456761 | NA | LOC729184 | CDC2 | 2.80E−06 | 0.72 | 4.57E−05 | 0.69 |
| rs1000032 | NA | KIAA1715 | EVX2 | 3.21E−06 | 0.62 | 9.26E−06 | 0.63 |
| rs2203208 | NA | LOC100127973 | LRIG3 | 3.54E−06 | 0.96 | 3.05E−06 | 1.00 |
| rs2687640 | intron | KIAA0644 | LOC100131724 | 3.55E−06 | 1.03 | 1.09E−06 | 1.13 |
| rs9310707 | intron | LOC727810 | LOC100130346 | 4.03E−06 | 0.53 | 1.33E−05 | 0.52 |
| rs7197696 | intron | LOC100129334 | LOC440337 | 5.95E−06 | 1.15 | 6.41E−06 | 1.16 |
| rs9991738 | NA | hCG_2025798 | LOC132386 | 7.26E−06 | 0.84 | 5.79E−06 | 0.86 |
| rs12597709 | intron | LOC100129334 | LOC440337 | 7.29E−06 | 1.14 | 7.36E−06 | 1.14 |
| rs13156044 | intron | LOC391738 | TRIO | 8.51E−06 | 0.60 | 7.40E−05 | 0.59 |
| rs12328055 | NA | FSHR | LOC130728 | 9.19E−06 | 0.99 | 2.27E−03 | 0.76 |
| rs4799369 | intron | LOC646842 | MAPRE2 | 1.14E−05 | 0.59 | 1.63E−03 | 0.44 |
| rs11610946 | NA | PARP11 | LOC399988 | 1.19E−05 | 0.96 | 1.21E−05 | 0.96 |
| rs750585 | intron | LOC728095 | CCDC99 | 1.24E−05 | 1.03 | 1.30E−05 | 1.04 |
| rs2757491 | intron | LOC100128178 | LOC100131486 | 1.25E−05 | 0.90 | 1.39E−02 | −0.68 |
| rs2757500 | intron | LOC100128178 | LOC100131486 | 1.25E−05 | 0.90 | 1.39E−02 | 0.28 |
| rs17752325 | intron | LOC644682 | LOC642828 | 1.38E−05 | 0.77 | 1.05E−05 | 0.82 |
| rs7204266 | intron | LOC653737 | LOC727844 | 1.44E−05 | 0.60 | 6.84E−06 | 0.69 |
| rs12754186 | intron | LOC130193 | C1orf151 | 1.65E−05 | 0.98 | 1.14E−05 | 0.99 |
| rs7202526 | intron | LOC100131413 | LOC100131080 | 1.67E−05 | 0.51 | 2.35E−05 | 0.52 |
| rs1001952 | NA | LRRC4C | LOC100131020 | 1.74E−05 | 0.87 | 1.74E−05 | 0.87 |
| rs11154658 | intron | CTGF | MOXD1 | 1.75E−05 | 0.98 | 1.51E−05 | 0.99 |
| rs7553399 | missense | ARHGEF16 | TPRG1L | 1.81E−05 | 0.95 | 1.46E−05 | 0.91 |
| rs1358206 | NA | LOC100129282 | HSP90AB5P | 1.81E−05 | 0.62 | 3.89E−03 | 0.45 |

TABLE 12-continued

| | | | | | | | |
|---|---|---|---|---|---|---|---|
| rs17867545 | NA | NT5C3P1 | NDST3 | 1.84E−05 | 1.20 | 1.57E−05 | 1.23 |
| rs16945809 | intron | TUSC5 | LOC727845 | 2.00E−05 | 0.80 | 2.16E−06 | 0.94 |
| rs7234672 | NA | LOC645355 | TTMA | 2.06E−05 | 0.72 | 1.03E−03 | 0.64 |
| rs13062101 | intron | LOC100130785 | UBE2E1 | 2.34E−05 | 0.45 | 4.35E−05 | 0.46 |
| rs10820743 | intron | NIPSNAP3B | SLC44A1 | 2.42E−05 | 0.48 | 8.05E−05 | 0.47 |
| rs7201930 | intron | LOC653737 | LOC727844 | 2.90E−05 | 0.60 | 4.51E−05 | 0.65 |
| rs12706180 | NA | ANKRD7 | LOC648442 | 3.03E−05 | 0.91 | 8.37E−04 | 0.97 |
| rs9933832 | intron | LOC653737 | LOC727844 | 3.24E−05 | 0.59 | 5.18E−05 | 0.64 |
| rs6706281 | NA | SLC40A1 | ASNSD1 | 3.27E−05 | 0.91 | 2.54E−05 | 0.94 |
| rs1437883 | NA | SLC40A1 | ASNSD1 | 3.35E−05 | 0.90 | 2.81E−05 | 0.93 |
| rs4407684 | near-gene-3 | LOC442233 | TBX18 | 3.48E−05 | 0.59 | 1.40E−03 | 0.49 |
| rs4149265 | intron | NIPSNAP3B | SLC44A1 | 3.57E−05 | 0.47 | 1.20E−04 | 0.46 |
| rs17202944 | NA | C8orf48 | SGCZ | 3.70E−05 | −0.82 | 2.53E−05 | −0.85 |
| rs4738274 | NA | XKR4 | TMEM68 | 3.72E−05 | 0.60 | 3.16E−03 | 0.49 |
| rs277311 | NA | LOC100131520 | LOC100130088 | 3.88E−05 | 0.62 | 3.47E−04 | 0.60 |
| rs2866223 | NA | EMCN | LOC728771 | 3.96E−05 | 0.56 | 2.40E−03 | 0.43 |
| rs7614155 | NA | LOC100129282 | HSP90AB5P | 4.05E−05 | 0.61 | 8.67E−03 | 0.42 |
| rs6966727 | NA | TSGA13 | KLF14 | 4.07E−05 | 1.31 | 1.26E−01 | 0.78 |
| rs6982610 | intron | LOC100131565 | TUSC3 | 4.39E−05 | 0.77 | 3.36E−05 | 0.78 |
| rs924945 | NA | LOC100132647 | CBLN2 | 4.48E−05 | 0.46 | 3.54E−05 | 0.49 |
| rs17021160 | NA | QPCT | CDC42EP3 | 4.52E−05 | 1.29 | 4.99E−05 | 1.30 |
| rs9921541 | intron | LOC653737 | LOC727844 | 4.52E−05 | 0.59 | 5.20E−05 | 0.64 |
| rs2250378 | near-gene-5 | KCNC2 | LOC100130268 | 4.63E−05 | 0.88 | 4.85E−05 | 0.89 |
| rs351572 | intron | hCG_1794003 | LOC646440 | 4.81E−05 | −0.46 | 1.43E−04 | −0.45 |
| rs11642239 | intron | LOC653737 | LOC727844 | 4.83E−05 | 0.48 | 1.14E−04 | 0.49 |
| rs1480802 | NA | ZFAT | LOC286094 | 4.97E−05 | 0.63 | 2.50E−05 | 0.70 |
| rs2886725 | NA | WDR70 | GDNF | 4.99E−05 | 0.97 | 4.89E−05 | 1.02 |
| rs1524145 | NA | MRPL50P1 | CRIM1 | 5.01E−05 | 0.84 | 5.05E−05 | 0.84 |
| rs12525751 | intron | ARMC2 | C6orf182 | 5.04E−05 | 0.51 | 1.31E−03 | 0.43 |
| rs2077923 | intron | LOC653737 | LOC727844 | 5.21E−05 | 0.59 | 1.20E−04 | 0.61 |
| rs7853963 | NA | LOC100128222 | TLE1 | 5.21E−05 | 0.72 | 5.12E−05 | 0.56 |
| rs1410171 | NA | LOC442233 | TBX18 | 5.23E−05 | 0.57 | 2.18E−03 | 0.47 |
| rs1904982 | NA | LOC642337 | LOC100130867 | 5.24E−05 | −0.75 | 3.54E−05 | −0.80 |
| rs12706181 | NA | ANKRD7 | LOC648442 | 5.28E−05 | 0.88 | 1.09E−03 | 0.95 |
| rs1345697 | intron | FBXO38 | ADRB2 | 5.49E−05 | −0.46 | 6.06E−04 | −0.41 |
| rs11255686 | NA | LOC389935 | KRT8P16 | 5.56E−05 | 0.80 | 5.51E−05 | 0.81 |
| rs181343 | NA | BARX2 | LOC729717 | 5.86E−05 | 0.50 | 1.32E−03 | 0.42 |
| rs7724465 | NA | IRX1 | LOC340094 | 5.92E−05 | 1.11 | 4.19E−05 | 1.15 |
| rs13258175 | NA | C8orf48 | SGCZ | 5.97E−05 | 0.72 | 3.14E−05 | 0.77 |
| rs7821773 | NA | TNKS | MSRA | 5.98E−05 | 0.71 | 1.75E−05 | 0.80 |
| rs1564470 | NA | ZFAT | LOC286094 | 6.02E−05 | 0.62 | 5.09E−06 | 0.75 |
| rs6763279 | NA | LOC100129282 | HSP90AB5P | 6.28E−05 | 0.46 | 5.01E−03 | 0.34 |
| rs2243628 | NA | LOC728777 | ITIH5 | 6.39E−05 | 0.53 | 1.87E−03 | 0.46 |
| rs10792038 | NA | OR5M11 | OR5M10 | 6.59E−05 | 0.61 | 1.81E−05 | 0.72 |
| rs13024296 | NA | LOC646696 | AP1S3 | 6.83E−05 | −0.97 | 4.35E−03 | −0.71 |
| rs7968026 | NA | LOC100128335 | SLC6A15 | 6.89E−05 | 0.57 | 3.63E−05 | 0.64 |
| rs41958 | NA | ANKRD7 | LOC648442 | 7.07E−05 | 0.87 | 1.26E−05 | 0.94 |
| rs2543540 | intron | EFNB3 | RPL29P2 | 7.09E−05 | −0.77 | 7.26E−05 | −0.77 |
| rs17615862 | NA | YWHAZP1 | LOC729165 | 7.21E−05 | 0.86 | 7.33E−05 | 0.86 |
| rs693996 | NA | OR5M6P | OR5M5P | 7.58E−05 | 0.60 | 2.16E−05 | 0.71 |
| rs1123110 | intron | WDR75 | ASNSD1 | 7.70E−05 | 0.72 | 7.56E−05 | 0.72 |
| rs7754913 | intron | CTGF | MOXD1 | 8.10E−05 | 0.58 | 1.07E−04 | 0.60 |
| rs9863361 | NA | LOC730168 | TBL1XR1 | 8.36E−05 | 1.63 | 9.80E−05 | 1.62 |
| rs2940774 | intron | GBA3 | PPARGC1A | 8.60E−05 | 0.62 | 9.16E−04 | 0.58 |
| rs1219769 | NA | VAV3 | SLC25A24 | 8.65E−05 | 0.62 | 6.64E−03 | 0.47 |
| rs2977983 | intron | H2AFZP2 | BTF3L2 | 8.76E−05 | 1.31 | 2.62E−03 | 1.36 |
| rs4831257 | NA | C8orf48 | SGCZ | 8.93E−05 | −0.72 | 6.57E−05 | −0.74 |
| rs8049793 | intron | LOC100131413 | LOC100131080 | 9.07E−05 | −0.68 | 6.74E−04 | −0.62 |
| rs7725683 | NA | PIK3R1 | LOC100130639 | 9.11E−05 | 0.82 | 9.54E−05 | 0.82 |
| rs2206593 | utr-3 | LOC100131939 | PLA2G4A | 9.14E−05 | 1.30 | 3.03E−04 | 1.49 |
| rs7038808 | NA | IL6RL1 | OR7E31P | 9.17E−05 | 0.68 | 4.55E−06 | 0.85 |
| rs8098087 | NA | LOC100132647 | CBLN2 | 9.23E−05 | 0.47 | 1.62E−04 | 0.49 |
| rs17252114 | NA | RPS27P4 | MRPS31P1 | 9.33E−05 | −0.43 | 6.44E−04 | −0.40 |
| rs9805752 | intron | FAM70B | CDC16 | 9.44E−05 | 0.86 | 4.96E−05 | 0.90 |
| rs12272563 | NA | WIT1 | EIF3M | 9.46E−05 | 0.85 | 8.00E−05 | 0.86 |
| rs222151 | NA | APP | CYYR1 | 9.49E−05 | −0.57 | 9.10E−06 | −0.73 |
| rs873930 | NA | LOC728777 | ITIH5 | 9.58E−05 | 0.40 | 4.49E−04 | 0.39 |
| rs10502634 | NA | LOC646842 | MAPRE2 | 9.58E−05 | 0.67 | 1.56E−05 | 0.57 |
| rs1349498 | NA | LOC100129169 | RAPGEF4 | 9.73E−05 | 0.50 | 1.51E−03 | 0.45 |
| rs2704783 | NA | LOC730124 | LOC727713 | 9.84E−05 | 0.87 | 1.00E−04 | 0.87 |

Fifty-seven out of the 100 variants had the same direction of effect in at least two out of the three trials (cutoff $p<1\times10^{-4}$). The top ten most statistically significant variants of that list in shown in Table 5. rs11662763 (G>A, MAF 0.11-0.14) was the most statistically significant ($p=9.19\times10^{-7}$, $\beta=0.67$), with the A allele increasing the risk of composite toxicity (FIG. 3). rs11662763 is 33 kb 3' from TTMA (FIG. 4A).

For the SNP-based analysis of grade ≤3, the Manhattan and Q-Q plots are shown in FIG. 5. 88 variants were identified as associated with composite toxicity (Table 13). Fifty-three out of 88 variants had the same direction of effect (either reduced or increased risk) in at least three out of the four studies (cutoff $p<1\times10^{-4}$). The top ten most statistically significant variants of that list are shown in Table 7. rs10867852 (G>A, MAF 0.06-0.08) was the most statistically significant ($p=1.46\times10^{-6}$, $\beta=1.16$), with the A allele increasing the risk of composite toxicity. rs10867852 is an intergenic variant located 430 kb 3' from RASEF (FIG. 6). rs7717673 (G>A, MAF 0.11-0.12) was the next most statistically significant ($p=3.93\times10^{-6}$, $\beta=0.94$) with the A allele increasing the risk of composite toxicity. rs7717673 is located in the intron of SLC25A48 (FIG. 6).

TABLE 13

SNPs associated with composite toxicity (grade ≥3)

| SNP | CH | BP | Effect allele | reference allele | MAF 80303 | MAF 40503 | MAF 90401 | gene | feature | Flanking gene | Flanking gene | p-value | effect (β) |
|---|---|---|---|---|---|---|---|---|---|---|---|---|---|
| rs6807110 | 3 | 120338347 | C | A | . | . | 0.06 | IGSF11 | intron | LOC728873 | C3orf30 | 1.29E-06 | 1.61 |
| rs10867852 | 9 | 84353502 | A | G | 0.08 | 0.07 | 0.06 | NA | NA | LOC442427 | RASEF | 1.46E-06 | 1.16 |
| rs1022306 | 11 | 83629022 | A | C | . | 0.13 | . | DLG2 | intron | LOC100130985 | LOC100130066 | 2.11E-06 | 1.32 |
| rs6954042 | 7 | 109951683 | G | A | . | 0.06 | . | NA | NA | LOC646620 | IMMP2L | 2.45E-06 | 1.76 |
| rs7717673 | 5 | 135239365 | A | G | 0.11 | 0.12 | 0.12 | SLC25A48 | intron | LOC153328 | IL9 | 3.93E-06 | 0.94 |
| rs2478835 | 10 | 30357955 | T | C | . | 0.40 | . | KIAA1462 | synonymous | SVIL | LOC729663 | 8.85E-06 | 1.22 |
| rs4842232 | 9 | 137279808 | A | G | 0.10 | . | NA | NA | NA | LOC401557 | C9orf62 | 9.83E-06 | 1.55 |
| rs4320922 | 11 | 104627661 | A | G | 0.49 | . | NA | NA | NA | OR2AL1P | GRIA4 | 1.27E-05 | -1.24 |
| rs6033941 | 20 | 14243645 | C | A | . | 0.29 | . | MACROD2 | intron | SCYE1P | FLRT3 | 1.40E-05 | 1.05 |
| rs2454331 | 8 | 89957664 | G | A | 0.43 | 0.40 | 0.43 | NA | NA | LOC100129100 | RIPK2 | 1.43E-05 | -0.77 |
| rs873224 | 8 | 142600146 | G | A | 0.11 | 0.10 | 0.08 | NA | NA | FLJ43860 | LOC100131146 | 1.48E-05 | 0.86 |
| rs10873360 | 14 | 25663831 | T | G | . | 0.11 | . | NA | NA | LOC401767 | NOVA1 | 1.49E-05 | 1.38 |
| rs966439 | 14 | 86235074 | G | A | 0.21 | 0.17 | 0.16 | NA | NA | LOC283585 | LOC283585 | 1.52E-05 | 0.70 |
| rs7849777 | 9 | 136812622 | A | G | 0.09 | 0.05 | 0.06 | COL5A1 | intron | RXRA | LOC100130622 | 1.56E-05 | 1.31 |
| rs10869538 | 9 | 70729551 | G | A | 0.15 | 0.16 | 0.15 | PIP5K1B | intron | LOC100131240 | PRKACG | 1.74E-05 | 0.74 |
| rs11664759 | 18 | 69223208 | A | G | 0.11 | 0.15 | 0.15 | NA | NA | LOC400655 | FBXO15 | 2.21E-05 | 0.83 |
| rs1978259 | 14 | 86265207 | A | C | 0.20 | . | 0.16 | NA | NA | LOC283585 | LOC283585 | 2.63E-05 | 0.81 |
| rs7174784 | 15 | 99119567 | G | A | . | . | 0.41 | NA | NA | ASB7 | LOC440313 | 2.74E-05 | 1.25 |
| rs17096208 | 14 | 73625022 | A | G | 0.08 | . | 0.07 | LIN52 | intron | ALDH6A1 | VSX2 | 2.87E-05 | 1.05 |
| rs4646864 | 14 | 73596456 | A | G | 0.08 | . | 0.07 | ALDH6A1 | near-gene-3 | ENTPD5 | ALDH6A1 | 2,87E-05 | 1.05 |
| rs17109031 | 12 | 52884634 | A | G | 0.13 | 0.08 | 0.10 | NA | NA | SMUG1 | LOC100132010 | 2.93E-05 | 0.85 |
| rs4696433 | 4 | 154307393 | A | G | 0.12 | 0.10 | 0.12 | NA | NA | FHDC1 | TRIM2 | 3.01E-05 | 0.90 |
| rs6739406 | 2 | 35467180 | A | G | 0.11 | 0.13 | 0.09 | NA | NA | LOC100130842 | MRPL50P1 | 3.11E-05 | 0.84 |
| rs10988111 | 9 | 130559781 | C | A | 0.45 | . | 0.46 | ZER1 | intron | ZDHHC12 | TBC1D13 | 3.21E-05 | -0.97 |
| rs491451 | 6 | 12836804 | A | G | 0.16 | 0.11 | 0.14 | PHACTR1 | intron | RPL15P3 | LOC100130357 | 3.45E-05 | 0.80 |
| rs16930838 | 8 | 65151961 | C | T | . | 0.11 | . | NA | NA | IFITM8P | LOC100130155 | 3.50E-05 | 1.31 |
| rs2505083 | 10 | 30375128 | C | T | . | 0.40 | . | KIAA1462 | intron | SVIL | LOC729663 | 3.55E-05 | 1.11 |
| rs10129969 | 14 | 77017051 | G | A | . | 0.06 | . | THSD3 | intron | AHSA1 | SPTLC2 | 3.73E-05 | 1.54 |
| rs1452243 | 12 | 83695187 | A | C | 0.38 | 0.34 | 0.39 | NA | NA | LOC100128335 | SLC6A15 | 3.73E-05 | 0.68 |
| rs11254929 | 10 | 7072177 | G | A | 0.16 | . | 0.17 | NA | NA | LOC439949 | SFMBT2 | 3.91E-05 | 0.94 |
| rs710392 | 5 | 87060900 | T | C | . | 0.17 | . | NA | NA | CCNH | TMEM161B | 4.02E-05 | 1.20 |
| rs1932065 | 1 | 70857226 | G | A | . | 0.23 | . | NA | NA | LOC391048 | PTGER3 | 4.03E-05 | 1.02 |
| rs12157031 | 0 | NA | T | C | . | 0.08 | . | NA | NA | RPS6KA3 | CNKSR2 | 4.33E-05 | 1.52 |
| rs7080002 | 10 | 109119252 | G | A | . | 0.06 | . | NA | NA | SORCS1 | LOC100128304 | 4.38E-05 | 1.64 |
| rs3739998 | 4 | 118873138 | G | C | . | 0.40 | . | NA | NA | NT5C3P1 | NDST3 | 4.38E-05 | 1.06 |
| rs17867545 | 14 | 61622536 | T | C | . | 0.10 | . | SYT16 | intron | MOCS3P | LOC100128793 | 4.57E-05 | 1.43 |
| rs2154110 | 6 | 2465335 | G | T | . | 0.25 | . | NA | NA | LOC100128372 | C6orf195 | 4.68E-05 | 1.17 |
| rs7764946 | 6 | 6613180 | T | C | . | 0.07 | . | NA | NA | LY86 | RP11-320C15.1 | 5.05E-05 | 1.55 |
| rs9405313 | 8 | 33984189 | A | C | 0.11 | 0.13 | 0.12 | NA | NA | CYCSP3 | LOC137107 | 5.07E-05 | 0.80 |
| rs4493901 | 6 | 22511446 | T | C | . | 0.11 | . | NA | NA | PRL | HDGEL1 | 5.10E-05 | 1.18 |
| rs2655439 | 6 | 14056368 | A | G | 0.15 | 0.14 | 0.13 | RNF182 | intron | CCDC90A | MRPL35P1 | 5.42E-05 | 0.75 |
| rs1192057 | 14 | 88559840 | A | G | . | 0.10 | . | NA | NA | TTC8 | LOC390501 | 5.55E-05 | 1.34 |
| rs11628605 | 4 | 56789252 | A | G | . | 0.32 | . | KIAA1211 | intron | CEP135 | MRPL22P1 | 5.56E-05 | 1.11 |
| rs17751450 | 9 | 25541627 | A | G | 0.36 | . | 0.38 | NA | NA | C9orf134 | TUSC1 | 5.66E-05 | 0.75 |
| rs7028018 | 20 | 40742146 | G | A | 0.29 | 0.38 | . | PTPRT | intron | LOC643172 | PPIAL | 5.76E-05 | 0.73 |
| rs2206428 | 12 | 72205105 | A | G | 0.25 | . | 0.30 | NA | NA | TRHDE | LOC100128674 | 5.90E-05 | 0.81 |
| rs12368298 | 10 | 76203313 | C | A | 0.19 | . | . | NA | NA | LOC645646 | MYS74 | 6.03E-05 | 1.31 |
| rs7075347 | 7 | 36284221 | A | G | 0.07 | . | 0.08 | EEPD1 | intron | LOC100131181 | KIAA0895 | 6.06E-05 | 1.01 |
| rs196584 | 9 | 117317136 | A | G | 0.07 | 0.13 | 0.09 | NA | NA | 43800 | C9orf27 | 6.13E-05 | 0.76 |
| rs9408872 | 20 | 14192971 | A | C | . | 0.22 | . | MACROD2 | intron | SCYE1P | FLRT3 | 6.39E-05 | 1.06 |
| rs1998238 | 11 | 104663936 | A | G | . | 0.29 | . | NA | NA | OR2AL1P | GRIA4 | 6.42E-05 | 0.99 |
| rs10895805 | 5 | 39716478 | A | G | . | 0.41 | . | NA | NA | LOC100129040 | LOC285634 | 6.42E-05 | -1.28 |
| rs10473145 | 1 | 25124011 | T | G | . | 0.15 | . | RUNX3 | intron | CLIC4 | LOC391020 | 6.68E-05 | 1.07 |
| rs742230 | 9 | 70717983 | C | T | . | 0.43 | . | PIP5K1B | intron | LOC100131240 | PRKACG | 6.69E-05 | -1.20 |
| rs1414954 | 1 | 156145769 | A | G | 0.13 | . | 0.11 | NA | NA | LOC649203 | hCG_1994895 | 6.72E-05 | 0.85 |
| rs4450009 | 12 | 74414178 | G | A | 0.16 | 0.13 | 0.13 | NA | NA | LOC100130336 | LOC100131830 | 6.72E-05 | 0.72 |
| rs4831949 | 13 | 80958452 | G | A | . | 0.08 | . | NA | NA | LOC100129023 | PTMAP5 | 6.80E-05 | 1.48 |
| rs9545728 | 20 | 40760195 | A | G | 0.19 | . | . | PTPRT | intron | LOC643172 | PPIAL | 6.85E-05 | 1.38 |

TABLE 13-continued

SNPs associated with composite toxicity (grade ≥3)

| SNP | CH | BP | Effect allele | reference allele | MAF 80303 | MAF 40503 | MAF 90401 | gene | feature | Flanking gene | Flanking gene | p-value | effect (β) |
|---|---|---|---|---|---|---|---|---|---|---|---|---|---|
| rs6072833 | 9 | 116819754 | A | G | 0.25 | . | 0.30 | NA | NA | TNFSF8 | TNC | 6.87E−05 | 0.80 |
| rs1107373 | 5 | 92355984 | A | G | 0.06 | 0.08 | 0.09 | NA | NA | CCT7P2 | LOC391811 | 7.14E−05 | 0.83 |
| rs12054859 | 10 | 30346810 | G | A | 0.07 | . | . | KIAA1462 | utr-3 | SVIL | LOC729663 | 7.28E−05 | 1.87 |
| rs2478839 | 13 | 66879378 | T | C | . | 0.42 | . | NA | NA | LOC400141 | LOC390411 | 7.37E−05 | 1.03 |
| rs13378216 | 6 | 143400706 | G | T | . | 0.06 | . | NA | NA | HIVEP2 | AIG1 | 7.41E−05 | 1.39 |
| rs12664681 | 18 | 55864775 | C | A | 0.06 | 0.06 | 0.08 | NA | NA | LOC728115 | LOC400652 | 7.65E−05 | 0.93 |
| rs17066548 | 13 | 95897355 | A | C | 0.05 | . | 0.05 | HS6ST3 | intron | UGCGL2 | HSP90AB6P | 7.74E−05 | 1.34 |
| rs732121 | 20 | 40763167 | G | A | 0.06 | . | 0.07 | PTPRT | intron | LOC643172 | PPIAL | 7.93E−05 | 1.12 |
| rs3092743 | 1 | 29428986 | A | G | 0.17 | . | 0.20 | MECR | intron | SFRS4 | PTPRU | 8.19E−05 | 0.79 |
| rs2819606 | 2 | 174388565 | T | C | . | 0.10 | . | NA | NA | LOC100129456 | LOC644056 | 8.19E−05 | 1.37 |
| rs16862115 | 5 | 168644898 | A | G | 0.20 | 0.21 | 0.24 | SLIT3 | intron | LOC728095 | CCDC99 | 8.61E−05 | 0.60 |
| rs750585 | 6 | 134606559 | G | A | . | 0.13 | . | NA | NA | SGK1 | LOC442261 | 8.66E−05 | 1.06 |
| rs9493871 | 16 | 78430806 | A | C | 0.09 | 0.07 | 0.08 | NA | NA | LOC440389 | LOC729847 | 8.66E−05 | 0.96 |
| rs11644568 | 6 | 1773164 | A | C | 0.06 | . | 0.05 | GMDS | intron | FLJ46552 | LOC100128372 | 8.83E−05 | 1.18 |
| rs9328072 | 2 | 50099333 | G | A | 0.28 | 0.26 | 0.31 | NRXN1 | intron | LOC130728 | LOC730100 | 9.04E−05 | 0.63 |
| rs7568888 | 4 | 109997382 | A | G | . | . | 0.15 | COL25A1 | intron | LOC100129714 | ZCCHC23 | 9.10E−05 | 1.17 |
| rs1377208 | 8 | 58380598 | C | A | 0.18 | . | . | NA | NA | C8orf71 | LOC100130588 | 9.11E−05 | 1.19 |
| rs1878628 | 11 | 104715682 | G | A | . | . | 0.07 | NA | NA | OR2AL1P | GRIA4 | 9.11E−05 | 1.35 |
| rs4603276 | 11 | 104778916 | G | A | . | 0.41 | . | NA | NA | OR2AL1P | GRIA4 | 9.13E−05 | −1.22 |
| rs7930393 | 8 | 24652844 | C | T | . | 0.41 | . | NA | NA | ADAM7 | NEFM | 9.13E−05 | −1.22 |
| rs10091523 | 9 | 116740531 | G | A | 0.34 | . | 0.36 | NA | NA | TNFSF8 | TNC | 9.31E−05 | 0.82 |
| rs4979476 | 13 | 35359822 | G | A | 0.09 | 0.09 | 0.08 | DCLK1 | intron | NBEA | SOHLH2 | 9.33E−05 | 0.73 |
| rs1171065 | 9 | 92388224 | C | A | 0.19 | 0.26 | 0.19 | NA | NA | LOC340515 | DIRAS2 | 9.34E−05 | 0.63 |
| rs16906689 | 5 | 37808537 | A | G | . | 0.09 | . | NA | NA | WDR70 | GDNF | 9.45E−05 | 1.43 |
| rs10472291 | 7 | 3583940 | A | C | . | 0.37 | . | SDK1 | intron | LOC100129603 | LOC730351 | 9.53E−05 | 1.04 |
| rs9654994 | 17 | 67535422 | G | A | 0.14 | 0.15 | 0.15 | NA | NA | hCG_1644301 | FLJ37644 | 9.64E−05 | 0.76 |
| rs12451606 | 1 | 61132767 | G | A | . | . | 0.03 | NA | NA | C1orf87 | NFIA | 9.67E−05 | 1.83 |
| rs1002005 | 8 | 24655238 | G | A | 0.06 | 0.08 | 0.07 | NA | NA | ADAM7 | NEFM | 9.75E−05 | 0.83 |
| rs4543550 | 10 | 93349774 | G | A | 0.34 | . | 0.36 | NA | NA | HECTD2 | PPP1R3C | 9.92E−05 | 0.82 |
| rs7903829 | 3 | 2307104 | A | C | 0.06 | 0.07 | 0.07 | CNTN4 | intron | LOC727810 | LOC100130346 | 9.97E−05 | 0.90 |

For the gene-based analysis of grade ≥2, the Q-Q plot is shown in FIG. 7. Table 9 shows the ten most statistically significant genes. SLC25A24 was the most significant ($p=4.00\times10^{-6}$).

Discussion

It is believed that this is the largest GWAS of bevacizumab-induced proteinuria and hypertension. The present study included 1,041 cancer patients, with different tumor types, from four randomized phase III clinical trials conducted at the Alliance. The relatively large sample size, the randomized design, and the standardized collection of the phenotypic and genotypic data are positive features that increase the value of these findings. The analysis of genetic associations that were consistent across different studies led to the identification of novel SNPs and genes associated with these toxicities.

This study has selected DNAH5, TRIO, RIPK4 and IL17F as genes involved bevacizumab-induced proteinuria. DNAH5 and TRIO are the closest genes from rs339947, the most statistically significant SNP associated with proteinuria ($p=7.66\times10^{-8}$). DNAH5 encodes a dynein protein (part of a microtubule-associated motor protein complex) that is important for the normal function of ciliated cells in many tissues, including kidney tubule. Mutations in DNAH5 cause a genetic disorder associated with polycystic kidney diseases. TRIO encodes a GDP to GTP exchange factor promoting the reorganization of the actin cytoskeleton, thereby playing a role in cell migration and growth. TRIO is highly expressed in podocytes and regulates the attachment of podocytes to glomerular basement membrane. TRIO also induces Rac 1 activity, which contributes to podocyte injury and proteinuria. DNAH5, or TRIO, or both could be involved in the mechanism of bevacizumab-induced proteinuria. Interestingly, our functional bioinformatic analysis that rs429023, in moderate LD with rs339947, is an eQTL increasing TRIO expression in the glomerulus (Table 14), potentially pointing towards TRIO as the putative gene of proteinuria.

TABLE 14

Bioinformatic analysis of rs13135230, rs2350620, and rs6770663 associated with hypertension, rs339947, rs12482855 and rs408130 associated with proteinuria, rs11662763 associated with composite toxicity, and SNPs in complete LD ($R^2 = 1.0$) according to LDlink.

| | | | | Data from Genome Browser, Regulome DB and/or HaploReg v4 | | | | |
|---|---|---|---|---|---|---|---|---|
| SNPs | eQTL | Region | Regulome DB Score | ChIP-seq | Transcription factor binding motifs | DNaseI sensitivity region | Chromatin state | Histone markers |
| Hypertension | | | | | | | | |
| rs13135230 | — | 3.8 kb 3' from LGI2 | No data | — | — | — | — | — |
| rs2350620 | — | — | 4 | FOXA1 | — | — | — | — |

TABLE 14-continued

Bioinformatic analysis of rs13135230, rs2350620, and rs6770663 associated with hypertension, rs339947, rs12482855 and rs408130 associated with proteinuria, rs11662763 associated with composite toxicity, and SNPs in complete LD ($R^2 = 1.0$) according to LDlink.

| | | | | Data from Genome Browser, Regulome DB and/or HaploReg v4 | | | | |
|---|---|---|---|---|---|---|---|---|
| SNPs | eQTL | Region | Regulome DB Score | ChIP-seq | Transcription factor binding motifs | DNaseI sensitivity region | Chromatin state | Histone markers |
| rs35026059 | — | | 2c | CTCF | CTCF | — | — | — |
| rs28695823 | — | ASPH intron 14 | 5 | SMARCC1 | — | Yes (fetal heart) | Enhancers (HUVEC, aorta and fetal heart) | H3K4me1, H3K4me3, H3K27ac, H3K9ac (HUVEC and heart tissue group) |
| rs6770663 | — | KCNAB1 intron 1 | 6 | — | — | — | — | H3K4me1 (HUVEC and aorta) |
| Proteinuria | | | | | | | | |
| rs339947 | — | 73 kb 5' from DNAH5 130 kb 5' from TRIO | 4 | USF1 | — | — | Repressed polycomb (HUVEC) | — |
| rs408130 | — | | No data | — | — | — | — | — |
| rs418173 | — | 60 kb 5' from DNAH5 140 kb 5' from TRIO | 5 | — | — | — | — | — |
| rs429023 | TRIO in glomerulus (NES = 2.1, p = 0.039) | | 5 | EBF1 | — | — | — | — |
| rs12482855 | — | 4.7 kb from RIPK4 5' | No data | — | — | — | — | H3K4me1 (fetal kidney) |
| Composite toxicity | | | | | | | | |
| rs11662763 | EPB41L3 in glomerulus (NES = 2.8, p = 0.0055) | 33 kb 3' from TTMA | No data | — | — | — | — | — |

For Table 14, SNPs in bold are the selected SNPs from our study and the SNPs not in bold are SNPs in LD with them. Expression quantitative trait loci (eQTL) information was retrieved from the GTEx v7 and NephQTL. The RegulomeDB score represents the evidence that a variant has a regulatory function (1-strong evidence, 6-weak evidence). Data from Genome Browser, RegulomeDB and/or HaploReg v4 includes computational and experimental data from ENCODE and Roadmap Epigenomics Consortium. Only ChIP-seq and transcription binding motifs from experimental data are reported. Only DNaseI sensitivity region, chromatin state and histone markers for relevant cell lines (HUVEC or heart tissue group) are reported. Composite toxicity is defined as the occurrence of either proteinuria or hypertension or both. NES: normalized effect size.

Figure 8:
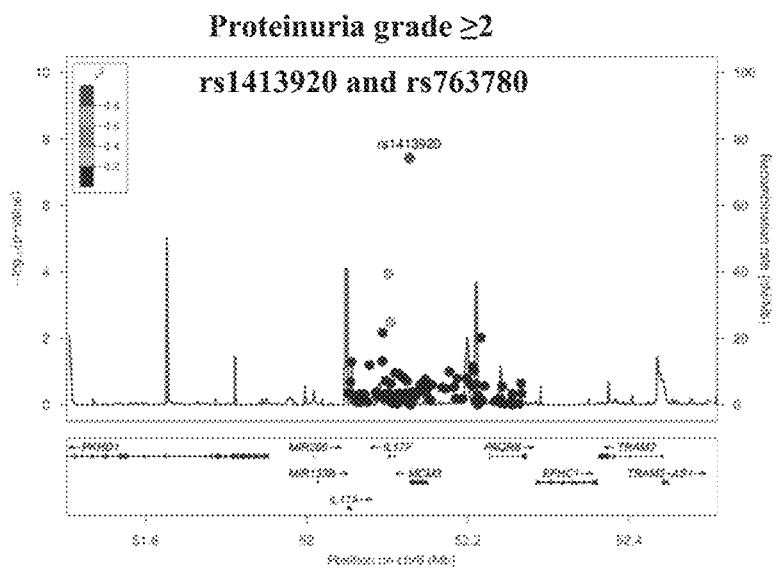
FIG. 8 shows LocusZoom plots using 400 kb window left and right from the IL17F and SLC25A24 limits associated with bevacizumab-induced proteinuria and composite toxicity, respectively, in gene-based analysis of grade ≥3. Each circle represents the p-value for one SNP, with the top SNP shown in purple and the SNPs in the region colored depending on their degree of linkage disequilibrium (LD) ($R^2$). X-axis denotes the position of the SNP in the region on chromosome; Y-axis denotes the p-value of the association. Composite toxicity is defined as the occurrence of either proteinuria or hypertension or both.
Figure 8:
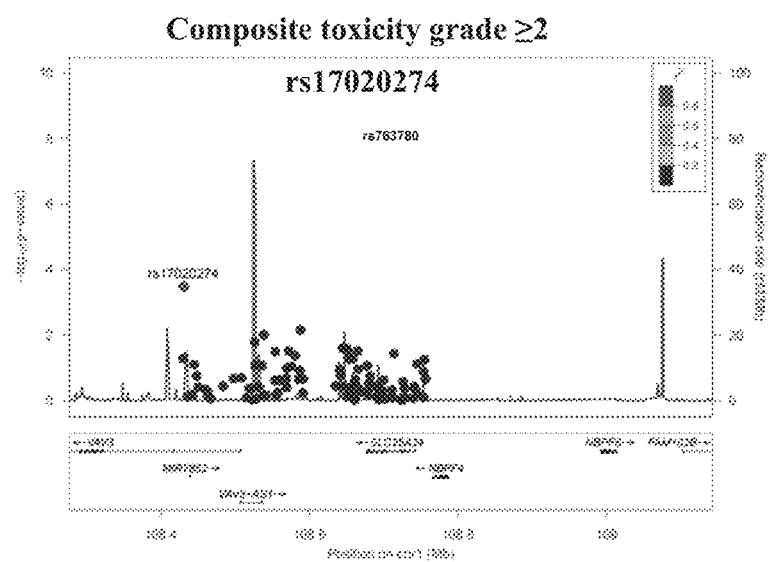

In addition to TRIO, RIPK4 is also another putative new gene for proteinuria. RIPK4 (selected by rs12482855, 4.7 kb 5') encodes a protein kinase that interacts with PKCδ, which is directly involved in renal damage by inducing apoptosis in podocytes and also in tubular cells. Finally, IL17F codes for interleukin-17F (IL-17F) and was selected by the gene based analysis. Using induced-nephrotoxic nephritis mouse model, IL-17F-deficient mice showed less severe nephritis, with lower albuminuria and better renal function, compared with wild-type mice. IL17F was the second most significant gene in our gene-based analysis after C1D, the biology of which cannot be reconciled with kidney damage by bevacizumab. Two less common variants (rs1413920 and rs763780, that did not pass the QC MAF<0.05 in SNP-based analysis) are driven the effect of IL17F in gene-based analysis. The G allele of rs1413920 (A>G, p=1.80×10−7, (ß=2.24, MAF 0.01-0.03) and of rs763780 (A>G, p=1.14× 10−4, (ß=1.41, MAF 0.05) decreased the risk of proteinuria. rs1413920 is intergenic located 1.3 kb 3' from MCM3 and 20 kb from IL17F (FIG. 8), with strong transcription in HUVEC. rs763780 is a non-synonymous variant that alters the histidine to arginine at amino acid 161 (H161R). The A allele (161H) has been associated with an anti-angiogenic effect by inhibition the angiogenesis in human endothelial cells. Inversely, patients who present the G allele (161R) could have an enhanced angiogenesis in these cells and be more prone to bevacizumab effect. The G allele was already associated with a better overall survival in CALGB 80303.

This study also proposes ASPH (selected by rs2350620, intronic, and by the gene-based 30 analysis) as novel candidate of bevacizumab-induced hypertension. ASPH encodes the junctin protein that forms a quaternary complex with triadin, calsequestrin and the ryanodine receptor (RyR), involved in the release of $Ca^{2+}$ from endoplasmic/sarcoplasmic reticulum. rs2350620 reduced the risk of bevacizumab-induced hypertension and has variants in complete LD that are located in regions of DNaseI sensitivity, chromatin state enhancers and enriched for histone modifications in HUVEC and cells from heart tissue group. The G allele of rs2350620 is likely to bind FOXA1 protein (in T-47D), which acts as a transcriptional activator. Therefore, rs2350620 might increase ASPH expression, which might contribute to confer a reduced risk of hypertension. Moreover, one of the variants in LD (rs35026059, →T) has 2c Regulome DB score (Table 14), due to strong evidence of binding of the T allele to CTCF motif, but not in relevant cell lines. CTCF can acts as a transcriptional activator or repressor and insulator.

Because genetic variants might have pleiotropic effects and hypertension and proteinuria share a common pathophysiology, we have also investigated the occurrence of the composite toxicity. rs11662763 had the same direction of effect in three trials, increasing the risk of either proteinuria or hypertension or both. rs1166276 is 33 kb from TIMA, also known as TMEM200C. rs11662763 was shown to be an eQTL for EPB41L3 in the glomerulus, increasing its expression (Table 14). EPB41L3 was also identified as a novel locus for kidney function, after an intronic SNP (rs9962915) was associated with lower glomerular filtration rate in a GWAS meta-analysis of more than 100,000 subjects. Furthermore. SLC25A24 was also selected by the gene-based analysis of the composite toxicity. SLC25A24 encodes a carrier protein that transports ATP-Mg exchanging it for phosphate.

The three most significant variants associated with composite toxicity (rs17084411, rs1927869 and rs17084371) had a p-value of $4.24$-$7.24 \times 10^{-8}$ but only in CALGB 40503.

In conclusion, as a result of this study, DNAH5. TRIO, RIPK4. IL17F. ASPH. TMA, EPB41L3 and SLC25A24, as well as all the top significant SNPs and genes associated with grade ≥3 toxicities are proposed as new genes involved in bevacizumab-induced proteinuria and hypertension. Despite many years of use of bevacizumab, proteinuria and hypertension still represent an obstacle to full delivery of effective therapy, and pose a threat for patients and their quality of life. Because these toxicities are also shared by many other anti-angiogenesis drugs, the availability of these results in the public domain will incentivize the application of these findings to other drugs with a similar mechanism of action.

Example 2

Sorafenib is an orally administered multikinase inhibitor that targets multiple tyrosine kinases involved in angiogenesis, apoptosis, and tumor cell proliferation, including the vascular endothelial growth factor receptor 2 (VEGFR2). It is approved by the U.S. Food and Drug Administration (FDA) for the treatment of several tumors, including metastatic renal cell carcinoma (mRCC), advanced hepatocellular carcinoma and differentiated thyroid cancer. The clear-cell histology of RCC is characterized by overexpression of VEGF, which interacts with VEGFR2 to stimulate tumor angiogenesis. In addition to sorafenib, sunitinib, pazopanib, axitinib, lenvatinib and cabozantinib are also approved for mRCC, sharing the same mechanisms of VEGF-pathway inhibition.

Hypertension is one of the most frequent toxicities induced by sorafenib. A meta-analysis showed a prevalence of sorafenib-induced all-grade and grade ≥3 hypertension of 19.1% and 4.3%, respectively. Patients with mRCC experience higher rates of hypertension when compared to other tumor types (all-grade: 24.9% vs 15.7%, high-grade: 8.6% versus 1.8%). Similar to sorafenib, other VEGF-pathway inhibitors can also induce hypertension, including bevacizumab, sunitinib and pazopanib.

The objective of this study was to identify and validate genetic biomarkers that are predictive of VEGF-pathway inhibitor-induced hypertension using a two-step, discovery-validation approach. Sorafenib-treated patients from the phase 3 Treatment Approaches in Renal Cancer Global Evaluation Trial (TARGET) were used as the discovery set, while a genome-wide association study (GWAS) of bevacizumab-treated patients from four Cancer and Leukemia Group B (CALGB, now Alliance for Clinical Trials in Oncology, Alliance) studies was used as a validation set.

TARGET was a double-blind, randomized, placebo-controlled phase III trial of patients with mRCC treated with 400 mg sorafenib orally twice daily or placebo. Hypertension was recorded according to CTCAE version 3.0. This analysis was conducted in patients who received at least one cycle (28 days) of sorafenib treatment. DNA was obtained from the peripheral blood of 140 patients treated with sorafenib. A total of 1,536 SNPs in 56 candidate genes were genotyped using the Illumina GoldenGate assay. Genes were selected based upon biological function, including genes involved in VEGF-pathway signaling, genes from additional signaling pathways targeted by sorafenib, genes associated with perycite survival, sorafenib disposition and toxicity, and genes associated with RCC prognosis/pathogenesis or general cancer prognosis. SNPs were excluded if the genotype call rate was <97.5% and were selected based upon a MAF >0.05 in Europeans from the 1,000 Genomes Project, and other criteria.

Figure 9A:
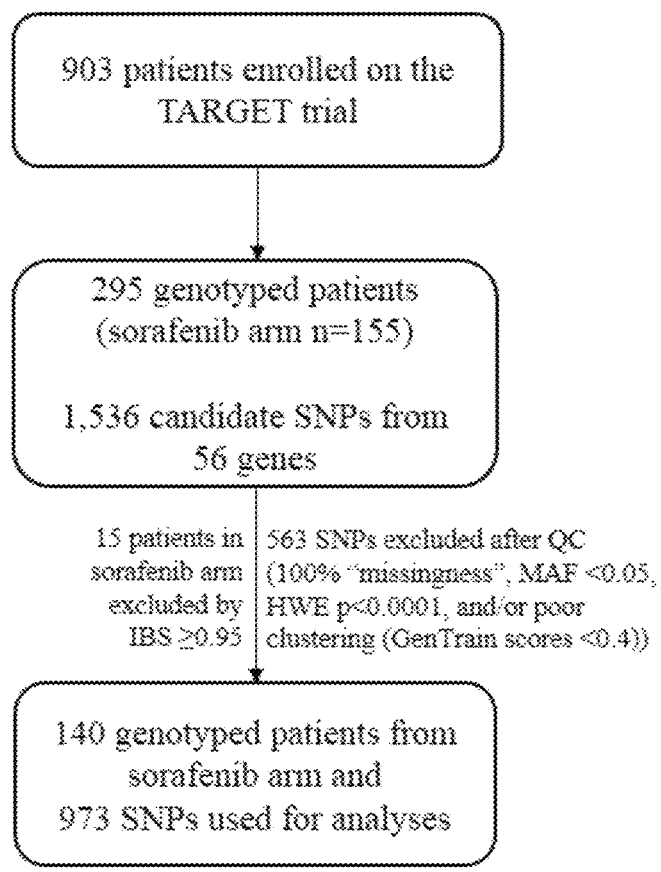
FIG. 9A provides a quality control flowchart for the TARGET study. Abbreviations: IBS: identical by state, MAF: minor allele frequency, HWE: Hardy-Weinberg Equilibrium. QC: quality control, SNP: single nucleotide polymorphism.

A flowchart showing the quality control for the study is provided as FIG. 9A. After quality control, a total of 973 of the 1,536 initial SNPs were used in this study. Tests for association between SNPs and grade ≥2 hypertension were performed in the sorafenib arm by calculating the odds ratio (OR) from a logistic regression analysis, where grade ≥2 hypertension was the binary outcome and SNPs were the independent variables, under an additive model. Age and gender were used as covariates. A p-value≤0.01 was used as a feature selection to identify SNPs for replication in the validation set.

For the validation cohort, the association between SNPs and hypertension was tested in genetic European patients treated with bevacizumab. A GWAS of four randomized phase III clinical trials from the CALGB/Alliance (CALGB 80303, 40503, 90401, and 40502) was used as the validation set. The details of the individual studies are described in Table 15. Patient eligibility, characteristics, stratifications and treatments can be found in the individual publications for all four trials. Blood pressure was measured on day 1 of each cycle in all four trials (and on day 15 in CALGB 80303), and hypertension was recorded according to CTCAE version 3.0. Bevacizumab-induced hypertension was defined as the occurrence of grade ≥2 hypertension after the start of treatment. DNA was obtained from peripheral blood. The genotyping platforms used in each study are described in Table 15. A cause-specific Cox model, where the outcome was defined as the pair of time event and the censoring indicator (defined as the time from the first administration of bevacizumab to the first incidence of the toxicity of interest, or other treatment-terminating events, whichever occurred first, under a competing risk model), was fitted to obtain the estimate of the SNP effect on hypertension in each individual study. The analyses were powered against an additive genetic model. The inverse variance formula was used to combine the SNP effect in each study to obtain the estimate (β) of the SNP-hypertension association. Age and sex were added as covariates in the model. The exponential function of β was used to calculate OR.

The SNPs from the TARGET study (discovery set) associated with grade ≥2 hypertension (p-value≤0.01) were tested in the CALGB GWAS (validation set). If the variant was not genotyped in the validation set, a SNP in high linkage disequilibrium (LD, $R^2$>0.8, Europeans in the 1,000 Genomes Project) according to LDlink, was selected for testing. In the validation set, SNPs with a p-value≤0.01 for association and the same direction of effect (increased or reduced risk) were considered as validated.

Functional annotation of SNPs was performed using the SCAN database. LDlink was used for analyses of LD. RegulomeDB and SNPnexus were used for functional inference. The Genotype-Tissue Expression project (GTEx v7) was used for expression quantitative trait loci (eQTL) analysis. atSNP was also used to quantify impact of SNPs on transcription factor binding.

A total of 140 mRCC patients treated with sorafenib in TARGET were included in this study. The characteristics of the patients, and the prevalence of grade ≥2 hypertension are shown in Table 15. Variants rs444904 (G>A, MAF 0.14) and rs1346563 (C>T, MAF 0.30) were both selected for testing in the validation set based on p<0.01 (Table 16). Both variants were associated with an increased risk of grade ≥2 hypertension (OR=3.88, 95%, CI 1.54-9.81, p=0.0057 and OR=3.50, 95%, CI 1.48-8.24, p=0.0064, respectively) (Table 16).

TABLE 15

Patient characteristics and trials.

| | Discovery set | Validation set (n = 1,041) | | | |
|---|---|---|---|---|---|
| Trial | (n = 140) TARGET | CALGB 80303 n = 154 | CALGB 40503 n = 105 | CALGB 90401 n = 316 | CALGB 40502 n = 466 |
| Hypertension (n, %) | | | | | |
| Grade ≥ 2 | 12 (8.6) | 26 (16.9) | 53 (50.5) | 47 (15.0) | 143 (30.7) |
| Grade 3 | 5 (3.6) | 19 (12.3) | 29 (27.6) | 22 (7.0) | 50 (10.7) |
| Age - Mean (SD) | 59.6 (9.8) | 64.1 (10.2) | 68.4 (8.3) | 56.9 (11.7) | 57.2 (10.7) |
| Gender    Male | 105 | 90 | 0 | 105 | 0 |
|          Female | 35 | 64 | 316 | 0 | 466 |
| Cancer type | Advanced and metastatic renal cell carcinoma | Advanced pancreatic cancer | Hormone receptor-positive advanced-stage breast cancer | Metastatic castration-resistant prostate cancer | Recurrent or metastatic breast cancer |
| Treatment | Sorafenib 400 mg orally twice daily administered in 6-week cycles for the first 24 weeks and in 8-week cycles thereafter | Gemcitabine 1,000 mg/m$^2$ on days 1, 8, and 15 plus either placebo or bevacizumab 10 mg/kg on days 1 and 15 | Letrozole 2.5 mg orally/day plus either placebo or bevacizumab 15 mg/kg every 21 days | Docetaxel 75 mg/m$^2$ in combination with prednisone 5 mg orally on day 1 plus either placebo or bevacizumab 15 mg/kg every 21 days | Paclitaxel 90 mg/m$^2$ or nab-paclitaxel 150 mg/m$^2$ or ixabepilone 16 mg/m$^2$ on days 1, 8, and 15 plus bevacizumab 10 mg/kg on days 1 and 15 |
| Genotyping platform | Illumina GoldenGate | Illumina HumanHap550-Quad | Illumina Human OmniExpressExome-8 | Illumina HumanHap610-Quad | Illumina Human OmniExpressExome-8 |

TABLE 16

SNPs associated with sorafenib-induced hypertension in the TARGET study. The SNPs in bold are the ones tested in the validation (p ≤ 0.01). Results are shown for associations with p-value < 0.05, adjusted for age and gender. Chr: Chromosome, NA: Intergenic SNP, MAF: minor allele frequency. OR: odds ratio, SNP: single nucleotide polymorphism.

| SNP | Chr | Gene | Feature | 5' Flanking gene | 3' Flanking gene | Base change | MAF | OR (95% CI) | p-value |
|---|---|---|---|---|---|---|---|---|---|
| rs444904 | 17 | PIK3R5 | Intron | PIK3R6 | LOC100129978 | G > A | 0.14 | 3.88 (1.54-9.81) | 0.0057 |
| rs1346563 | 16 | ADAMTS18 | Intron | VN2R10P | NUDT7 | C > T | 0.30 | 3.50 (1.48-8.24) | 0.0064 |
| rs2330951 | 7 | EGFR | Intron | LOC643168 | LOC100133256 | A > C | 0.23 | 4.23 (1.78-10.05) | 0.0118 |
| rs11125039 | 2 | PRKCE | Intron | SRBD1 | EPAS1 | A > G | 0.24 | 3.51 (1.49-8.25) | 0.0122 |
| rs56367980 | 7 | EGFR | Intron | LOC643168 | LOC100133256 | G > A | 0.12 | 3.33 (1.27-8.76) | 0.0188 |
| rs16917099 | 10 | NA | NA | R7KN2 | ZNF365 | T > C | 0.13 | 3.58 (1.37-9.35) | 0.0207 |
| rs2740761 | 7 | EGFR | Intron | LOC643168 | LOC100130121 | C > T | 0.18 | 3.46 (1.39-8.59) | 0.0222 |
| rs3754565 | 2 | PRKCE | Intron | SRBD1 | EPAS1 | G > T | 0.11 | 4.07 (1.48-11.19) | 0.0222 |
| rs3754566 | 2 | PRKCE | Intron | SRBD1 | EPAS1 | G > A | 0.11 | 4.07 (1.48-11.19) | 0.0222 |
| rs4596024 | 2 | PRKCE | Intron | SRBD1 | EPAS1 | A > G | 0.11 | 4.07 (1.48-11.19) | 0.0222 |
| rs251312 | 5 | NA | NA | NLN | ERBB2IP | C > T | 0.48 | 3.26 (1.31-8.14) | 0.0223 |
| rs12366035 | 11 | VEGFB | reference | DNAJC4 | FKBP2 | C > T | 0.34 | 3.09 (1.31-7.24) | 0.0227 |
| rs35539903 | 4 | KDR | Intron | LOC100132311 | LOC100128865 | A > G | 0.15 | 3.44 (1.33-8.90) | 0.0254 |
| rs35597368 | 4 | PDGFRA | Missense | LOC442108 | KIT | T > C | 0.10 | 3.69 (1.32-10.29) | 0.0256 |
| rs3797102 | 5 | FLT4 | Intron | SCGB3A1 | OR2AI1P | T > C | 0.42 | 2.78 (1.17-6.59) | 0.0262 |
| rs3804158 | 4 | NUDT6/FGF2 | Intron/UTR-3 | BBS12 | SPATA5 | A > G | 0.43 | 0.30 (0.11-0.84) | 0.0272 |
| rs45492196 | 1 | PIK3C2B | Reference | PPP1R15B | LOC100130573 | G > A | 0.05 | 3.68 (1.07-12.60) | 0.0279 |
| rs7187665 | 16 | WWOX | Intron | LOC100131126 | LOC645947 | T > C | 0.45 | 0.34 (0.13-0.89) | 0.0298 |
| rs11980616 | 7 | GNAI1 | Intron | LOC100128030 | GNAT3 | A > G | 0.13 | 3.24 (1.24-8.50) | 0.0322 |
| rs659441 | 3 | NA | NA | UMPS | ITGB5 | G > C | 0.40 | 0.28 (0.11-0.73) | 0.0327 |
| rs315498 | 17 | NA | NA | LOC100130112 | C17orf79 | T > C | 0.33 | 0.24 (0.07-0.84) | 0.0335 |
| rs41348645 | 1 | FGF2/NUDT6 | UTR-3/Intron | BBS12 | SPATA5 | G > A | 0.41 | 0.31 (0.11-0.87) | 0.0350 |
| rs3950680 | 11 | PIK3C2A | Intron | RPS13 | LOC732199 | G > A | 0.36 | 2.61 (1.12-6.06) | 0.0385 |
| rs6743202 | 2 | TGFA | Intron | LOC100128042 | ADD2 | A > T | 0.32 | 0.27 (0.08-0.93) | 0.0421 |

TABLE 16-continued

SNPs associated with sorafenib-induced hypertension in the TARGET study.
The SNPs in bold are the ones tested in the validation (p ≤ 0.01). Results are shown for
associations with p-value < 0.05, adjusted for age and gender. Chr: Chromosome, NA:
Intergenic SNP, MAF: minor allele frequency. OR: odds ratio, SNP: single nucleotide
polymorphism.

| SNP | Chr | Gene | Feature | 5' Flanking gene | 3' Flanking gene | Base change | MAF | OR (95% CI) | p-value |
|---|---|---|---|---|---|---|---|---|---|
| rs11644322 | 16 | WWOX | Intron | LOC645947 | LOC729251 | C > T | 0.21 | 2.66 (1.10-6.42) | 0.0431 |
| rs446086 | 2 | TGF4 | Intron | LOC100128042 | ADD2 | C > A | 0.23 | 0.19 (0.04-0.84) | 0.0431 |
| rs3804452 | 6 | MAPK14 | utr-3 | SLC26A8 | MAPK13 | C > T | 0.11 | 2.86 (1.04-7.84) | 0.0439 |
| rs2293348 | 7 | EGFR | Intron | LOC100133256 | LOC100130121 | G > A | 0.36 | 0.32 (0.11-0.96) | 0.0466 |
| rs16947173 | 16 | WWOX | Intron | LOC100131126 | LOC645947 | A > G | 0.20 | 0.12 (0.02-0.93) | 0.0480 |
| rs11644207 | 16 | WWOX | Intron | LOC100131126 | LOC645947 | T > G | 0.24 | 0.22 (0.05-0.64) | 0.0484 |
| rs8193040 | 6 | NA | NA | IL17A | LOC730141 | T > G | 0.48 | 0.39 (0.16-0.97) | 0.0499 |

Figure 9B:
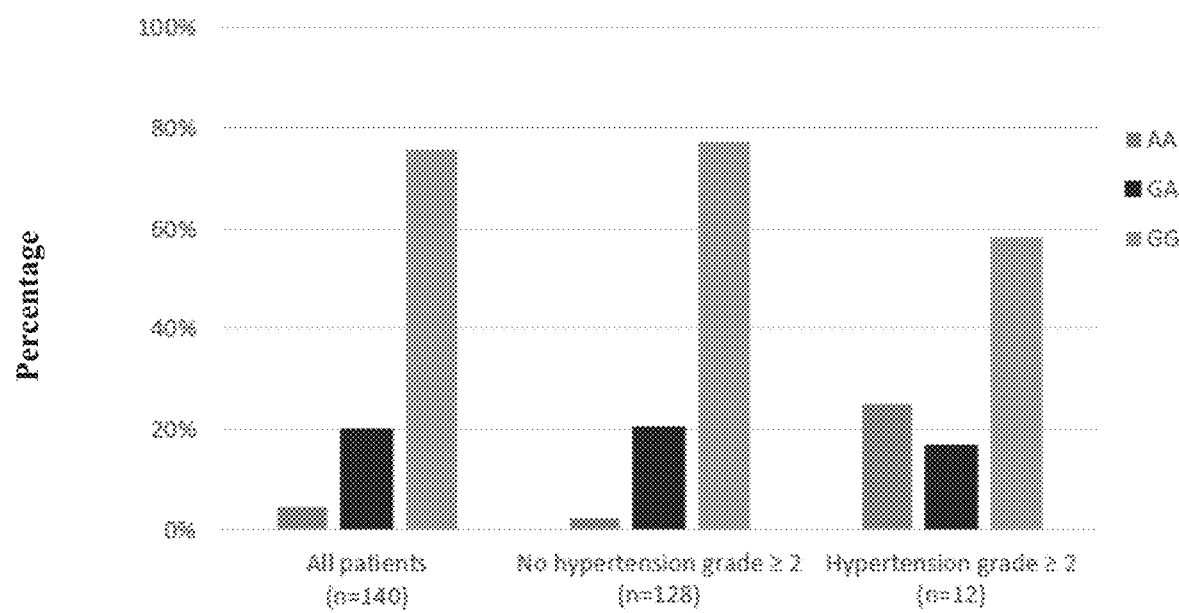
FIG. 9B is a bar graph showing the frequency of rs444904 AA, GA, and GG genotypes associated with sorafenib-induced hypertension.
Figure 10:
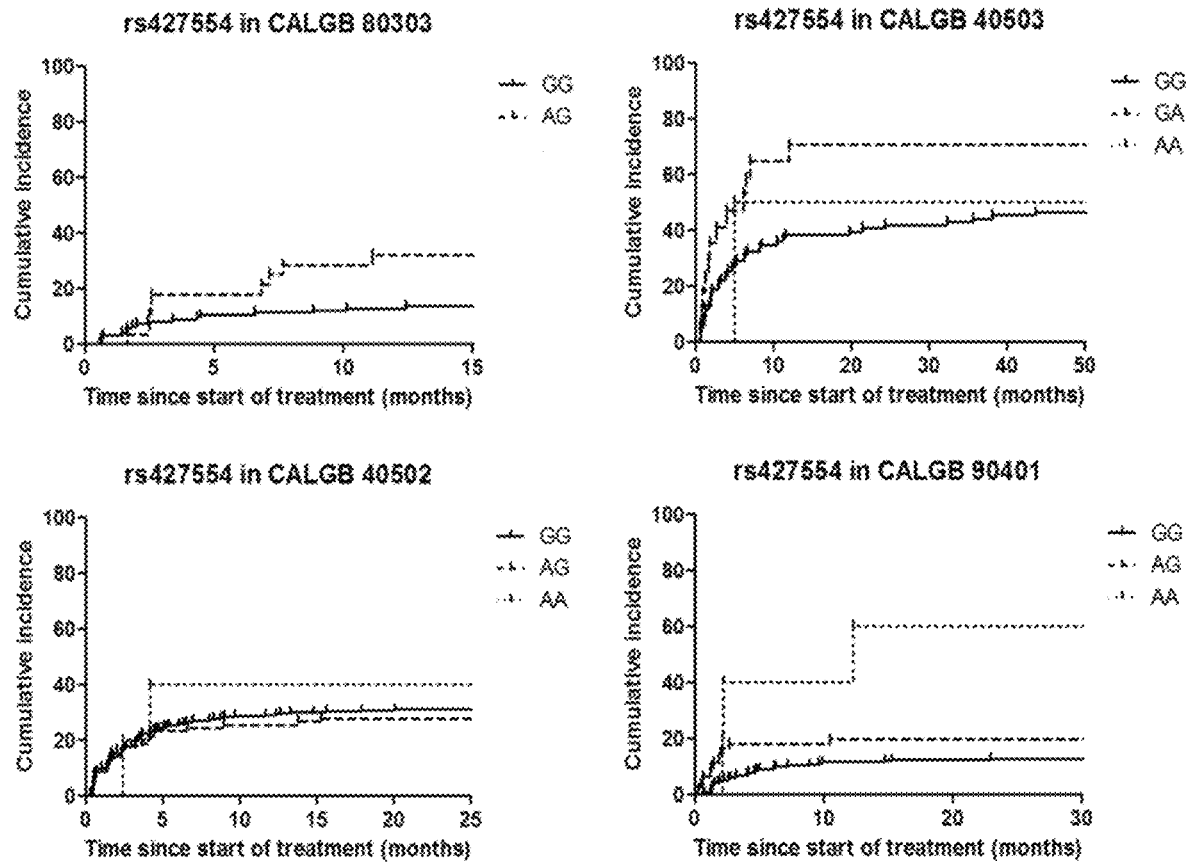
FIG. 10 shows the effect of genotypes of rs427554 associated with bevacizumab-induced hypertension.

A total of 1,041 patients treated with bevacizumab in the CALGB trials were included in this study. Because neither rs444904 nor rs1346563 were genotyped on the GWAS platforms, rs427554 (G>A, MAF 0.10-0.11 in complete LD $R^2=1.0$ with rs444904) and rs4888628 (A>G, MAF 0.26-0.29, LD $R^2=0.96$ with rs1346563) were used as proxies. Variant rs427554 was associated with an increased risk of hypertension (p=0.008, β=0.33, OR=1.39, CI 1.09-1.78) (FIG. 10). This result is consistent with the discovery set, where the frequencies of patients without hypertension with the AA and GA genotypes are 2.3% and 20.3%, respectively, versus 25.0% and 16.7% in patients with hypertension (FIG. 9B).

Table 17 provides bioinformatic analyses for both rs444904 and rs427554. There is evidence in GTex that rs444904 and rs427554 are both eQTLs for PIK3R5 in whole blood, with the A allele of both variants associated with decreased gene expression. DNase 1 hypersensitivity peaks indicate that both rs444904 and rs427554 are located in areas of open chromatin, thus permitting selective binding of transcription factors, while ChIP-seq revealed that the two SNPs are potential loci for binding with putative transcription factors. RegulomeDB, utilizing data from the ENCODE-motif database, indicates that rs427554 is located in the binding motif for the SP transcription factor. Additional data from the JASPAR database (using atSNP) predicts preferential binding of SP1 to the G allele of rs444904 rather than the A allele (p=0.01 for the G allele, and p=0.30 for the A allele). The majority of non-coding variation scores provided by SNPnexus shows a higher evidence of regulatory function of rs427554 compared to rs444904 (Table 17).

TABLE 17

Bioinformatic analysis of rs444904 and rs427554. The RegulomeDB score represents the evidence that a SNP has a regulatory function
(1-strong evidence, 6-weak evidence). SNPnexus non-coding variation scoring
predicts functional impact of non-coding SNPs using 8 non-coding
SNP scoring algorithms. Higher scores in CADD (range 0-99), FitCons (range
0-1), Eigen (range 0-1), FATHMM (range 0-1), GWAVA (3 scores,
range 0-1), funSeq2 (range 0-5) ReMM (range 0-1) mean that the SNP is
most likely to be functional/deleterious, while a lower score in DeepSEA
(range 0-1) means that the SNP is most likely to be functional/deleterious. eQTL:
expression quantitative trait loci, NES: normalized effect siz

| SNP (Regulome DB score) | eQTL (GTEx) | RegulomeDB/ENCODE | | | SNPnextus non-coding variation rankings | | | | | | | |
|---|---|---|---|---|---|---|---|---|---|---|---|---|
| | | ChIP-seq | DNase I Sensitivity region | Motif | CADD | FitCons | EIGEN | FATHMM | GWAVA | DeepSEA | FlanSeq2 | ReMM |
| rs444904 (4) | Whole blood (p = 2.7 × $10^{-12}$, NES = −0.16) | POLR2A, RELA, EP300, TCF12, EBF1, IKZF2, IKZF1, TAF1, MEF2C, TBL1XR1, FOXM1, ZNF687, TARDBP, NFATC1, MTA3, ZEB1, MTA2, YY1, CBFB, RUNX3, GATAD2B, CHD2, ELF1, BCLAF1, ETS1, ARNT, EGR1, IRF4, PBX3, TCF7, NFIC, BHLHE40, POU2F2, CREM, BCL3, MEF2A, ETV6. | Yes | — | 0.775 | 0.102 | 0.176 | 0.110 | 0.38/ 0.48/ 0.44 | 0.035 | 1.560 | 0.019 |
| rs427554 (2c) | Whole blood (p = | POLR2A, GATA1, SPI1, IKZF1, IKZF2, ZBTB40, | Yes | SP1 | 2.641 | 0.102 | 0.614 | 0.141 | 0.45/ 0.53/ 0.41 | 0.118 | 1.560 | 0.122 |

TABLE 17-continued

Bioinformatic analysis of rs444904 and rs427554. The RegulomeDB score represents the evidence that a SNP has a regulatory function (1-strong evidence, 6-weak evidence). SNPnexus non-coding variation scoring predicts functional impact of non-coding SNPs using 8 non-coding SNP scoring algorithms. Higher scores in CADD (range 0-99), FitCons (range 0-1), Eigen (range 0-1), FATHMM (range 0-1), GWAVA (3 scores, range 0-1), funSeq2 (range 0-5) ReMM (range 0-1) mean that the SNP is most likely to be functional/deleterious, while a lower score in DeepSEA (range 0-1) means that the SNP is most likely to be functional/deleterious. eQTL: expression quantitative trait loci, NES: normalized effect siz

| SNP (Regulome DB score) | eQTL (GTEx) | RegulomeDB/ENCODE | | | | | | | | | | |
|---|---|---|---|---|---|---|---|---|---|---|---|---|
| | | ChIP-seq | DNase I Sensitivity region | Motif | CADD | FitCons | EIGEN | FATHMM | GWAVA | DeepSEA | FlanSeq2 | ReMM |
| | $9.4 \times 10^{-13}$, NES = -0.17) | TCF7, MLLT1, EP300, ELF1, LEF1, PAX5, BCLAF1, DPF2, TRIM22, RELB, ARNT, MXI1, FOXM1, NR2F1, SMARCA5, ZMYM3, SP1, MEF2A, RBM25, TARDBP, NBN, TAF1, BHLHE40, BCL3, RUNX3, KLF5, BATF, ETV6, NFATC3, ZFHX2, ZBTB33, ETS1, IRF4, NKRF, VEZF1, ZBED1, SKIL, ZNF207, CREM, ETV1, CBFB, HDGF, TBX21, ARID3A, BCL11A, POU2F2, EGR1, COMMD3-BMI1, BMI1, ATF2, REST, RFX1, MAZ, EBF1, ZNF143, EED. | | | | | | | | | | |

The results of the study identified a common intronic SNP (rs444904) located in PIK3R5 that increased the risk of grade ≥2 hypertension in patients treated with the VEGF-pathway inhibitors sorafenib and bevacizumab.

Bioinformatic analyses of rs444904 and rs427554 in PIK3R5 showed that both SNPs are located in a region that binds numerous transcription factors, indicating a potential regulatory role for each SNP in gene expression (Table 17). rs427554 is located within a binding motif for SP1, and rs444904 may alter an SP binding motif as described above. Considering that both SNPs are in complete LD with each other, it is plausible to suggest that the G allele of both variants ma increase binding of the SP1 transcription factor to DNA.

Figure 11:
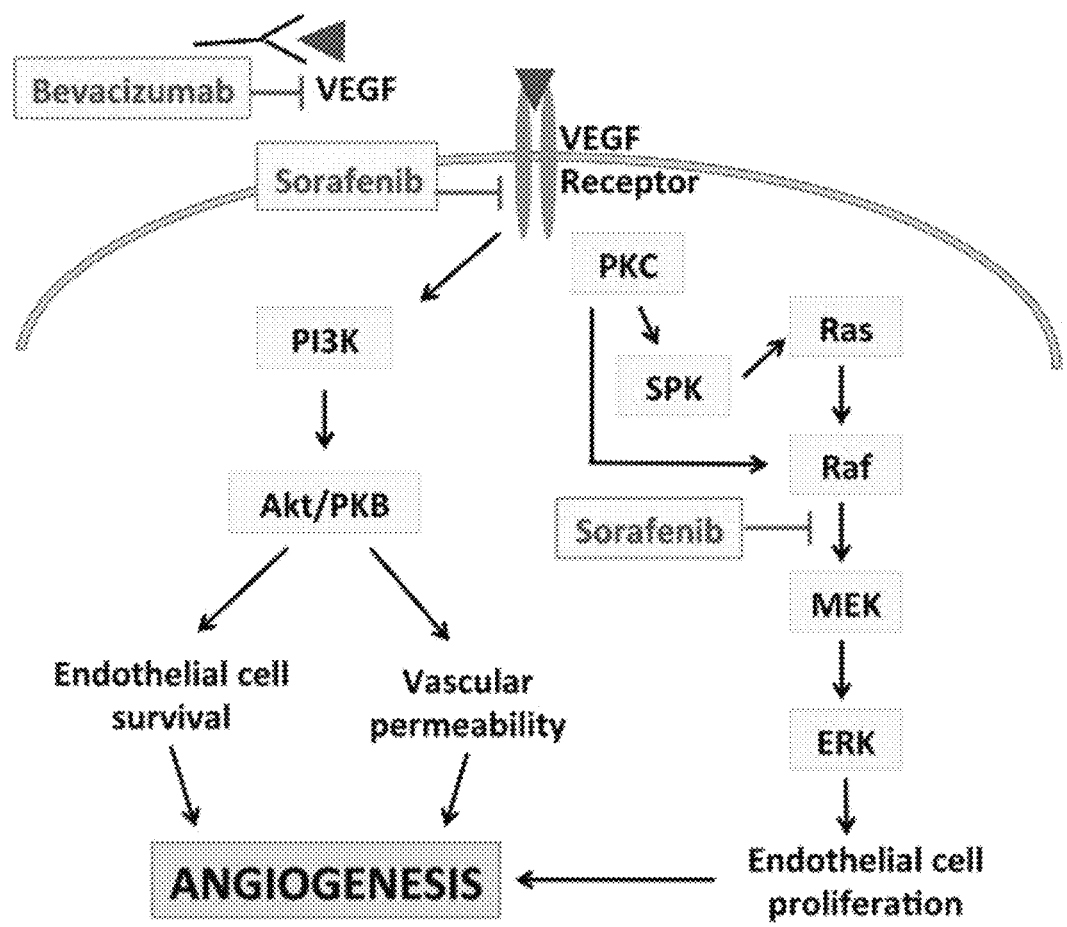
FIG. 11 is a graphic showing the mechanism of action of sorafenib and bevacizumab[65].
Figure 12:
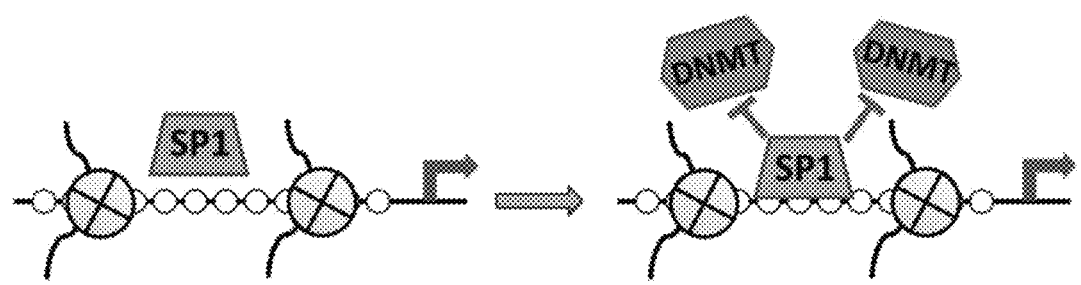
FIG. 12 is a graphic showing the function of the SP1 transcription factor.[67] DNMT: DNA methyl transferase.

In embodiments, the data provided herein proposes a novel mechanism through which rs444904 and rs427554 regulate the expression of PIK3R5 and mediate hypertension induced by sorafenib, bevacizumab, or other VEGF pathway inhibitors. The G allele of both SNPs allows the binding of SP1, which, by inhibiting the action of DNMT, activates PIK3R5 transcription (FIG. 12). Conversely, the A allele decreases the binding of the SP1, which allows DNA methylation by DNMT, downregulating PIK3R5 transcription, (FIGS. 11 and 12).

The validation of rs444904 in an external dataset utilizing a different VEGF-pathway inhibitor (such as bevacizumab) provides additional evidence of clinical applicability of biomarkers of hypertension induced by different anti-angiogenic drugs. Taken together, the study provides evidence for rs444904 in PIK3R5 as a biomarker of hypertension induced by sorafenib, bevacizumab, and other VEGF pathway inhibitors. Common genetic variants in PIK3R5, rs444904 and rs427554 in complete LD with each other ($R^2$=1.00), increased the risk of sorafenib and bevacizumab-induced hypertension in two independent datasets, and ma be used as predictor biomarkers of hypertension induced by the whole class of VEGF-pathway inhibitors Example 3

Two SNPs associated with grade ≥2 hypertension in Example 1 above, rs2350620 and rs6770663, were evaluated for replication in European ancestry patients from ECOG-ACRIN E5103. A summary of the cohort evaluated is provided as Table 18.

TABLE 18

GWAS patients of European ancestry treated with bevacizumab from ECOG-ACRIN E5103. ECOG Eastern Cooperative Oncology Group, ACRIN American College of Radiology Imaging Network, SBP systolic blood pressure, SD standard deviation.

|  | Validation set ECOG-5103 | |
| --- | --- | --- |
|  | SBP ≥ 160 mm Hg<br>n = 582 | Grade ≥ 3<br>n = 564 |
| Hypertension* (n, %) | 195 (33.5) | 177 (37.8) |
| Age - Mean (SD) | 55.3 | 55.1 |
| Gender    Male | 0 | 0 |
|               Female | 582 | 564 |
| Cancer type | Breast cancer | |
| Treatment | Doxorubicin (60 mg/m$^2$) and cyclophosphamide (600 mg/m$^2$) for four cycles, followed by 12 weeks (4 cycles) of weekly paclitaxel. Concurrently to chemotherapy, patients received either placebo (arm A) or bevacizumab 10-15 mg/kg (arms B and C). Patients in arm C continued bevacizumab monotherapy (15 mg/kg every 3 weeks) for an additional 10 cycles. | |
| Genotype platform | Illumina Human Omni1-Quad and Illumina Human OmniExpress | |

Variants rs2350620 and rs6770663 were selected because they were among the top ten SNPs that also had a concordant effect in three out of four studies (p-value<0.05 for each study) (Table 5). FIG. 13 shows the cumulative incidence of grade ≥2 hypertension for rs2350620 and rs6770663. Table 19 shows the results of the SNPs tested for replication. The G allele of rs6770663 (A>G, MAF 0.08-0.09) was associated with a higher risk of SBP ≥160 mm Hg (odds ratio. OR=1.76, p-value=0.005) in ECOG-ACRIN E5103 (Table 20), similar to the increased risk of grade ≥2 hypertension in our study ($\beta$=0.57, p-value=4.79×10$^{-6}$) (Table 5).

TABLE 19

Top two SNPs ranked by unadjusted p-value with a concordant effect in three out of four studies for grade ≥ 2 hypertension in the CALGB trials tested for replication in the ECOG-ACRIN E5103 GWAS. ECOG Eastern Cooperative Oncology Group, ACRIN American College of Radiology Imaging Network, MAF minor allele frequency, SBP systolic blood pressure, OR odds ratio. The row in bold is the one SNP that replicated in ECOG-ACRIN E5103.

| SNP | Risk allele | MAF ECOG-ACRIN E5103 | OR (SBP ≥ 160 mm Hg) | p-value (SBP ≥ 160 mm Hg) |
| --- | --- | --- | --- | --- |
| Grade ≥ 2 | | | | |
| rs2350620 | T | 0.33 | 1.14 | 0.235 |
| rs6770663 | G | 0.10 | 1.76 | 0.005 |

TABLE 20

Frequency of rs6770663 AA, GA, and GG genotypes associated with bevacizumab-induced hypertension in ECOG-ACRIN E5103. ECOG Eastern Cooperative Oncology Group, ACRIN American College of Radiology Imaging Network, SBP systolic blood pressure.

|  | rs6770663 | | |
| --- | --- | --- | --- |
|  | NA | GA | GG |
| SBP ≥ 160 (cases, n = 195) | 147 (75.4%) | 45 (23.1%) | 3 (1.5%) |
| No hypertension (controls, n = 387) | 327 (84.5%) | 59 (15.2%) | 1 (0.3%) |

Table 21 shows published studies that reported associations between 37 SNPs and bevacizumab-induced hypertension with p-value<0.05. Out of 37 SNPs, 26 of them had either the same SNP or a proxy for it. Three of the 26 SNPs were associated with composite toxicity (but with neither hypertension nor proteinuria) with the same direction of the effect (either reduced or increased risk) in the herein provided study (Table 22).

TABLE 21

SNPs previously associated with bevacizumab-induced hypertension in the literature. VEGF vascular endothelial growth factor, NO nitric oxide, CTCAE Common Toxicity Criteria for Adverse Events, FOLFIRI 5-fluorouracil (5-FU) + irinotecan, FOLFOX 5-EU + oxaliplatin, XELOX capecitabine + oxaliplatin, SBP systolic blood pressure. Not on platform means that either the reported SNP or SNPs in high LD ($R^2$ > 0.8) were not on the genotype platforms in our study.

| Reference | SNP selection method | Genes associated | Hypertension phenotype | Concomitant treatment | Number of bevacizumab treated patients | Clinical trial discovery set |
| --- | --- | --- | --- | --- | --- | --- |
| Li et al. (2018) | Sequencing of 174 candidate genes (VEGF signaling, endothelial cell biology, NO signaling or essential hypertension genes) | HSP90AB1 PRKCA CACNA1C HSP90AB1 CCL2 PDE3B NOSIP FLT4 | Grade ≥ 3 (CTCAE v3.0) | FOLFIRI or FOLFOX6 | 61 | Discovery: CALGB 80405 Validation: CALGE3 40502, CALGB 90401, and ECOG-5103 |
| Frey et al. (2017) | 103 SNPs in 11 genes (VEGF and essential | GRK4 KLKB1 VEGF WNK1 | Grade ≥ 1 (CTCAE v3.0) | Cisplatin and taxotere/ doxorubicin, and cyclophosphamide/ | 114 | 6 clinical trials at Memorial Sloan- |

TABLE 21-continued

SNPs previously associated with bevacizumab-induced hypertension in the literature. VEGF vascular endothelial growth factor, NO nitric oxide, CTCAE Common Toxicity Criteria for Adverse Events, FOLFIRI 5-fluorouracil (5-FU) + irinotecan, FOLFOX 5-EU + oxaliplatin, XELOX capecitabine + oxaliplatin, SBP systolic blood pressure. Not on platform means that either the reported SNP or SNPs in high LD ($R^2 > 0.8$) were not on the genotype platforms in our study.

| Reference | SNP selection method | Genes associated | Hypertension phenotype | Concomitant treatment | Number of bevacizumab treated patients | Clinical trial discovery set |
|---|---|---|---|---|---|---|
| | hypertension associated genes) | | | paclitaxel and cisplatin/erlotinib/ letrozole/S-1 and oxaliplatin | | Kettering Cancer Center |
| Berger et al. (2017) | 12 SNPs in 8 autophagy-related genes | FIP 200 ATG13 | Grade ≥ 2 (CTCAE v3.0) | FOLFIRI | 219 | TRIBE |
| Gampenrieder et al. (2017) | 10 SNPs in VEGFA, FLT1, STK39, EDN1, and UMOD | VEGF4 | Grade ≥ 3 | Capecitabine or taxane | 163 | Retrospective selection of patients from hospital records |
| Sibertin-Blanc et al. (2015) | 10 SNPs in VEGF4, FLT1, KDR, and HIF1A | VEGF4 | Grade ≥ 1 (CTCAE v3.0) | 5-FU based chemotherapy (the majority FOLFIRI) | 89 | Retrospective selection of patients from hospital records |
| Lambrechts et al. (2014) | 236 SNPs in 14 genes (VEGF and essential hypertension associated genes). | EGLN3 KDR EPAS1 FLT1 FLT4 EGF WNK1 | Grade ≥ 1 (CTCAE v3.0) | XELOX or FOLFOX4/ gemcitabine and erlotinib/cisplatin and gemcitabine/ interferon α-2a/ docetaxel/ capecitabine and cisplatin | 807 | NO16966, AViTA, AVAiL, AVOREN, AVADO, AVAGAST |
| Morita et al. (2013) | 5 SNPs in VEGF4 | VEGF4 | Grade ≥ 2 (CTCAE v4.0) | FOLFIRI or FOLFOX6 or 5-FU or XELOX | 60 | Retrospective selection of patients from hospital records |
| Etienne-Grimaldi et al. (2011) | 5 SNPs in VEGF4 | VEGF4 | Grade ≥ 1 (CTCAE v3.0) | Paclitaxel or docetaxel or navelbine | 137 | ATHENA |
| Schneider et al. (2008) | 7 SNPs in VEGF and KDR | VEGF4 | Grade ≥ 3 (CTCAE v2.0) | Paclitaxel | 180 | ECOG-2100 |

TABLE 22

Previously reported variants associated with bevacizumab-induced hypertension. The associations with a p-value < 0.05 and same direction of effect for grade ≥ 2 composite toxicity in our study are shown. Proxy rs9900205 was genotyped only in CALGB 90401, and proxy rs833070 was genotyped only in CALGB 40503.

| SNP (literature) | Region | Base change | Risk (literature) | Risk (our study) |
|---|---|---|---|---|
| rs59189065 | PRKCA intronic | G > A | Increased grade ≥ 3 hypertension in CALGB 80405 | Proxy rs9900205 ($R^2 = 0.82$) Increased grade ≥ 2 composite toxicity in CALGB 90401 ($\beta = 0.49$, p = 0.02) |
| rs9381299 | 3 kb 5' from HSP90AB1 and 10 kb 3' from of SLC29A1 | T > C | Increased grade ≥ 3 hypertension in CALGB 80405 (discovery set), and in CALGB 40502 and ECOG 5103 (validation sets), but not in CALGB 90401 | Increased grade ≥ 2 composite toxicity in CALGB 80303, 40503, and 90401 ($\beta = 0.39$, p = 0.02) |

TABLE 22-continued

Previously reported variants associated with bevacizumab-induced hypertension.
The associations with a p-value < 0.05 and same direction of effect for grade ≥ 2
composite toxicity in our study are shown. Proxy rs9900205 was genotyped only
in CALGB 90401, and proxy rs833070 was genotyped only in CALGB 40503.

| SNP (literature) | Region | Base change | Risk (literature) | Risk (our study) |
|---|---|---|---|---|
| rs833061 | 5' of VEGFA | C > T | Decreased grade ≥ 2 (7) and grade ≥ 3 (6) hypertension | Proxy rs833070 ($R^2$ = 0.98) Decreased grade ≥ 2 composite toxicity in CALGB 40503 ($\beta$ = −0.44, p = 0.03) |

Taken together, the studies provided herein were the largest genome-wide analysis of bevacizumab-induced hypertension and proteinuria, which included 1,041 cancer patients from four randomized phase III clinical trials. The large sample size, randomized design, and standardized collection of the phenotypic and genotypic data facilitated the testing of genetic associations of drug response in patients. The use of genomic data from different studies allowed the evaluation of concordance of the effect, increasing the validity of these associations. For the first time, a variant in KCNAB1 for bevacizumab-induced hypertension was identified from an independent, external dataset provided and provided evidence of clinical actionability. Accordingly, the results of the study provide a critical identification of SNPs and gene variants that can be used to provide improved and safer methods for treating patients with bevacizumab or other VEGF pathway inhibitor drugs. For example, patients indicated for or being treated with an inhibitor of the VEGF pathway (e.g., bevacizumab) can be assessed for the presence of rs6770663, and treatment modified accordingly (e.g., pre-treatment with anti-hypertensive supportive therapy and/or dose modification and/or delivery of an alternative to the VEGF pathway inhibitor).

Importantly, the study established replication of the effect of rs6770663 (A>G), intronic in KCNAB1, as a variant for the risk of hypertension. Similar to the CALGB studies where it increased the risk of grade ≥2 hypertension, rs6770663 was also associated with a higher risk of SBP ≥160 mm Hg in ECOG-ACRIN E5103 (Table 14, FIG. 13).

In addition to KCNAB1, the studies provided herein identified other new candidate genes associated with VEGF pathway inhibitor-induced toxicity. This selection was based upon the strength and probability of the associations, the biological plausibility of gene, and the bioinformatic prediction of the SNP effect on the gene function or expression. Under this set of evaluations, ASPH was also identified as a new gene for VEGF pathway inhibitor-induced hypertension, based upon the signal of intronic rs2350620 (FIG. 13). Variant rs2350620 (A>G) reduced the risk of bevacizumab-induced hypertension and has SNPs in complete LD located in regulatory regions in HUVEC, aorta and the heart (Table 14). Also, rs2350620 is in complete LD with a deletion in ASPH (rs35026059, T>−), and CTCF can act as an insulator of the expression of ASPH because of binding in the presence the T allele (Table 14).

Despite many years of use of bevacizumab, hypertension and proteinuria still represent an obstacle to full delivery of effective therapy and pose a threat for patients and their quality of life. The studies provided herein identified rs6770663 in KCNAB1 as a novel marker of bevacizumab-induced hypertension that can be used to guide decisions on the risk assessment of patients treated with any VEGF pathway inhibitor. Other novel candidate genes are ASPH for hypertension, and TRIO and DNAH5 for proteinuria. Because these toxicities are also shared by many other antiangiogenesis drugs, the availability of these results in the public domain will expedite their translation into clinical application for other drugs with a similar mechanism of action.

In summary, the results of the studies provided herein showed that variant rs6770663 in KCNAB1 was associated with an increased the risk of hypertension (p=4.79×10$^{-6}$). This was validated in ECOG-ACRIN E5103 (p=0.005). Variant rs2350620 in APSH was associated with a decreased risk of hypertension (p=1.44×10$^{-6}$) and rs339947 (between DNAH5 and TRIO) was associated with an increased risk of proteinuria (p=7.66×10$^{-8}$). Three variants previously associated with bevacizumab-induced hypertension were associated with composite toxicity (but not hypertension) with the same direction of effect in our study. To the knowledge of the inventors, this was the largest GWAS of bevacizumab-treated patients from randomized trials. The study has identified new genes involved in bevacizumab-induced hypertension and proteinuria. Genetic variation in KCNAB1 can be regarded to as a new validated biomarker to predict the risk of bevacizumab-induced hypertension.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Various modifications and variations of the described compositions, methods, and uses of the technology will be apparent to those skilled in the art without departing from the scope and spirit of the technology as described. Although the technology has been described in connection with specific exemplary embodiments, it should be understood that the disclosure as claimed should not be unduly limited to such specific embodiments. Indeed, various modifications of the described modes for carrying out the disclosure that are obvious to those skilled in pharmacology, biochemistry, medical science, or related fields are intended to be within the scope of the following claims.

REFERENCES

1. F Ferrara N, Adamis A P. Ten years of anti-vascular endothelial growth factor therapy. *Nat Rev Drug Discov* 2016, 15, 385-403.

2. Ellis L M, Kirkpatrick P. Bevacizumab. *Nat Rev Drug Discov* 2005, 3, 995-996.
3. Zhu X, Wu S, Dahut W L, Parikh C R. Risks of Proteinuria and Hypertension With Bevacizumab, an Antibody Against Vascular Endothelial Growth Factor: Systematic Review and Meta-Analysis. *Am J Kidney Dis* 2007, 49, 186-19.
4. Izzedine H, Ederhy S, Goldwasser F, Soria J C, Milano G, Cohen A et al. Management of hypertension in angiogenesis inhibitor-treated patients. *Ann Oncol* 2009, 20, 807-815.
5. Hurwitz H, Fehrenbacher L, Novotny W, Cartwright T. Hainsworth J, Heim W et al. Bevacizumab plus Irinotecan, Fluorouracil, and Leucovorin for Metastatic Colorectal Cancer. *N Engl J Med* 2004, 350, 2335-2342.
6. Syrigos K N, Karapanagiotou E, Boura P, Manegold C, Harrington K. Bevacizumab-induced hypertension: pathogenesis and management. *Biodrugs* 2011, 25, 159-169.
7. Schneider B P, Wang M. Radovich M, Sledge G W, Badve S, Thor A et al. Association of vascular endothelial growth factor and vascular endothelial growth factor receptor-2 genetic polymorphisms with outcome in a trial of paclitaxel compared with paclitaxel plus bevacizumab in advanced breast cancer: ECOG 2100. *J Chn Oncol* 2008, 28, 4672-4678.
8. Jain L, Sissung T M, Danesi R, Kohn E C, Dahut W L, Kummar S et al. Hypertension and hand-foot skin reactions related to VEGFR2 genotype and improved clinical outcome following bevacizumab and sorafenib. *J Exp. Chn Cancer Res* 2010, 29, 95.
9. Morita S. Uehara K, Nakayama G, Shibata T, Oguri T, Inada-Inoue M et al. Association between bevacizumab-related hypertension and vascular endothelial growth factor (VEGF) gene polymorphisms in Japanese patients with metastatic colorectal cancer. *Cancer Chemother Pharmacol* 2013, 71, 405-411.
10. Lambrechts D, Moisse M. Delmar P. Miles D W, Leighl N, Escudier B et al. Genetic markers of bevacizumab-induced hypertension. Angiogenesis 2014, 17, 685-694.
11. Sibertin-Blanc C, Mancini J, Fabre A, Lagarde A. Del Grande J, Levy N et al. Vascular Endothelial Growth Factor A c. 237C T polymorphism is associated with bevacizumab efficacy and related hypertension in metastatic colorectal cancer. *Dig Liver Dis* 2015, 47, 331-337.
12. Gampenrieder S P, Hufnagl C. Brechelmancher S, Huemer F. Hackl H, Rinnerthaler G et al. Endothelin-1 genetic polymorphism as predictive marker for bevacizumab in metastatic breast cancer. *Pharmacogenomics J* 2017, 17, 344-350.
13. Etienne-Grimaldi M C, Formento P, Degeorges A, Pierga J Y, Delva R, Pivot X et al. Prospective analysis of the impact of VEGF-A gene polymorphisms on the pharmacodynamics of bevacizumab-based therapy in metastatic breast cancer patients. *Br J Clin Pharmacol* 2011, 71, 921-928.
14. Frey M K, Dao F. Olvera N, Konner J A, Dickler M N, Levine D A et al. Genetic predisposition to bevacizumab-induced hypertension. *Gynecol Oncol* 2017, 147, 621-625.
15. Schneider B P, Li L, Shen F. Miller K D, Radovich M, O'Neill A et al. Genetic variant predicts bevacizumab-induced hypertension in ECOG-5103 and ECOG-2100. *Br J Cancer* 2014, 111, 1241-1248.
16. Li M, Kroetz D L. Bevacizumab-induced hypertension: Clinical presentation and molecular understanding. *Pharmacol Ther* 2018, 182, 152-160.
17. Kindler H L, Niedzwiecki D, Hollis D, Sutherland S, Schrag D, Hurwitz H B et al. Gemcitabine plus bevacizumab compared with gemcitabine plus placebo in patients with advanced pancreatic cancer: Phase III trial of the Cancer and Leukemia Group B (CALGB 80303). *J Clin Oncol* 2010, 28, 3617-3622.
18. Dickler M N, Barry W T, Cirrincione C T, Ellis M J, Moynahan M E, Innocenti F et al. Phase III trial evaluating letrozole as first-line endocrine therapy with or without bevacizumab for the treatment of postmenopausal women with hormone receptor-positive advanced-stage breast cancer: CALGB 40503 (Alliance). *J Clin Oncol* 2016, 34, 2602-2609.
19. Kelly W K, Halabi S, Carducci M. George D, Mahoney J F Stadler W M et al. Randomized, double-blind, placebo-controlled phase III trial comparing docetaxel and prednisone with or without bevacizumab in men with metastatic castration-resistant prostate cancer: CALGB 90401. *J Chn Oncol* 2012, 30, 1534-1540
20. Rugo H S, Barry W T, Moreno-Aspitia A, Lyss A P, Cirrincione C, Leung E et al. Randomized phase III trial of paclitaxel once per week compared with nanoparticle albumin-bound nab-paclitaxel once per week or ixabepilone with bevacizumab as first line chemotherapy for locally recurrent or metastatic breast cancer: CALGB 40502/NCCTGN063H (Alliance). *J OM Oncol* 2015, 33, 2361-2369.
21. Innocenti F, Jiang C, Sibley A B, Denning S, Etheridge A S, Watson D et al. An initial genetic analysis of gemcitabine-induced high-grade neutropenia in pancreatic cancer patients in CALGB 80303 (Alliance). *Pharmacogenet Genomics* 2019, 29, 123-131.
22. Innocenti F, Owzar K, Cox N L, Evans P, Kubo M, Zembutsu H et al. A genome-wide association study of overall survival in pancreatic cancer patients treated with gemcitabine in CALGB 80303. OM *Cancer Res* 2012, 18, 577-584.
23. Baldwin R M, Owzar K. Zembutsu H, Chhibber A, Kubo M, Jiang C et al. A genome-wide association study identifies novel loci for paclitaxel-induced sensory peripheral neuropathy in CALGB 40101. OM *Cancer Res* 2012, 18, 5099-5109.
24. Rashkin S R, Chua K C, Ho C. Mulkey F, Jiang C. Mushiroda T et al. A Pharmacogenetic Prediction Model of Progression-Free Survival in Breast Cancer using Genome-Wide Genotyping Data from CALGB 40502 (Alliance). *Clin Pharmacol Ther* 2019, 105, 738-745.
25. Price A L, Patterson N J, Plenge R M, Weinblatt M E, Shadick N A, Reich D. Principal components analysis corrects for stratification in genome-wide association studies. *Nat Genet* 2006, 38, 904-909.
26. European Bioinformatics Institute, ftp://ftp.ebi.ac.uk/pub/databases/genenames/new/tsv/locus groups/protein-coding gene.txt. Accessed on May 7 (2018).
27. Carlson M, Maintainer B P. TxDb.Hsapiens.UCSC.hg18.knownGene: Annotation package for TxDb object(s). R package version 3.2.2. (2015).
28. Carlson M, Maintainer B P. TxDb.Hsapiens.UCSC.hg19.knownGene: Annotation package for TxDb object(s). R package version 3.2.2. (2015).
29. Yi C, Sibley A. Owzar K. snplist: Tools to Create Gene Sets. R package version 0.18.1. (2017).

30. Wu M C, Lee S, Cai T. Li Y, Boehnke M, Lin X. Rare-variant association testing for sequencing data with the sequence kernel association test. *Am J Hum Genet* 2011, 89, 82-93.
31. Tang Z Z, Lin D Y. MASS: Meta-analysis of score statistics for sequencing studies. Bioinformatics 2013, 29, 1803-1805.
32. Zhang W, Gamazon E R, Zhang X, Konkashbaev A, Liu C. Szilagyi K L et al. SCAN database: Facilitating integrative analyses of cytosine modification and expression QTL. *Database* 2015, 27, bav025.
33. Machiela M J, Chanock S J. LDlink: A web-based application for exploring population-specific haplotype structure and linking correlated alleles of possible functional variants. *Bioinformatics* 2015, 31, 3555-3557.
34. James Kent W. Sugnet C W, Furey T S, Roskin K M, Pringle T H, Zahler A M et al. The human genome browser at UCSC. *Genome Res* 2002, 12, 996-1006.
35. Boyle A P, Hong E L, Hariharan M, Cheng Y, Schaub M A, Kasowski M et al. Annotation of functional variation in personal genomes using RegulomeDB. *Genome Res* 2012, 22, 1790-1797.
36. Ward L D, Kellis M. HaploReg: A resource for exploring chromatin states, conservation, and regulatory motif alterations within sets of genetically linked variants. *Nucleic Acids Res* 2012, 40, D930-D934.
37. GTEx Consortium. The Genotype-Tissue Expression (GTEx) pilot analysis: Multitissue gene regulation in humans. Science 2015, 8, 648-660.
38. Gillies C E, Putler R, Menon R, Otto E, Yasutake Kl, Nair V et al. An eQTL Landscape of Kidney Tissue in Human Nephrotic Syndrome. *Am J Hum Genet* 2018, 103, 232-244.
39. Leigh M W, Pittman J E, Carson J L, Ferkol T W, Dell S D, Davis S D et al. Clinical and genetic aspects of primary ciliary dyskinesia/kartagener syndrome. *Genet Med* 2009, 11, 473-87.
40. Maier M, Baldwin C, Aoudjit L, Takano T. The role of trio, a rho guanine nucleotide exchange factor, in glomerular podocytes. *Int J Mol Sci* 2018, 19, E479.
41. Robins R, Baldwin C, Aoudjit L, Cote J F, Gupta I R, Takano T. Rac1 activation in podocytes induces the spectrum of nephrotic syndrome. *Kidney Int* 2017, 92, 349-364.
42. Yu H, Suleiman H, Kim A H, Miner J H, Dani A, Shaw A S et al. Rac1 Activation in Podocytes Induces Rapid Foot Process Effacement and Proteinuria. *Mol Cell Biol* 2013, 33, 4755-4764.
43. Li X, Pabla N, Wei Q, Dong G, Messing R O, Wang C Y et al. PKC-δ Promotes Renal Tubular Cell Apoptosis Associated with Proteinuria. *J Am Soc Nephrol* 2010, 21, 1115-1124.
44. Riedel J H, Paust H J, Krohn S, Turner J E, Kluger M A, Steinmetz O M et al. IL-17F Promotes Tissue Injury in Autoimmune Kidney Diseases. *J Am Soc Nephrol* 2016, 27, 3666-3677.
45. Stames T, Robertson M J, Sledge G, Kelich S, Nakshatri H, Broxmeyer H E et al. Cutting Edge: IL-17F, a Novel Cytokine Selectively Expressed in Activated T Cells and Monocytes, Regulates Angiogenesis and Endothelial Cell Cytokine Production. *J Immunol* 2001, 167, 4137-4140.
46. Oyadomari S, Araki E, Mori M. Endoplasmic reticulum stress-mediated apoptosis in pancreatic β-cells. *Apoptosis* 2002, 7, 335-345.
47. Bucci M, Gratton J P, Rudic R D, Acevedo L, Roviezzo F, Cirino G et al. In vivo delivery of the caveolin-1 scaffolding domain inhibits nitric oxide synthesis and reduces inflammation. Nat Med 2000, 6, 1362-1367.
48. 49. Yang Y A, Zhao J C, Fong K W, Kim J, Li S, Song C et al. FOXA1 potentiates lineage-specific enhancer activation through modulating TET1 expression and function. Nucleic Acids Res 2016, 44, 8153-8164.
49. Holwerda S J, de Laat W. CTCF: The protein, the binding partners, the binding sites and their chromatin loops. *Philos Trans R Soc Lond B Biol Sci* 2013, 368, 20120369.
50. Gorski M, Most P J V, Teumer A, Chu A Y, Li M, Mijatovic V et al. Corrigendum: 1000 Genomes-based meta-analysis identifies 10 novel loci for kidney function. *Sci Rep.* 2017, 7, 46835.
51. De Francesco E M, Maggiolini M. Tanowitz H B, Sotgia F, Lisanti M P. Targeting hypoxic cancer stem cells (CSCs) with Doxycycline: Implications for optimizing anti-angiogenic therapy. *Oncotarget* 2017, 8, 56126-56142.
52. Calbet J A L. Chronic hypoxia increases blood pressure and noradrenaline spillover in healthy humans. *J Physiol* 2003, 551, 379-386.
53. Gueler F, Shushakova N, Mengel M, Hueper K. Chen R. Liu X et al. A novel therapy to attenuate acute kidney injury and ischemic allograft damage after allogenic kidney transplantation in mice. *PLoS One* 2015, 10, e0115709.
54. Chen R, Liliental J E, Kowalski P E, Lu Q, Cohen S N. Regulation of transcription of hypoxia-inducible factor-la (HIF-1 a) by heat shock factors HSF2 and HSF4. *Oncogene* 2011, 30, 2570-2580.
55. Huang C Y, Pal P Y, Kuo C H, Ho T J, Lin J Y, Lin D Y et al. p53-mediated miR-18 repression activates HSF2 for IGF-IIR-dependent myocyte hypertrophy in hypertension induced heart failure. *Cell Death Dis* 2017, 8, e2990.
56. Berger M D, Lenz H J. The safety of monoclonal antibodies for treatment of colorectal cancer. *Expert Opin Drug Saf* 2016, 15, 799-808.
57. An M M, Zou Z, Shen H, Liu P, Chen M L, Cao Y B et al. Incidence and risk of significantly raised blood pressure in cancer patients treated with bevacizumab: An updated meta-analysis. *Eur J Clin Pharmacol* 2010, 66, 813-821.
58. Schneider B P, Li L, Radovich M, Shen F, Miller K D, Flockhart D A et al. Genome-Wide Association Studies for Taxane-Induced Peripheral Neuropathy in ECOG-5103 and ECOG-1199. *Clin Cancer Res* 2015, 21, 5082-5091.
59. Han J Y, Shin E S, Lee Y S, Ghang H Y, Kim S Y, Hwang J A et al. A genome-wide association study for irinotecan-related severe toxicities in patients with advanced non-small-cell lung cancer. *Pharmacogenomics J* 2013, 13, 417-422.
60. Tesařová P, Tesař V. Proteinuria and hypertension in patients treated with inhibitors of the VEGF signalling pathway—incidence, mechanisms and management. *Folia Biol (Praha)* 2013, 59, 15-25.
61. D J et al. Genetic Variants of VEGFA and FLT4 Are Determinants of Survival in Renal Cell Carcinoma Patients Treated with Sorafenib. *Cancer Res* 2019, 79, 231-41.
62. GTEx Consortium. The Genotype-Tissue Expression (GTEx) pilot analysis: Multitissue gene regulation in humans. *Science* 2015, 8, 648-60.
63. Machiela M J et al. LDlink: A web-based application for exploring population-specific haplotype structure and 64. Angiogenisis Inhibitor. https://www.wikiwand.com/en/Angiogenesis_inhibitor. Accessed on Aug. 7 (2019).
65. James Kent W et al. The human genome browser at UCSC. Genome Res 2002, 12, 996-1006.
66. Blattler A et al. Cross-talk between site-specific transcription factors and DNA methylation states. *J Biol Chem* 2013 288, 34287-94.
67. Mir O, Coriat R, Cabanes L et al. An Observational Study of Bevacizumab-Induced Hypertension as a Clinical Biomarker of Antitumor Activity. Oncologist 2011; 16: 1325-1332.
68. Hertz D L, Owzar K, Lessans S et al. Pharmacogenetic discovery in CALGB (alliance) 90401 and mechanistic validation of a VAC14 polymorphism that increases risk of docetaxel-induced neuropathy. Clin *Cancer Res* 2016; 22: 4890-4900.
69. Thul P J, Akesson L, Wiking M et al. A subcellular map of the human proteome. Science 2017; 356: pii:eaal3321.
70. González C, Baez-Nieto D, Valencia I et al. K+ channels: Function-structural overview. Compr Physiol 2012; 2: 2087-2149.
71. Tipparaju S M, Liu S Q, Barski O A et al. NADPH binding to β-subunit regulates inactivation of voltage-gated K+ channels. Biochem Biophys Res Commun 2007:359: 267-276.
72. Sobey C G. Potassium channel function in vascular disease. Arterioscler Thromb Vasc Biol 2001: 21: 28-38.
73. Martens J R, Gelband C H. Alterations in rat interlobar artery membrane potential and K+ channels in genetic and nongenetic hypertension. Circ Res 1996; 79: 295-301.
74. Banerjee B, Peiris D N, Koo S H et al. Genomic imbalances in key ion channel genes and telomere shortening in sudden cardiac death victims. Cytogenet Genome Res 2009: 122: 350-355.
75. Tur J, Chapalamadugu K C, Padawer T et al. Deletion of Kvβ1.1 subunit leads to electrical and haemodynamic changes causing cardiac hypertrophy in female murine hearts. Exp Physiol 2016; 101: 494-508.
76. Kulakovskiy I V, Vorontsov I E, Yevshin I S et al. HOCOMOCO: Towards a complete collection of transcription factor binding models for human and mouse via large-scale ChIP-Seq analysis. Nucleic Acids Res 2018; 46: D252-D259.
77. Niu Z, Li A Zhang S X et al. Serum response factor micromanaging cardiogenesis. Curr Opin Cell Biol 2007; 19: 618-627.
78. Rouillard A D, Gundersen G W, Fernandez N F et al. The harmonizome: a collection of processed datasets gathered to serve and mine knowledge about genes and proteins. Database (Oxford) 2016: pii: baw100.
79. Sherry S T, Ward M H, Kholodov M et al. dbSNP: the NCBI database of genetic variation. Nucleic Acids Res 2001: 29: 308-311.
80. Reddish F N, Miller C L, Gorkhali R et al. Calcium dynamics mediated by the endoplasmic/sarcoplasmic reticulum and related diseases. Int J Mol Sci 2017; pii: E1024.
81. West A G, Gaszner M, Felsenfeld G. Insulators: Many functions, many mechanisms. Genes Dev 2002; 16: 271-288.
82. Brahmer J R, Dahlberg S E, Gray R J et al. Sex differences in outcome with bevacizumab therapy: Analysis of patients with advanced-stage non-small cell lung cancer treated with or without bevacizumab in combination with paclitaxel and carboplatin in the eastern cooperative oncology group trial 459. J Thorac Oncol 2011; 6: 1031-08.
83. Li M, Mulkey F, Jiang C et al. Identification of a genomic region between SLC29A1 and HsP90AB1 associated with risk of bevacizumab-induced hypertension: CALGB 80405 (Alliance). Clin Cancer Res 2018; 24: 4734-4744
84. Wilhelm S M, Carter C, Tang L Y, et al. BAY 43-9006 exhibits broad spectrum oral antitumor activity and targets the RAF/MEK/ERK pathway and receptor tyrosine kinases involved in tumor progression and angiogenesis. *Cancer Res* 2004; 64:7099-109. https://doi.org/10.1158/0008-5472.CAN-04-1443.
85. Nexavar (Sorafenib). <https://www.accessdata.fda.gov/drugsatfda_docs/label/2018/021923s020lbl.pdf>. Accessed 16 May 2020.
86. Costa L J, Drabkin H A. Renal Cell Carcinoma: New Developments in Molecular Biology and Potential for Targeted Therapies. Oncologist 2007; 12:1404-15. https://doi.org/10.1634/theoncologist.12-12-1404.
87. Li Y, Li S, Zhu Y, et al. Incidence and risk of sorafenib-induced hypertension: A systematic review and meta-analysis. J Clin Hypertens 2014; 16:177-85. https://doi.org/10.1111/jch.12273.
88. Qi W X, Lin F, Sun Y J, et al. Incidence and risk of hypertension with pazopanib in patients with cancer: A meta-analysis. Cancer Chemother Pharmacol 2013; 71:431-9. https://doi.org/10.1007/s00280-012-2025-5.
89. Zhu X, Stergiopoulos K, Wu S. Risk of hypertension and renal dysfunction with an angiogenesis inhibitor sunitinib: Systematic review and meta-analysis. Acta Oncol (Madr) 2009; 8:9-17. https://doi.org10.1080/02841860802314720.
90. Maitland M L, Kasza K E, Karrison T, et al. Ambulatory monitoring detects sorafenib-induced blood pressure elevations on the first day of treatment. Clin Cancer Res 2009; 15:6250-7. https://doi.org/10.1158/1078-0432.CCR-09-0058.
91. Karar J, Maity A. PI3K/AKT/mTOR Pathway in Angiogenesis. Front Mol Neurosci 2011; 4:51. https://doi.org/10.3389/fnmol.2011.00051.
92. Horowitz J R, Rivard A, Van Der Zee R, et al. Vascular endothelial growth factor/vascular permeability factor produces nitric oxide-dependent hypotension: Evidence for a maintenance role in quiescent adult endothelium. Arterioscler Thromb Vasc Biol 1997:17:2793-800. https://doi.org/10.1161/01.ATV.17.11.2793.
93. Rini B I. Quantifying hypertension in patients with cancer treated with sorafenib. Lancet Oncol 2008; 9:86-7. https://doi.org/10.1016/S1470-2045(08)70009-3.
94. Qin C, Cao Q. Li P, et al. The influence of genetic variants of sorafenib on clinical outcomes and toxic effects in patients with advanced renal cell carcinoma. Sci Rep 2016; 6:20089. https://doi.org/10.1038/srep20089.
95. Robinson E S, Khankin E V, Karumanchi S A, et al. Hypertension induced by vascular endothelial growth factor signaling pathway inhibition: Mechanisms and potential use as a biomarker. Semin Nephrol 2010:30: 591-601. https://doi.org/10.1016j.semnephrol.2010.09.007.
96. Escudier B, Eisen T, Stadler W M, et al. Sorafenib in advanced clear-cell renal-cell carcinoma. N Engl J Med 2007; 356:125-34. https://doi.org/10.1056/NEJMoa060655.
97. Crona D J, Skol A D, Leppanen V M, et al. Genetic variants of VEGFA and FLT4 are determinants of survival in renal cell carcinoma patients treated with sorafenib. Cancer Res 2019; 79:231-41. https://doi.org/10.11580008-5472.CAN-18-1089.
98. Quintanilha J C F, Wang J, Sibley A B et al. Bevacizumab-induced hypertension and proteinuria: A genome-wide analysis of more than 1,000 patients. Submitted to J Nat Cancer Inst.
99. Baldwin R M, Owzar K, Zembutsu H, et al. A genome-wide association study identifies novel loci for paclitaxel-induced sensory peripheral neuropathy in CALGB 40101. Clin Cancer Res 2012; 18:5099-109. https://doi.org/10.11581078-0432.CCR-12-1590.
100. Dayem Ullah A Z, Oscanoa J, Wang J, et al. SNPnexus: Assessing the functional relevance of genetic variation to facilitate the promise of precision medicine. Nucleic Acids Res 2018; 46:W109-W113. https://doi.org/10.1093/nar/gky399.
101. Ardlie K G, DeLuca D S, Segrà A V., Sullivan T J, Young T R, Gelfand E T, et al. The Genotype-Tissue Expression (GTEx) pilot analysis: Multitissue gene regulation in humans. Science 2015; 8:648-60. https://doi.org/10.1126/science.1262110.
102. Zuo C, Shin S, Keleş S. AtSNP: Transcription factor binding affinity testing for regulatory SNP detection. Bioinformatics 2015; 31:3353-5. https://doi.org/10.1093/bioinformatics/btv328.
103. Zhong H, Chiles K. Feldser D, et al. Modulation of hypoxia-inducible factor 1α expression by the epidermal growth factor/phosphatidylinositol 3-kinase/PTEN/AKT/FRAP pathway in human prostate cancer cells: Implications for tumor angiogenesis and therapeutics. Cancer Res 2000; 60:1541-1545.
104. Forsythe J A, Jiang B H, Iyer N V, et al. Activation of vascular endothelial growth factor gene transcription by hypoxia-inducible factor 1. Mol Cell Biol 1996; 16:4604-4613. https://doi.org/10.1128/mcb.16.9.4604.
105. Shymanets A, Prajwal, Bucher K, et al. P87 and p101 subunits are distinct regulators determining class 1 B phosphoinositide 3-kinase (PI3K) specificity. J Biol Chem 2013; 288:31059-68. https://doi.org/10.1074/jbc.M113.508234.
106. Serban D, Leng J, Cheresh D. H-ras regulates angiogenesis and vascular permeability by activation of distinct downstream effectors. Circ Res 2008:102:1350-8. https://doi.org/10.1161/CIRCRESAHA.107.169664.

What is claimed is:

1. A method for reducing the risk of vascular endothelial growth factor (VEGF) pathway inhibitor-induced hypertension in a subject in need of treatment with a VEGF pathway inhibitor, the method comprising:
   (i) identifying the subject as having a single nucleotide polymorphism (SNP) at rs6770663, wherein the base identified at rs6770663 is a guanine; and
   (ii) administering one or more antihypertensive agents to the subject identified as having a guanine at rs6770663.

2. The method of claim 1, wherein the SNP lowers expression of KCNAB1 relative to wildtype.

3. The method of claim 1, wherein the anti-hypertensive agent is selected from the group consisting of diuretics, beta blockers, alpha and beta blockers, calcium channel blockers, Angiotensin-converting enzyme (ACE) inhibitors, angiotensin II receptor antagonists (ARBs), adrenergic receptor antagonists, vasodilators, renin inhibitors, aldosterone receptor antagonists, alpha-2 adrenergic receptor agonists, central alpha-2 agonists and other centrally acting drugs, and endothelin receptor blockers.

4. The method of claim 1, wherein the subject was receiving a first antihypertensive agent prior to administration of the VEGF-pathway inhibitor, and wherein administering one or more antihypertensive agents comprises adding a second antihypertensive agent to the subject's treatment regimen, increasing the dose of the first antihypertensive agent, switching the subject to a different antihypertensive agent relative to the first antihypertensive agent, and/or switching the subject to an antihypertensive agent that is in a different class of therapeutic agent relative to the first antihyertensive agent.

5. The method of claim 1, wherein the subject is administered the antihypertensive agent prior to or concurrently with the VEGF pathway inhibitor.

6. The method of claim 1, wherein the VEGF-pathway inhibitor is selected from the group consisting of bevacizumab, bevacizumab-awwb, bevacizumab-bvzr, ranibizumab, aflibercept, ziv-aflibercept, lenalidomide, lenvatinib, ramucirumab, cabozantinib, pazopanib, sunitinib malate, regorafenib, axitinib, tipiracil and trifluridine, ponatinib, vandetanib, sorafenib, everolimus, thalidomide, temsirolimus, interferon alfa, interferon alfa-2B, interferon alfa-N3, peginterferon alfa-2B, peginterferon alfa-2A, rhEndostatin, cediranib, semaxanib, pomalidomide, alitretinoin, imiquimod, sinecatechins, vismodegib, sonidegib, pegaptanib sodium, dexamethasone intravitreal implant, fluocinolone acetonide, conbercept, brolucizumab-dbll, selpercatinib, nintedanib, apatinib, and motesanib.

* * * * *